US011054424B2

(12) United States Patent
Benkirane et al.

(10) Patent No.: US 11,054,424 B2
(45) Date of Patent: Jul. 6, 2021

(54) CELL IDENTIFICATION METHOD

(71) Applicant: Centre National De La Recherche Scientifique (CNRS), Paris (FR)

(72) Inventors: Monsef Benkirane, Saint Gely du Fesc (FR); Gael Petitjean, Montpellier (FR)

(73) Assignee: CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 94 days.

(21) Appl. No.: 15/538,742

(22) PCT Filed: Dec. 17, 2015

(86) PCT No.: PCT/FR2015/053579

§ 371 (c)(1),
(2) Date: Jun. 22, 2017

(87) PCT Pub. No.: WO2016/102829

PCT Pub. Date: Jun. 30, 2016

(65) Prior Publication Data

US 2017/0350889 A1 Dec. 7, 2017

(30) Foreign Application Priority Data

Dec. 22, 2014 (FR) ....................................... 1463138

(51) Int. Cl.

| | |
|---|---|
| ***C12Q 1/68*** | (2018.01) |
| ***G01N 33/569*** | (2006.01) |
| ***C12Q 1/70*** | (2006.01) |
| ***C12Q 1/6897*** | (2018.01) |
| ***C07K 16/10*** | (2006.01) |
| ***C12N 7/04*** | (2006.01) |
| ***G01N 33/50*** | (2006.01) |

(52) U.S. Cl.

CPC ... *G01N 33/56988* (2013.01); *C07K 16/1045* (2013.01); *C12N 7/04* (2013.01); *C12Q 1/6897* (2013.01); *C12Q 1/703* (2013.01); *G01N 33/505* (2013.01); *G01N 33/569* (2013.01); *G01N 33/56972* (2013.01); *C12Q 2521/507* (2013.01); *C12Q 2600/136* (2013.01); *G01N 2333/16* (2013.01); *G01N 2333/70514* (2013.01); *G01N 2333/70517* (2013.01); *G01N 2333/70589* (2013.01); *G01N 2333/70596* (2013.01); *G01N 2500/10* (2013.01)

(58) Field of Classification Search
None
See application file for complete search history.

(56) References Cited

FOREIGN PATENT DOCUMENTS

| | | | |
|---|---|---|---|
| EP | 1 715 053 | A1 | 10/2006 |
| WO | 2006/067572 | A2 | 6/2006 |
| WO | 2013/148197 | A1 | 10/2013 |

OTHER PUBLICATIONS

Ikawa et al. (Human Molecular Genetics, 2019, vol. 28, No. 1 R24-R30).*

Matteo et al (Expert Opin. Biol. Ther. 2012, vol. 12, No. 7, pp. 841-858).*

Hauber, et al., Highly Significant Antiviral Activity of HIV-1 LTR-Specific Tre-Recombinase in Humanized Mice, PLOS Pathogens/www.plospathogens.org, Sep. 2013, vol. 9, Issue 9, e1003587, pp. 1-18, Switzerland.

Wall, et al., Monosynaptic Circuit Tracing in Vivo Through Cre-dependent Targeting and Complementation of Modified Rabies Virus, Proceedings of the National Academy of Sciences, vol. 107, Issue 50, pp. 21848-21853, USA.

Laird, et al., Rapid Quantification of the Latent Reservoir for HIV-1 Using a Viral Outgrowth Assay, PLOS/www.plospathogens.org, May 2013, vol. 9, Issue 5, e1003398, pp. 1-11, USA.

* cited by examiner

*Primary Examiner* — Celine X Qian

(74) *Attorney, Agent, or Firm* — Dinsmore & Shohl LLP

(57) ABSTRACT

The present invention relates to the use of a nucleic acid molecule encoding a first reporter gene, bordered by at least one first pair and one second pair of sequences targeting a site-specific recombinase in order to detect cells of a mammal infected with a virus responsible for an immunodeficiency.

6 Claims, 11 Drawing Sheets

Specification includes a Sequence Listing.

CELL IDENTIFICATION METHOD

The present invention relates to a method for identifying cells.

Research into acquired immune deficiency syndrome, AIDS, is a path fraught with challenges. Despite progress in therapies and the few rare cases of functional recovery, infection by the human immunodeficiency virus HIV still remains a public health problem. Seropositive people may currently live as long as others, but absolutely have to follow their treatment for their whole lives. This is because, if they stop treatment, the viral load increases rapidly, and the patients will then develop AIDS.

Antivirals, and in particular highly active therapies HAART, make it possible to control the viral load and make the virus undetectable by conventional screening techniques. This does not however mean that the virus has been eliminated from the host.

A portion of the viral DNAs insert themselves into the genome of some cells and remain there in the latent state, that is to say that the virus is present but is not replicating. Using this strategy, HIV becomes "resistant" to therapies which essentially target the mechanisms of infection and multiplication of the virus.

Moreover, latent HIV is invisible to the immune system, because the infected cell does not present any viral antigens, which are the only signs for the immune system to consider that the cell has been infected and must thus be eliminated.

"Resistant" cells are referred to as viral reservoirs.

There is also a need to determine the nature of these cells, in order to propose a suitable therapy to eliminate these reservoirs, with a view to completely eradicating the infection.

Application WO 2013/148197 proposes the use of a bromodomain inhibitor with a view to reactivating the latent virus and thus to eradicating the reservoir cells.

Application US 2009/010941 proposes treating the cells infected with HIV with a TRAIL agonist, optionally combined with histone deacetylase inhibitors, in order to induce apoptosis of the reservoir cells.

However, these documents only propose treatments which target all cells, without knowing the exact nature of the reservoir cells. There is also a risk of proposing treatments which are not very specific and which will only increase the undesirable effects already associated with antiretroviral therapies.

Consequently, there is still a need to determine the nature of the reservoir cells.

One of the aims of the invention is to overcome this lack.

The aim of the invention is to propose a method making it possible to effectively determine the reservoir cells of viruses inducing an immunodeficiency.

Another aim of the invention is to propose a model for studying these cells.

Thus, the invention relates to the use of a nucleic acid molecule comprising a first sequence encoding a first reporter, under the control of at least one element necessary for transcription, the first sequence being bordered by

- at least one first pair of sequences targeting a site-specific recombinase, said first pair comprising a P1-1 sequence and a P1-2 sequence,
- at least one second pair of sequences targeting a site-specific recombinase, said second pair comprising a P2-1 sequence and a P2-2 sequence, the sequences of each of said first and second pairs of sequences being oppositely oriented relative to one another, the sequences of the first pair of sequences targeting a site-specific recombinase are unable to recombine with the sequences of the second pair of sequences targeting a site-specific recombinase, and in which the sequences of the second pair of sequences targeting a site-specific recombinase are unable to recombine with the sequences of the first pair of sequences targeting a site-specific recombinase, one sequence from the first pair and one sequence from the second pair of sequences targeting a site-specific recombinase being located upstream of said first nucleic acid sequence, and one sequence from the first pair and one sequence from the second pair of sequences targeting a site-specific recombinase being located downstream of said first nucleic acid sequence, such that the sequences of the same pair never surround the two sequences of the other pair, the sequence of said first nucleic acid molecule being such that, in the absence of combination induced by said site-specific recombinase, it has an open reading frame encoding said first reporter in a 3'-5' orientation, and is therefore unable to enable the transcription and translation of the reporter gene in order to obtain said first reporter, optionally combined with a recombinase, or advantageously combined with a virus responsible for an immunodeficiency, said virus comprising, in its genome, a gene encoding said site-specific recombinase, for the detection, especially the in vitro detection, of cells from a mammal infected by a virus responsible for an immunodeficiency in said mammal, said cells being the reservoir cells of said virus, or for carrying out a method for the detection, especially the in vitro detection, of cells from a mammal infected by a virus responsible for an immunodeficiency in said mammal, said cells being the reservoir cells of said virus, said cells especially being hematopoietic cells.

Advantageously, the invention relates to the use of a nucleic acid molecule comprising a first sequence encoding a first reporter, under the control of at least one element necessary for transcription, the first sequence being bordered by

- at least one first pair of sequences targeting a site-specific recombinase, said first pair comprising a P1-1 sequence and a P1-2 sequence,
- at least one second pair of sequences targeting a site-specific recombinase, said second pair comprising a P2-1 sequence and a P2-2 sequence, the sequences of each of said first and second pairs of sequences being oppositely oriented relative to one another, the sequences of the first pair of sequences targeting a site-specific recombinase are unable to recombine with the sequences of the second pair of sequences targeting a site-specific recombinase, and in which the sequences of the second pair of sequences targeting a site-specific recombinase are unable to recombine with the sequences of the first pair of sequences targeting a site-specific recombinase, one sequence from the first pair and one sequence from the second pair of sequences targeting a site-specific recombinase being located upstream of said first nucleic acid sequence, and one sequence from the first pair and one sequence from the second pair of sequences targeting a site-specific recombinase being located downstream of said first nucleic acid sequence, such that the sequences of the same pair never surround the two sequences of the other pair, the sequence of said first nucleic acid molecule being such that, in the absence of combination induced by said site-specific recombinase, it has an open reading frame coding for said first reporter in a 3'-5' orientation, and is therefore unable to enable the transcription and translation of the reporter gene encoding said first reporter, combined with a virus responsible for an immunodeficiency, said virus comprising, in its genome, a gene encoding said site-specific recombinase, for the detection, especially the in vitro detection, of cells from a mammal infected by a virus responsible for an immunodeficiency in said mammal, said cells being the reservoir cells of said virus.

The invention is based on the surprising observation made by the inventors that a gene construct which enables the expression of a reporter specifically targeting the cells infected by a virus inducing an immunodeficiency makes it possible to detect the reservoir cells of said virus.

Advantageously, by combining a nucleic acid molecule comprising a sequence encoding a reporter, which is able to be recombined, and a recombinase, it is possible to specifically identify the target cells of said virus and thereby isolate the reservoir cells thereof.

The invention is therefore based on the use of a nucleic acid molecule which comprises a reporter gene sequence encoding a reporter. The sequence of this reporter gene, or more precisely the open reading frame encoding the reporter, is positioned in the 3'→5' direction. Thus, under normal conditions, if the nucleic acid molecule is introduced into a cell, or if it is placed in the presence of an in vitro transcription/translation system, no functional protein corresponding to the reporter gene will be able to be expressed. This principle is well known to those skilled in the art: transcription and translation occur in the 5'→3' direction.

In order to enable the expression of the reporter gene, it will be necessary to carry out genetic recombination within the nucleic acid molecule.

For this purpose, the inventors have made use of site-specific recombination using site-specific recombinase enzymes. The recombination mechanisms involved in the context of recombination of the same molecule are as follows:

- excision and resolution which are two relatively similar phenomena in terms of the mechanism used, even though they represent unrelated biological events. In both cases, the two recombination sites are borne by the same initial replicon, and must be direct repeats relative to one another. After synapsis by the recombinase, two independent replicons will be produced, which are either identical in the case of dimer resolution, or different in the case of excision, and
- inversion which also requires the two recombination sites to be borne by the same replicon. However, in order for an inversion to take place, it is necessary for these sites to be inverted repeats relative to one another. Their assembly in synapsis will give rise to topological stresses which will lead to the inversion of the genetic material located between the two sites, rather than the deletion thereof.

These two mechanisms are illustrated in FIG. 1.

Thus, since the sequence encoding the reporter is in a 3'→5' orientation, which is incompatible with transcription and translation, it will be necessary, in order for said reporter gene to be able to be expressed, to carry out an inversion. Thus, as is mentioned above, the sequence encoding the reporter is therefore flanked by a pair of sequences which can be recognized by a recombinase, the two sequences being inverted repeats relative to one another, or oppositely oriented relative to one another.

By way of example, if the recombination sequence referred to as "SEQUENCE", the nucleic acid molecule would be artificially written in the following way, for the purposes of this example:

5'-SEQUENCE—ENEG RETROPER (which corresponds to the reporter gene in the 3'→5' direction)—ECNEUQES-3'.

After recombination, in the presence of the appropriate recombinase, the recombined sequence will be as follows:

5'-ECNEUQES—REPORTER GENE (which corresponds to the reporter gene in the 5'→3' direction)—SEQUENCE-3'.

Nonetheless, it is understood from this example that as long as recombination is present, inversion by recombination will be possible, and the sequence of the reporter gene could be inverted indefinitely.

In order to overcome this drawback, the inventors have made use of the ability that certain site-specific recombinases have to recognize specific pairs of sequences. In this case, the recombinase is able to carry out recombinations by means of a first pair of recombination sequences, or by means of a second or third, etc. pair of sequences, but the recombinase is unable to carry out recombination using sequences of two different pairs.

In other words, if the sequence encoding the reporter of the invention is flanked by a recombination sequence of a first pair on one side and a recombination sequence on the other side, without the second sequence of each of the pairs being present, no recombination (inversion or excision) will be possible.

By making use of these properties, the inventors propose to use a nucleic acid molecule encoding a reporter, the reading frame of which is in a 3'→5' orientation, which is bordered by two pairs of recombination sequences recognized by the same recombinase.

As has been mentioned above, it is necessary for the sequences of the same sequence pair enabling site-specific recombination by a recombinase to be oppositely oriented relative to one another.

In addition, it is necessary for the sequences of the same pair to not be included between the sequences of the other pair. Indeed, if this were the case, the sequence of the reporter gene would then be inverted by a first pair, and inverted again by the second pair.

Thus, the nucleic acid molecule of the invention is such that it comprises a first pair of site-specific sequences consisting of a sequence P1.1 and of a sequence P1.2, and a second pair of site-specific sequences consisting of a sequence P2.1 and of a sequence P2.2, such that the reporter gene is flanked by the two pairs of sequences and that said sequences are oriented in the following way:

5'-P1.1-P2.1-"reporter gene to be recombined"-P1.2-P2.2-3', or

5'-P1.1-P2.2-"reporter gene to be recombined"-P1.2-P2.1-3', or

5'-P1.2-P2.1-"reporter gene to be recombined"-P1.1-P2.2-3', or

5'-P1.2-P2.2-"reporter gene to be recombined"-P1.1-P2.1-3', or

5'-P2.1-P1.1-"reporter gene to be recombined"-P2.2-P1.2-3', or

5'-P2.1-P1.2-"reporter gene to be recombined"-P2.2-P1.1-3', or

5'-P2.2-P1.1-"reporter gene to be recombined"-P2.1-P1.2-3', or

5'-P2.2-P1.2-"reporter gene to be recombined"-P2.1-P1.1-3'.

In this configuration, and as illustrated in FIG. 2, a first inversion will take place by virtue of the sequences of one of the two site-specific pairs of sequences. At the end of this recombination, the sequences of the other pair, initially oppositely oriented relative to one another, are in the same orientation. These sequences of the other pair also flank one of the sequences of the pair of sequences which enabled the inversion. It will then be possible to carry out an excision by means of the other pair of sequences, and the resulting molecule will comprise one sequence from the pair which enabled the inversion, and one sequence which enabled the excision, surrounding the sequence of the reporter gene positioned in the 5'→3' direction.

Since the sequences of the two pairs are not compatible with one another, that is to say that it is not possible to carry out recombination using one sequence from one pair and one sequence from another pair, the sequence of the reporter gene is "fixed" in a 5'→3' orientation and is no longer able to be inverted. The reporter can then be expressed.

In the invention, "reporter gene" is intended to mean the nucleic acid molecule encoding the protein "reporter".

Within the context of the abovementioned use, it is the reporter which is detected.

The reporters may especially be any one of the proteins known to those skilled in the art which make it possible to identify cells, and especially autofluorescent proteins such as green, red, yellow, far red, cyan fluorescent proteins, etc., originating from jellyfish or coral, or else enzymes such as luciferase from the sea pansy (*Renilla reniformis*) or firefly, or else enzymes such as β-galactosidase. This list is non-limiting.

Advantageously, the first reporter in the invention is red fluorescent protein RFP.

The sequence of the reporter gene, encoding the first abovementioned reporter, is placed under the control of elements enabling its transcription. This means that the sequence of the reporter gene is under the control of a promoter and optionally of enhancers, which, in the presence of transcription complexes, will make it possible to produce a messenger RNA corresponding to said reporter gene, said RNA subsequently being translated into said first reporter.

The element(s) necessary for transcription may be

- either included between the sequences of the site-specific recombination sequence pairs, advantageously 3' to the sequence of the non-inverted reporter gene, but upstream of the sequence of the pair of sequences which will serve for excision, such that after inversion, the element(s) will be in the 5' position
- or upstream of said sequences, such that it(they) will not be inverted during recombination.

The abovementioned first nucleic acid molecule and therefore ready to be recombined.

It is advantageous to introduce into the target cells, that is to say the cells which it is envisaged to detect, a site-specific recombinase for specific recombination of sites contained in the first nucleic acid sequence.

Since the aim of the invention is to detect reservoir cells of viruses causing an immunodeficiency in an infected mammal, it is advantageous for the target cells to be cells of the immune system. Thus, the recombinase may be introduced into the cells of interest by any means known to those skilled in the art.

An advantageous means for targeting the expression of the recombinase in the cells of interest is to infect the cells with a virus which is specific to said cells, said virus being genetically modified such that, in addition to the genes necessary for its life-cycle, it expresses said recombinase.

It is therefore particularly advantageous, within the context of detecting reservoir cells of an immunodeficiency virus, such as human immunodeficiency virus (HIV), simian immunodeficiency virus (SIV) or feline immunodeficiency virus (FIV), to use said virus which comprises, in its genome, an additional gene encoding the recombinase of interest.

Due to its specificity for hematopoietic cells, one of the abovementioned viruses will target all the target cells and especially the reservoir cells. If the cells also comprise the abovementioned first nucleic acid molecule, due to the action of the recombinase, the cells targeted by the virus will express the reporter and will then be readily detectable by those skilled in the art.

In one advantageous embodiment, the invention relates to the abovementioned use, in which the first nucleic acid sequence is bordered

- upstream of its first nucleotide in its 5' region by one of the sequences from the first pair of sequences targeting a site-specific recombinase and by one of the sequences from the second pair of sequences targeting a site-specific recombinase, and
- downstream of its last nucleotide in its 3' region by the other sequence from the first pair of sequences targeting a site-specific recombinase and the other sequence from the second pair of sequences targeting a site-specific recombinase.

Advantageously, the invention relates to the abovementioned use, in which the site-specific recombinase is chosen from Cre recombinase from the P1 bacteriophage, FLP recombinase from *Saccharomyces cerevisiae*, R recombinase from *Zygosaccharomyces rouxii* pSR1, A recombinase from *Kluyveromyces drosophilarium* pKD1, A recombinase from *Kluyveromyces waltii* pKW1, λ Int integrase, recombinase from the GIN recombination system from the Mu phage, bacterial β recombinase or a variant of any one of these recombinases.

Advantageously, the invention relates to the abovementioned use, in which said nucleic acid molecule also comprises a second sequence encoding a second reporter under the control of at least one element necessary for transcription.

In this advantageous embodiment, outside the regions involved in the site-specific recombination, the abovementioned first nucleic acid molecule comprises a second reporter gene sequence encoding a second reporter. Unlike the sequence encoding the first reporter, the second reporter gene sequence is already in the 5'→3' direction and the second reporter is expressed regardless of the presence or absence of the recombinase. This second reporter especially has the benefit of detecting cells which have been transformed by the abovementioned first nucleic acid molecule.

As a summary of the preceding description, the invention relates to the use, for the detection of reservoir cells of an immunodeficiency virus of mammals, especially primates (humans or monkeys) and felines, or for carrying out a method for the in vitro detection of said reservoir cells, said virus being especially HIV, SIV, or FIV:

- of a nucleic acid molecule comprising, in the 5'-3' direction:
  - a first sequence from a first pair of sequences for site-specific recombination, followed by
  - a first sequence from a second pair of sequences for site-specific recombination, followed by the sequence of the first reporter gene, the open reading frame of which is oriented in the 3'→5' direction, followed by a second sequence from a first pair of sequences for site-specific recombination, this second sequence being oppositely oriented to the orientation of the first sequence from the first pair, followed by a second sequence from a second pair of sequences for site-specific recombination, this second sequence being oppositely oriented to the orientation of the first sequence from the second pair, optionally, a virus of the abovementioned immunodeficiency, modified and enabling the expression of the site-specific recombinase recognizing the sequences of said first and second pair of sequences for site-specific recombination.

This viral sequence is advantageously one of the following sequences:

HIV NL4-3-Nef-IRES-Cre (SEQ ID NO: 21),

HIV NL4-3-Nef (codon opt)-IRES-Cre (SEQ ID NO: 22),

HIV NL4-3-Nef-CMV-Cre (SEQ ID NO: 23),

HIV NL4-3-Nef (codon opt)-CMV-Cre (SEQ ID NO: 24),

SIVmac239-Nef-IRES-Cre (SEQ ID NO: 25),

SIVmac239-Nef (codon opt)-IRES-Cre (SEQ ID NO: 26),

SIVmac239-Nef-CMV-Cre (SEQ ID NO: 27), and

SIVmac239-Nef (codon opt)-CMV-Cre (SEQ ID NO: 28).

In another advantageous embodiment, the invention relates to the abovementioned use, in which the site-specific recombinase is the Cre recombinase from the P1 bacteriophage.

Advantageously, the Cre recombinase from the P1 bacteriophage comprises or consists of either one of sequences SEQ ID NO: 18 and SEQ ID NO: 20, respectively encoded by is encoded the following nucleic acid sequences: SEQ ID NO: 17 and SEQ ID NO: 19.

The sequence encoding the Cre recombinase is either inserted into the viral genome, under the control of an autonomous promoter, or under the control of the expression of the Nef protein, in the form of a Nef-IRES Cre sequence.

Advantageously, the invention relates to the abovementioned use, in which the sequences of the first pair of sequences targeting a site-specific recombinase and the sequences of the second pair of sequences targeting a site-specific recombinase are chosen from Lox P1, Lox P2272, Lox 66, Lox 71, Lox 511, Lox 512, Lox 514 and mutated sequences of the Lox P1 site, bearing at least one point mutation in the spacer sequence.

The pairs of sequences targeting a site-specific recombinase which are advantageous to the invention and which are recognized by the Cre recombinase of the P1 phage, are the sequences Lox P1 and Lox P2272, represented by the following sequences:

```
Lox P1:
                                   (SEQ ID NO: 1)
ATAACTTCGTATAGCATACATTATACGAAGTTAT,
and

Lox P2272:
                                   (SEQ ID NO: 2)
ATAACTTCGTATAAAGTATCCTATACGAAGTTAT.
```

The complementary sequences thereto (sequence in the opposite orientation) are as follows:

Lox P1 complementary sequence: ATAACTTCGTATAATGTATGCTATACGAAGTTAT (SEQ ID NO: 3), and Lox P2272 complementary sequence:

```
                                   (SEQ ID NO: 4)
     ATAACTTCGTATAGGATACTTTATACGAAGTTAT.
```

In another advantageous embodiment, the invention relates to the abovementioned use, in combination with one or more compounds inhibiting the multiplication of said virus.

Mono-, bi-, tri- or multitherapies proposed for the treatment of HIV infections are transposable to FIV and SIV viral infections. Examples are given below.

Thus, in one advantageous embodiment, the invention relates to the use for the detection, especially the in vitro detection, of cells from a mammal infected by a virus responsible for an immunodeficiency in said mammal, said cells being the reservoir cells of said virus, or for carrying out a method for the detection, especially the in vitro detection, of cells from a mammal infected by a virus responsible for an immunodeficiency in said mammal, said cells being the reservoir cells of said virus of a nucleic acid molecule comprising a first sequence encoding a first reporter, under the control of at least one element necessary for transcription, the first sequence being bordered by a first pair of Lox P1 sequences targeting the Cre recombinase of the P1 phage, said first pair comprising a P1-1 sequence and a P1-2 sequence, a second pair of Lox P2272 sequences targeting the Cre recombinase of the P1 phage, said second pair comprising a P2-1 sequence and a P2-2 sequence, the sequences of each of said pairs of Lox P1 and Lox P2272 sequences being oppositely oriented relative to one another, the sequences of the Lox P1 pair being unable to recombine with the sequences of the Lox P2272 pair, the sequence encoding a first reporter essentially comprising or consisting of the sequence SEQ ID NO: 5, represented below
TTATCTGTGCCCCAGTTTGCTAGG-
GAGGTCGCAGTACTTGGCCACAGCCATC
TCGTGCTGCTCGACGTAGGTCTCTTTGTCGGCC
TCCTTGATTCTTTCCAGTC TGTGGTC-
CACGAAGTGGAAGCCGGGCATCTT-
GAGGTTCTTAGCGGGTTTCT
TGGATCTGTATGTGGTCTT-
GAAGGAGCAGTGCAGGTAGCCCCCGCC-
CACGA GCTTCAGGGC-
CATCTGGCTGTGGCCTCTCAGGCCGCCGTCAG
CGGGGTAC
AGCATCTCGGTGTTGGCCTCCCAGCCGCGTGT
TTTCTTCTGCATCACAGGG CCGTTGGATGG-
GAAGTTCACCCCGTTGATCTTGACGTTGTA-
GATGATGCAGC CGTTCTG-
GAAGCTGGTGTCCTGGGTAGCGGTCAGCACGC
CCCCGTCTTCGT ATGTGGTGATTCTCTCC-
CATGTGAAGCCCTCAGGGAAGGACTGCT-
TAAAGAA GTCGGGGATGCCCTGGGTGTGGTT-
GATGAAGGCTTTGCTGCCGTACATGAA
GCTGGTAGCCAGGATGTCGAAGGCGAAGGG-
GAGAGGGCCGCCCTCGACC ACCTTGATCTT-
CATGGTCTGGGTGCCCTCGTAGGGCTTGCCTTC GCCCTCG GATGTGCACTT-GAAGTGGTGGTTGTTCACGGTGCCCTC-CATGTACAGCTTCA TGTGCATGTTCTCCTT-GATCAGCTCGCTCAT.

optionally combined with the Cre recombinase of the P1 phage, or advantageously combined with a virus responsible for said immunodeficiency, said virus comprising, in its genome, a gene encoding said recombinase, Cre recombinase of the P1 phage, optionally combined with one or more compounds inhibiting the multiplication of said virus, or antiretroviral agents, or antiretrovirals.

The sequence SEQ ID NO: 5 corresponds to the sequence of the open reading frame encoding red fluorescent protein (RFP) in its 3'→5' orientation. Thus, before recombination, this sequence, which is read in the 5'→3' direction according to the principles of transcription, will not be able to encode the RFP reporter.

Advantageously, it is also envisaged that the sequence encoding a first reporter essentially comprising or consisting of the sequence SEQ ID NO: 31 corresponds to the sequence of the open reading frame encoding firefly luciferase in its 3'→5' orientation. After recombination, the sequence will be oriented in the 5'→3' direction (SEQ ID NO: 46) and will encode a functional luciferase of sequence SEQ ID NO: 47.

Advantageously, the nucleic acid molecule comprises a second sequence encoding a second reporter under the control of at least one element necessary for transcription. The second sequence especially encodes an autofluorescent protein, an enzyme, or any other peptide which is able to be easily detected with molecular biology techniques known to those skilled in the art. Unlike the sequence of the first reporter gene, the sequence encoding a second reporter is in the 5'→3' direction, and enables the expression of the reporter independently of the recombination. This second sequence is under the control of a promoter, optionally one or more enhancers, which enables constitutive expression of said second reporter. In addition, this sequence encoding the second reporter is located outside the framing regions defined by the site-specific recombinase target sequences.

Advantageously, said second sequence essentially comprises or consists of the sequence SEQ ID NO: 8, which corresponds to the open reading frame encoding enhanced green fluorescent protein (eGFP).

In yet another embodiment, the invention relates to the use as defined above, in which said nucleic acid molecule essentially comprises, or essentially consists of, one of the following sequences:

```
                                  (SEQ ID NO: 6)
pHR-4lox-RFP/GFP-WPRE,

                                 (SEQ ID NO: 32)
pHR-4lox-CMV-RFP-PGK-GFP-WPRE

                                 (SEQ ID NO: 33)
pHR-4lox-SFFV-RFP-PGK-GFP-WPRE

                                 (SEQ ID NO: 34)
pHR-4lox-SFFV-RFP-CMV-GFP-WPRE

                                 (SEQ ID NO: 35)
pHR-4lox-CMV-lucif-PGK-GFP-WPRE,

                                  (SEQ ID NO: 7)
pSDT-4lox-RFP/GFP-WPRE,

                                 (SEQ ID NO: 36)
HR-4lox-CMV-RFP-PGK-GFP-WPRE
```

-continued

```
                                 (SEQ ID NO: 37)
HR-4lox-SFFV-RFP-PGK-GFP-WPRE

                                 (SEQ ID NO: 38)
HR-4lox-SFFV-RFP-CMV-GFP-WPRE

                                 (SEQ ID NO: 39)
HR-4lox-CMV-lucif-PGK-GFP-WPRE,
and

                                 (SEQ ID NO: 40)
SDT-4lox-RFP/GFP-WPRE.
```

Advantageously, the molecules pHR-4lox-RFP/GFP-WPRE (SEQ ID NO: 6), pHR-4lox-CMV-RFP-PGK-GFP-WPRE (SEQ ID NO: 32), pHR-4lox-SFFV-RFP-PGK-GFP-WPRE (SEQ ID NO: 33), pHR-4lox-SFFV-RFP-CMV-GFP-WPRE (SEQ ID NO: 34), pHR-410x-CMV-lucif-PGK-GFP-WPRE (SEQ ID NO: 35), HR-4lox-CMV-RFP-PGK-GFP-WPRE (SEQ ID NO: 36), HR-4lox-SFFV-RFP-PGK-GFP-WPRE (SEQ ID NO: 37), HR-4lox-SFFV-RFP-CMV-GFP-WPRE (SEQ ID NO: 38) and HR-4lox-CMV-lucif-PGK-GFP-WPRE (SEQ ID NO: 39) are used for the detection, or for carrying out a method for the detection, of human cells infected by HIV. These sequences are such that:

the sequence SEQ ID NO: 6 or 32 corresponds to the sequence SEQ ID NO: 36 contained in the pHR vector, the sequence SEQ ID NO: 33 corresponds to the sequence SEQ ID NO: 37 contained in the pHR vector, the sequence SEQ ID NO: 34 corresponds to the sequence SEQ ID NO: 38 contained in the pHR vector, and the sequence SEQ ID NO: 35 corresponds to the sequence SEQ ID NO: 39 contained in the pHR vector.

The pHR vector is a vector comprising a genetic base from the HIV-1 virus, derived from the pHR-ET vector (Bachracha et al. 2005 Virology. 332(1), 418-429), itself derived from the pHR-CMV-lacz vector (Naldini, et al. 1996. Science, 272(5259), pp. 263-267). The "lox-turboRFP-lox-promotor" cassette has been introduced into the pHR-ET.

Advantageously, the molecules pSDT-4lox-RFP/GFP-WPRE and SDT-4lox-RFP/GFP-WPRE are used for the detection, or for carrying out a method for the detection, of simian cells infected by SIV. The sequence SEQ ID NO: 7 corresponds to the sequence SEQ ID NO: 40 contained in the pSDT vector.

The pSDT vector is a vector comprising a genetic base from the SIV virus derived from the pGAE-SFFV-eGFP vector (Verhoeyen et al. 2012. Hum Gene Ther. 23(7):754-68.), itself derived from the pSIV-RMES-GAE vector (Mangeot et al. 2002. Mol. Ther.; 5:283-290.). The "lox-turboRFP-lox-promotor" cassette has been introduced into the pGAE-SFFV-eGFP.

In yet another embodiment, the invention relates to the use as defined above, in which said nucleic acid molecule essentially comprises, or essentially consists of, one of the sequences SEQ ID NO: 36,37,38,39 or 40.

Examples of nucleic acid molecules of the invention are illustrated in FIG. 3, which shows recombination, and in FIG. 4.

The invention also relates to a hematopoietic cell comprising, in its genome, a) a first recombined sequence resulting from the recombination of a first sequence encoding a first reporter gene, under the control of at least one element necessary for transcription, the first sequence being flanked by at least one first pair of sequences targeting a site-specific recombinase, said first pair comprising a P1-1 sequence and a P1-2 sequence, at least one second pair of sequences targeting a site-specific recombinase, said second pair comprising a P2-1 sequence and a P2-2 sequence, the sequences of each of said first and second pairs of sequences being oppositely oriented relative to one another, the sequences of the first pair of sequences targeting a site-specific recombinase are unable to recombine with the sequences of the second pair of sequences targeting a site-specific recombinase, and in which the sequences of the second pair of sequences targeting a site-specific recombinase are unable to recombine with the sequences of the first pair of sequences targeting a site-specific recombinase, one sequence from the first pair and one sequence from the second pair of sequences targeting a site-specific recombinase being located upstream of said first nucleic acid sequence, and one sequence from the first pair and one sequence from the second pair of sequences targeting a site-specific recombinase being located downstream of said first nucleic acid sequence, such that the sequences of the same pair never flank the two sequences of the other pair, the sequence of said first nucleic acid molecule being such that, in the absence of combination induced by said one site-specific recombinase, it has an open reading frame coding for said first reporter gene in a 3'-5' orientation, by the site-specific recombination encoded by a gene contained in the genome of a virus causing an immunodeficiency in a mammal, said recombined sequence comprising a first sequence having an open reading frame coding for said first reporter gene in a 5'-3' orientation, said first sequence being bordered by a single sequence from a first pair of sequences targeting a site-specific recombinase and a single sequence from a second pair of sequences targeting a site-specific recombinase, such that if, upstream of its first nucleotide in its 5' region, said first recombined sequence is bordered by a sequence from a first pair of sequences targeting a site-specific recombinase, said recombined sequence is bordered downstream of its last 3' nucleotide by a sequence from a second pair of sequences targeting a site-specific recombinase, and if, upstream of its first nucleotide in its 5' region, said first recombined sequence is bordered by a sequence from a second pair of sequences targeting a site-specific recombinase, said recombined sequence is bordered downstream of its last 3' nucleotide by a sequence from a first pair of sequences targeting a site-specific recombinase, in which said sequences from said first and second pairs of sequences targeting a site-specific recombinase are in the same orientation, and b) optionally the genome of a virus causing an immunodeficiency in a mammal comprising a gene coding for a site-specific recombinase, said hematopoietic cell especially being resistant to antiviral therapy against said virus.

In the invention, hematopoietic cell is intended to mean any blood cell from the myeloid or lymphoid lineage, which groups together eosinophils, neutrophils, basophils, monocytes, macrophages, B and T lymphocytes, NK cells, mastocytes, plasmocytes, cells derived from proerythroblasts and megakaryocytes and also all precursors of said cells, including hematopoietic stem cells, especially CD34+ cells. In the invention, “comprising in its genome” is intended to mean that the nucleic acid molecules are integrated into the DNA of the hematopoietic cell. Thus, when the latter divides, it will transmit to its progeny the nucleic acid molecules which have been integrated.

The abovementioned hematopoietic cell is especially a reservoir cell of said virus.

The abovementioned cells are cells which have undergone recombination by the recombinase and in which the sequence of the reporter gene which was initially in the 3'→5' direction is now in the 5'→3' direction. This cell is thus able to express the reporter. If the reporter is an autofluorescent protein, the hematopoietic cell will thus be autofluorescent.

Advantageously, the abovementioned cell comprises a single Lox P1 sequence of sequence SEQ ID NO: 1 or 3, and a single Lox P2272 sequence of sequence SEQ ID NO: 2 or 4.

Advantageously, the sequence of the reporter gene, oriented in the 5'→3' direction at the end of recombination, essentially comprises or consists of the sequence SEQ ID NO: 9.

In yet another advantageous embodiment, the invention relates to the abovementioned hematopoietic cell, in which the nucleic acid molecule essentially comprises or consists of one of the following sequences:

```
                                    SEQ ID NO: 29,
pHR-4lox-RFP/GFP flox

                                    (SEQ ID NO: 41)
HR-4lox-CMV-RFP-PGK-GFP-WPRE floxed

                                    (SEQ ID NO: 42)
HR-4lox-SFFV-RFP-PGK-GFP-WPRE floxed

                                    (SEQ ID NO: 43)
HR-4lox-SFFV-RFP-CMV-GFP-WPRE floxed

                                    (SEQ ID NO: 44)
HR-4lox-CMV-lucif-PGK-GFP-WPRE flox,

                                    (SEQ ID NO: 30)
pSDT-4lox-RFP/GFP-WPRE-floxed,
and

                                    (SEQ ID NO: 45)
SDT-4lox-CMV-RFP-PGK-GFP-WPRE floxed.
```

In yet another advantageous embodiment, the invention relates to the abovementioned hematopoietic cell, in which the nucleic acid molecule essentially comprises or consists of one of the following sequences: SEQ ID NO: 41, SEQ ID NO: 42, SEQ IDNO: 43, SEQ ID NO: 44 or SEQ ID NO: 45.

In yet another advantageous embodiment, the invention relates to the abovementioned hematopoietic cell, also comprising, in its genome, any one of the following sequences:

```
                                    (SEQ ID NO: 21)
HIV NL4-3-Nef-IRES-Cre,

                                    (SEQ ID NO: 22)
HIV NL4-3-Nef (codon opt)-IRES-Cre,

                                    (SEQ ID NO: 23)
HIV NL4-3-Nef-CMV-Cre,
and

                                    (SEQ ID NO: 24)
HIV NL4-3-Nef (codon opt)-CMV-Cre.

                                    (SEQ ID NO: 25)
SIVmac239-Nef-IRES-Cre,
```

-continued (SEQ ID NO: 26)
SIVmac239-Nef (codon opt)-IRES-Cre, (SEQ ID NO: 27)
SIVmac239-Nef-CMV-Cre,
and (SEQ ID NO: 28)
SIVmac239-Nef (codon opt)-CMV-Cre.

Advantageously, the invention relates to the abovementioned hematopoietic cell also comprising the sequence of a virus inducing an immunodeficiency as defined above.

More particularly, the invention relates to the hematopoietic cell comprising:

any one of the sequences SEQ ID NO: 41 to 44, any one of the sequences SEQ ID NO: 21 to 24.

More particularly, the invention relates to the hematopoietic cell comprising:

the sequence SEQ ID NO: 45 and any one of the sequences SEQ ID NO: 25 to 28.

The invention relates to a hematopoietic cell comprising, in its genome, a nucleic acid molecule as defined above.

Within the context of the process making it possible to obtain the abovementioned hematopoietic cells, the hematopoietic cells of this aspect of the invention are the "intermediate products" of the recombination by the recombinase.

The abovementioned hematopoietic cell is especially a cell comprising a nucleic acid molecule comprising a first sequence encoding a first reporter, under the control of at least one element necessary for transcription, the first sequence being bordered by at least one first pair of sequences targeting a site-specific recombinase, said first pair comprising a P1-1 sequence and a P1-2 sequence, at least one second pair of sequences targeting a site-specific recombinase, said second pair comprising a P2-1 sequence and a P2-2 sequence, the sequences of each of said first and second pairs of sequences being oppositely oriented relative to one another, the sequences of the first pair of sequences targeting a site-specific recombinase are unable to recombine with the sequences of the second pair of sequences targeting a site-specific recombinase, and in which the sequences of the second pair of sequences targeting a site-specific recombinase are unable to recombine with the sequences of the first pair of sequences targeting a site-specific recombinase, one sequence from the first pair and one sequence from the second pair of sequences targeting a site-specific recombinase being located upstream of said first nucleic acid sequence, and one sequence from the first pair and one sequence from the second pair of sequences targeting a site-specific recombinase being located downstream of said first nucleic acid sequence, such that the sequences of the same pair never flank the two sequences of the other pair, the sequence of said first nucleic acid molecule being such that, in the absence of combination induced by said site-specific recombinase, it has an open reading frame encoding said first reporter in a 3'-5' orientation, and is therefore unable to enable the transcription and translation of the reporter gene in order to obtain said first reporter.

This hematopoietic cell advantageously comprises the abovementioned nucleic acid molecule which also comprises a second sequence encoding a second reporter under the control of at least one element necessary for transcription.

The pairs of sequences targeting a site-specific recombinase which are advantageous to the invention and which are recognized by the Cre recombinase of the P1 phage, are the sequences Lox P1 and Lox P2272, represented by the following sequences:

Lox P1:
(SEQ ID NO: 1)
ATAACTTCGTATAGCATACATTATACGAAGTTAT,
and

Lox P2272:
(SEQ ID NO: 2)
ATAACTTCGTATAAAGTATCCTATACGAAGTTAT.

The complementary sequences thereto (sequence in the opposite orientation) are as follows:

Lox P1 complementary sequence: ATAACTTCGTATAATGTATGCTATACGAAGTTAT (SEQ ID NO: 3), and Lox P2272 complementary sequence:

(SEQ ID NO: 4)
ATAACTTCGTATAGGATACTTTATACGAAGTTAT.

Advantageously, the sequence of the reporter gene, in its 3'→5' orientation, is the sequence SEQ ID NO: 5 or 31.

More advantageously, the abovementioned hematopoietic cell comprises an abovementioned nucleic acid molecule comprising any one of the sequences SEQ ID NO: 6, SEQ ID NO: 7, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40.

In addition, the abovementioned hematopoietic cell may comprise the sequence of a viral genome which contains a gene coding for a site-specific recombinase. This viral sequence is advantageously one of the following sequences:

(SEQ ID NO: 21)
HIV NL4-3-Nef-IRES-Cre, (SEQ ID NO: 22)
HIV NL4-3-Nef (codon opt)-IRES-Cre, (SEQ ID NO: 23)
HIV NL4-3-Nef-CMV-Cre, (SEQ ID NO: 24)
HIV NL4-3-Nef (codon opt)-CMV-Cre, (SEQ ID NO: 25)
SIVmac239-Nef-IRES-Cre, (SEQ ID NO: 26)
SIVmac239-Nef (codon opt)-IRES-Cre, (SEQ ID NO: 27)
SIVmac239-Nef-CMV-Cre,
and (SEQ ID NO: 28)
SIVmac239-Nef (codon opt)-CMV-Cre.

Advantageously, the abovementioned cell is a human cell comprising, in its genome, the sequence SEQ ID NO: 6, and advantageously any one of the sequences SEQ ID NO: 10 to 12 and 21 to 24.

Advantageously, the abovementioned cell is a human cell comprising, in its genome, the sequence SEQ ID NO: 32, and advantageously any one of the sequences SEQ ID NO: 10 to 12 and 21 to 24.

Advantageously, the abovementioned cell is a human cell comprising, in its genome, the sequence SEQ ID NO: 33, and advantageously any one of the sequences SEQ ID NO: 10 to 12 and 21 to 24.

Advantageously, the abovementioned cell is a human cell comprising, in its genome, the sequence SEQ ID NO: 34, and advantageously any one of the sequences SEQ ID NO: 10 to 12 and 21 to 24.

Advantageously, the abovementioned cell is a human cell comprising, in its genome, the sequence SEQ ID NO: 35, and advantageously any one of the sequences SEQ ID NO: 10 to 12 and 21 to 24.

Advantageously, the abovementioned cell is a human cell comprising, in its genome, the sequence SEQ ID NO: 36, and advantageously any one of the sequences SEQ ID NO: 10 to 12 and 21 to 24.

Advantageously, the abovementioned cell is a human cell comprising, in its genome, the sequence SEQ ID NO: 37, and advantageously any one of the sequences SEQ ID NO: 10 to 12 and 21 to 24.

Advantageously, the abovementioned cell is a human cell comprising, in its genome, the sequence SEQ ID NO: 38, and advantageously any one of the sequences SEQ ID NO: 10 to 12 and 21 to 24.

Advantageously, the abovementioned cell is a human cell comprising, in its genome, the sequence SEQ ID NO: 39, and advantageously any one of the sequences SEQ ID NO: 10 to 12 and 21 to 24.

Advantageously, the abovementioned cell is a simian cell comprising, in its genome, the sequence SEQ ID NO: 7, and advantageously any one of the sequences SEQ ID NO: 13 to 16 and 25 to 28.

Advantageously, the abovementioned cell is a simian cell comprising, in its genome, the sequence SEQ ID NO: 40, and advantageously any one of the sequences SEQ ID NO: 13 to 16 and 25 to 28.

The invention also relates to a nonhuman mammal, the hematopoietic system of which comprises, essentially consists of, or consists of hematopoietic cells as defined above.

The abovementioned mammals thus consist of cells of an essentially identical genotype, except for all or a portion of their hematopoietic cells which comprise:

either the abovementioned nucleic acid molecule or the sequence of the reporter gene is oriented in the 3'→5' direction; this is especially the case for all the hematopoietic cells of said animal, either the abovementioned nucleic acid molecule or the sequence of the reporter gene is oriented in the 3'→5' direction, and the genome of said virus induces immunodeficiency; this is especially the case for the hematopoietic cells which express cell receptors for said virus, either the abovementioned nucleic acid molecule or the sequence of the reporter gene is oriented in the 5'→3' direction, and the genome of said virus induces immunodeficiency; this is especially the case for the hematopoietic cells which express cell receptors for said virus; these cells are the cells resulting from the recombination.

The advantageous mammals for the invention are monkeys, mice or cats.

It is well known from the prior art that it is possible to reconstruct the entirety of the hematopoietic system of a mammal by injecting hematopoietic stem cells, or CD34+ cells, into this animal following sublethal irradiation.

Indeed, when the mammals are irradiated with gamma rays at certain doses, all the cells of the bone marrow are destroyed (myeloablative irradiation) and the mammal will no longer be capable of producing new hematopoietic cells. However, the injection of CD34+ stem cells, while respecting the rules of histocompatibility, has the effect of the CD34+ stem cells colonizing the bone marrow and giving rise to new hematopoietic cells which are capable of replacing the dead cells at the end of irradiation. Examples of experimental protocols are given by way of indication in the examples for mice, macaques, and cats.

The graft of the hematopoietic stem cells is either an autograft; the mammal is grafted with its own hematopoietic stem cells, which have been genetically modified, or an allograft; the mammal is grafted with genetically modified hematopoietic stem cells from another mammal of the same species, or a xenograft; the mammal is grafted with genetically modified hematopoietic stem cells from another mammal of a different species.

The allograft and autograft are particularly advantageous within the context of the invention when the mammal is a monkey or a cat.

The xenograft makes it possible to reproduce a hematopoietic system from one species in another species, and especially to reproduce the human hematopoietic system in an immunodeficient mouse, in particular a Nod Scid mouse, nude mice or $Rag_{2-/-}\gamma c_{-/-}$ mice. In this example, after grafting, the mice will have human hematopoietic cells which will thus be able to be infected by a human immunodeficiency virus.

Advantageously, the invention relates to the use of an abovementioned mammal for the detection, especially the in vitro detection, of reservoir cells of said virus inducing an immunodeficiency in said mammal, or for carrying out a method enabling the detection, especially the in vitro detection, of reservoir cells of said virus inducing an immunodeficiency in said mammal.

The abovementioned mammals may be used to isolate the reservoir cells of said viruses inducing the immunodeficiency.

After treatment with one or more antiretroviral agents, the infected cells decline and disappear with the exception of the reservoir cells. Thus, starting from a blood sample or a marrow sample from said infected mammals treated with antiretrovirals, it will be possible, by means of suitable techniques, to isolate the cells which express the reporter, these cells being the cells which have been infected by the virus which expresses the recombinase, and in which the recombination of the nucleic acid molecule has undergone a recombination.

If the reporter is an auto fluorescent protein, it will then be possible to isolate the reservoir cells by means of a flow cytometer/cell sorter according to routine protocols for those skilled in the art.

Thus, the invention moreover relates to a method for the identification, especially the in vitro identification, of reservoir cells of a virus inducing immunodeficiency in a mammal, said method comprising a step of detecting the reporter gene encoded by a first recombined sequence as defined above in a population of hematopoietic cells.

As mentioned above, the abovementioned hematopoietic cells having undergone recombination are liable to be reservoir cells for the virus inducing the immunodeficiency.

Advantageously, the process of the invention comprises a step for selecting said reservoir cells contained in a population of hematopoietic cells, by detecting, using suitable means, the reporter which is expressed in the cells which are:

infected by the virus inducing the immunodeficiency, and which also expresses the recombinase, and transformed with the abovementioned nucleic acid molecule.

Only those cells which have undergone recombination of the reporter gene will be detectable because only these cells will express the reporter.

Advantageously, the invention relates to an abovementioned process comprising the following steps:

a step of transformation of hematopoietic stem cells, especially CD34+, with an abovementioned nucleic acid molecule, a step of reconstructing the hematopoietic system of a mammal which has undergone myeloablation, with the abovementioned hematopoietic stem cells, infection of the mammal having reconstructed marrow, in the following step, with a virus inducing an immunodeficiency in the mammal from which the hematopoietic stem cells originate, said virus expressing a site-specific recombinase, a step of treating the abovementioned infected mammal with a treatment inhibiting the development of said virus, a step of detecting hematopoietic cells expressing the reporter.

At the end of this process, the identified cells are hematopoietic cells, recombined for the reporter gene, infected by the virus and capable of "reactivating", and resistant to treatments against said virus. These are the reservoir cells of said virus.

In another aspect of the invention, it is also possible to propose a method for characterizing reservoir hematopoietic cells obtained by the abovementioned process, using a collection of antibodies directed against differentiation markers CD expressed at the surface of these cells.

The characterization of the reservoir cells thus makes it possible to determine their genetic type, and to propose compositions or drugs which kill specifically without having any effect on the mortality of the other cells of the mammal.

The abovementioned advantageous embodiments relating to the use, the cells, and the nonhuman mammals, apply mutatis mutandis to the present method.

Another subject of the invention is a kit for identifying and/or isolating the reservoir cells of a virus inducing an immunodeficiency in a mammal, comprising:

a nucleic acid molecule as defined above, and especially comprising any one of the sequences SEQ ID NO: 6, SEQ ID NO: 7, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40, and at least one nucleic acid molecule comprising the sequence of said virus inducing an immunodeficiency in a mammal, and comprising, in its genome, a gene coding for said site-specific recombinase, and especially at least any one of the following sequences:

```
                                    (SEQ ID NO: 10)
pBR-NL4-3-Nef-IRES-Cre,

                                    (SEQ ID NO: 11)
pBR-NL4-3-Nef (codon opt)-IRES-Cre,

                                    (SEQ ID NO: 12)
pBR-NL4-3-Nef-CMV-Cre,

                                    (SEQ ID NO: 13)
pBR-SIVmac239-Nef-IRES-Cre,

                                    (SEQ ID NO: 14)
pBR-SIVmac239-Nef (codon opt)-IRES-Cre,

                                    (SEQ ID NO: 15)
pBR-SIVmac239-Nef-CMV-Cre,

                                    (SEQ ID NO: 16)
pBR-SIVmac239-Nef (codon opt)-CMV-Cre,

                                    (SEQ ID NO: 21)
HIV NL4-3-Nef-IRES-Ore,

                                    (SEQ ID NO: 22)
HIV NL4-3-Nef (codon opt)-IRES-Ore,

                                    (SEQ ID NO: 23)
HIV NL4-3-Nef-CMV-Ore,

                                    (SEQ ID NO: 24)
HIV NL4-3-Nef (codon opt)-CMV-Ore,

                                    (SEQ ID NO: 25)
SIVmac239-Nef-IRES-Ore,

                                    (SEQ ID NO: 26)
SIVmac239-Nef (codon opt)-IRES-Ore,

                                    (SEQ ID NO: 27)
SIVmac239-Nef-CMV-Ore,
and

                                    (SEQ ID NO: 28)
SIVmac239-Nef (codon opt)-CMV-Cre,
```

optionally combined with means for detecting said reporter gene.

Advantageously, the abovementioned kit comprises: a nucleic acid molecule comprising the sequence SEQ ID NO: 6 and a nucleic acid molecule comprising the sequence of said virus inducing an immunodeficiency in a mammal, and comprising, in its genome, a gene coding for said specific recombinase, said viral sequence comprising the sequence of the Cre recombinase comprising any one of the following sequences:

```
                                    (SEQ ID NO: 10)
pBR-NL4-3-Nef-IRES-Cre,

                                    (SEQ ID NO: 11)
pBR-NL4-3-Nef (codon opt)-IRES-Cre,

                                    (SEQ ID NO: 12)
pBR-NL4-3-Nef-CMV-Cre,
```

-continued (SEQ ID NO: 21)
HIV NL4-3-Nef-IRES-Cre, (SEQ ID NO: 22)
HIV NL4-3-Nef (codon opt)-IRES-Cre, (SEQ ID NO: 23)
HIV NL4-3-Nef-CMV-Cre,
and (SEQ ID NO: 24)
HIV NL4-3-Nef (codon opt)- CMV-Cre.

Advantageously, the abovementioned kit comprises: a nucleic acid molecule comprising the sequence SEQ ID NO: 32 and a nucleic acid molecule comprising the sequence of said virus inducing an immunodeficiency in a mammal, and comprising, in its genome, a gene coding for said specific recombinase, said viral sequence comprising the sequence of the Cre recombinase comprising any one of the following sequences:

(SEQ ID NO: 10)
pBR-NL4-3-Nef-IRES-Cre, (SEQ ID NO: 11)
pBR-NL4-3-Nef (codon opt)-IRES-Cre, (SEQ ID NO: 12)
pBR-NL4-3-Nef-CMV-Cre, (SEQ ID NO: 21)
HIV NL4-3-Nef-IRES-Cre, (SEQ ID NO: 22)
HIV NL4-3-Nef (codon opt)-IRES-Cre, (SEQ ID NO: 23)
HIV NL4-3-Nef-CMV-Cre,
and (SEQ ID NO: 24)
HIV NL4-3-Nef (codon opt)-CMV-Cre.

Advantageously, the abovementioned kit comprises: a nucleic acid molecule comprising the sequence SEQ ID NO: 33 and a nucleic acid molecule comprising the sequence of said virus inducing an immunodeficiency in a mammal, and comprising, in its genome, a gene coding for said specific recombinase, said viral sequence comprising the sequence of the Cre recombinase comprising any one of the following sequences:

(SEQ ID NO: 10)
pBR-NL4-3-Nef-IRES-Cre, (SEQ ID NO: 11)
pBR-NL4-3-Nef (codon opt)-IRES-Cre, (SEQ ID NO: 12)
pBR-NL4-3-Nef-CMV-Cre, (SEQ ID NO: 21)
HIV NL4-3-Nef-IRES-Cre, (SEQ ID NO: 22)
HIV NL4-3-Nef (codon opt)-IRES-Cre, (SEQ ID NO: 23)
HIV NL4-3-Nef-CMV-Cre,
and (SEQ ID NO: 24)
HIV NL4-3-Nef (codon opt)-CMV-Cre.

Advantageously, the abovementioned kit comprises: a nucleic acid molecule comprising the sequence SEQ ID NO: 34 and a nucleic acid molecule comprising the sequence of said virus inducing an immunodeficiency in a mammal, and comprising, in its genome, a gene coding for said specific recombinase, said viral sequence comprising the sequence of the Cre recombinase comprising any one of the following sequences:

(SEQ ID NO: 10)
pBR-NL4-3-Nef-IRES-Cre, (SEQ ID NO: 11)
pBR-NL4-3-Nef (codon opt)-IRES-Cre, (SEQ ID NO: 12)
pBR-NL4-3-Nef-CMV-Cre, (SEQ ID NO: 21)
HIV NL4-3-Nef-IRES-Cre, (SEQ ID NO: 22)
HIV NL4-3-Nef (codon opt)-IRES-Cre, (SEQ ID NO: 23)
HIV NL4-3-Nef-CMV-Cre,
and (SEQ ID NO: 24)
HIV NL4-3-Nef (codon opt)-CMV-Cre.

Advantageously, the abovementioned kit comprises: a nucleic acid molecule comprising the sequence SEQ ID NO: 35 and a nucleic acid molecule comprising the sequence of said virus inducing an immunodeficiency in a mammal, and comprising, in its genome, a gene coding for said specific recombinase, said viral sequence comprising the sequence of the Cre recombinase comprising any one of the following sequences:

(SEQ ID NO: 10)
pBR-NL4-3-Nef-IRES-Cre, (SEQ ID NO: 11)
pBR-NL4-3-Nef (codon opt)-IRES-Cre, (SEQ ID NO: 12)
pBR-NL4-3-Nef-CMV-Cre, (SEQ ID NO: 21)
HIV NL4-3-Nef-IRES-Cre, (SEQ ID NO: 22)
HIV NL4-3-Nef (codon opt)-IRES-Cre, (SEQ ID NO: 23)
HIV NL4-3-Nef-CMV-Cre,
and (SEQ ID NO: 24)
HIV NL4-3-Nef (codon opt)-CMV-Cre.

Advantageously, the abovementioned kit comprises: a nucleic acid molecule comprising the sequence SEQ ID NO: 36 and a nucleic acid molecule comprising the sequence of said virus inducing an immunodeficiency in a mammal, and comprising, in its genome, a gene coding for said specific recombinase, said viral sequence comprising the sequence of the Cre recombinase comprising any one of the following sequences:

pBR-NL4-3-Nef-IRES-Cre, (SEQ ID NO: 10)

pBR-NL4-3-Nef (codon opt)-IRES-Cre, (SEQ ID NO: 11)

pBR-NL4-3-Nef-CMV-Cre, (SEQ ID NO: 12)

HIV NL4-3-Nef-IRES-Cre, (SEQ ID NO: 21)

HIV NL4-3-Nef (codon opt)-IRES-Cre, (SEQ ID NO: 22)

HIV NL4-3-Nef-CMV-Cre, (SEQ ID NO: 23)
and

HIV NL4-3-Nef (codon opt)-CMV-Cre. (SEQ ID NO: 24)

Advantageously, the abovementioned kit comprises: a nucleic acid molecule comprising the sequence SEQ ID NO: 37 and a nucleic acid molecule comprising the sequence of said virus inducing an immunodeficiency in a mammal, and comprising, in its genome, a gene coding for said specific recombinase, said viral sequence comprising the sequence of the Cre recombinase comprising any one of the following sequences:

pBR-NL4-3-Nef-IRES-Cre, (SEQ ID NO: 10)

pBR-NL4-3-Nef (codon opt)-IRES-Cre, (SEQ ID NO: 11)

pBR-NL4-3-Nef-CMV-Cre, (SEQ ID NO: 12)

HIV NL4-3-Nef-IRES-Cre, (SEQ ID NO: 21)

HIV NL4-3-Nef (codon opt)-IRES-Cre, (SEQ ID NO: 22)

HIV NL4-3-Nef-CMV-Cre, (SEQ ID NO: 23)
and

HIV NL4-3-Nef (codon opt)-CMV-Cre. (SEQ ID NO: 24)

Advantageously, the abovementioned kit comprises: a nucleic acid molecule comprising the sequence SEQ ID NO: 38 and a nucleic acid molecule comprising the sequence of said virus inducing an immunodeficiency in a mammal, and comprising, in its genome, a gene coding for said specific recombinase, said viral sequence comprising the sequence of the Cre recombinase comprising any one of the following sequences:

pBR-NL4-3-Nef-IRES-Cre, (SEQ ID NO: 10)

pBR-NL4-3-Nef (codon opt)-IRES-Cre, (SEQ ID NO: 11)

pBR-NL4-3-Nef-CMV-Cre, (SEQ ID NO: 12)

-continued

HIV NL4-3-Nef-IRES-Cre, (SEQ ID NO: 21)

HIV NL4-3-Nef (codon opt)-IRES-Cre, (SEQ ID NO: 22)

HIV NL4-3-Nef-CMV-Cre, (SEQ ID NO: 23)
and

HIV NL4-3-Nef (codon opt)-CMV-Cre. (SEQ ID NO: 24)

Advantageously, the abovementioned kit comprises: a nucleic acid molecule comprising the sequence SEQ ID NO: 39 and a nucleic acid molecule comprising the sequence of said virus inducing an immunodeficiency in a mammal, and comprising, in its genome, a gene coding for said specific recombinase, said viral sequence comprising the sequence of the Cre recombinase comprising any one of the following sequences:

pBR-NL4-3-Nef-IRES-Cre, (SEQ ID NO: 10)

pBR-NL4-3-Nef (codon opt)-IRES-Cre, (SEQ ID NO: 11)

pBR-NL4-3-Nef-CMV-Cre, (SEQ ID NO: 12)

HIV NL4-3-Nef-IRES-Cre, (SEQ ID NO: 21)

HIV NL4-3-Nef (codon opt)-IRES-Cre, (SEQ ID NO: 22)

HIV NL4-3-Nef-CMV-Cre, (SEQ ID NO: 23)
and

HIV NL4-3-Nef (codon opt)-CMV-Cre. (SEQ ID NO: 24)

Advantageously, the abovementioned kit comprises: a nucleic acid molecule comprising the sequence SEQ ID NO: 7 and a nucleic acid molecule comprising the sequence of said virus inducing an immunodeficiency in a mammal, and comprising, in its genome, a gene coding for said specific recombinase, said viral sequence comprising the sequence of the Cre recombinase comprising any one of the following sequences:

pBR-SIVmac239-Nef-IRES-Cre, (SEQ ID NO: 13)

pBR-SIVmac239-Nef (codon opt)-IRES-Cre, (SEQ ID NO: 14)

pBR-SIVmac239-Nef-CMV-Cre, (SEQ ID NO: 15)

pBR-SIVmac239-Nef (codon opt)-CMV-Cre, (SEQ ID NO: 16)

SIVmac239-Nef-IRES-Ore, (SEQ ID NO: 25)

SIVmac239-Nef (codon opt)-IRES-Ore, (SEQ ID NO: 26)

-continued (SEQ ID NO: 27)
SIVmac239-Nef-CMV-Ore,
and (SEQ ID NO: 28)
SIVmac239-Nef (codon opt)-CMV-Ore.

Advantageously, the abovementioned kit comprises: a nucleic acid molecule comprising the sequence SEQ ID NO: 40 and a nucleic acid molecule comprising the sequence of said virus inducing an immunodeficiency in a mammal, and comprising, in its genome, a gene coding for said specific recombinase, said viral sequence comprising the sequence of the Cre recombinase comprising any one of the following sequences:

(SEQ ID NO: 13)
pBR-SIVmac239-Nef-IRES-Cre, (SEQ ID NO: 14)
pBR-SIVmac239-Nef (codon opt)-IRES-Cre, (SEQ ID NO: 15)
pBR-SIVmac239-Nef-CMV-Cre, (SEQ ID NO: 16)
pBR-SIVmac239-Nef (codon opt)-CMV-Cre, (SEQ ID NO: 25)
SIVmac239-Nef-IRES-Ore, (SEQ ID NO: 26)
SIVmac239-Nef (codon opt)-IRES-Ore, (SEQ ID NO: 27)
SIVmac239-Nef-CMV-Ore,
and (SEQ ID NO: 28)
SIVmac239-Nef (codon opt)-CMV-Ore.

When the kit comprises a nucleic acid molecule enabling, after recombination, an autofluorescent protein reporter, the detection means may be instructions in the form of a computer program product on a suitable support, making it possible to select, especially by flow cytometry, the reservoir cells, that is to say the hematopoietic cells expressing the reporter gene.

The kit may also comprise means making it possible to purify hematopoietic stem cells, which cells will be transformed by said nucleic acid molecule.

In one advantageous embodiment, the abovementioned kit also comprises one or more antiretrovirals, especially the antiretrovirals indicated in the examples.

The invention will be better understood in light of the following three examples and seventeen figures.

BRIEF DESCRIPTION OF THE FIGURES

FIG. 5A is an image of detection of GFP in non-transduced and non-transfected or non-infected cells (control).

FIG. 5B is an image of detection of GFP in transduced and non-transfected or non-infected cells (recombination control).

FIG. 5C is an image of detection of GFP in transduced and transfected cells (with a plasmid containing the viral genome).

FIG. 5D is an image of detection of GFP in transduced cells infected with a virus.

FIG. 5E is an image of detection of RFP in non-transduced and non-transfected or non-infected cells (control).

FIG. 5F is an image of detection of RFP in transduced and non-transfected or non-infected cells (recombination control).

FIG. 5G is an image of detection of RFP in transduced and transfected cells (with a plasmid containing the viral genome).

FIG. 5H is an image of detection of RFP in transduced cells infected with a virus.

FIG. 6A is the result obtained by flow cytometry for the cells illustrated in FIGS. 5A and 5E.

FIG. 6B is the result obtained by flow cytometry for the cells illustrated in FIGS. 5B and 5F.

FIG. 6C is the result obtained by flow cytometry for the cells illustrated in FIGS. 5C and 5G.

FIG. 6D is the result obtained by flow cytometry for the cells illustrated in FIGS. 5D and 5H.

FIG. 8A is an image of detection of GFP in non-transduced and non-infected cells (control).

FIG. 8B is an image of detection of GFP in transduced and non-infected cells (recombination control).

FIG. 8C is an image of detection of GFP in transduced cells infected with a virus.

FIG. 8D is an image of detection of RFP in non-transduced and non-infected cells (control).

FIG. 8E is an image of detection of RFP in transduced and non-infected cells (recombination control).

FIG. 8F is an image of detection of RFP in transduced cells infected with a virus.

FIG. 9A is the result obtained by flow cytometry for the cells illustrated in FIGS. 8A and 8D.

FIG. 9B is the result obtained by flow cytometry for the cells illustrated in FIGS. 9B and 8E.

FIG. 9C is the result obtained by flow cytometry for the cells illustrated in FIGS. 5C and 5F.

FIG. 10A is an image of detection of GFP in non-transduced and non-infected cells (control).

FIG. 10B is an image of detection of GFP at 24 hours in cells transduced with a multiplicity of infection of 5 and non-infected.

FIG. 10C is an image of detection of GFP at 48 hours in cells transduced with a multiplicity of infection of 5 and non-infected.

FIG. 11A is the result obtained by flow cytometry for the cells illustrated in FIGS. 10A and 10D.

FIG. 11B is the result obtained by flow cytometry for the cells illustrated in FIGS. 10B and 10E.

FIG. 11C is the result obtained by flow cytometry for the cells illustrated in FIGS. 10C and 10F.

FIG. 12A is an image of detection of GFP in non-transduced and non-infected cells (control).

FIG. 12B is an image of detection of GFP in transduced and non-infected cells.

FIG. 12C is an image of detection of GFP in transduced cells infected with a virus.

FIG. 13A is the result obtained by flow cytometry for the cells illustrated in FIGS. 12A and 12D.

FIG. 13B is the result obtained by flow cytometry for the cells illustrated in FIGS. 12B and 12E.

FIG. 13C is the result obtained by flow cytometry for the cells illustrated in FIGS. 12C and 12F.

FIG. 14A is an image of detection of the non-floxed forms in cells which have not been transduced by the nucleic acid molecule and which are not infected (control).

FIG. 14B is an image of detection of the non-floxed forms in cells which have been transduced by the nucleic acid molecule and which are not infected.

FIG. 14C is an image of detection of the floxed forms in cells which have been transduced by the nucleic acid molecule and which are not infected.

FIG. 14D is an image of detection of the non-floxed forms in cells which have been transduced by the nucleic acid molecule and which are infected.

FIG. 14E is an image of detection of the floxed forms in cells which have been transduced by the nucleic acid molecule and which are infected.

FIG. 15A is an image of detection of GFP in non-transduced and non-infected cells (control).

FIG. 15B is an image of detection of GFP in transduced cells which have not been infected by a virus after 48 hours of culture.

FIG. 15C is an image of detection of RFP in non-transduced and non-infected cells (control).

FIG. 15D is an image of detection of RFP in transduced cells which have not been infected by a virus after 48 hours of culture.

FIG. 16A is the result obtained by flow cytometry for the cells illustrated in FIG. 15A.

FIG. 16B is the result obtained by flow cytometry for the cells illustrated in FIG. 15B.

FIG. 18A represents a fluorescence micrograph detecting GFP (showing transfection with the reporter of the invention) in non-transfected MT4C5 cells which have not been infected by an HIV virus.

FIG. 18B represents a fluorescence micrograph detecting GFP (showing transfection with the reporter of the invention) in MT4C5 cells transfected with the reporter and which have not been infected by an HIV virus.

FIG. 18C represents a fluorescence micrograph detecting GFP (showing transfection with the reporter of the invention) in MT4C5 cells transfected with the reporter and which have been infected by a control HIV virus.

FIG. 18D represents a fluorescence micrograph detecting GFP (showing transfection with the reporter of the invention) in MT4C5 cells transfected with the reporter and which have been infected by an HIV virus expressing Cre recombinase.

FIG. 18E represents a fluorescence micrograph detecting RFP (showing recombination of the reporter of the invention) in non-transfected MT4C5 cells which have not been infected by an HIV virus.

FIG. 18F represents a fluorescence micrograph detecting RFP (showing recombination of the reporter of the invention) in MT4C5 cells transfected with the reporter and which have not been infected by an HIV virus.

FIG. 18G represents a fluorescence micrograph detecting RFP (showing recombination of the reporter of the invention) in MT4C5 cells transfected with the reporter and which have been infected by an HIV virus.

FIG. 18H represents a fluorescence micrograph detecting RFP (showing recombination of the reporter of the invention) in MT4C5 cells transfected with the reporter and which have been infected by an HIV virus expressing Cre recombinase.

EXAMPLES

Example 1

Method for Identifying Human Reservoir Cells

A—Materials and Methods

Figure 1:
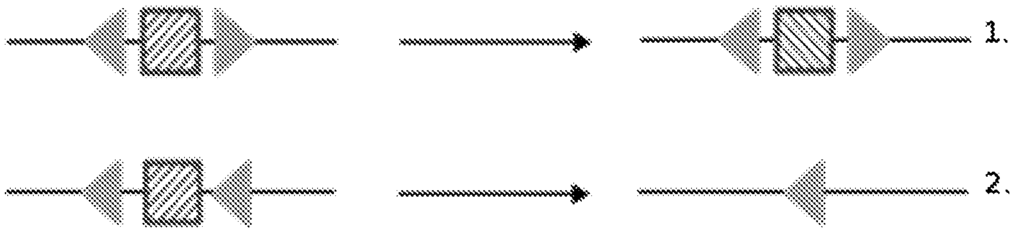
FIG. 1 represents the modes of recombination by deletion (1.) and inversion (2.) by site-specific recombination.
Figure 2:
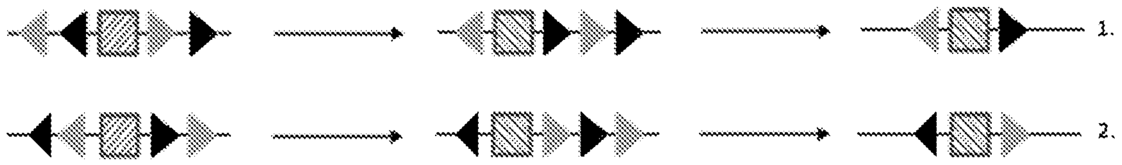
FIG. 2 represents the modes of recombination by inversion which are possible when the nucleic acid molecule comprises two pairs of sequences for site-specific recombination.
Figure 3:
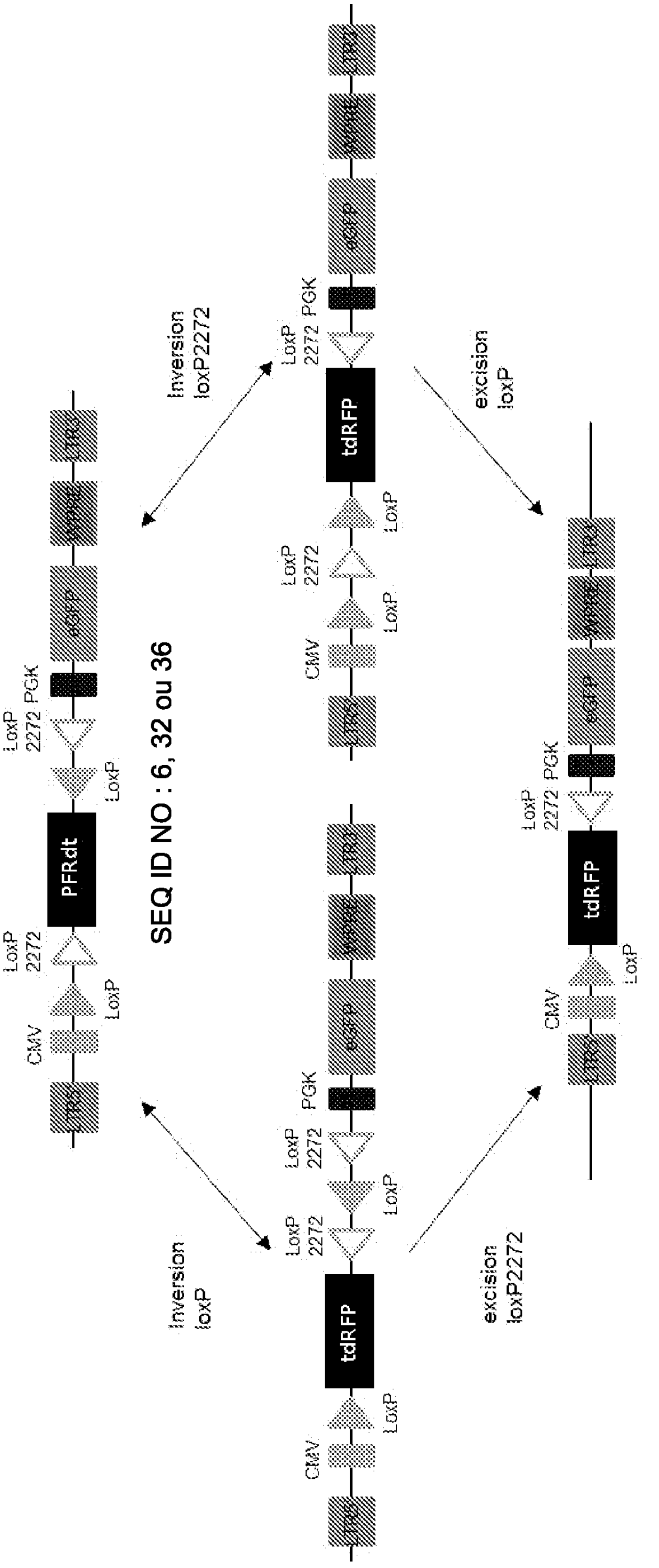
FIG. 3 represents one of the constructs of the invention and the mechanisms of recombination of the reporter gene.
Figure 4:
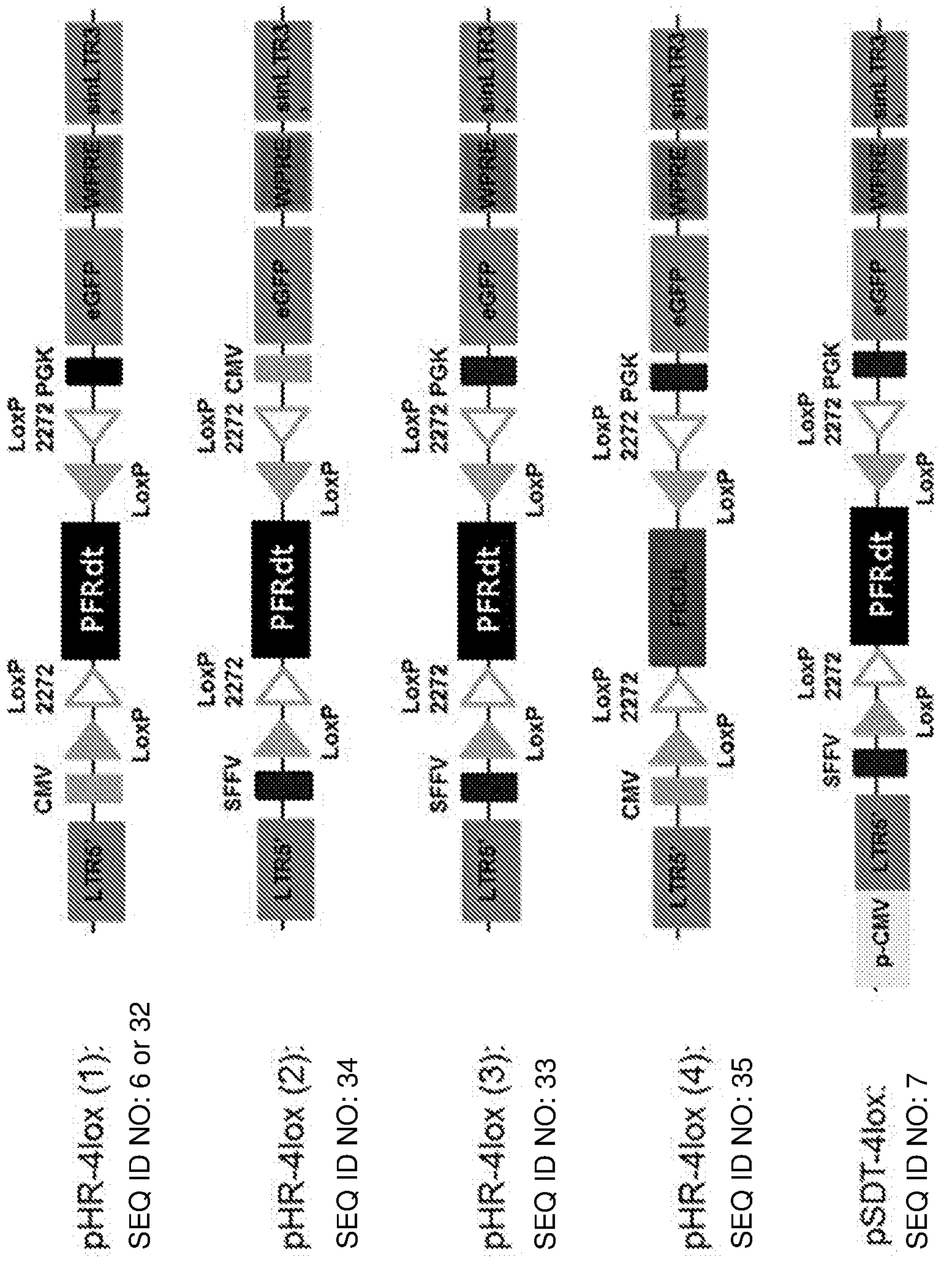
FIG. 4 represents five examples of construct (nucleic acid molecule) according to the invention based on detection of the reservoir cells of HIV1.

1. Isolation and pre-stimulation of CD34+ cells from bone marrow or taken from cord blood.

Bags of fresh cord blood are recovered via the hospital network.

- Prepare 20 ml of Ficoll in a Falcon 50 tube.
- Dilute the bone marrow/cord blood in PBS to give a volume of 30 ml (at least ½/⅓ dilution).
- Gently deposit the 30 ml of marrow on the Ficoll gel.
- Centrifuge for a minimum of 30 min at 1800 rpm, RT and without braking.
- Recover the ring of cells using a 10 ml pipette and deposit it in a new Falcon 50.
- Supplement the volume with PBS to give 50 ml.
- Centrifuge for 10 min at 1800 rpm.
- Empty out the supernatant using a pipette and break up the pellet.
- If there are too many erythrocytes, add 5 ml of lysing solution, homogenize well and leave for a maximum of 5 min. Add at least 10 ml of PBS to stop the reaction.
- Centrifuge for 10 min at 1800 rpm.
- Empty out the supernatant and break up the pellet.
- Resuspend in a final 1 ml of isolation buffer (cf 2).
- Count the mononuclear cells (CBMNC/BMMC) with exclusion of dead cells using trypan blue.
- Set aside 2×100 000 BMMC cells in microtube for labelling. Supplement q.s of PBS to give 100 µl, in order to avoid drying.

Isolation of the CD34+ Cells by Dynal Magnetic Beads Method (Positive Selection):

- Beforehand: prepare the isolation buffer: PBS 2% BSA 0.6% Citrate or EDTA (100 IU/ml Penicillin-Streptomycin), filtered over 0.2 µm membrane.
- In a 1.8 ml Eppendorf tube: add 100 µl of Dynabeads/ml of BMMC (capacity 4.107<CMMO<4.108 CBMNC/BMMC).
- Wash 3 times with 1 ml of isolation buffer over the Dynal magnet (Add 1 ml of buffer, homogenize well; apply the magnet against the Eppendorf tube and allow the beads to be attracted to the magnet for 1 minute; recover the negative fraction using a P100—move the magnet away from the Eppendorf tube; resuspend the cells+beads in 1 ml of isolation buffer).

- Immediately add the BMMCs to the bead pellet.
- Vortex gently for 2-3 seconds.
- Incubate for 30 minutes at 4° C. (gentle stirring, 10-20 rpm).
- During this time, identify the control labelling microtubes.
- Wash 5 to 7 times in buffer over the magnet (apply the magnet against the Eppendorf tube and allow the beads to be attracted to the magnet for 1 minute—recover the negative fraction using a P1000—move the magnet away from the Eppendorf tube—resuspend the cells+beads in 1 ml of isolation buffer—homogenize well).

- (keep the first negative fraction in an Eppendorf tube for control labelling
- Set aside 100 000 cells in at least 100 µl)
- Remove the tube of CD34 cells magnetic beads
- Resuspend in a small amount of buffer (maximum 100 µl total volume)
- Add 100 µl of DETACHaBEAD
- Incubate for 45 min at RT (>20° C.) or 15 min at 37° C., with gentle stirring at 10 rpm, or manually every 5 min.
- Add 400 µl of isolation buffer RT (neutralizes the reaction).
- Place the tube over the magnet and leave for one minute.
- Take off the unfixed fraction 1 into a new, labeled Eppendorf tube.
- Remove the Eppendorf tube from the magnetic field.
- Add 500 µl of isolation buffer to the Eppendorf tube containing the beads and stir gently.
- Place the tube over the magnet again and take off the unfixed fraction 2 and add to the fraction 1.
- Place the tube containing the fractions 1+2 over the magnet and recover the unfixed fraction in a new Eppendorf tube: positive fraction.
- Set aside a small number of cells for control labelling (50 000) and adjust the volume to a minimum of 100 µl.
- Count the cells of the positive fraction in ½ trypan blue (10 µl of cells+10 µl of TB). Concentrate the positive fraction, if required, by centrifugation.
- Labelling of CD34 (IgG1) in order to verify the purity of the positive fractions and evaluate the separation yield: CBMNC/BMMC fraction, negative fraction, positive fraction labeled with anti-CD34, IgG1-PE isotype control. Analyze by flow cytometry.

Pre-stimulation and Transduction of CD34+ Cells:

- Extemporaneously prepare the IMDM medium, 1% bovine serum albumin (BSA), supplemented with bovine pancreatic insulin (10 µg/ml), human transferrin (200 µg/ml), and L-glutamine (2 mM). Add 50 ng/ml (rh) of recombinant human (rh) SCF, 50 ng/ml of rh Flt3-L, 10 ng/ml of rh IL-3, and 10 ng/ml of rh IL-6. Preheat the medium.

Seed to 0.5-1.106 cells/ml and leave in culture on 48-well plates for 24 hours at 37° C.

Wash the cells with complete medium and add vector with a multiplicity of infection (MOI)=5-10 in a final volume of 500 μl. Leave in culture overnight at 37° C.

Add 500 μl of complete medium and place back in culture.

Monitor the expression of GFP in the transduced cells by flow cytometry.

2. Reconstruction of the immune system of Rag2-/- γc-/- mice by allograft of transduced CD34 cells.

The experimental procedures are set up in accordance with local regulations on animal experimentation. The cord blood samples are collected following signature of an informed consent letter and in accordance with the recommendations of the local ethics committee. A method is briefly described below:

Irradiate newborn (1-3 days old) NOG mice with 1 Gy.

Intrahepatic injection of $2.5\pm0.5\times10^5$ transduced CD34+ cells.

Check, approximately 15 weeks after transplantation, taking of the graft of human immune cells by flow cytometry (CD45, CD3, CD4, CD8 and CD19 labelling).

3. Infection of the mice by the HIV-1-Cre virus.

The dose and the route of infection are able to be modified as a function of the scientific aims of the experimentation. A method is briefly described below:

Infect the mice intraperitoneally with 20 ng of p24/animal.

Monitor the viral load in kinetic conditions by quantification of the viral RNAs in the plasma of the infected animals.

B—Results

In order to test the construct of the invention, the lentiviral vector pHR-4lox-RFP/GFP on HIV-1 base was constructed by cloning fragments derived from pHL-HH (Luche et al. 2007. Eur J Immunol. 2007 January;37(1):43-53.) and pHRET-GFP (supplied by C. Mettling). This non-replicative vector (inactivated 3'LTR) was devised in the following way, from 5' to 3':

Prokaryotic plasmid/SV40.

Lactamase gene.

Eco1 origin.

SV40 origin of replication.

xanthine-guanine phosphoribosyltransferase.

SV40 intron.

SV40 poly A.

active HIV-1 5'LTR (NL4-3).

PBS-gag encapsidation sequence y of HIV-1 (NL4-3).

SA and RRE of the HIV-1 env gene (NL4-3).

DNA flap.

CMV promoter.

loxP-loxP2272-turboRFP (inverted sequence)-loxP-loxP2272 cassette.

PGK promoter.

eGFP gene.

WPRE sequence.

inactivated HIV-1 3'LTR (NL4-3).

This construct is represented by the sequences SEQ ID NO: 6, and SEQ ID NO: 32.

Figure 5:
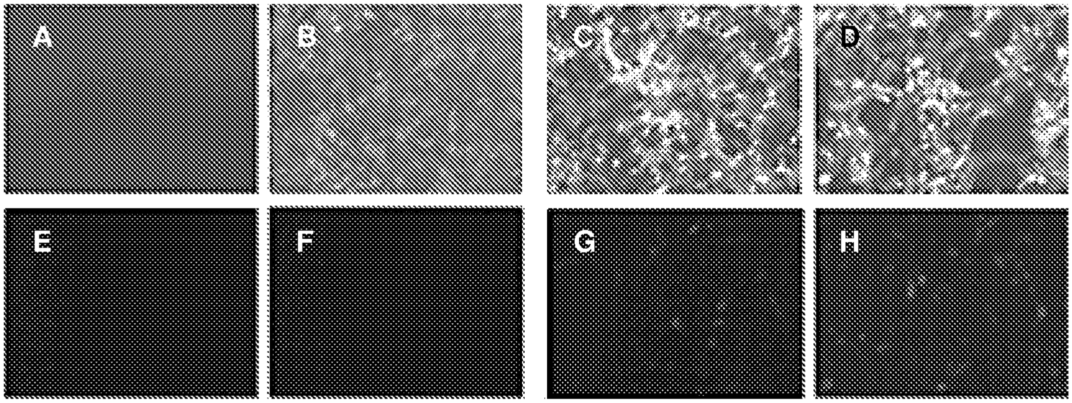
FIGS. 5A to 5H are fluorescence micrographs showing the recombination of the reporter gene when the nucleic acid molecule is transduced in human 293T cells and when the cells have been transfected or infected by an HIV-1 virus expressing Cre recombinase.
Figure 6:
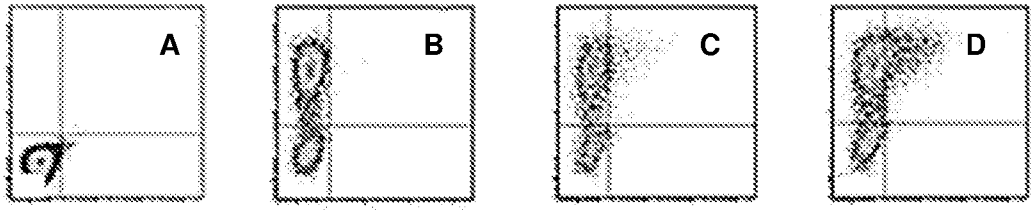
FIGS. 6A to 6D are graphs showing flow cytometry images for the cells expressing GFP (y-axis) and RFP (x-axis). The doubly labeled cells are indicated in each figure in the top right square.
Figure 7:
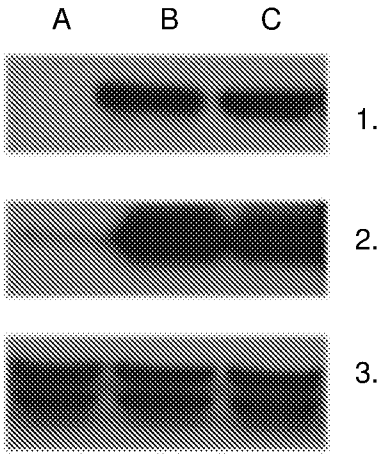
FIG. 7 is a western blot showing the expression of Cre recombinase (1.) and of the HIV p24 protein (2.) in the cells illustrated in FIGS. 5B and 5F (A), in FIGS. 5C and 5G (B) and in FIGS. 5D and 5H (C). As control, loading is controlled by the detection of ERK ½ kinases (3.).

The functioning of the pHR-4lox-RFP/GFP construct was confirmed on the human 293T cell line and of the primary cells (peripheral blood mononuclear cells from healthy donors) in combination with pBR-HIV-1-NL4-3-Nef-IRES-Cre under different conditions: overexpression by transfection/infection and transduction/infection. FIGS. 5 to 7 present the confirmation of the construct on 293T cells under these different conditions.

Figure 8:
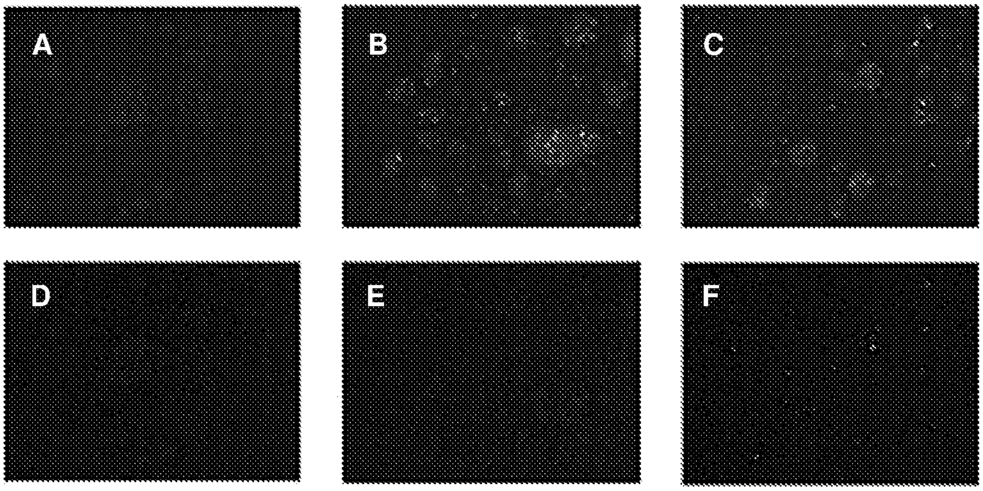
FIGS. 8A to 8F are fluorescence micrographs showing the recombination of the reporter gene when the nucleic acid molecule is transduced in human peripheral blood mononuclear cells and when the cells have been infected by an HIV-1 virus expressing Cre recombinase.
Figure 9:
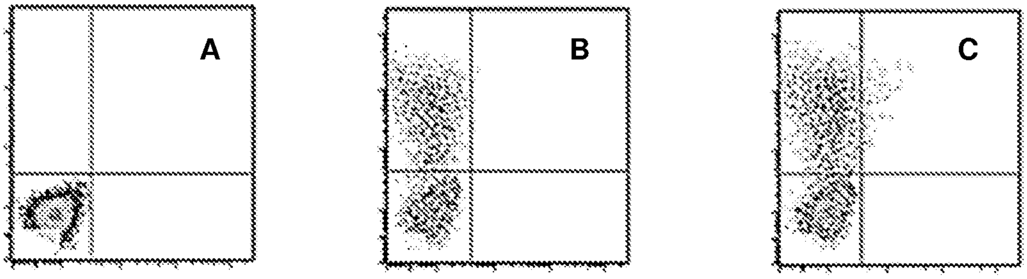
FIGS. 9A to 9C are graphs showing flow cytometry images for the cells expressing GFP (y-axis) and RFP (x-axis). The doubly labeled cells are indicated in each figure in the top right square.
Figure 10:
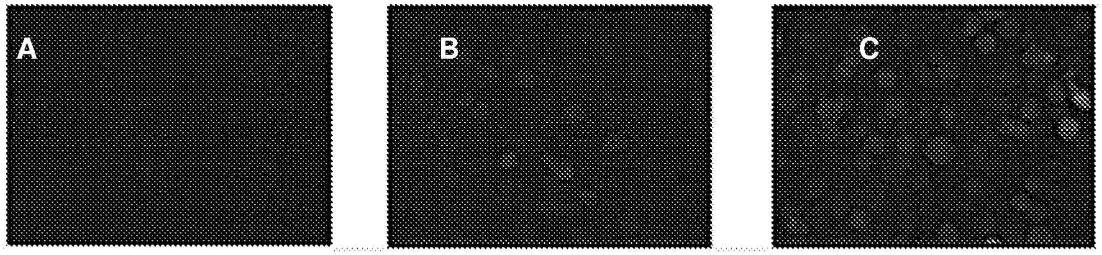
FIGS. 10A to 10C are fluorescence micrographs showing the good level of transduction (GFP expression) in the human CD34+ cells which will be used for the reconstructions. The expression of GFP in human CD34+ cells transduced by the nucleic acid molecule is checked 24 and 48 hours post-transduction.
FIG. 10D is an image of detection of RFP in non-transduced and non-infected cells (control).
FIG. 10E is an image of detection of RFP at 24 hours in cells transduced with a multiplicity of infection of 5 and non-infected.
FIG. 10F is an image of detection of RFP at 48 hours in cells transduced with a multiplicity of infection of 5 and non-infected.
Figure 11:
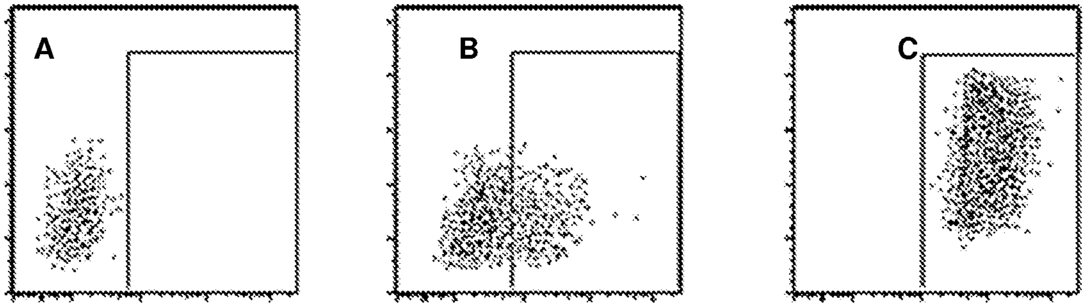
FIGS. 11A to 11C are graphs showing flow cytometry images for the cells according to their particle size (y-axis) and GFP (x-axis). The doubly labeled cells are indicated in each figure in the top right square.

FIGS. 8 and 9 present the confirmation of the pHR-4lox-RFP/GFP construct in primary cells from healthy donors by fluorescence microscopy and by flow cytometry. Similarly, since the aim is to use this construct to transduce CD34+ hematopoietic precursors derived from human cord blood in order to humanize the Rag2-/- γc-/- mice, the lentivector was tested in kinetic conditions (24 and 48 hours post-transduction) with a multiplicity of infection (MOI) of 5 (FIGS. 10 and 11) on cells activated beforehand for 24 h. The vector has proved to be perfectly well suited to the transduction of these cells which will be the source of the humanization and reconstruction of a complete immune system in the grafted mice.

The viral load of the humanized mice infected by NL4-3-Nef-IRES-Cre was tested. The results are contained in the following table 1:

TABLE 1

| animal | Number of weeks after infection | HIV-1-RNA (copies/ml) |
|---|---|---|
| #1824 | 2 weeks | 47940 |
| | 7 weeks | 473480 |
| #1833 | 2 weeks | Not tested |
| | 2 weeks | 3540 |

The humanized mice are treated via the diet. Food pellets were developed by mixing 2.5 g of 3TC, 2.5 g of TDF, 2.5 g of AZT, and 5 g of RTV in 5 kg de earth-rich proteins (vitamin-fortified food, Nafag 3432, Provimi Kliba AG, Switzerland). The pellets will then be sterilized by gamma irradiation (25 kGy). All the batches of food product pellets will be analyzed by HPLC in order to check the doses of medicaments. Food and water will be given ad libitum. The moleculesTMC278-LA and TMC181-LA are administered subcutaneously at 160 and 400 mg/kg, respectively.

The treatment is administered continuously starting from 30 to 40 days post-infection.

Once treated, the viral load of the mice is measured in order to verify the effectiveness of the treatment, and the reservoir cells are isolated by flow cytometry by selecting the cells expressing the reporter (RFP).

Example 2

Method for Identifying Simian Reservoir Cells

A—Materials and Methods

1. Isolation and pre-stimulation of CD34+ cells from bone marrow.

For each monkey, put to sleep by ketamine hydrochloride at 15 mg/kg, 3 ml of bone marrow are taken off from the iliac crest (or 8 ml from the humerus) into a tube (10% sodium citrate).

Prepare 20 ml of Ficoll in a Falcon 50 tube.

Dilute the bone marrow/cord blood in PBS to give a volume of 30 ml (at least ½-⅓ dilution).

Gently deposit the 30 ml of marrow on the Ficoll gel.

Centrifuge for a minimum of 30 min at 1800 rpm, RT and without braking.

Recover the ring of cells using a 10 ml pipette and deposit it in a new Falcon 50.

Supplement the volume with PBS to give 50 ml.

Centrifuge for 10 min at 1800 rpm.

Empty out the supernatant using a pipette and break up the pellet.

If there are too many erythrocytes, add 5 ml of lysing solution, homogenize well and leave for a maximum of 5 min. Add at least 10 ml of PBS to stop the reaction.

Centrifuge for 10 min at 1800 rpm.

Empty out the supernatant and break up the pellet.

Resuspend in a final 1 ml of isolation buffer (cf 2).

Count the mononuclear cells (CBMNC/BMMC) with exclusion of dead cells using trypan blue.

Set aside 2×100 000 BMMC cells in microtube for labelling. Supplement q.s of PBS to give 100 μl, in order to avoid drying.

Isolation of the CD34+ cells by Dynal magnetic beads method (positive selection):

Beforehand: prepare the isolation buffer: PBS 2% BSA 0.6% Citrate or EDTA (100 IU/ml Penicillin-Streptomycin), filtered over 0.2 μm membrane.

In a 1.8 ml Eppendorf tube: add 100 μl of Dynabeads/ml of BMMC (capacity $4\times10^7$<CMMO<$4\times10^8$ CBMNC/BMMC).

Wash 3 times with 1 ml of isolation buffer over the Dynal magnet (Add 1 ml of buffer, homogenize well; apply the magnet against the Eppendorf tube and allow the beads to be attracted to the magnet for 1 minute; recover the negative fraction using a P1000—move the magnet away from the Eppendorf tube; resuspend the cells+beads in 1 ml of isolation buffer).

Immediately add the BMMCs to the bead pellet.

Vortex gently for 2-3 seconds.

Incubate for 30 minutes at 4° C. (gentle stirring, 10-20 rpm).

During this time, identify the control labelling microtubes.

Wash 5 to 7 times in buffer over the magnet (apply the magnet against the Eppendorf tube and allow the beads to be attracted to the magnet for 1 minute—recover the negative fraction using a P1000—move the magnet away from the Eppendorf tube—resuspend the cells+beads in 1 ml of isolation buffer—homogenize well).

(keep the first negative fraction in an Eppendorf tube for control labelling

Set aside 100 000 cells in at least 100 μl)

Remove the tube of CD34 cells magnetic beads

Resuspend in a small amount of buffer (maximum 100 μl total volume)

Add 100 μl of DETACHaBEAD

Incubate for 45 min at RT (>20° C.) or 15 min at 37° C., with gentle stirring at 10 rpm, or manually every 5 min.

Add 400 μl of isolation buffer RT (neutralizes the reaction).

Place the tube over the magnet and leave for one minute.

Take off the unfixed fraction 1 into a new, labeled Eppendorf tube.

Remove the Eppendorf tube from the magnetic field.

Add 500 μl of isolation buffer to the Eppendorf tube containing the beads and stir gently.

Place the tube over the magnet again and take off the unfixed fraction 2 and add to the fraction 1.

Place the tube containing the fractions 1+2 over the magnet and recover the unfixed fraction in a new Eppendorf tube: positive fraction.

Set aside a small number of cells for control labelling (50 000) and adjust the volume to a minimum of 100 μl.

Count the cells of the positive fraction in ½ trypan blue (10 μl of cells+10 μl of TB). Concentrate the positive fraction, if required, by centrifugation.

Labelling of CD34 (IgG1) in order to verify the purity of the positive fractions and evaluate the separation yield: CBMNC/BMMC fraction, negative fraction, positive fraction labeled with anti-CD34, IgG1-PE isotype control. Analyze by flow cytometry.

Pre-Stimulation and Transduction of CD34+ Cells:

Extemporaneously prepare the IMDM medium, 1% bovine serum albumin (BSA), supplemented with bovine pancreatic insulin (10 μg/ml), human transferrin (200 μg/ml), and L-glutamine (2 mM). Add 50 ng/ml (rh) of recombinant human (rh) SCF, 50 ng/ml of rh Flt3-L, 10 ng/ml of rh IL-3, and 10 ng/ml of rh IL-6. Preheat the medium.

Seed to 0.5-$1\times10^6$ cells/ml and leave in culture on 48-well plates for 24 hours at 37° C.

Wash the cells with complete medium and add vector with an MOI=5-10 in a final volume of 500 μl. Leave in culture overnight at 37° C.

Add 500 μl of complete medium and place back in culture.

Monitor the expression of GFP in the transduced cells by flow cytometry.

2. Reconstruction of the macaque immune system by autograft of transduced CD34 cells.

The experimental procedures (able to be modified) are set up in accordance with European regulations on experimentation using primates (Official Journal of the European Communities, L358, 18 Dec. 1986).

Sedate the animal using ketamine (Imalgene; 10 mg/kg, im) and place it in a restraint chair.

Apply the myeloablative treatment in the form of full body exposure to gamma radiation ($^{60}$Co) with unilateral anterior direction. Deliver a total dose of 6 Gy at a rate of 25.92 cGy/minute.

After clinical monitoring of the animal, inject all the autologous CD34s which were transduced in vitro by intramedullary administration at the humerus.

3. Infection of the macaques by the SIVmac239-Cre virus.

The dose and the route of infection are able to be modified as a function of the scientific aims of the experimentation. A method is briefly described below:

Infect the macaques intravenously (50 $AID_{50}$) or mucosally (50-5000 $AID_{50}$).

Monitor the viral load in kinetic conditions by quantification of the viral RNAs in the plasma of the infected animals.

B—Results

The pSDT-4lox-RFP/GFP lentivrial vector on SIVmac251 base (FIG. 5) was obtained by cloning the fragment derived from pHR-4lox-RFP/GFP and from pGAE-SFFV-GFP-WPRE (supplied by E. Verhoyen). This high-titer (SIVmac251 CMV-5'LTR) non-replicative vector (SIVmac251 inactivated 3'LTR) was devised in the following way, from 5' to 3':

Prokaryotic plasmid.

F1 origin.

Lactamase gene.

CMV promoter.

5'LTR (SIVmac251).

PBS-gag encapsidation sequence of SIVmac251.

cPPT/CTS.

RRE sequence of SIVmac251.

SFFV promoter.

loxP-loxp2272-turboRFP-loxP-loxP2272 cassette.

PGK promoter.

eGFP gene.

WPRE.

PPT and TTTTAT tract.

Inactivated 3'LTR (SIVmac251).

This construct is represented by the sequence SEQ ID NO: 7.

Figure 12:
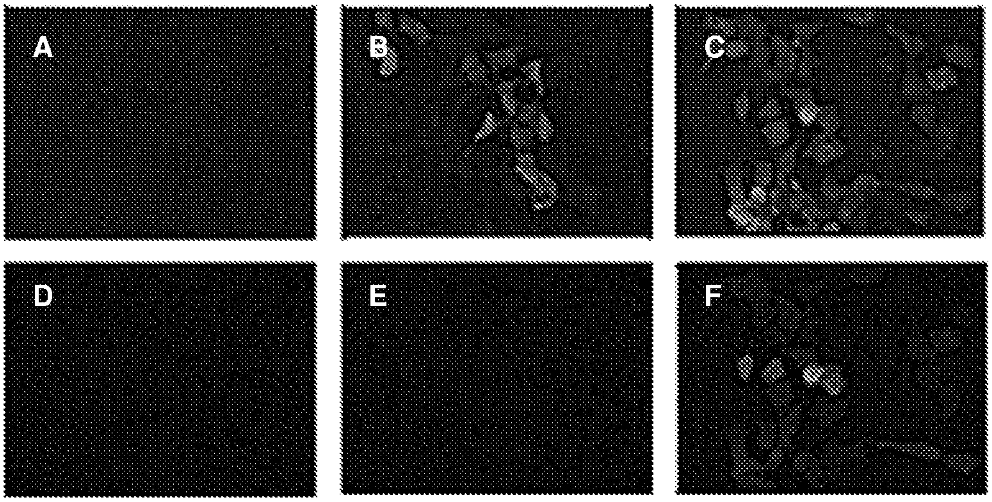
FIGS. 12A to 12C are fluorescence micrographs showing the recombination of the reporter gene when the nucleic acid molecule is transduced in 293T cells and when the cells have been infected by an SIVmac virus expressing Cre recombinase.
FIG. 12D is an image of detection of RFP in non-transduced and non-infected cells (control).
FIG. 12E is an image of detection of RFP in transduced and non-infected cells.
FIG. 12F is an image of detection of RFP in transduced cells infected with a virus.
Figure 13:
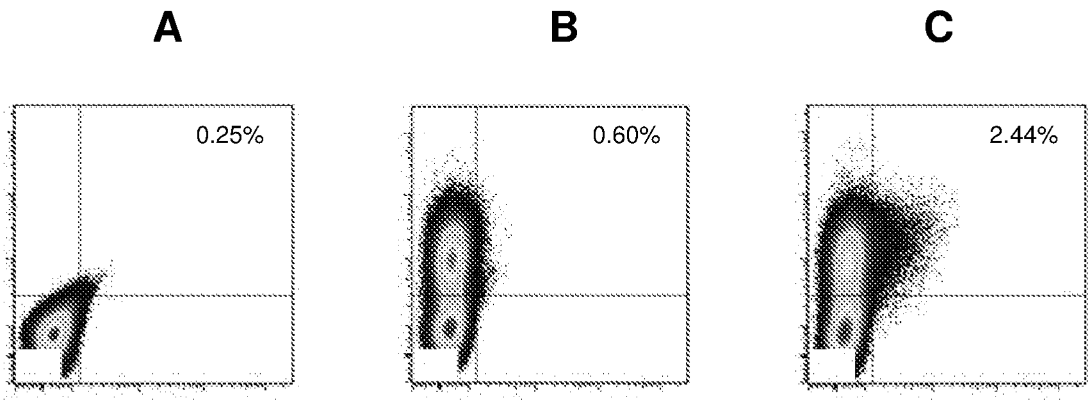
FIGS. 13A to 13C are graphs showing flow cytometry images for the cells expressing RFP (y-axis) and GFP (x-axis). The doubly labeled cells are indicated in each figure in the top right square.
Figure 14:
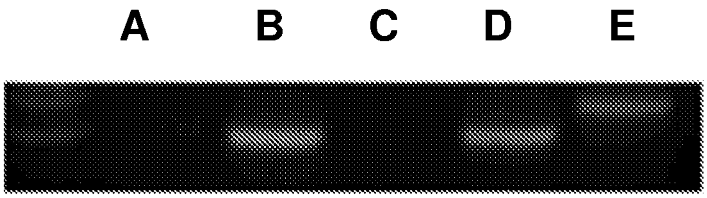
FIG. 14 is a PCR image showing detection of the non-floxed and floxed forms of the nucleic acid molecule in the 293T cells transduced by the nucleic acid molecule and infected with the virus expressing Cre recombinase.
Figure 15:
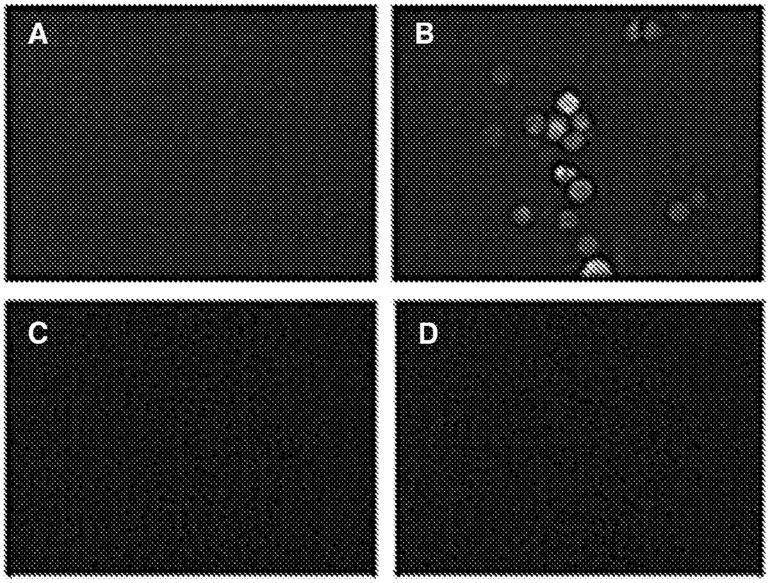
FIGS. 15A to 15D are fluorescence micrographs showing the good level of transduction (GFP expression) in the macaque CD34+ cells which will be used for the reconstructions. The expression of GFP in macaque CD34+ cells transduced by the nucleic acid molecule is checked 48 hours post-transduction.
Figure 16:
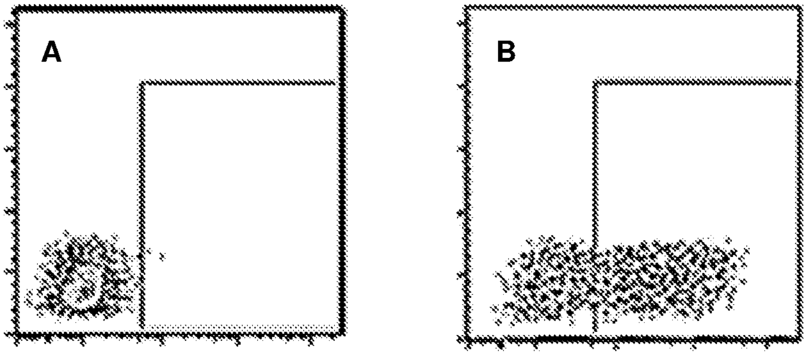
FIGS. 16A to 16B are graphs showing flow cytometry images for the cells depending on granularity (y-axis) and GFP (x-axis). The cells expressing GFP are indicated in each figure in the top right square.

In the same way as for the vector on HIV-1 base, the functioning of the SDT-4lox-RFP/GFP vector was confirmed on the 293T line and transduction/infection with SIVmac239-Nef-IRES-Cre (FIGS. 12, 13 and 14). The capacity for transduction of the CD34+ cells purified from macaque bone marrow was demonstrated after 24 h of pre-stimulation (FIGS. 15 and 16). The transduced CD34+ cells will be used for autografts in macaques irradiated beforehand, in order to reconstruct their immune system from these precursors bearing the transgene.

Figure 17:
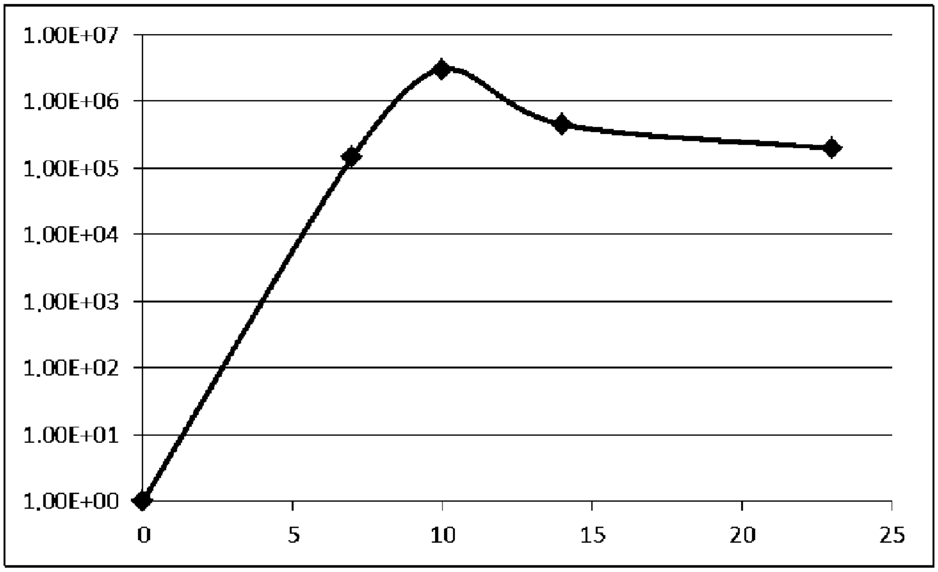
FIG. 17 is a graph showing the replication of the SIV virus expressing Cre recombinase evaluated by the number of copies of viral RNA/ml of plasma (y-axis) after infection in macaques, as a function of time (in days).
Figure 18:
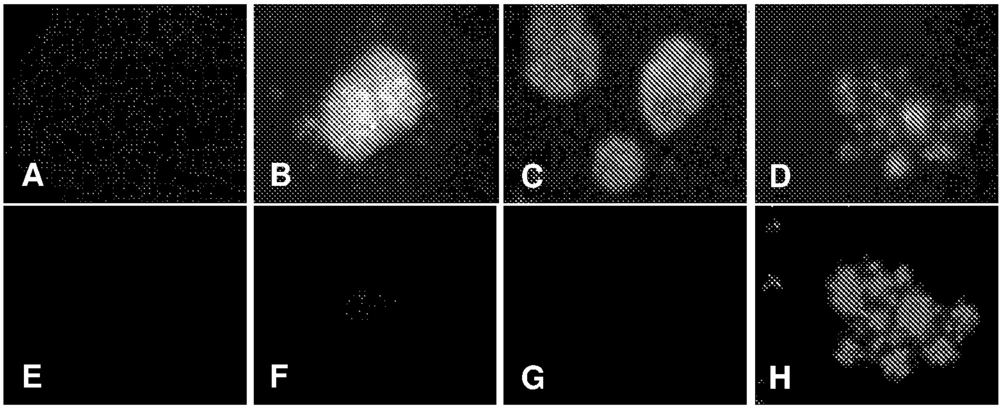
FIGS. 18A to 18H represent fluorescence micrographs showing the level of transduction (GFP expression) and of recombination (RFP expression) in MT4C5 cells.
Figure 19:
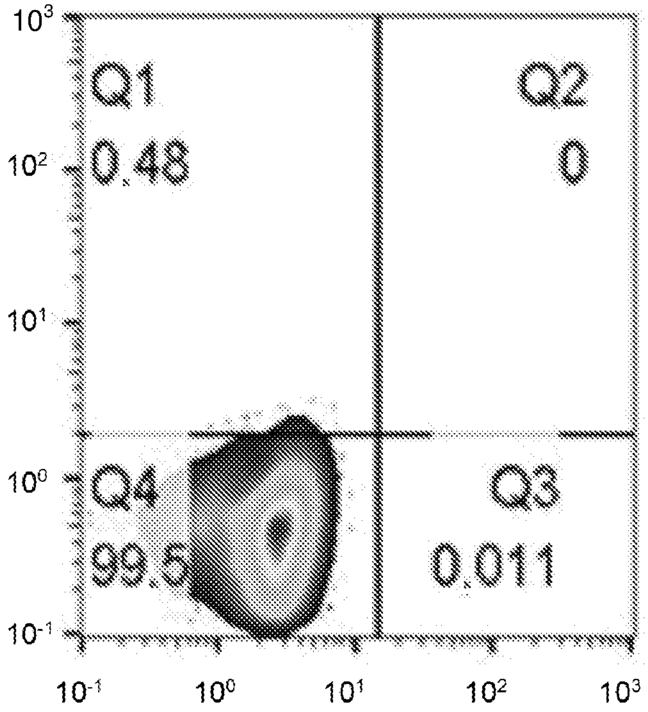
FIG. 19 represents a flow cytometry image according to RFP expression (y-axis: recombination of the reporter) and HIV p24 protein expression (x-axis: viral replication) from MT4C5 cells transfected with the reporter but which have not been infected with HIV.

This vector SDT-4lox-RFP/GFP is soon to be tested in vivo. The virus SIVmac239-Nef-IRES-Cre is being validated. One macaque was infected with this virus, which shows normal replication dynamics (FIG. 17).

The infected animals will be treated with AZT (4.5 mg/kg) and 3TC (2.5 mg/kg) twice daily by subcutaneous injection and also with indinavir (60 mg/kg) twice daily, orally.

Once treated, the viral load of the mice is measured in order to verify the effectiveness of the treatment, and the reservoir cells are isolated by flow cytometry by selecting the cells expressing the reporter (RFP).

Example 3

Method for Identifying Feline Reservoir Cells

The characteristics of infection by the feline immunodeficiency virus (FIV) are similar to those of infection by HIV-1 (see review by McDonnel et al, *Retrovirology* 2013, 10:69.). After an acute phase, infection is characterized by a long chronic phase leading to an AIDS state after depletion of the CD4+ T lymphocyte compartment. In the same way as for HIV-1, reservoir cells have been revealed during the chronic phase, even in the absence of treatment (McDonnel et al, *Viruses* 2012, 4:878-888). The method of example 1 can therefore be transposed to the FIV model.

In addition, it is possible to obtain feline hematopoietic cells transformed with the nucleic acid molecule. These transgenesis experiments are carried out according to the protocol described by Wongsrikeo et al., Nat Methods. 2011 Sep. 11;8(10):853-9), and briefly summarized below.

Gamete Isolation and Embryo Generation:

Recover gonads originating from cat sterilizations.

Recover the total oocytes after repeated cutting up of ovarian tissue in PBS supplemented with BSA at 4 mg/ml and L-gentamicin at 50 μg/ml.

Retain the stage I and stage II oocytes.

Mature the oocytes by culturing them for 28 hours at 38° C. in modified TCM-199 medium containing 10 μg/ml of human chorionic gonadotropin, 0.5 IU/ml of equine chorionic gonadotropin, 10 μg/ml of epidermal growth factor and 4 mg/ml of BSA.

Eliminate the cells of the cumulus 18 to 20 hours after beginning maturation.

Inject a volume of 100 μl of vector directly into the perivitelline space of the oocyte, 12 hours before fertilization.

Wash and place the oocytes back in culture.

After 28 hours of culture, wash spermatozoa in Brackett-Oliphant medium supplemented with 137 μg/ml of sodium pyruvate, 4 mg/ml of BSA and 50 μg/ml of L-gentamicin with centrifugation at 1800 rpm for 5 minutes.

Eliminate the supernatant and take up the pellet in 500 μl of fertilization medium (G-IVF plus) and place in an incubator for 30 minutes.

Adjust the spermatozoa concentration to $2\times10^6$/ml.

Transfer 10 pre-stimulated oocytes into each 100 μl spermatozoa pellet and culture for 12 hours.

Recover the zygotes and culture them after washing in modified Earle's balanced sodium salt medium (MK-1) supplemented with 4 mg/ml BSA and 50 μg/ml of gentamicin for 3 days.

Recover the embryos and culture them in MK-1 medium supplemented with 5% FBS and 50 μg/ml of gentamicin for 4 days.

Transfer of the embryos carrying the transgene.

Females from e to 3 years are the recipients.

Stimulate the females by intravenous injection, 96 to 120 hours before in vitro fertilization, of 150 IU of equine chorionic gonadotropin and 100 IU of human chorionic gonadotropin 72 hours later.

Anesthetize the females with 5 mg/kg of ketamine, 0.03 mg/kg of medetomidine and 0.01 mg/kg of buprenorphine intramuscularly and under 1 to 3% isoflurane atmosphere.

After ventral incision and clearing of the Fallopian tubes, transfer 15 to 25 embryos in 10 to 20 μl of medium per tube.

Monitor the progression of the pregnancy according to the customary criteria.

Check the expression of GFP in the newborns.

Infection of cats by the FIV virus.

The dose and the route of infection are able to be modified as a function of the scientific aims of the experimentation. A method is briefly described below:

Infect the cats intravenously (50 AID50) or mucosally (50-5000 AID50).

Monitor the viral load in kinetic conditions by quantification of the viral RNAs in the plasma of the infected animals.

The animals are then treated with one or more antiretrovirals. After treatment, the reservoir cells are detected by detecting the reporter.

Example 4

In Vitro Characterization of Infected Cells Which are not Producing Virus; That is to Say, Reservoir Cells The inventors then isolated the reservoir cells:

$10^6$ MT4C5 cells (T lymphocyte line) were transduced by the double color HR4lox vector with a multiplicity of infection of 5. The cells were left in culture overnight before being washed then placed back in culture at a concentration of 0.5×10$^6$ cells/ml. Four days post-translation, the transduction frequency was determined by flow cytometry by monitoring the expression of GFP. Under these conditions, the frequency of cells carrying the HR4lox vector was 80%. The cells were kept in culture at a concentration of 0.5×10$^6$ cells/ml. 10$^6$ HR4lox-MT4C5 cells were infected with HIV-1-NL4-3 (R5) at a concentration of 500 ng of p24/106 cells as control, by HIV-1-NL4-3-Nefopt-CMV-Cre at a concentration of 500 ng of p24/10$^6$ cells, or were not infected (negative control). The cells were left in culture overnight before being washed then placed back in culture at a concentration of 0.5×10$^6$ cells/ml.

From 4 to 10 days post-infection, the frequency of cells expressing intracellular p24 (productively infected cells) and/or RFP was determined in GFP+ cells by flow cytometry. For this purpose, the cells were fixed, permeabilized and labeled with an anti-p24 gag protein antibody.

Figure 20:
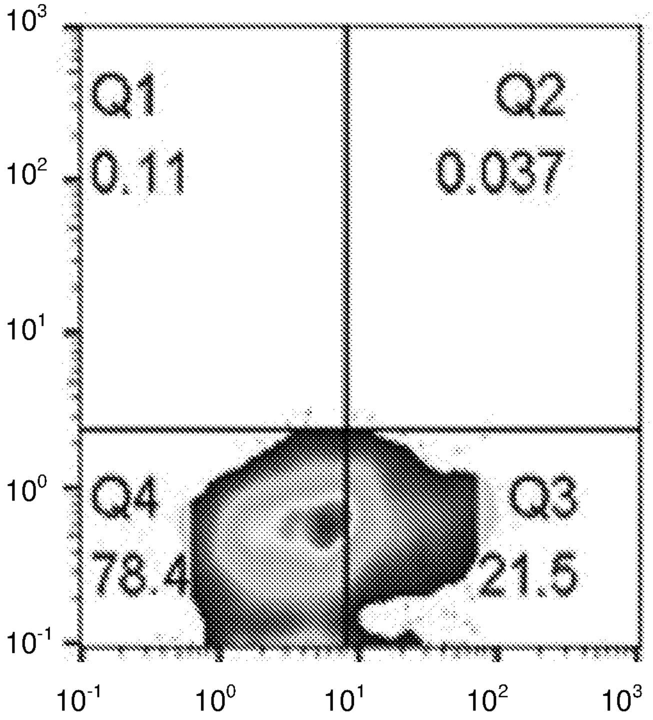
FIG. 20 represents a flow cytometry image according to RFP expression (y-axis: recombination of the reporter) and HIV p24 protein expression (x-axis: viral replication) from MT4C5 cells transfected with the reporter and infected with the control HIV.
Figure 21:
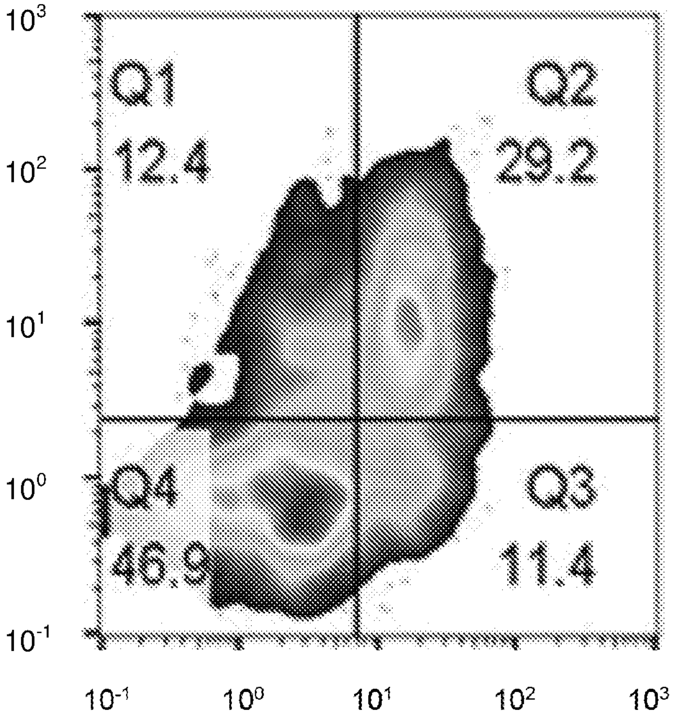
FIG. 21 represents a flow cytometry image according to RFP expression (y-axis: recombination of the reporter) and HIV p24 protein expression (x-axis: viral replication) from MT4C5 cells transfected with the reporter and infected with the HIV expressing Cre recombinase.

The results are shown in FIGS. 20 and 21.

These results clearly show that the reporter transgene is recombined and capable of expressing RFP (FIG. 21). In addition, it is noted that there are two cell populations in which recombination of the transgene has taken place:

- the cells in which the virus is replicating (square Q2 of FIG. 21), which represent approximately 29% of the population, and
- the cells which have been infected and recombined, but in which the virus is not replicating (square Q1 of FIG. 21), which represent approximately 12% of the population and correspond to the reservoir cells.

The invention is not limited to the embodiments presented and other embodiments will become clearly apparent to those skilled in the art.

The invention claimed is:

1. A method for detection of cells that constitute the reservoir of a virus inducing immunodeficiency in a donor mammal by using a recombinant virus expressing site-specific recombinase, the donor mammal being a human, the method comprising:

(a) introducing into hematopoietic stem cells from the donor mammal:

a nucleic acid molecule comprising a first reporter gene, the nucleic acid molecule comprising a first sequence encoding the first reporter gene, under the control of at least one element necessary for transcription, the first sequence being bordered by:

at least one first pair of sequences targeting a site-specific recombinase, the first pair comprising a P1-1 sequence and a P1-2 sequence, at least one second pair of sequences targeting a site-specific recombinase, the second pair comprising a P2-1 sequence and a P2-2 sequence, the sequences of each of the first and second pairs of sequences being oppositely oriented relative to one another, the sequences of the first pair of sequences targeting a site-specific recombinase being unable to recombine with the sequences of the second pair of sequences targeting a site-specific recombinase, and the sequences of the second pair of sequences targeting a site-specific recombinase being unable to recombine with the sequences of the first pair of sequences targeting a site-specific recombinase, one sequence from the first pair and one sequence from the second pair of sequences targeting a site-specific recombinase being located upstream of the first nucleic acid sequence, and one sequence from the first pair and one sequence from the second pair of sequences targeting a site-specific recombinase being located downstream of the first nucleic acid sequence, such that the sequences of the same pair never flank the two sequences of the other pair, the sequence of the first nucleic acid molecule being such that, in the absence of combination induced by the site-specific recombinase, it has an open reading frame coding for the first reporter gene in a 3'-5' orientation;

(b) myeloablating the hematopoietic system of a recipient mammal, the recipient mammal being a mouse, and reconstructing the hematopoietic system of the recipient mammal, said reconstructing using the hematopoietic stem cells of the donor mammal prepared in (a);

(c) infecting the recipient mammal having a reconstructed bone marrow in (b) with a virus inducing an immunodeficiency in the donor mammal, the virus expressing a site-specific recombinase;

(d) treating the recipient mammal infected in (c) with a treatment inhibiting development of the virus; and (e) detecting, in the recipient mammal, hematopoietic cells expressing the first reporter and being resistant to the treatment inhibiting development of the virus.

2. The method as claimed in claim 1, in which the site-specific recombinase is the Cre recombinase from the P1 bacteriophage.

3. The method as claimed in claim 1, in which the sequences of the first pair of sequences targeting a site-specific recombinase and the sequences of the second pair of sequences targeting a site-specific recombinase are chosen from Lox P1, Lox P2272, Lox 66, Lox 71, Lox 511, Lox 512, Lox 514 and mutated sequences of the Lox P1 site, bearing at least one point mutation in the spacer sequence.

4. The method as claimed in claim 1, in which the nucleic acid molecule comprises one of the following sequences: SEQ ID NO: 6, SEQ ID NO: 7, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, or SEQ ID NO: 40.

5. The method as claimed in claim 1, wherein the virus inducing the immunodeficiency in the mammal is a HIV-1 virus.

6. The method as claimed in claim 1, wherein the virus inducing the immunodeficiency in the mammal is a HIV-1 or HIV-2 virus.

* * * * *

SEQUENCE LISTING

```
<160> NUMBER OF SEQ ID NOS: 47

<210> SEQ ID NO 1
<211> LENGTH: 34
<212> TYPE: DNA
<213> ORGANISM: Artificial Sequence
<220> FEATURE:
<223> OTHER INFORMATION: LoxP1 forward sequence

<400> SEQUENCE: 1

ataacttcgt atagcataca ttatacgaag ttat                                34


<210> SEQ ID NO 2
<211> LENGTH: 34
<212> TYPE: DNA
<213> ORGANISM: Artificial Sequence
<220> FEATURE:
<223> OTHER INFORMATION: Lox P2272 forward sequence

<400> SEQUENCE: 2

ataacttcgt ataaagtatc ctatacgaag ttat                                34


<210> SEQ ID NO 3
<211> LENGTH: 34
<212> TYPE: DNA
<213> ORGANISM: Artificial Sequence
<220> FEATURE:
<223> OTHER INFORMATION: Lox P reverse sequence

<400> SEQUENCE: 3

ataacttcgt ataatgtatg ctatacgaag ttat                                34


<210> SEQ ID NO 4
<211> LENGTH: 34
<212> TYPE: DNA
<213> ORGANISM: Artificial Sequence
<220> FEATURE:
<223> OTHER INFORMATION: Lox P2272 reverse sequence

<400> SEQUENCE: 4

ataacttcgt ataggatact ttatacgaag ttat                                34


<210> SEQ ID NO 5
<211> LENGTH: 696
<212> TYPE: DNA
<213> ORGANISM: Artificial Sequence
<220> FEATURE:
<223> OTHER INFORMATION: reverse RFP
```

<400> SEQUENCE: 5
ttatctgtgc cccagtttgc tagggaggtc gcagtacttg gccacagcca tctcgtgctg 60
ctcgacgtag gtctctttgt cggcctcctt gattctttcc agtctgtggt ccacgaagtg 120
gaagccgggc atcttgaggt tcttagcggg tttcttggat ctgtatgtgg tcttgaagga 180
gcagtgcagg tagcccccgc ccacgagctt cagggccatc tggctgtggc ctctcaggcc 240
gccgtcagcg gggtacagca tctcggtgtt ggcctcccag ccgcgtgttt tcttctgcat 300
cacagggccg ttggatggga agttcacccc gttgatcttg acgttgtaga tgatgcagcc 360
gttctggaag ctggtgtcct gggtagcggt cagcacgccc ccgtcttcgt atgtggtgat 420
tctctcccat gtgaagccct cagggaagga ctgcttaaag aagtcgggga tgccctgggt 480
gtggttgatg aaggctttgc tgccgtacat gaagctggta gccaggatgt cgaaggcgaa 540
ggggagaggg ccgccctcga ccaccttgat cttcatggtc tgggtgccct cgtagggctt 600
gccttcgccc tcggatgtgc acttgaagtg gtggttgttc acggtgccct ccatgtacag 660
cttcatgtgc atgttctcct tgatcagctc gctcat 696

<210> SEQ ID NO 6
<211> LENGTH: 11336
<212> TYPE: DNA
<213> ORGANISM: Artificial Sequence
<220> FEATURE:
<223> OTHER INFORMATION: sequence for screening human cells

<400> SEQUENCE: 6
ttaattccgt gtattctata gtgtcaccta aatcgtatgt gtatgataca taaggttatg 60
tattaattgt agccgcgttc taacgacaat atgtacaagc ctaattgtgt agcatctggc 120
ttactgaagc agaccctatc atctctctcg taaactgccg tcagagtcgg tttggttgga 180
cgaaccttct gagtttctgg taacgccgtc ccgcacccgg aaatggtcag cgaaccaatc 240
agcagggtca tcgctagcca gatcctctac gccggacgca tcgtggccgg catcaccggc 300
gccacaggtg cggttgctgg cgcctatatc gccgacatca ccgatgggga agatcgggct 360
cgccacttcg ggctcatgag cgcttgtttc ggcgtgggta tggtggcagg ccccgtggcc 420
gggggactgt tgggcgccat ctccttgcat gcaccattcc ttgcggcggc ggtgctcaac 480
ggcctcaacc tactactggg ctgcttccta atgcaggagt cgcataaggg agagcgtcga 540
atggtgcact ctcagtacaa tctgctctga tgccgcatag ttaagccagc cccgacaccc 600
gccaacaccc gctgacgcgc cctgacgggc ttgtctgctc ccggcatccg cttacagaca 660
agctgtgacc gtctccggga gctgcatgtg tcagaggttt tcaccgtcat caccgaaacg 720
cgcgagacga aagggcctcg tgatacgcct atttttatag gttaatgtca tgataataat 780
ggtttcttag acgtcaggtg gcacttttcg gggaaatgtg cgcggaaccc ctatttgttt 840
atttttctaa atacattcaa atatgtatcc gctcatgaga caataaccct gataaatgct 900
tcaataatat tgaaaaagga agagtatgag tattcaacat ttccgtgtcg cccttattcc 960
cttttttgcg gcattttgcc ttcctgtttt tgctcaccca gaaacgctgg tgaaagtaaa 1020
agatgctgaa gatcagttgg gtgcacgagt gggttacatc gaactggatc tcaacagcgg 1080
taagatcctt gagagttttc gccccgaaga acgttttcca atgatgagca cttttaaagt 1140
tctgctatgt ggcgcggtat tatcccgtat tgacgccggg caagagcaac tcggtcgccg 1200
catacactat tctcagaatg acttggttga gtactcacca gtcacagaaa agcatcttac 1260
ggatggcatg acagtaagag aattatgcag tgctgccata accatgagtg ataacactgc 1320

-continued

```
ggccaactta cttctgacaa cgatcggagg accgaaggag ctaaccgctt ttttgcacaa   1380
catgggggat catgtaactc gccttgatcg ttgggaaccg gagctgaatg aagccatacc   1440
aaacgacgag cgtgacacca cgatgcctgt agcaatggca acaacgttgc gcaaactatt   1500
aactggcgaa ctacttactc tagcttcccg gcaacaatta atagactgga tggaggcgga   1560
taaagttgca ggaccacttc tgcgctcggc ccttccggct ggctggttta ttgctgataa   1620
atctggagcc ggtgagcgtg ggtctcgcgg tatcattgca gcactggggc cagatggtaa   1680
gccctcccgt atcgtagtta tctacacgac ggggagtcag gcaactatgg atgaacgaaa   1740
tagacagatc gctgagatag gtgcctcact gattaagcat tggtaactgt cagaccaagt   1800
ttactcatat atactttaga ttgatttaaa acttcatttt taatttaaaa ggatctaggt   1860
gaagatcctt tttgataatc tcatgaccaa aatcccttaa cgtgagtttt cgttccactg   1920
agcgtcagac cccgtagaaa agatcaaagg atcttcttga gatccttttt ttctgcgcgt   1980
aatctgctgc ttgcaaacaa aaaaaccacc gctaccagcg gtggtttgtt tgccggatca   2040
agagctacca actctttttc cgaaggtaac tggcttcagc agagcgcaga taccaaatac   2100
tgtccttcta gtgtagccgt agttaggcca ccacttcaag aactctgtag caccgcctac   2160
atacctcgct ctgctaatcc tgttaccagt ggctgctgcc agtggcgata agtcgtgtct   2220
taccgggttg gactcaagac gatagttacc ggataaggcg cagcggtcgg gctgaacggg   2280
gggttcgtgc acacagccca gcttggagcg aacgacctac accgaactga gatacctaca   2340
gcgtgagcat tgagaaagcg ccacgcttcc cgaagggaga aaggcggaca ggtatccggt   2400
aagcggcagg gtcggaacag gagagcgcac gagggagctt ccagggggaa acgcctggta   2460
tctttatagt cctgtcgggt ttcgccacct ctgacttgag cgtcgatttt tgtgatgctc   2520
gtcagggggg cggagcctat ggaaaaacgc cagcaacgcg gcctttttac ggttcctggc   2580
cttttgctgg ccttttgctc acatgttctt tcctgcgtta tcccctgatt ctgtggataa   2640
ccgtattacc gcctttgagt gagctgatac cgctcgccgc agccgaacga ccgagcgcag   2700
cgagtcagtg agcgaggaag cggaagagcg cccaatacgc aaaccgcctc tccccgcgcg   2760
ttggccgatt cattaatgca gctgtggaat gtgtgtcagt tagggtgtgg aaagtcccca   2820
ggctccccag caggcagaag tatgcaaagc atgcatctca attagtcagc aaccaggtgt   2880
ggaaagtccc caggctcccc agcaggcaga agtatgcaaa gcatgcatct caattagtca   2940
gcaaccatag tcccgcccct aactccgccc atcccgcccc taactccgcc cagttccgcc   3000
cattctccgc cccatggctg actaattttt tttatttatg cagaggccga ggccgcctcg   3060
gcctctgagc tattccagaa gtagtgagga ggcttttttg gaggcctagg cttttgcaaa   3120
aagcttggac acaagacagg cttgcgagat atgtttgaga ataccacttt atcccgcgtc   3180
agggagaggc agtgcgtaaa aagacgcgga ctcatgtgaa atactggttt ttagtgcgcc   3240
agatctctat aatctcgcgc aacctatttt cccctcgaac actttttaag ccgtagataa   3300
acaggctggg acacttcaca tgagcgaaaa atacatcgtc acctgggaca tgttgcagat   3360
ccatgcacgt aaactcgcaa gccgactgat gccttctgaa caatggaaag gcattattgc   3420
cgtaagccgt ggcggtctgt accgggtgcg ttactggcgc gtgaactggg tattcgtcat   3480
gtcgataccg tttgtatttc cagctacgat cacgacaacc agcgcgagct taaagtgctg   3540
aaacgcgcag aaggcgatgg cgaaggcttc atcgttattg atgacctggt ggataccggt   3600
ggtactgcgg ttgcgattcg tgaaatgtat ccaaaagcgc actttgtcac catcttcgca   3660
```

-continued aaaccggctg gtcgtccgct ggttgatgac tatgttgttg atatcccgca agatacctgg 3720
attgaacagc cgtgggatat gggcgtcgta ttcgtcccgc caatctccgg tcgctaatct 3780
tttcaacgcc tggcactgcc gggcgttgtt ctttttaact tcaggcgggt tacaatagtt 3840
tccagtaagt attctggagg ctgcatccat gacacaggca aacctgagcg aaaccctgtt 3900
caaaccccgc tttaaacatc ctgaaacctc gacgctagtc cgccgcttta atcacggcgc 3960
acaaccgcct gtgcagtcgg cccttgatgg taaaaccatc cctcactggt atcgcatgat 4020
taaccgtctg atgtggatct ggcgcggcat tgacccacgc gaaatcctcg acgtccaggc 4080
acgtattgtg atgagcgatg ccgaacgtac cgacgatgat ttatacgata cggtgattgg 4140
ctaccgtggc ggcaactgga tttatgagtg ggccccggat ctttgtgaag gaaccttact 4200
tctgtggtgt gacataattg gacaaactac ctacagagat ttaaagctct aaggtaaata 4260
taaaattttt aagtgtataa tgtgttaaac tactgattct aattgtttgt gtattttaga 4320
ttccaaccta tggaactgat gaatgggagc agtggtggaa tgcctttaat gaggaaaacc 4380
tgttttgctc agaagaaatg ccatctagtg atgatgaggc tactgctgac tctcaacatt 4440
ctactcctcc aaaaaagaag agaaaggtag aagaccccaa ggactttcct tcagaattgc 4500
taagtttttt gagtcatgct gtgtttagta atagaactct tgcttgcttt gctatttaca 4560
ccacaaagga aaaagctgca ctgctataca agaaaattat ggaaaaatat tctgtaacct 4620
ttataagtag gcataacagt tataatcata acatactgtt ttttcttact ccacacaggc 4680
atagagtgtc tgctattaat aactatgctc aaaaattgtg tacctttagc tttttaattt 4740
gtaaaggggt taataaggaa tatttgatgt atagtgcctt gactagagat cataatcagc 4800
cataccacat ttgtagaggt tttacttgct ttaaaaaacc tcccacacct ccccctgaac 4860
ctgaaacata aaatgaatgc aattgttgtt gttaacttgt ttattgcagc ttataatggt 4920
tacaaataaa gcaatagcat cacaaatttc acaaataaag catttttttc actgcattct 4980
agttgtggtt tgtccaaact catcaatgta tcttatcatg tctggatcaa ctggataact 5040
caagctaacc aaaatcatcc caaacttccc accccatacc ctattaccac tgccaattac 5100
ctagtggttt catttactct aaacctgtga ttcctctgaa ttattttcat tttaaagaaa 5160
ttgtatttgt taaatatgta ctacaaactt agtagttgga agggctaatt cactcccaaa 5220
gaagacaaga tatccttgat ctgtggatct accacacaca aggctacttc cctgattagc 5280
agaactacac accagggcca ggggtcagat atccactgac ctttggatgg tgctacaagc 5340
tagtaccagt tgagccagat aaggtagaag aggccaataa aggagagaac accagcttgt 5400
tacaccctgt gagcctgcat gggatggatg acccggagag agaagtgtta gagtggaggt 5460
ttgacagccg cctagcattt catcacgtgg cccgagagct gcatccggag tacttcaaga 5520
actgctgata tcgagcttgc tacaagggac tttccgctgg ggactttcca gggaggcgtg 5580
gcctgggcgg gactggggag tggcgagccc tcagatcctg catataagca gctgcttttt 5640
gcctgtactg ggtctctctg gttagaccag atctgagcct gggagctctc tggctaacta 5700
gggaacccac tgcttaagcc tcaataaagc ttgccttgag tgcttcaagt agtgtgtgcc 5760
cgtctgttgt gtgactctgg taactagaga tccctcagac ccttttagtc agtgtggaaa 5820
atctctagca gtggcgcccg aacagggact tgaaagcgaa agggaaacca gaggagctct 5880
ctcgacgcag gactcggctt gctgaagcgc gcacggcaag aggcgagggg cggcgactgg 5940
tgagtacgcc aaaaattttg actagcggag gctagaagga gagagatggg tgcgagagcg 6000
tcagtattaa gcgggggaga attagatcgc gatgggaaaa aattcggtta aggccagggg 6060

-continued gaaagaaaaa atataaatta aaacatatag tatgggcaag cagggagcta gaacgattcg 6120
cagttaatcc tggcctgtta gaaacatcag aaggctgtag acaaatactg ggacagctac 6180
aaccatccct tcagacagga tcagaagaac ttagatcatt atataataca gtagcaaccc 6240
tctattgtgt gcatcaaagg atagagataa aagacaccaa ggaagcttta gacaagatag 6300
aggaagagca aaacaaaagt aagaccaccg cacagcaagc ggccgctgat cttcagacct 6360
ggaggaggag atatgaggga caattggaga agtgaattat ataaatataa agtagtaaaa 6420
attgaaccat taggagtagc acccaccaag gcaaagagaa gagtggtgca gagagaaaaa 6480
agagcagtgg gaataggagc tttgttcctt gggttcttgg gagcagcagg aagcactatg 6540
ggcgcagcgt caatgacgct gacggtacag gccagacaat tattgtctgg tatagtgcag 6600
cagcagaaca atttgctgag ggctattgag gcgcaacagc atctgttgca actcacagtc 6660
tggggcatca agcagctcca ggcaagaatc ctggctgtgg aaagatacct aaaggatcaa 6720
cagctcctgg ggatttgggg ttgctctgga aaactcattt gcaccactgc tgtgccttgg 6780
aatgctagtt ggagtaataa atctctggaa cagatttgga atcacacgac ctggatggag 6840
tgggacagag aaattaacaa ttacacaagc ttaatacact ccttaattga agaatcgcaa 6900
aaccagcaag aaaagaatga acaagaatta ttggaattag ataaatgggc aagtttgtgg 6960
aattggttta acataacaaa ttggctgtgg tatataaaat tattcataat gatagtagga 7020
ggcttggtag gtttaagaat agtttttgct gtactttcta tagtgaatag agttaggcag 7080
ggatattcac cattatcgtt tcagacccac ctcccaaccc cgaggggacc cgacaggccc 7140
gaaggaatag aagaagaagg tggagagaga gacagagaca gatccattcg attagtgaac 7200
ggatctcgac ggtatcgccg aattcacaaa tggcagtatt catccacaat tttaaaagaa 7260
aaggggggat tggggggtac agtgcagggg aaagaatagt agacataata gcaacagaca 7320
tacaaactaa agaattacaa aaacaaatta caaaaattca aaattttcgg gtttattaca 7380
gggacagcag agatccactt tatcgataag cttgggagtt ccgcgttaca taacttacgg 7440
taaatggccc gcctggctga ccgcccaacg acccccgccc attgacgtca ataatgacgt 7500
atgttcccat agtaacgcca atagggactt tccattgacg tcaatgggtg gagtatttac 7560
ggtaaactgc ccacttggca gtacatcaag tgtatcatat gccaagtacg ccccctattg 7620
acgtcaatga cggtaaatgg cccgcctggc attatgccca gtacatgacc ttacgggact 7680
ttcctacttg gcagtacatc tacgtattag tcatcgctat taccatggtg atgcggtttt 7740
ggcagtacac caatgggcgt ggatagcggt ttgactcacg gggatttcca agtctccacc 7800
ccattgacgt caatgggagt ttgttttggc accaaaatca acgggacttt ccaaaatgtc 7860
gtaacaactc cgccccattg acgcaaatgg gcggtaggcg tgtacggtgg gaggtctata 7920
taagcagagc tcgtttagtg aaccgtcaga tcgcctggag acgccatcca cgctgttttg 7980
acctccatag aagacaccga ctctagctag aggatccgga ctagtaactc gaggatgggg 8040
actgacccgg gctgcaggaa ttcataactt cgtataatgt atgctatacg aagttatagt 8100
taagccttat tgtttatcat cctcattcaa cgacgcgaag gtgtaccttg gcgagaataa 8160
cttcgtatag gatactttat acgaagttat ttatctgtgc cccagtttgc tagggaggtc 8220
gcagtacttg gccacagcca tctcgtgctg ctcgacgtag gtctctttgt cggcctcctt 8280
gattctttcc agtctgtggt ccacgaagtg gaagccgggc atcttgaggt tcttagcggg 8340
tttcttggat ctgtatgtgg tcttgaagga gcagtgcagg tagcccccgc ccacgagctt 8400

-continued

```
cagggccatc tggctgtggc ctctcaggcc gccgtcagcg gggtacagca tctcggtgtt   8460
ggcctcccag ccgcgtgttt tcttctgcat cacagggccg ttggatggga agttcacccc   8520
gttgatcttg acgttgtaga tgatgcagcc gttctggaag ctggtgtcct gggtagcggt   8580
cagcacgccc ccgtcttcgt atgtggtgat tctctcccat gtgaagccct cagggaagga   8640
ctgcttaaag aagtcgggga tgccctgggt gtggttgatg aaggctttgc tgccgtacat   8700
gaagctggta gccaggatgt cgaaggcgaa ggggagaggg ccgccctcga ccaccttgat   8760
cttcatggtc tgggtgccct cgtagggctt gccttcgccc tcggatgtgc acttgaagtg   8820
gtggttgttc acggtgccct ccatgtacag cttcatgtgc atgttctcct tgatcagctc   8880
gctcatggtg gcatatgata acttcgtata gcatacatta tacgaagtta tattaagggt   8940
tattgaatat gatcggaagt caacgggtcg atggtgatgc ttggctcgaa taacttcgta   9000
taaagtatcc tatacgaagt tatactttgg ccgcggctcg agggggttgg ggttgcgcct   9060
tttccaaggc agccctgggt ttgcgcaggg acgcggctgc tctgggcgtg gttccgggaa   9120
acgcagcggc gccgaccctg ggtctcgcac attcttcacg tccgttcgca gcgtcacccg   9180
gatcttcgcc gctacccttg tgggcccccc ggcgacgctt cctgctccgc ccctaagtcg   9240
ggaaggttcc ttgcggttcg cggcgtgccg gacgtgacaa acggaagccg cacgtctcac   9300
tagtaccctc gcagacggac agcgccaggg agcaatggca gcgcgccgac cgcgatgggc   9360
tgtggccaat agcggctgct cagcagggcg cgccgagagc agcggccggg aaggggcggt   9420
gcgggaggcg gggtgtgggg cggtagtgtg ggccctgttc ctgcccgcgc ggtgttccgc   9480
attctgcaag cctccggagc gcacgtcggc agtcggctcc ctcgttgacc gaatcaccga   9540
cctctctccc caggggggatc caccggtcgc caccatggtg agcaagggcg aggagctgtt   9600
caccggggtg gtgcccatcc tggtcgagct ggacggcgac gtaaacggcc acaagttcag   9660
cgtgtccggc gagggcgagg gcgatgccac ctacggcaag ctgaccctga agttcatctg   9720
caccaccggc aagctgcccg tgccctggcc caccctcgtg accaccctga cctacggcgt   9780
gcagtgcttc agccgctacc ccgaccacat gaagcagcac gacttcttca agtccgccat   9840
gcccgaaggc tacgtccagg agcgcaccat cttcttcaag gacgacggca actacaagac   9900
ccgcgccgag gtgaagttcg agggcgacac cctggtgaac cgcatcgagc tgaagggcat   9960
cgacttcaag gaggacggca acatcctggg gcacaagctg gagtacaact acaacagcca  10020
caacgtctat atcatggccg acaagcagaa gaacggcatc aaggtgaact tcaagatccg  10080
ccacaacatc gaggacggca gcgtgcagct cgccgaccac taccagcaga acacccccat  10140
cggcgacggc cccgtgctgc tgcccgacaa ccactacctg agcacccagt ccgccctgag  10200
caaagacccc aacgagaagc gcgatcacat ggtcctgctg gagttcgtga ccgccgccgg  10260
gatcactctc ggcatggacg agctgtacaa gtaagatatc aagcttatcg ataatcaacc  10320
tctggattac aaaatttgtg aaagattgac tggtattctt aactatgttg ctccttttac  10380
gctatgtgga tacgctgctt taatgccttt gtatcatgct attgcttccc gtatggcttt  10440
cattttctcc tccttgtata aatcctggtt gctgtctctt tatgaggagt tgtggcccgt  10500
tgtcaggcaa cgtggcgtgg tgtgcactgt gtttgctgac gcaaccccca ctggttgggg  10560
cattgccacc acctgtcagc tcctttccgg gactttcgct ttccccctcc ctattgccac  10620
ggcggaactc atcgccgcct gccttgcccg ctgctggaca ggggctcggc tgttgggcac  10680
tgacaattcc gtggtgttgt cggggaaatc atcgtccttt ccttggctgc tcgcctgtgt  10740
tgccacctgg attctgcgcg ggacgtcctt ctgctacgtc ccttcggccc tcaatccagc  10800
```

-continued

```
ggaccttcct tcccgcggcc tgctgccggc tctgcggcct cttccgcgtc ttcgccttcg  10860

ccctcagacg agtcggatct ccctttgggc cgcctccccg catcgatacc gtcgacctcg  10920

agaacctaga aaaacatgga gcaatcacaa gtagcaatac agcagctacc aatgctgatt  10980

gtgcctggct agaagcacaa gaggaggagg aggtgggttt tccagtcaca cctcaggtac  11040

ctttaagacc aatgacttac aaggcagctg tagatcttag ccacttttta aaagaaaagg  11100

ggggactgga agggctaatt cactcccaac gaagacaaga tctttttgct tgtactgggt  11160

ctctctggtt agaccagatc tgagcctggg agctctctgg ctaactaggg aacccactgc  11220

ttaagcctca ataaagcttg ccttgagtgc ttcaagtagt gtgtgcccgt ctgttgtgtg  11280

actctggtaa ctagagatcc ctcagaccct tttagtcagt gtggaaaatc tctaga      11336
```

<210> SEQ ID NO 7
<211> LENGTH: 9303
<212> TYPE: DNA
<213> ORGANISM: Artificial Sequence
<220> FEATURE:
<223> OTHER INFORMATION: sequence for screening simian cells

<400> SEQUENCE: 7

```
ggaaattgta aacgttaata ttttgttaaa attcgcgtta aatttttgtt aaatcagctc     60

atttttaac caataggccg aaatcggcaa aatcccttat aaatcaaaag aatagaccga    120

gatagggttg agtgttgttc cagtttggaa caagagtcca ctattaaaga acgtggactc    180

caacgtcaaa gggcgaaaaa ccgtctatca gggcgatggc ccactacgtg aaccatcacc    240

ctaatcaagt tttttggggt cgaggtgccg taaagcacta aatcggaacc ctaaagggag    300

cccccgattt agagcttgac ggggaaagcc ggcgaacgtg gcgagaaagg aagggaagaa    360

agcgaaagga gcgggcgcta gggcgctggc aagtgtagcg gtcacgctgc gcgtaaccac    420

cacacccgcc gcgcttaatg cgccgctaca gggcgcgtcg cgccattcgc cattcaggct    480

gcgcaactgt tgggaagggc gatcggtgcg ggcctcttcg ctattacgcc agctggcgaa    540

agggggatgt gctgcaaggc gattaagttg ggtaacgcca gggttttccc agtcacgacg    600

ttgtaaaacg acggccagtg aattgtaata cgactcacta tagggcgaat tggagctcca    660

ccgcggtggc ggccgctcta gaattcccat tgcatacgtt gtatccatat cataatatgt    720

acatttatat tggctcatgt ccaacattac cgccatgttg acattgatta ttgactagtt    780

attaatagta atcaattacg gggtcattag ttcatagccc atatatggag ttccgcgtta    840

cataacttac ggtaaatggc ccgcctggct gaccgcccaa cgacccccgc ccattgacgt    900

caataatgac gtatgttccc atagtaacgc caatagggac tttccattga cgtcaatggg    960

tggagtattt acggtaaact gcccacttgg cagtacatca agtgtatcat atgccaagta   1020

cgccccctat tgacgtcaat gacggtaaat ggcccgcctg gcattatgcc cagtacatga   1080

ccttatggga ctttcctact tggcagtaca tctacgtatt agtcatcgct attaccatgg   1140

tgatgcggtt ttggcagtac atcaatgggc gtggatagcg gtttgactca cggggatttc   1200

caagtctcca ccccattgac gtcaatggga gtttgttttg gcaccaaaat caacgggact   1260

ttccaaaatg tcgtaacaac tccgccccat tgacgcaaat gggcggtagg cgtgtacggt   1320

gggaggtcta tataagcaga gctcgtttag tgaaccgcag tcgctctgcg gagaggctgg   1380

cagattgagc cctgggaggt tctctccagc actagcaggt agagcctggg tgttccctgc   1440

tagactctca ccagcacttg gccagtgctg ggcagagtgg ctccacgctt gcttgcttaa   1500
```

-continued

```
agacctcttc aataaagctg ccattttaga agtaagccag tgtgtgttcc catctctcct   1560
agtcgccgcc tggtcaactc ggtactcggt aataagaaga ccctggtctg ttaggaccct   1620
ttctgctttg agaaaccgaa gcaggaaaat ccctagcaga ttggcgcccg aacagggact   1680
tgaaggagag tgagagactc ctgagtacgg ctgagtgaag gcagtaaggg cggcaggaac   1740
caaccacgac ggagtgctcc tataaaggcg cgggtcggta ccagacggcg tgaggagcgg   1800
gagaggagga ggcctccggt tgcagtaagt gcaacacaaa aaagaaatag ctgtcttgtt   1860
atccaggaag ggataataag atagagtggg agatgggcgc gagaaactcc gtcttgtcag   1920
ggaagaaagc agatgaattg aaaaaattat taatcgcatg aattttaaaa gaaggggagg   1980
aataggggat atgactccag cagaaagatt aattaacatg atcactacag aacaagaaat   2040
acaatttcaa caatcaaaaa actcaaaatt taaaaatttt cgggtctatt acagagctca   2100
cgcgtgattg gagttgggag attataaatt agtagagatc actccgattg gcttggcccc   2160
cacagatgtg aagaggtaca ctactggtgg cacctcaaga aataaaagag ggtctttgt    2220
gctagggttc ttgggttttc tcgcaacggc aggttctgca atgggcgcgg cgtcgttgac   2280
gctgaccgct cagtcccgga ctttattggc tgggatagtg cagcaacagc aacagctgtt   2340
ggacgtggtc aagagacaac aagaattgtt gcgactgacc gtctggggaa caaagaacct   2400
ccagactagg gtcactgcca tcgagaagta cttaaaggac caggcgcagc taaatgcttg   2460
ggatgtgcg tttagacaag tctgccacac tactgtacca tggccaaatg caagtctaac   2520
accagactgg aacaatgata cttggcaaga gtgggagcga aaggttgact tcttggagga   2580
aaatataaca gccctcctag aagaggcaca aattcaacaa gagaagaaca tgtatgaatt   2640
acaaaagttg aatagctggg atgtgtttgg caattggttt gaccttgctt cttggataaa   2700
gtatatacaa tatggaattt atgtagttgt aggagtaata ctgttaagaa tagtgatcta   2760
tatagtacaa atgctagcta agttaaggca ggggtatagg ccagtgttct cttccccacc   2820
ctcttatttc cagtagactc atacccaaca ggacccggca ctgccaacca gagaaggcaa   2880
agaaggagac ggtggagaag gcggtggatc ctattatcga attcctgcag ccccgataaa   2940
ataaaagatt ttatttagtc tccagaaaaa ggggggaatg aaagacccca cctgtaggtt   3000
tggcaagcta gctgcagtaa cgccattttg caaggcatgg aaaaatacca aaccaagaat   3060
agagaagttc agatcaaggg cgggtacatg aaaatagcta acgttgggcc aaacaggata   3120
tctgcggtga gcagtttcgg ccccggcccg gggccaagaa cagatggtca ccgcagtttc   3180
ggccccggcc cgaggccaag aacagatggt ccccagatat ggcccaaccc tcagcagttt   3240
cttaagaccc atcagatgtt tccaggctcc cccaaggacc tgaaatgacc ctgcgcctta   3300
tttgaattaa ccaatcagcc tgcttctcgc ttctgttcgc gcgcttctgc ttcccgagct   3360
ctataaaaga gctcacaacc cctcactcgg cgcgccagtc ctccgacaga ctgagtcgcc   3420
cgggggggat ccaccgggct gcaggaattc gatatcaagc ttatcgatga ttctagacat   3480
gcatatctag cgtcccgggc tgcaggaatt cataacttcg tataatgtat gctatacgaa   3540
gttatagtta agccttattg tttatcatcc tcattcaacg acgcgaaggt gtaccttggc   3600
gagaataact tcgtatagga tactttatac gaagttattt atctgtgccc cagtttgcta   3660
gggaggtcgc agtacttggc cacagccatc tcgtgctgct cgacgtaggt ctctttgtcg   3720
gcctccttga ttctttccag tctgtggtcc acgaagtgga agccgggcat cttgaggttc   3780
ttagcgggtt tcttggatct gtatgtggtc ttgaaggagc agtgcaggta gcccccgccc   3840
acgagcttca gggccatctg gctgtggcct ctcaggccgc cgtcagcggg gtacagcatc   3900
```

-continued

```
tcggtgttgg cctcccagcc gcgtgttttc ttctgcatca cagggccgtt ggatgggaag   3960
ttcaccccgt tgatcttgac gttgtagatg atgcagccgt tctggaagct ggtgtcctgg   4020
gtagcggtca gcacgccccc gtcttcgtat gtggtgattc tctcccatgt gaagccctca   4080
gggaaggact gcttaaagaa gtcggggatg ccctgggtgt ggttgatgaa ggctttgctg   4140
ccgtacatga agctggtagc caggatgtcg aaggcgaagg ggagagggcc gccctcgacc   4200
accttgatct tcatggtctg ggtgccctcg tagggcttgc cttcgccctc ggatgtgcac   4260
ttgaagtggt ggttgttcac ggtgccctcc atgtacagct tcatgtgcat gttctccttg   4320
atcagctcgc tcatggtggc atatgataac ttcgtatagc atacattata cgaagttata   4380
ttaagggtta ttgaatatga tcggaagtca acgggtcgat ggtgatgctt ggctcgaata   4440
acttcgtata aagtatccta tacgaagtta tactttggcc gcggctcgag ggggttgggg   4500
ttgcgccttt tccaaggcag ccctgggttt gcgcagggac gcggctgctc tgggcgtggt   4560
tccgggaaac gcagcggcgc cgaccctggg tctcgcacat tcttcacgtc cgttcgcagc   4620
gtcacccgga tcttcgccgc taccettgtg ggcccccegg cgacgcttcc tgctccgccc   4680
ctaagtcggg aaggttcctt gcggttcgcg gcgtgccgga cgtgacaaac ggaagccgca   4740
cgtctcacta gtaccctcgc agacggacag cgccagggag caatggcagc gcgccgaccg   4800
cgatgggctg tggccaatag cggctgctca gcagggcgcg ccgagagcag cggccgggaa   4860
ggggcggtgc gggaggcggg gtgtggggcg gtagtgtggg ccctgttcct gcccgcgcgg   4920
tgttccgcat tctgcaagcc tccggagcgc acgtcggcag tcggctccct cgttgaccga   4980
atcaccgacc tctctcccca gggggatcca ccggtcgcca ccatggtgag caagggcgag   5040
gagctgttca ccggggtggt gcccatcctg gtcgagctgg acggcgacgt aaacggccac   5100
aagttcagcg tgtccggcga gggcgagggc gatgccacct acggcaagct gaccctgaag   5160
ttcatctgca ccaccggcaa gctgcccgtg ccctggccca ccctcgtgac caccctgacc   5220
tacggcgtgc agtgcttcag ccgctacccc gaccacatga agcagcacga cttcttcaag   5280
tccgccatgc ccgaaggcta cgtccaggag cgcaccatct tcttcaagga cgacggcaac   5340
tacaagaccc gcgccgaggt gaagttcgag ggcgacaccc tggtgaaccg catcgagctg   5400
aagggcatcg acttcaagga ggacggcaac atcctggggc acaagctgga gtacaactac   5460
aacagccaca acgtctatat catggccgac aagcagaaga acggcatcaa ggtgaacttc   5520
aagatccgcc acaacatcga ggacggcagc gtgcagctcg ccgaccacta ccagcagaac   5580
acccccatcg gcgacggccc cgtgctgctg cccgacaacc actacctgag cacccagtcc   5640
gccctgagca aagaccccaa cgagaagcgc gatcacatgg tcctgctgga gttcgtgacc   5700
gccgccggga tcactctcgg catggacgag ctgtacaagt aaagcggccg cgactctaga   5760
gtcgacctgc aggcatgcaa gcttgatatc aagcttatcg ataatcaacc tctggattac   5820
aaaatttgtg aaagattgac tggtattctt aactatgttg ctccttttac gctatgtgga   5880
tacgctgctt taatgccttt gtatcatgct attgcttccc gtatggcttt cattttctcc   5940
tccttgtata aatcctggtt gctgtctctt tatgaggagt tgtggcccgt tgtcaggcaa   6000
cgtggcgtgg tgtgcactgt gtttgctgac gcaacccccca ctggttgggg cattgccacc   6060
acctgtcagc tcctttccgg gactttcgct ttccccctcc ctattgccac ggcggaactc   6120
atcgccgcct gccttgcccg ctgctggaca ggggctcggc tgttgggcac tgacaattcc   6180
gtggtgttgt cggggaaatc atcgtccttt ccttggctgc tcgcctgtgt tgccacctgg   6240
```

-continued

```
attctgcgcg ggacgtcctt ctgctacgtc ccttcggccc tcaatccagc ggaccttcct   6300
tcccgcggcc tgctgccggc tctgcggcct cttccgcgtc ttcgccttcg ccctcagacg   6360
agtcggatct ccctttgggc cgcctccccg catcgatacc gtcgacctcg agttttataa   6420
aagaaaaggg gggactggaa gggatttatt acagtgcaag aagacataga atcttagaca   6480
tgtacttaga aaaggaagaa ggcatcatac cagattggca ggattacacc tcaggaccag   6540
gaattagata cccaaagaca tttggctggc tatggaaatt agtccctgta aatgtatcag   6600
atgaggcaca ggaggatgag aggcattatt taatgcagcc agctcaaact tccaagtggg   6660
atgacccttg ggagagaggtt ctagcgtgga agtttgatcc aactctagcc tacacttatg   6720
aggcatatgc tagataccca gaagagttgg aagcaagtca ggcctgtcag aactgcattt   6780
cgctctgtat tcagtcgctc tgcggagagg ctggcagatt gagccctggg aggttctctc   6840
cagcactagc aggtagagcc tgggtgttcc ctgctagact ctcaccagca cttggccagt   6900
gctgggcaga gtggctccac gcttgcttgc ttaaagacct cttcaataaa gctgccattt   6960
tagaagtaag ccagtgtgtg ttcccatctc tcctagtcgc cgcctggtca actcggtact   7020
cggtaataag aagaccctgg tctgttagga ccctttctgc tttgagaaac cgaagcagga   7080
aaatccctag catggtaccc agcttttgtt ccctttagtg agggttaatt ccgagcttgg   7140
cgtaatcatg gtcatagctg tttcctgtgt gaaattgtta tccgctcaca attccacaca   7200
acatacgagc cggaagcata aagtgtaaag cctggggtgc ctaatgagtg agctaactca   7260
cattaattgc gttgcgctca ctgcccgctt tccagtcggg aaacctgtcg tgccagctgc   7320
attaatgaat cggccaacgc gcggggagag gcggtttgcg tattgggcgc tcttccgctt   7380
cctcgctcac tgactcgctg cgctcggtcg ttcggctgcg gcgagcggta tcagctcact   7440
caaaggcggt aatacggtta tccacagaat caggggataa cgcaggaaag aacatgtgag   7500
caaaaggcca gcaaaaggcc aggaaccgta aaaaggccgc gttgctggcg tttttccata   7560
ggctccgccc ccctgacgag catcacaaaa atcgacgctc aagtcagagg tggcgaaacc   7620
cgacaggact ataaagatac caggcgtttc cccctggaag ctccctcgtg cgctctcctg   7680
ttccgaccct gccgcttacc ggatacctgt ccgcctttct cccttcggga agcgtggcgc   7740
tttctcatag ctcacgctgt aggtatctca gttcggtgta ggtcgttcgc tccaagctgg   7800
gctgtgtgca cgaacccccc gttcagcccg accgctgcgc cttatccggt aactatcgtc   7860
ttgagtccaa cccggtaaga cacgacttat cgccactggc agcagccact ggtaacagga   7920
ttagcagagc gaggtatgta ggcggtgcta cagagttctt gaagtggtgg cctaactacg   7980
gctacactag aaggacagta tttggtatct gcgctctgct gaagccagtt accttcggaa   8040
aaagagttgg tagctcttga tccggcaaac aaaccaccgc tggtagcggt ggtttttttg   8100
tttgcaagca gcagattacg cgcagaaaaa aaggatctca agaagatcct ttgatctttt   8160
ctacggggtc tgacgctcag tggaacgaaa actcacgtta agggattttg gtcatgagat   8220
tatcaaaaag gatcttcacc tagatccttt taaattaaaa atgaagtttt aaatcaatct   8280
aaagtatata tgagtaaact tggtctgaca gttaccaatg cttaatcagt gaggcaccta   8340
tctcagcgat ctgtctattt cgttcatcca tagttgcctg actccccgtc gtgtagataa   8400
ctacgatacg ggagggctta ccatctggcc ccagtgctgc aatgataccg cgagacccac   8460
gctcaccggc tccagattta tcagcaataa accagccagc cggaagggcc gagcgcagaa   8520
gtggtcctgc aactttatcc gcctccatcc agtctattaa ttgttgccgg gaagctagag   8580
taagtagttc gccagttaat agtttgcgca acgttgttgc cattgctaca ggcatcgtgg   8640
```

-continued tgtcacgctc gtcgtttggt atggcttcat tcagctccgg ttcccaacga tcaaggcgag 8700
ttacatgatc ccccatgttg tgcaaaaaag cggttagctc cttcggtcct ccgatcgttg 8760
tcagaagtaa gttggccgca gtgttatcac tcatggttat ggcagcactg cataattctc 8820
ttactgtcat gccatccgta agatgctttt ctgtgactgg tgagtactca accaagtcat 8880
tctgagaata gtgtatgcgg cgaccgagtt gctcttgccc ggcgtcaata cgggataata 8940
ccgcgccaca tagcagaact ttaaaagtgc tcatcattgg aaaacgttct tcggggcgaa 9000
aactctcaag gatcttaccg ctgttgagat ccagttcgat gtaacccact cgtgcaccca 9060
actgatcttc agcatctttt actttcacca gcgtttctgg gtgagcaaaa acaggaaggc 9120
aaaatgccgc aaaaaaggga ataagggcga cacggaaatg ttgaatactc atactcttcc 9180
tttttcaata ttattgaagc atttatcagg gttattgtct catgagcgga tacatatttg 9240
aatgtattta gaaaaataaa caaatagggg ttccgcgcac atttccccga aaagtgccac 9300
ctg 9303

<210> SEQ ID NO 8
<211> LENGTH: 720
<212> TYPE: DNA
<213> ORGANISM: Artificial Sequence
<220> FEATURE:
<223> OTHER INFORMATION: recombinant enhanced GFP

<400> SEQUENCE: 8
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaagtaa 720

<210> SEQ ID NO 9
<211> LENGTH: 696
<212> TYPE: DNA
<213> ORGANISM: Artificial Sequence
<220> FEATURE:
<223> OTHER INFORMATION: RFP

<400> SEQUENCE: 9
atgagcgagc tgatcaagga gaacatgcac atgaagctgt acatggaggg caccgtgaac 60
aaccaccact tcaagtgcac atccgagggc gaaggcaagc cctacgaggg cacccagacc 120
atgaagatca aggtggtcga gggcggccct ctccccttcg ccttcgacat cctggctacc 180
agcttcatgt acggcagcaa agccttcatc aaccacaccc agggcatccc cgacttcttt 240
aagcagtcct tccctgaggg cttcacatgg gagagaatca ccacatacga agacgggggc 300

-continued

```
gtgctgaccg ctacccagga caccagcttc cagaacggct gcatcatcta caacgtcaag    360

atcaacgggg tgaacttccc atccaacggc cctgtgatgc agaagaaaac acgcggctgg    420

gaggccaaca ccgagatgct gtaccccgct gacggcggcc tgagaggcca cagccagatg    480

gccctgaagc tcgtgggcgg gggctacctg cactgctcct tcaagaccac atacagatcc    540

aagaaacccg ctaagaacct caagatgccc ggcttccact tcgtggacca cagactggaa    600

agaatcaagg aggccgacaa agagacctac gtcgagcagc acgagatggc tgtggccaag    660

tactgcgacc tccctagcaa actggggcac agataa                              696
```

<210> SEQ ID NO 10
<211> LENGTH: 13978
<212> TYPE: DNA
<213> ORGANISM: Artificial Sequence
<220> FEATURE:
<223> OTHER INFORMATION: pBR HIV -NL4-3-Nef-IRES-Cre

<400> SEQUENCE: 10

```
gcgttggaag ggctaattca ctcccaaaga agacaagata tccttgatct gtggatctac     60

cacacacaag gctacttccc tgattggcag aactacacac cagggccagg ggtcagatat    120

ccactgacct ttggatggtg ctacaagcta gtaccagttg agccagataa ggtagaagag    180

gccaataaag gagagaacac cagcttgtta caccctgtga gcctgcatgg aatggatgac    240

cctgagagag aagtgttaga gtggaggttt gacagccgcc tagcatttca tcacgtggcc    300

cgagagctgc atccggagta ctacaaagac tgctgacatc gagctttcta caagggactt    360

tccgctgggg actttccagg gaggtgtggc ctgggcggga ctggggagtg gcgagccctc    420

agatgctaca tataagcagc tgctttttgc ctgtactggg tctctctggt tagaccagat    480

ctgagcctgg gagctctctg gctaactagg gaacccactg cttaagcctc aataaagctt    540

gccttgagtg ctcaaagtag tgtgtgcccg tctgttgtgt gactctggta actagagatc    600

cctcagaccc ttttagtcag tgtggaaaat ctctagcagt ggcgcccgaa cagggacttg    660

aaagcgaaag taaagccaga ggagatctct cgacgcagga ctcggcttgc tgaagcgcgc    720

acggcaagag gcgagggggcg gcgactggtg agtacgccaa aaattttgac tagcggaggc    780

tagaaggaga gagatgggtg cgagagcgtc ggtattaagc gggggagaat tagataaatg    840

ggaaaaaatt cggttaaggc cagggggaaa gaaacaatat aaactaaaac atatagtatg    900

ggcaagcagg gagctagaac gattcgcagt taatcctggc cttttagaga catcagaagg    960

ctgtagacaa atactgggac agctacaacc atcccttcag acaggatcag aagaacttag   1020

atcattatat aatacaatag cagtcctcta ttgtgtgcat caaaggatag atgtaaaaga   1080

caccaaggaa gccttagata agatagagga agagcaaaac aaaagtaaga aaaaggcaca   1140

gcaagcagca gctgacacag gaaacaacag ccaggtcagc caaaattacc ctatagtgca   1200

gaacctccag gggcaaatgg tacatcaggc catatcacct agaactttaa atgcatgggt   1260

aaaagtagta gaagagaagg ctttcagccc agaagtaata cccatgtttt cagcattatc   1320

agaaggagcc accccacaag atttaaatac catgctaaac acagtggggg gacatcaagc   1380

agccatgcaa atgttaaaag agaccatcaa tgaggaagct gcagaatggg atagattgca   1440

tccagtgcat gcagggccta ttgcaccagg ccagatgaga gaaccaaggg gaagtgacat   1500

agcaggaact actagtaccc ttcaggaaca aataggatgg atgacacata atccacctat   1560

cccagtagga gaaatctata aaagatggat aatcctggga ttaaataaaa tagtaagaat   1620

gtatagccct accagcattc tggacataag acaaggacca aaggaaccct ttagagacta   1680
```

-continued

```
tgtagaccga ttctataaaa ctctaagagc cgagcaagct tcacaagagg taaaaaattg   1740
gatgacagaa accttgttgg tccaaaatgc gaacccagat tgtaagacta ttttaaaagc   1800
attgggacca ggagcgacac tagaagaaat gatgacagca tgtcagggag tgggggggacc  1860
cggccataaa gcaagagttt tggctgaagc aatgagccaa gtaacaaatc cagctaccat   1920
aatgatacag aaaggcaatt ttaggaacca aagaaagact gttaagtgtt tcaattgtgg   1980
caaagaaggg cacatagcca aaaattgcag ggcccctagg aaaaagggct gttggaaatg   2040
tggaaaggaa ggacaccaaa tgaaagattg tactgagaga caggctaatt ttttagggaa   2100
gatctggcct tcccacaagg gaaggccagg gaattttctt cagagcagac cagagccaac   2160
agccccacca gaagagagct tcaggtttgg ggaagagaca acaactccct ctcagaagca   2220
ggagccgata gacaaggaac tgtatccttt agcttccctc agatcactct ttggcagcga   2280
cccctcgtca caataaagat aggggggcaa ttaaaggaag ctctattaga tacaggagca   2340
gatgatacag tattagaaga aatgaatttg ccaggaagat ggaaaccaaa aatgataggg   2400
ggaattggag gttttatcaa agtaggacag tatgatcaga tactcataga aatctgcgga   2460
cataaagcta taggtacagt attagtagga cctacacctg tcaacataat tggaagaaat   2520
ctgttgactc agattggctg cactttaaat tttcccatta gtcctattga gactgtacca   2580
gtaaaattaa agccaggaat ggatggccca aaagttaaac aatggccatt gacagaagaa   2640
aaaataaaag cattagtaga aatttgtaca gaaatggaaa aggaaggaaa aatttcaaaa   2700
attgggcctg aaaatccata caatactcca gtatttgcca taaagaaaaa agacagtact   2760
aaatggagaa aattagtaga tttcagagaa cttaataaga gaactcaaga tttctgggaa   2820
gttcaattag gaataccaca tcctgcaggg ttaaaacaga aaaaatcagt aacagtactg   2880
gatgtgggcg atgcatattt ttcagttccc ttagataaag acttcaggaa gtatactgca   2940
tttaccatac ctagtataaa caatgagaca ccagggatta gatatcagta caatgtgctt   3000
ccacagggat ggaaaggatc accagcaata ttccagtgta gcatgacaaa aatcttagag   3060
ccttttagaa aacaaaatcc agacatagtc atctatcaat acatggatga tttgtatgta   3120
ggatctgact tagaaatagg gcagcataga acaaaaatag aggaactgag acaacatctg   3180
ttgaggtggg gatttaccac accagacaaa aaacatcaga aagaacctcc attcctttgg   3240
atgggttatg aactccatcc tgataaatgg acagtacagc ctatagtgct gccagaaaag   3300
gacagctgga ctgtcaatga catacagaaa ttagtgggaa aattgaattg ggcaagtcag   3360
atttatgcag ggattaaagt aaggcaatta tgtaaacttc ttaggggaac caaagcacta   3420
acagaagtag taccactaac agaagaagca gagctagaac tggcagaaaa cagggagatt   3480
ctaaaagaac cggtacatgg agtgtattat gacccatcaa aagacttaat agcagaaata   3540
cagaagcagg ggcaaggcca atggacatat caaatttatc aagagccatt taaaaatctg   3600
aaaacaggaa aatatgcaag aatgaagggt gcccacacta atgatgtgaa acaattaaca   3660
gaggcagtac aaaaaatagc cacagaaagc atagtaatat ggggaaagac tcctaaattt   3720
aaattaccca tacaaaagga aacatgggaa gcatggtgga cagagtattg gcaagccacc   3780
tggattcctg agtgggagtt tgtcaatacc cctcccttag tgaagttatg gtaccagtta   3840
gagaaagaac ccataatagg agcagaaact ttctatgtag atggggcagc caatagggaa   3900
actaaattag gaaaagcagg atatgtaact gacagaggaa gacaaaaagt tgtcccccta   3960
acggacacaa caaatcagaa gactgagtta caagcaattc atctagcttt gcaggattcg   4020
```

-continued

```
ggattagaag taaacatagt gacagactca caatatgcat tgggaatcat tcaagcacaa   4080
ccagataaga gtgaatcaga gttagtcagt caaataatag agcagttaat aaaaaaggaa   4140
aaagtctacc tggcatgggt accagcacac aaaggaattg gaggaaatga acaagtagat   4200
aaattggtca gtgctggaat caggaaagta ctatttttag atggaataga taaggcccaa   4260
gaagaacatg agaaatatca cagtaattgg agagcaatgg ctagtgattt taacctacca   4320
cctgtagtag caaaagaaat agtagccagc tgtgataaat gtcagctaaa aggggaagcc   4380
atgcatggac aagtagactg tagcccagga atatggcagc tagattgtac acatttagaa   4440
ggaaaagtta tcttggtagc agttcatgta gccagtggat atatagaagc agaagtaatt   4500
ccagcagaga cagggcaaga aacagcatac ttcctcttaa aattagcagg aagatggcca   4560
gtaaaaacag tacatacaga caatggcagc aatttcacca gtactacagt taaggccgcc   4620
tgttggtggg cggggatcaa gcaggaattt ggcattccct acaatcccca aagtcaagga   4680
gtaatagaat ctatgaataa agaattaaag aaaattatag gacaggtaag agatcaggct   4740
gaacatctta agacagcagt acaaatggca gtattcatcc acaattttaa aagaaaaggg   4800
gggattgggg ggtacagtgc aggggaaaga atagtagaca taatagcaac agacatacaa   4860
actaaagaat tacaaaaaca aattacaaaa attcaaaatt ttcgggttta ttacagggac   4920
agcagagatc cagtttggaa aggaccagca aagctcctct ggaaaggtga aggggcagta   4980
gtaatacaag ataatagtga cataaaagta gtgccaagaa gaaaagcaaa gatcatcagg   5040
gattatggaa aacagatggc aggtgatgat tgtgtggcaa gtagacagga tgaggattaa   5100
cacatggaaa agattagtaa aacaccatat gtatatttca aggaaagcta aggactggtt   5160
ttatagacat cactatgaaa gtactaatcc aaaaataagt tcagaagtac acatcccact   5220
aggggatgct aaattagtaa taacaacata ttggggtctg catacaggag aaagagactg   5280
gcatttgggt cagggagtct ccatagaatg gaggaaaaag agatatagca cacaagtaga   5340
ccctgaccta gcagaccaac taattcatct gcactatttt gattgttttt cagaatctgc   5400
tataagaaat accatattag gacgtatagt tagtcctagg tgtgaatatc aagcaggaca   5460
taacaaggta ggatctctac agtacttggc actagcagca ttaataaaac caaaacagat   5520
aaagccacct ttgcctagtg ttaggaaact gacagaggac agatggaaca agccccagaa   5580
gaccaagggc cacagaggga gccatacaat gaatggacac tagagctttt agaggaactt   5640
aagagtgaag ctgttagaca ttttcctagg atatggctcc ataacttagg acaacatatc   5700
tatgaaactt acggggatac ttgggcagga gtggaagcca taataagaat tctgcaacaa   5760
ctgctgttta tccatttcag aattgggtgt cgacatagca gaataggcgt tactcgacag   5820
aggagagcaa gaaatggagc cagtagatcc tagactagag ccctggaagc atccaggaag   5880
tcagcctaaa actgcttgta ccaattgcta ttgtaaaaag tgttgctttc attgccaagt   5940
ttgtttcatg acaaaagcct taggcatctc ctatggcagg aagaagcgga gacagcgacg   6000
aagagctcat cagaacagtc agactcatca agcttctcta tcaaagcagt aagtagtaca   6060
tgtaatgcaa cctataatag tagcaatagt agcattagta gtagcaataa taatagcaat   6120
agttgtgtgg tccatagtaa tcatagaata taggaaaata ttaagacaaa gaaaaataga   6180
caggttaatt gatagactaa tagaaagagc agaagacagt ggcaatgaga gtgaaggaga   6240
agtatcagca cttgtggaga tgggggtgga aatggggcac catgctcctt gggatattga   6300
tgatctgtag tgctacagaa aaattgtggg tcacagtcta ttatggggta cctgtgtgga   6360
aggaagcaac caccactcta ttttgtgcat cagatgctaa agcatatgat acagaggtac   6420
```

```
ataatgtttg ggccacacat gcctgtgtac ccacagaccc caacccacaa gaagtagtat   6480
tggtaaatgt gacagaaaat tttaacatgt ggaaaaatga catggtagaa cagatgcatg   6540
aggatataat cagtttatgg gatcaaagcc taaagccatg tgtaaaatta accccactct   6600
gtgttagttt aaagtgcact gatttgaaga atgatactaa taccaatagt agtagcggga   6660
gaatgataat ggagaaagga gagataaaaa actgctcttt caatatcagc acaagcataa   6720
gagataaggt gcagaaagaa tatgcattct tttataaact tgatatagta ccaatagata   6780
ataccagcta taggttgata agttgtaaca cctcagtcat tacacaggcc tgtccaaagg   6840
tatcctttga gccaattccc atacattatt gtgccccggc tggttttgcg attctaaaat   6900
gtaataataa gacgttcaat ggaacaggac catgtacaaa tgtcagcaca gtacaatgta   6960
cacatggaat caggccagta gtatcaactc aactgctgtt aaatggcagt ctagcagaag   7020
aagatgtagt aattagatct gccaatttca cagacaatgc taaaaccata atagtacagc   7080
tgaacacatc tgtagaaatt aattgtacaa gacccaacaa caatacaaga aaaagtatcc   7140
gtatccagag gggaccaggg agagcatttg ttacaatagg aaaaatagga aatatgagac   7200
aagcacattg taacattagt agagcaaaat ggaatgccac tttaaaacag atagctagca   7260
aattaagaga acaatttgga aataataaaa caataatctt taagcaatcc tcaggagggg   7320
acccagaaat tgtaacgcac agttttaatt gtggagggga atttttctac tgtaattcaa   7380
cacaactgtt taatagtact tggtttaata gtacttggag tactgaaggg tcaaataaca   7440
ctgaaggaag tgacacaatc acactcccat gcagaataaa acaatttata aacatgtggc   7500
aggaagtagg aaaagcaatg tatgcccctc ccatcagtgg acaaattaga tgttcatcaa   7560
atattactgg gctgctatta acaagagatg gtggtaataa caacaatggg tccgagatct   7620
tcagacctgg aggaggcgat atgagggaca attggagaag tgaattatat aaatataaag   7680
tagtaaaaat tgaaccatta ggagtagcac ccaccaaggc aaagagaaga gtggtgcaga   7740
gagaaaaaag agcagtggga ataggagctt tgttccttgg gttcttggga gcagcaggaa   7800
gcactatggg cgcagcgtca atgacgctga cggtacaggc cagacaatta ttgtctgata   7860
tagtgcagca gcagaacaat ttgctgaggg ctattgaggc gcaacagcat ctgttgcaac   7920
tcacagtctg gggcatcaaa cagctccagg caagaatcct ggctgtggaa agatacctaa   7980
aggatcaaca gctcctgggg atttggggtt gctctggaaa actcatttgc accactgctg   8040
tgccttggaa tgctagttgg agtaataaat ctctggaaca gatttggaat aacatgacct   8100
ggatggagtg ggacagagaa attaacaatt acacaagctt aatacactcc ttaattgaag   8160
aatcgcaaaa ccagcaagaa aagaatgaac aagaattatt ggaattagat aaatgggcaa   8220
gtttgtggaa ttggtttaac ataacaaatt ggctgtggta tataaaatta ttcataatga   8280
tagtaggagg cttggtaggt ttaagaatag tttttgctgt actttctata gtgaatagag   8340
ttaggcaggg atattcacca ttatcgtttc agacccacct cccaatcccg aggggacccg   8400
acaggcccga aggaatagaa gaagaaggtg gagagagaga cagagacaga tccattcgat   8460
tagtgaacgg atccttagca cttatctggg acgatctgcg gagcctgtgc ctcttcagct   8520
accaccgctt gagagactta ctcttgattg taacgaggat tgtggaactt ctgggacgca   8580
gggggtggga agccctcaaa tattggtgga atctcctaca gtattggagt caggaactaa   8640
agaatagtgc tgttaacttg ctcaatgcca cagccatagc agtagctgag gggacagata   8700
gggttataga agtattacaa gcagcttata gagctattcg ccacatacct agaagaataa   8760
```

-continued

```
gacagggctt ggaaaggatt ttgctataag atgggtggca agtggtcaaa aagtagtgtg   8820
attggatggc ctgctgtaag ggaaagaatg agacgagctg agccagcagc agatggggtg   8880
ggagcagtat ctcgagacct agaaaaacat ggagcaatca caagtagcaa tacagcagct   8940
aacaatgctg cttgtgcctg gctagaagca caagaggagg aagaggtggg ttttccagtc   9000
acacctcagg tacctttaag accaatgact tacaaggcag ctgtagatct tagccacttt   9060
ttaaaagaaa aggggggact ggaagggcta attcactccc aaagaaggca agatatcctt   9120
gatctgtgga tctaccacac acaaggctac ttccctgatt ggcagaacta cacaccaggg   9180
ccaggggtca gatatccact gacctttgga tggtgctaca agctagtacc agctgagcca   9240
gataaggtag aagaggccaa taaaggagag aacaccagct tgttacaccc tgtgagcctg   9300
catggaatgg atgaccctga gagagaagtg ttagagtgga ggtttgacag ccgcctagca   9360
tttcatcacg tggcccgaga gctgcatccg gagtacttca agaactgctg aacgcgtcgg   9420
atcccggagt actacaaaga ctgctgacgc gaattccgcc cccccccta acgttactgg    9480
ccgaagccgc ttggaataag gccggtgtgc gtttgtctat atgttatttt ccaccatatt   9540
gccgtctttt ggcaatgtga gggcccggaa acctggccct gtcttcttga cgagcattcc   9600
taggggtctt tcccctctcg ccaaaggaat gcaaggtctg ttgaatgtcg tgaaggaagc   9660
agttcctctg gaagcttctt gaagacaaac aacgtctgta gcgacccttt gcaggcagcg   9720
gaaccccca cctggcgaca ggtgcctctg cggccaaaag ccacgtgtat aagatacacc    9780
tgcaaaggcg gcacaacccc agtgccacgt tgtgagttgg atagttgtgg aaagagtcaa   9840
atggctctcc tcaagcgtat tcaacaaggg gctgaaggat gcccagaagg taccccattg   9900
tatgggatct gatctggggc ctcggtgcac atgctttaca tgtgtttagt cgaggttaaa   9960
aaacgtctag gccccccgaa ccacggggac gtggttttcc tttgaaaaac acgatgataa  10020
taccatggtg cccaagaaga agaggaaagt ctccaacctg ctgactgtgc accaaaacct  10080
gcctgccctc cctgtggatg ccacctctga tgaagtcagg aagaacctga tggacatgtt  10140
cagggacagg caggccttct ctgaacacac ctggaagatg ctcctgtctg tgtgcagatc  10200
ctgggctgcc tggtgcaagc tgaacaacag gaaatggttc cctgctgaac ctgaggatgt  10260
gagggactac ctcctgtacc tgcaagccag aggcctggct gtgaagacca tccaacagca  10320
cctgggccag ctcaacatgc tgcacaggag atctggcctg cctcgccctt ctgactccaa  10380
tgctgtgtcc ctggtgatga ggagaatcag aaaggagaat gtggatgctg gggagagagc  10440
caagcaggcc ctggcctttg aacgcactga ctttgaccaa gtcagatccc tgatggagaa  10500
ctctgacaga tgccaggaca tcaggaacct ggccttcctg ggcattgcct acaacaccct  10560
gctgcgcatt gccgaaattg ccagaatcag agtgaaggac atctcccgca ccgatggtgg  10620
gagaatgctg atccacattg gcaggaccaa gaccctggtg tccacagctg gtgtggagaa  10680
ggccctgtcc ctgggggtta ccaagctggt ggagagatgg atctctgtgt ctggtgtggc  10740
tgatgacccc aacaactacc tgttctgccg ggtcagaaag aatggtgtgg ctgccccttc  10800
tgccacctcc caactgtcca cccgggccct ggaagggatc tttgaggcca cccaccgcct  10860
gatctatggt gccaaggatg actctgggca gagatacctg gcctggtctg gccactctgc  10920
cagagtgggt gctgccaggg acatggccag ggctggtgtg tccatccctg aaatcatgca  10980
ggctggtggc tggaccaatg tgaacattgt gatgaactac atcagaaacc tggactctga  11040
gactggggcc atggtgaggc tgctcgagga tggggactga cccgggtagc cactttttaa  11100
aagaaaaggg gggactggaa gggctaattc actcccaaag aagacaagat atcccatccg  11160
```

-continued

```
gagtacttca agaactgctg acatcgagct tgctacaagg gactttccgc tggggacttt  11220
ccagggaggc gtggcctggg cgggactggg gagtggcgag ccctcagatg ctgcatataa  11280
gcagctgctt tttgcctgta ctgggtctct ctggttagac cagatctgag cctgggagct  11340
ctctggctaa ctagggaacc cactgcttaa gcctcaataa agcttgcctt gagtgcttca  11400
agtagtgtgt gcccgtctgt tgtgtgactc tggtaactag agatccctca gaccctttta  11460
gtcagtgtgg aaaatctcta gcagttctag agcggccgct cgcgaattct tgaagacgaa  11520
agggcctcgt gatacgccta tttttatagg ttaatgtcat gataataatg gtttcttaga  11580
cgtcaggtgg cacttttcgg ggaaatgtgc gcggaacccc tatttgttta tttttctaaa  11640
tacattcaaa tatgtatccg ctcatgagac aataaccctg ataaatgctt caataatatt  11700
gaaaaaggaa gagtatgagt attcaacatt tccgtgtcgc ccttattccc ttttttgcgg  11760
cattttgcct tcctgttttt gctcacccag aaacgctggt gaaagtaaaa gatgctgaag  11820
atcagttggg tgcacgagtg ggttacatcg aactggatct caacagcggt aagatccttg  11880
agagttttcg ccccgaagaa cgttttccaa tgatgagcac ttttaaagtt ctgctatgtg  11940
gcgcggtatt atcccgtgtt gacgccgggc aagagcaact cggtcgccgc atacactatt  12000
ctcagaatga cttggttgag tactcaccag tcacagaaaa gcatcttacg gatggcatga  12060
cagtaagaga attatgcagt gctgccataa ccatgagtga taacactgcg gccaacttac  12120
ttctgacaac gatcggagga ccgaaggagc taaccgcttt tttgcacaac atgggggatc  12180
atgtaactcg ccttgatcgt tgggaaccgg agctgaatga agccatacca aacgacgagc  12240
gtgacaccac gatgcctgca gcaatggcaa caacgttgcg caaactatta actggcgaac  12300
tacttactct agcttcccgg caacaattaa tagactggat ggaggcggat aaagttgcag  12360
gaccacttct gcgctcggcc cttccggctg gctggtttat tgctgataaa tctggagccg  12420
gtgagcgtgg gtctcgcggt atcattgcag cactggggcc agatggtaag ccctcccgta  12480
tcgtagttat ctacacgacg gggagtcagg caactatgga tgaacgaaat agacagatcg  12540
ctgagatagg tgcctcactg attaagcatt ggtaactgtc agaccaagtt tactcatata  12600
tactttagat tgatttaaaa cttcattttt aatttaaaag gatctaggtg aagatccttt  12660
ttgataatct catgaccaaa atcccttaac gtgagttttc gttccactga gcgtcagacc  12720
ccgtagaaaa gatcaaagga tcttcttgag atcctttttt tctgcgcgta atctgctgct  12780
tgcaaacaaa aaaaccaccg ctaccagcgg tggtttgttt gccggatcaa gagctaccaa  12840
ctctttttcc gaaggtaact ggcttcagca gagcgcagat accaaatact gtccttctag  12900
tgtagccgta gttaggccac cacttcaaga actctgtagc accgcctaca tacctcgctc  12960
tgctaatcct gttaccagtg gctgctgcca gtggcgataa gtcgtgtctt accgggttgg  13020
actcaagacg atagttaccg gataaggcgc agcggtcggg ctgaacgggg ggttcgtgca  13080
cacagcccag cttggagcga acgacctaca ccgaactgag atacctacag cgtgagctat  13140
gagaaagcgc cacgcttccc gaagggagaa aggcggacag gtatccggta agcggcaggg  13200
tcggaacagg agagcgcacg agggagcttc caggggggaaa cgcctggtat ctttatagtc  13260
ctgtcgggtt tcgccacctc tgacttgagc gtcgattttt gtgatgctcg tcaggggggc  13320
ggagcctatg gaaaaacgcc agcaacgcgg cctttttacg gttcctggcc ttttgctggc  13380
cttttgctca catgttcttt cctgcgttat cccctgattc tgtggataac cgtattaccg  13440
cctttgagtg agctgatacc gctcgccgca gccgaacgac cgagcgcagc gagtcagtga  13500
```

gcgaggaagc ggaagagcgc ctgatgcggt attttctcct tacgcatctg tgcggtattt 13560
cacaccgcat atggtgcact ctcagtacaa tctgctctga tgccgcatag ttaagccagt 13620
atacactccg ctatcgctac gtgactgggt catggctgcg ccccgacacc cgccaacacc 13680
cgctgacgcg ccctgacggg cttgtctgct cccggcatcc gcttacagac aagctgtgac 13740
cgtctccggg agctgcatgt gtcagaggtt ttcaccgtca tcaccgaaac gcgcgaggca 13800
gatcccgcaa gaggcccggc agtaccggca taaccaagcc tatgcctaca gcatccaggg 13860
tgacggtgcc gaggatgacg atgagcgcat tgttagattt catacacggt gcctgactgc 13920
gttagcaatt taactgtgat aaactaccgc attaaagctt gtcgacagcg ctacgcgc 13978

<210> SEQ ID NO 11
<211> LENGTH: 13978
<212> TYPE: DNA
<213> ORGANISM: Artificial Sequence
<220> FEATURE:
<223> OTHER INFORMATION: pBR HIV NL4-3-Nef IRES-Cre

<400> SEQUENCE: 11
gcgttggaag ggctaattca ctcccaaaga agacaagata tccttgatct gtggatctac 60
cacacacaag gctacttccc tgattggcag aactacacac cagggccagg ggtcagatat 120
ccactgacct ttggatggtg ctacaagcta gtaccagttg agccagataa ggtagaagag 180
gccaataaag gagagaacac cagcttgtta caccctgtga gcctgcatgg aatggatgac 240
cctgagagag aagtgttaga gtggaggttt gacagccgcc tagcatttca tcacgtggcc 300
cgagagctgc atccggagta ctacaaagac tgctgacatc gagctttcta caagggactt 360
tccgctgggg actttccagg gaggtgtggc ctgggcggga ctggggagtg gcgagccctc 420
agatgctaca tataagcagc tgctttttgc ctgtactggg tctctctggt tagaccagat 480
ctgagcctgg gagctctctg gctaactagg gaacccactg cttaagcctc aataaagctt 540
gccttgagtg ctcaaagtag tgtgtgcccg tctgttgtgt gactctggta actagagatc 600
cctcagaccc ttttagtcag tgtggaaaat ctctagcagt ggcgcccgaa cagggacttg 660
aaagcgaaag taaagccaga ggagatctct cgacgcagga ctcggcttgc tgaagcgcgc 720
acggcaagag gcgaggggcg gcgactggtg agtacgccaa aaattttgac tagcggaggc 780
tagaaggaga gagatgggtg cgagagcgtc ggtattaagc gggggagaat tagataaatg 840
ggaaaaaatt cggttaaggc cagggggaaa gaaacaatat aaactaaaac atatagtatg 900
ggcaagcagg gagctagaac gattcgcagt taatcctggc cttttagaga catcagaagg 960
ctgtagacaa atactgggac agctacaacc atcccttcag acaggatcag aagaacttag 1020
atcattatat aatacaatag cagtcctcta ttgtgtgcat caaaggatag atgtaaaaga 1080
caccaaggaa gccttagata agatagagga agagcaaaac aaaagtaaga aaaaggcaca 1140
gcaagcagca gctgacacag gaaacaacag ccaggtcagc caaaattacc ctatagtgca 1200
gaacctccag gggcaaatgg tacatcaggc catatcacct agaactttaa atgcatgggt 1260
aaaagtagta gaagagaagg ctttcagccc agaagtaata cccatgtttt cagcattatc 1320
agaaggagcc accccacaag atttaaatac catgctaaac acagtggggg gacatcaagc 1380
agccatgcaa atgttaaaag agaccatcaa tgaggaagct gcagaatggg atagattgca 1440
tccagtgcat gcagggccta ttgcaccagg ccagatgaga gaaccaaggg gaagtgacat 1500
agcaggaact actagtaccc ttcaggaaca aataggatgg atgacacata atccacctat 1560
cccagtagga gaaatctata aaagatggat aatcctggga ttaaataaaa tagtaagaat 1620

```
gtatagccct accagcattc tggacataag acaaggacca aaggaaccct ttagagacta   1680
tgtagaccga ttctataaaa ctctaagagc cgagcaagct tcacaagagg taaaaaattg   1740
gatgacagaa accttgttgg tccaaaatgc gaacccagat tgtaagacta ttttaaaagc   1800
attgggacca ggagcgacac tagaagaaat gatgacagca tgtcagggag tgggggggacc   1860
cggccataaa gcaagagttt tggctgaagc aatgagccaa gtaacaaatc cagctaccat   1920
aatgatacag aaaggcaatt ttaggaacca aagaaagact gttaagtgtt tcaattgtgg   1980
caaagaaggg cacatagcca aaaattgcag ggcccctagg aaaaagggct gttggaaatg   2040
tggaaaggaa ggacaccaaa tgaaagattg tactgagaga caggctaatt ttttagggaa   2100
gatctggcct tcccacaagg gaaggccagg gaattttctt cagagcagac cagagccaac   2160
agccccacca gaagagagct tcaggtttgg ggaagagaca acaactccct ctcagaagca   2220
ggagccgata gacaaggaac tgtatccttt agcttccctc agatcactct ttggcagcga   2280
cccctcgtca caataaagat aggggggcaa ttaaaggaag ctctattaga tacaggagca   2340
gatgatacag tattagaaga aatgaatttg ccaggaagat ggaaaccaaa aatgataggg   2400
ggaattggag gttttatcaa agtaggacag tatgatcaga tactcataga aatctgcgga   2460
cataaagcta taggtacagt attagtagga cctacacctg tcaacataat tggaagaaat   2520
ctgttgactc agattggctg cactttaaat tttcccatta gtcctattga gactgtacca   2580
gtaaaattaa agccaggaat ggatggccca aaagttaaac aatggccatt gacagaagaa   2640
aaaataaaag cattagtaga aatttgtaca gaaatggaaa aggaaggaaa aatttcaaaa   2700
attgggcctg aaaatccata caatactcca gtatttgcca taaagaaaaa agacagtact   2760
aaatggagaa aattagtaga tttcagagaa cttaataaga gaactcaaga tttctgggaa   2820
gttcaattag gaataccaca tcctgcaggg ttaaaacaga aaaaatcagt aacagtactg   2880
gatgtgggcg atgcatattt ttcagttccc ttagataaag acttcaggaa gtatactgca   2940
tttaccatac ctagtataaa caatgagaca ccagggatta gatatcagta caatgtgctt   3000
ccacagggat ggaaaggatc accagcaata ttccagtgta gcatgacaaa aatcttagag   3060
ccttttagaa aacaaaatcc agacatagtc atctatcaat acatggatga tttgtatgta   3120
ggatctgact tagaaatagg gcagcataga acaaaaatag aggaactgag acaacatctg   3180
ttgaggtggg gatttaccac accagacaaa aaacatcaga aagaacctcc attcctttgg   3240
atgggttatg aactccatcc tgataaatgg acagtacagc ctatagtgct gccagaaaag   3300
gacagctgga ctgtcaatga catacagaaa ttagtgggaa aattgaattg ggcaagtcag   3360
atttatgcag ggattaaagt aaggcaatta tgtaaacttc ttaggggaac caaagcacta   3420
acagaagtag taccactaac agaagaagca gagctagaac tggcagaaaa cagggagatt   3480
ctaaaagaac cggtacatgg agtgtattat gacccatcaa aagacttaat agcagaaata   3540
cagaagcagg ggcaaggcca atggacatat caaatttatc aagagccatt taaaaatctg   3600
aaaacaggaa aatatgcaag aatgaagggt gcccacacta atgatgtgaa acaattaaca   3660
gaggcagtac aaaaaatagc cacagaaagc atagtaatat ggggaaagac tcctaaattt   3720
aaattaccca tacaaaagga aacatgggaa gcatggtgga cagagtattg gcaagccacc   3780
tggattcctg agtgggagtt tgtcaatacc cctcccttag tgaagttatg gtaccagtta   3840
gagaaagaac ccataatagg agcagaaact ttctatgtag atggggcagc caatagggaa   3900
actaaattag gaaaagcagg atatgtaact gacagaggaa gacaaaaagt tgtcccccta   3960
```

-continued

```
acggacacaa caaatcagaa gactgagtta caagcaattc atctagcttt gcaggattcg   4020
ggattagaag taaacatagt gacagactca caatatgcat tgggaatcat tcaagcacaa   4080
ccagataaga gtgaatcaga gttagtcagt caaataatag agcagttaat aaaaaaggaa   4140
aaagtctacc tggcatgggt accagcacac aaaggaattg gaggaaatga acaagtagat   4200
aaattggtca gtgctggaat caggaaagta ctatttttag atggaataga taaggcccaa   4260
gaagaacatg agaaatatca cagtaattgg agagcaatgg ctagtgattt taacctacca   4320
cctgtagtag caaaagaaat agtagccagc tgtgataaat gtcagctaaa aggggaagcc   4380
atgcatggac aagtagactg tagcccagga atatggcagc tagattgtac acatttagaa   4440
ggaaaagtta tcttggtagc agttcatgta gccagtggat atatagaagc agaagtaatt   4500
ccagcagaga cagggcaaga aacagcatac ttcctcttaa aattagcagg aagatggcca   4560
gtaaaaacag tacatacaga caatggcagc aatttcacca gtactacagt taaggccgcc   4620
tgttggtggg cggggatcaa gcaggaattt ggcattccct acaatcccca aagtcaagga   4680
gtaatagaat ctatgaataa agaattaaag aaaattatag gacaggtaag agatcaggct   4740
gaacatctta agacagcagt acaaatggca gtattcatcc acaattttaa aagaaaaggg   4800
gggattgggg ggtacagtgc aggggaaaga atagtagaca taatagcaac agacatacaa   4860
actaaagaat tacaaaaaca aattacaaaa attcaaaatt ttcgggttta ttacagggac   4920
agcagagatc cagtttggaa aggaccagca aagctcctct ggaaaggtga aggggcagta   4980
gtaatacaag ataatagtga cataaaagta gtgccaagaa gaaaagcaaa gatcatcagg   5040
gattatggaa aacagatggc aggtgatgat tgtgtggcaa gtagacagga tgaggattaa   5100
cacatggaaa agattagtaa aacaccatat gtatatttca aggaaagcta aggactggtt   5160
ttatagacat cactatgaaa gtactaatcc aaaaataagt tcagaagtac acatcccact   5220
aggggatgct aaattagtaa taacaacata ttggggtctg catacaggag aaagagactg   5280
gcatttgggt cagggagtct ccatagaatg gaggaaaaag agatatagca cacaagtaga   5340
ccctgaccta gcagaccaac taattcatct gcactatttt gattgttttt cagaatctgc   5400
tataagaaat accatattag gacgtatagt tagtcctagg tgtgaatatc aagcaggaca   5460
taacaaggta ggatctctac agtacttggc actagcagca ttaataaaac caaaacagat   5520
aaagccacct ttgcctagtg ttaggaaact gacagaggac agatggaaca agccccagaa   5580
gaccaagggc cacagaggga gccatacaat gaatggacac tagagctttt agaggaactt   5640
aagagtgaag ctgttagaca ttttcctagg atatggctcc ataacttagg acaacatatc   5700
tatgaaactt acggggatac ttgggcagga gtggaagcca taataagaat tctgcaacaa   5760
ctgctgttta tccatttcag aattgggtgt cgacatagca gaataggcgt tactcgacag   5820
aggagagcaa gaaatggagc cagtagatcc tagactagag ccctggaagc atccaggaag   5880
tcagcctaaa actgcttgta ccaattgcta ttgtaaaaag tgttgctttc attgccaagt   5940
ttgtttcatg acaaaagcct taggcatctc ctatggcagg aagaagcgga gacagcgacg   6000
aagagctcat cagaacagtc agactcatca agcttctcta tcaaagcagt aagtagtaca   6060
tgtaatgcaa cctataatag tagcaatagt agcattagta gtagcaataa taatagcaat   6120
agttgtgtgg tccatagtaa tcatagaata taggaaaata ttaagacaaa gaaaaataga   6180
caggttaatt gatagactaa tagaaagagc agaagacagt ggcaatgaga gtgaaggaga   6240
agtatcagca cttgtggaga tgggggtgga aatggggcac catgctcctt gggatattga   6300
tgatctgtag tgctacagaa aaattgtggg tcacagtcta ttatggggta cctgtgtgga   6360
```

```
aggaagcaac caccactcta ttttgtgcat cagatgctaa agcatatgat acagaggtac   6420
ataatgtttg ggccacacat gcctgtgtac ccacagaccc caacccacaa gaagtagtat   6480
tggtaaatgt gacagaaaat tttaacatgt ggaaaaatga catggtagaa cagatgcatg   6540
aggatataat cagtttatgg gatcaaagcc taaagccatg tgtaaaatta accccactct   6600
gtgttagttt aaagtgcact gatttgaaga atgatactaa taccaatagt agtagcggga   6660
gaatgataat ggagaaagga gagataaaaa actgctcttt caatatcagc acaagcataa   6720
gagataaggt gcagaaagaa tatgcattct tttataaact tgatatagta ccaatagata   6780
ataccagcta taggttgata agttgtaaca cctcagtcat tacacaggcc tgtccaaagg   6840
tatcctttga gccaattccc atacattatt gtgccccggc tggttttgcg attctaaaat   6900
gtaataataa gacgttcaat ggaacaggac catgtacaaa tgtcagcaca gtacaatgta   6960
cacatggaat caggccagta gtatcaactc aactgctgtt aaatggcagt ctagcagaag   7020
aagatgtagt aattagatct gccaatttca cagacaatgc taaaaccata atagtacagc   7080
tgaacacatc tgtagaaatt aattgtacaa gacccaacaa caatacaaga aaaagtatcc   7140
gtatccagag gggaccaggg agagcatttg ttacaatagg aaaaatagga aatatgagac   7200
aagcacattg taacattagt agagcaaaat ggaatgccac tttaaaacag atagctagca   7260
aattaagaga acaatttgga aataataaaa caataatctt taagcaatcc tcaggagggg   7320
acccagaaat tgtaacgcac agttttaatt gtggaggggga atttttctac tgtaattcaa   7380
cacaactgtt taatagtact tggtttaata gtacttggag tactgaaggg tcaaataaca   7440
ctgaaggaag tgacacaatc acactcccat gcagaataaa acaatttata aacatgtggc   7500
aggaagtagg aaaagcaatg tatgcccctc ccatcagtgg acaaattaga tgttcatcaa   7560
atattactgg gctgctatta acaagagatg gtggtaataa caacaatggg tccgagatct   7620
tcagacctgg aggaggcgat atgagggaca attggagaag tgaattatat aaatataaag   7680
tagtaaaaat tgaaccatta ggagtagcac ccaccaaggc aaagagaaga gtggtgcaga   7740
gagaaaaaag agcagtggga ataggagctt tgttccttgg gttcttggga gcagcaggaa   7800
gcactatggg cgcagcgtca atgacgctga cggtacaggc cagacaatta ttgtctgata   7860
tagtgcagca gcagaacaat ttgctgaggg ctattgaggc gcaacagcat ctgttgcaac   7920
tcacagtctg gggcatcaaa cagctccagg caagaatcct ggctgtggaa agatacctaa   7980
aggatcaaca gctcctgggg atttggggtt gctctggaaa actcatttgc accactgctg   8040
tgccttggaa tgctagttgg agtaataaat ctctggaaca gatttggaat aacatgacct   8100
ggatggagtg ggacagagaa attaacaatt acacaagctt aatacactcc ttaattgaag   8160
aatcgcaaaa ccagcaagaa aagaatgaac aagaattatt ggaattagat aaatgggcaa   8220
gtttgtggaa ttggtttaac ataacaaatt ggctgtggta tataaaatta ttcataatga   8280
tagtaggagg cttggtaggt ttaagaatag tttttgctgt actttctata gtgaatagag   8340
ttaggcaggg atattcacca ttatcgtttc agacccacct cccaatcccg aggggacccg   8400
acaggcccga aggaatagaa gaagaaggtg gagagagaga cagagacaga tccattcgat   8460
tagtgaacgg atccttagca cttatctggg acgatctgcg gagcctgtgc ctcttcagct   8520
accaccgctt gagagactta ctcttgattg taacgaggat tgtggaactt ctgggacgca   8580
gggggtggga agccctcaaa tattggtgga atctcctaca gtattggagt caggaactaa   8640
agaatagtgc tgttaacttg ctcaatgcca cagccatagc agtagctgag gggacagata   8700
```

-continued

```
gggttataga agtattacaa gcagcttata gagctattcg ccacatacct agaagaataa   8760
gacagggctt ggaaaggatt ttgctataag atgggtggca agtggtcaaa aagtagtgtg   8820
attggatggc ctgctgtaag ggaaagaatg agacgagctg agccagcagc agatggggtg   8880
ggagcagtat ctcgagacct agaaaaacat ggagcaatca caagtagcaa tacagcagct   8940
aacaatgctg cttgtgcctg gctagaagca caagaggagg aagaggtggg ttttccagtc   9000
acacctcagg tacctttaag accaatgact tacaaggcag ctgtagatct gagccatttc   9060
ctgaaggaga agggaggcct tgagggcctg attcacagcc agcggcgcca agacatcctt   9120
gacttgtgga tttaccatac acaggggtac ttccccgact ggcagaacta tacaccagga   9180
cccggagtga gataccccct gaccttcgga tggtgttaca aactggttcc agtggagcct   9240
gataaggtcg aagaggcaaa caaaggcgag aatacatctt tgctgcatcc tgtgtcactg   9300
cacgggatgg acgaccctga gcgggaggtg cttgagtgga ggttcgactc tcgactggcc   9360
tttcaccacg tagcaaggga gctgcaccct gagtatttta aaaattgttg aacgcgtcgg   9420
atcccggagt actacaaaga ctgctgacgc gaattccgcc ccccccccta acgttactgg   9480
ccgaagccgc ttggaataag gccggtgtgc gtttgtctat atgttatttt ccaccatatt   9540
gccgtctttt ggcaatgtga gggcccggaa acctggccct gtcttcttga cgagcattcc   9600
taggggtctt tcccctctcg ccaaaggaat gcaaggtctg ttgaatgtcg tgaaggaagc   9660
agttcctctg gaagcttctt gaagacaaac aacgtctgta gcgacccttt gcaggcagcg   9720
gaacccccca cctggcgaca ggtgcctctg cggccaaaag ccacgtgtat aagatacacc   9780
tgcaaaggcg gcacaacccc agtgccacgt tgtgagttgg atagttgtgg aaagagtcaa   9840
atggctctcc tcaagcgtat tcaacaaggg gctgaaggat gcccagaagg taccccattg   9900
tatgggatct gatctggggc ctcggtgcac atgctttaca tgtgtttagt cgaggttaaa   9960
aaacgtctag gccccccgaa ccacggggac gtggttttcc tttgaaaaac acgatgataa  10020
taccatggtg cccaagaaga agaggaaagt ctccaacctg ctgactgtgc accaaaacct  10080
gcctgccctc cctgtggatg ccacctctga tgaagtcagg aagaacctga tggacatgtt  10140
cagggacagg caggccttct ctgaacacac ctggaagatg ctcctgtctg tgtgcagatc  10200
ctgggctgcc tggtgcaagc tgaacaacag gaaatggttc cctgctgaac ctgaggatgt  10260
gagggactac ctcctgtacc tgcaagccag aggcctggct gtgaagacca tccaacagca  10320
cctgggccag ctcaacatgc tgcacaggag atctggcctg cctcgccctt ctgactccaa  10380
tgctgtgtcc ctggtgatga ggagaatcag aaaggagaat gtggatgctg ggagagagagc  10440
caagcaggcc ctggcctttg aacgcactga ctttgaccaa gtcagatccc tgatggagaa  10500
ctctgacaga tgccaggaca tcaggaacct ggccttcctg ggcattgcct acaacaccct  10560
gctgcgcatt gccgaaattg ccagaatcag agtgaaggac atctcccgca ccgatggtgg  10620
gagaatgctg atccacattg gcaggaccaa gaccctggtg tccacagctg gtgtggagaa  10680
ggccctgtcc ctgggggtta ccaagctggt ggagagatgg atctctgtgt ctggtgtggc  10740
tgatgacccc aacaactacc tgttctgccg ggtcagaaag aatggtgtgg ctgccccttc  10800
tgccacctcc caactgtcca cccgggccct ggaagggatc tttgaggcca cccaccgcct  10860
gatctatggt gccaaggatg actctgggca gagatacctg gcctggtctg gccactctgc  10920
cagagtgggt gctgccaggg acatggccag ggctggtgtg tccatccctg aaatcatgca  10980
ggctggtggc tggaccaatg tgaacattgt gatgaactac atcagaaacc tggactctga  11040
gactggggcc atggtgaggc tgctcgagga tggggactga cccgggtagc cactttttaa  11100
```

-continued aagaaaaggg gggactggaa gggctaattc actcccaaag aagacaagat atcccatccg 11160
gagtacttca agaactgctg acatcgagct tgctacaagg gactttccgc tggggacttt 11220
ccagggaggc gtggcctggg cgggactggg gagtggcgag ccctcagatg ctgcatataa 11280
gcagctgctt tttgcctgta ctgggtctct ctggttagac cagatctgag cctgggagct 11340
ctctggctaa ctagggaacc cactgcttaa gcctcaataa agcttgcctt gagtgcttca 11400
agtagtgtgt gcccgtctgt tgtgtgactc tggtaactag agatccctca gaccctttta 11460
gtcagtgtgg aaaatctcta gcagttctag agcggccgct cgcgaattct tgaagacgaa 11520
agggcctcgt gatacgccta tttttatagg ttaatgtcat gataataatg gtttcttaga 11580
cgtcaggtgg cacttttcgg ggaaatgtgc gcggaacccc tatttgttta tttttctaaa 11640
tacattcaaa tatgtatccg ctcatgagac aataaccctg ataaatgctt caataatatt 11700
gaaaaaggaa gagtatgagt attcaacatt tccgtgtcgc ccttattccc ttttttgcgg 11760
cattttgcct tcctgttttt gctcacccag aaacgctggt gaaagtaaaa gatgctgaag 11820
atcagttggg tgcacgagtg ggttacatcg aactggatct caacagcggt aagatccttg 11880
agagttttcg ccccgaagaa cgttttccaa tgatgagcac ttttaaagtt ctgctatgtg 11940
gcgcggtatt atcccgtgtt gacgccgggc aagagcaact cggtcgccgc atacactatt 12000
ctcagaatga cttggttgag tactcaccag tcacagaaaa gcatcttacg gatggcatga 12060
cagtaagaga attatgcagt gctgccataa ccatgagtga taacactgcg gccaacttac 12120
ttctgacaac gatcggagga ccgaaggagc taaccgcttt tttgcacaac atgggggatc 12180
atgtaactcg ccttgatcgt tgggaaccgg agctgaatga agccatacca aacgacgagc 12240
gtgacaccac gatgcctgca gcaatggcaa caacgttgcg caaactatta actggcgaac 12300
tacttactct agcttcccgg caacaattaa tagactggat ggaggcggat aaagttgcag 12360
gaccacttct gcgctcggcc cttccggctg gctggtttat tgctgataaa tctggagccg 12420
gtgagcgtgg gtctcgcggt atcattgcag cactggggcc agatggtaag ccctcccgta 12480
tcgtagttat ctacacgacg gggagtcagg caactatgga tgaacgaaat agacagatcg 12540
ctgagatagg tgcctcactg attaagcatt ggtaactgtc agaccaagtt tactcatata 12600
tactttagat tgatttaaaa cttcattttt aatttaaaag gatctaggtg aagatccttt 12660
ttgataatct catgaccaaa atcccttaac gtgagttttc gttccactga gcgtcagacc 12720
ccgtagaaaa gatcaaagga tcttcttgag atcctttttt tctgcgcgta atctgctgct 12780
tgcaaacaaa aaaaccaccg ctaccagcgg tggtttgttt gccggatcaa gagctaccaa 12840
ctctttttcc gaaggtaact ggcttcagca gagcgcagat accaaatact gtccttctag 12900
tgtagccgta gttaggccac cacttcaaga actctgtagc accgcctaca tacctcgctc 12960
tgctaatcct gttaccagtg gctgctgcca gtggcgataa gtcgtgtctt accgggttgg 13020
actcaagacg atagttaccg gataaggcgc agcggtcggg ctgaacgggg ggttcgtgca 13080
cacagcccag cttggagcga acgacctaca ccgaactgag atacctacag cgtgagctat 13140
gagaaagcgc cacgcttccc gaagggagaa aggcggacag gtatccggta agcggcaggg 13200
tcggaacagg agagcgcacg agggagcttc caggggggaaa cgcctggtat ctttatagtc 13260
ctgtcgggtt tcgccacctc tgacttgagc gtcgattttt gtgatgctcg tcaggggggc 13320
ggagcctatg gaaaaacgcc agcaacgcgg cctttttacg gttcctggcc ttttgctggc 13380
cttttgctca catgttcttt cctgcgttat cccctgattc tgtggataac cgtattaccg 13440

```
cctttgagtg agctgatacc gctcgccgca gccgaacgac cgagcgcagc gagtcagtga  13500
gcgaggaagc ggaagagcgc ctgatgcggt attttctcct tacgcatctg tgcggtattt  13560
cacaccgcat atggtgcact ctcagtacaa tctgctctga tgccgcatag ttaagccagt  13620
atacactccg ctatcgctac gtgactgggt catggctgcg ccccgacacc cgccaacacc  13680
cgctgacgcg ccctgacggg cttgtctgct cccggcatcc gcttacagac aagctgtgac  13740
cgtctccggg agctgcatgt gtcagaggtt ttcaccgtca tcaccgaaac gcgcgaggca  13800
gatcccgcaa gaggcccggc agtaccggca taaccaagcc tatgcctaca gcatccaggg  13860
tgacggtgcc gaggatgacg atgagcgcat tgttagattt catacacggt gcctgactgc  13920
gttagcaatt taactgtgat aaactaccgc attaaagctt gtcgacagcg ctacgcgc    13978
```

<210> SEQ ID NO 12
<211> LENGTH: 14057
<212> TYPE: DNA
<213> ORGANISM: Artificial Sequence
<220> FEATURE:
<223> OTHER INFORMATION: pBR-HIV NL4-3-Nef-CMV-Cre

<400> SEQUENCE: 12

```
gcgttggaag ggctaattca ctcccaaaga agacaagata tccttgatct gtggatctac     60
cacacacaag gctacttccc tgattggcag aactacacac cagggccagg ggtcagatat    120
ccactgacct ttggatggtg ctacaagcta gtaccagttg agccagataa ggtagaagag    180
gccaataaag gagagaacac cagcttgtta caccctgtga gcctgcatgg aatggatgac    240
cctgagagag aagtgttaga gtggaggttt gacagccgcc tagcatttca tcacgtggcc    300
cgagagctgc atccggagta ctacaaagac tgctgacatc gagctttcta caagggactt    360
tccgctgggg actttccagg gaggtgtggc ctgggcggga ctggggagtg gcgagccctc    420
agatgctaca tataagcagc tgctttttgc ctgtactggg tctctctggt tagaccagat    480
ctgagcctgg gagctctctg gctaactagg gaacccactg cttaagcctc aataaagctt    540
gccttgagtg ctcaaagtag tgtgtgcccg tctgttgtgt gactctggta actagagatc    600
cctcagaccc ttttagtcag tgtggaaaat ctctagcagt ggcgcccgaa cagggacttg    660
aaagcgaaag taaagccaga ggagatctct cgacgcagga ctcggcttgc tgaagcgcgc    720
acggcaagag gcgagggggcg gcgactggtg agtacgccaa aaattttgac tagcggaggc    780
tagaaggaga gagatgggtg cgagagcgtc ggtattaagc gggggagaat tagataaatg    840
ggaaaaaatt cggttaaggc cagggggaaa gaaacaatat aaactaaaac atatagtatg    900
ggcaagcagg gagctagaac gattcgcagt taatcctggc cttttagaga catcagaagg    960
ctgtagacaa atactgggac agctacaacc atcccttcag acaggatcag aagaacttag   1020
atcattatat aatacaatag cagtcctcta ttgtgtgcat caaaggatag atgtaaaaga   1080
caccaaggaa gccttagata agatagagga agagcaaaac aaaagtaaga aaaaggcaca   1140
gcaagcagca gctgacacag gaaacaacag ccaggtcagc caaaattacc ctatagtgca   1200
gaacctccag gggcaaatgg tacatcaggc catatcacct agaactttaa atgcatgggt   1260
aaaagtagta gaagagaagg ctttcagccc agaagtaata cccatgtttt cagcattatc   1320
agaaggagcc accccacaag atttaaatac catgctaaac acagtggggg gacatcaagc   1380
agccatgcaa atgttaaaag agaccatcaa tgaggaagct gcagaatggg atagattgca   1440
tccagtgcat gcagggccta ttgcaccagg ccagatgaga gaaccaaggg gaagtgacat   1500
agcaggaact actagtaccc ttcaggaaca aataggatgg atgacacata atccacctat   1560
```

-continued

```
cccagtagga gaaatctata aaagatggat aatcctggga ttaaataaaa tagtaagaat   1620
gtatagccct accagcattc tggacataag acaaggacca aaggaaccct ttagagacta   1680
tgtagaccga ttctataaaa ctctaagagc cgagcaagct tcacaagagg taaaaaattg   1740
gatgacagaa accttgttgg tccaaaatgc gaacccagat tgtaagacta ttttaaaagc   1800
attgggacca ggagcgacac tagaagaaat gatgacagca tgtcagggag tgggggggacc   1860
cggccataaa gcaagagttt tggctgaagc aatgagccaa gtaacaaatc cagctaccat   1920
aatgatacag aaaggcaatt ttaggaacca aagaaagact gttaagtgtt tcaattgtgg   1980
caaagaaggg cacatagcca aaaattgcag ggcccctagg aaaaagggct gttggaaatg   2040
tggaaaggaa ggacaccaaa tgaaagattg tactgagaga caggctaatt ttttagggaa   2100
gatctggcct tcccacaagg gaaggccagg gaattttctt cagagcagac cagagccaac   2160
agccccacca gaagagagct tcaggtttgg ggaagagaca acaactccct ctcagaagca   2220
ggagccgata gacaaggaac tgtatccttt agcttccctc agatcactct ttggcagcga   2280
cccctcgtca caataaagat aggggggcaa ttaaaggaag ctctattaga tacaggagca   2340
gatgatacag tattagaaga aatgaatttg ccaggaagat ggaaaccaaa aatgataggg   2400
ggaattggag gttttatcaa agtaggacag tatgatcaga tactcataga aatctgcgga   2460
cataaagcta taggtacagt attagtagga cctacacctg tcaacataat tggaagaaat   2520
ctgttgactc agattggctg cactttaaat tttcccatta gtcctattga gactgtacca   2580
gtaaaattaa agccaggaat ggatggccca aaagttaaac aatggccatt gacagaagaa   2640
aaaataaaag cattagtaga aatttgtaca gaaatggaaa aggaaggaaa aatttcaaaa   2700
attgggcctg aaaatccata caatactcca gtatttgcca taaagaaaaa agacagtact   2760
aaatggagaa aattagtaga tttcagagaa cttaataaga gaactcaaga tttctgggaa   2820
gttcaattag gaataccaca tcctgcaggg ttaaaacaga aaaaatcagt aacagtactg   2880
gatgtgggcg atgcatattt ttcagttccc ttagataaag acttcaggaa gtatactgca   2940
tttaccatac ctagtataaa caatgagaca ccagggatta gatatcagta caatgtgctt   3000
ccacagggat ggaaaggatc accagcaata ttccagtgta gcatgacaaa aatcttagag   3060
ccttttagaa aacaaaatcc agacatagtc atctatcaat acatggatga tttgtatgta   3120
ggatctgact tagaaatagg gcagcataga acaaaaatag aggaactgag acaacatctg   3180
ttgaggtggg gatttaccac accagacaaa aaacatcaga aagaacctcc attcctttgg   3240
atgggttatg aactccatcc tgataaatgg acagtacagc ctatagtgct gccagaaaag   3300
gacagctgga ctgtcaatga catacagaaa ttagtgggaa aattgaattg ggcaagtcag   3360
atttatgcag ggattaaagt aaggcaatta tgtaaacttc ttaggggaac caaagcacta   3420
acagaagtag taccactaac agaagaagca gagctagaac tggcagaaaa cagggagatt   3480
ctaaaagaac cggtacatgg agtgtattat gacccatcaa aagacttaat agcagaaata   3540
cagaagcagg ggcaaggcca atggacatat caaatttatc aagagccatt taaaaatctg   3600
aaaacaggaa aatatgcaag aatgaagggt gcccacacta atgatgtgaa acaattaaca   3660
gaggcagtac aaaaaatagc cacagaaagc atagtaatat ggggaaagac tcctaaattt   3720
aaattaccca tacaaaagga aacatgggaa gcatggtgga cagagtattg gcaagccacc   3780
tggattcctg agtgggagtt tgtcaatacc cctcccttag tgaagttatg gtaccagtta   3840
gagaaagaac ccataatagg agcagaaact ttctatgtag atggggcagc caatagggaa   3900
```

-continued

```
actaaattag gaaaagcagg atatgtaact gacagaggaa gacaaaaagt tgtcccccta   3960
acggacacaa caaatcagaa gactgagtta caagcaattc atctagcttt gcaggattcg   4020
ggattagaag taaacatagt gacagactca caatatgcat tgggaatcat tcaagcacaa   4080
ccagataaga gtgaatcaga gttagtcagt caaataatag agcagttaat aaaaaaggaa   4140
aaagtctacc tggcatgggt accagcacac aaaggaattg gaggaaatga acaagtagat   4200
aaattggtca gtgctggaat caggaaagta ctatttttag atggaataga taaggcccaa   4260
gaagaacatg agaaatatca cagtaattgg agagcaatgg ctagtgattt taacctacca   4320
cctgtagtag caaaagaaat agtagccagc tgtgataaat gtcagctaaa aggggaagcc   4380
atgcatggac aagtagactg tagcccagga atatggcagc tagattgtac acatttagaa   4440
ggaaaagtta tcttggtagc agttcatgta gccagtggat atatagaagc agaagtaatt   4500
ccagcagaga cagggcaaga aacagcatac ttcctcttaa aattagcagg aagatggcca   4560
gtaaaaacag tacatacaga caatggcagc aatttcacca gtactacagt taaggccgcc   4620
tgttggtggg cggggatcaa gcaggaattt ggcattccct acaatcccca aagtcaagga   4680
gtaatagaat ctatgaataa agaattaaag aaaattatag gacaggtaag agatcaggct   4740
gaacatctta agacagcagt acaaatggca gtattcatcc acaattttaa aagaaaaggg   4800
gggattgggg ggtacagtgc aggggaaaga atagtagaca taatagcaac agacatacaa   4860
actaaagaat tacaaaaaca aattacaaaa attcaaaatt ttcgggttta ttacagggac   4920
agcagagatc cagtttggaa aggaccagca aagctcctct ggaaaggtga aggggcagta   4980
gtaatacaag ataatagtga cataaaagta gtgccaagaa gaaaagcaaa gatcatcagg   5040
gattatggaa aacagatggc aggtgatgat tgtgtggcaa gtagacagga tgaggattaa   5100
cacatggaaa agattagtaa aacaccatat gtatatttca aggaaagcta aggactggtt   5160
ttatagacat cactatgaaa gtactaatcc aaaaataagt tcagaagtac acatcccact   5220
aggggatgct aaattagtaa taacaacata ttggggtctg catacaggag aaagagactg   5280
gcatttgggt cagggagtct ccatagaatg gaggaaaaag agatatagca cacaagtaga   5340
ccctgaccta gcagaccaac taattcatct gcactatttt gattgttttt cagaatctgc   5400
tataagaaat accatattag gacgtatagt tagtcctagg tgtgaatatc aagcaggaca   5460
taacaaggta ggatctctac agtacttggc actagcagca ttaataaaac caaaacagat   5520
aaagccacct ttgcctagtg ttaggaaact gacagaggac agatggaaca agccccagaa   5580
gaccaagggc cacagaggga gccatacaat gaatggacac tagagctttt agaggaactt   5640
aagagtgaag ctgttagaca ttttcctagg atatggctcc ataacttagg acaacatatc   5700
tatgaaactt acggggatac ttgggcagga gtggaagcca taataagaat tctgcaacaa   5760
ctgctgttta tccatttcag aattgggtgt cgacatagca gaataggcgt tactcgacag   5820
aggagagcaa gaaatggagc cagtagatcc tagactagag ccctggaagc atccaggaag   5880
tcagcctaaa actgcttgta ccaattgcta ttgtaaaaag tgttgctttc attgccaagt   5940
ttgtttcatg acaaaagcct taggcatctc ctatggcagg aagaagcgga gacagcgacg   6000
aagagctcat cagaacagtc agactcatca agcttctcta tcaaagcagt aagtagtaca   6060
tgtaatgcaa cctataatag tagcaatagt agcattagta gtagcaataa taatagcaat   6120
agttgtgtgg tccatagtaa tcatagaata taggaaaata ttaagacaaa gaaaaataga   6180
caggttaatt gatagactaa tagaaagagc agaagacagt ggcaatgaga gtgaaggaga   6240
agtatcagca cttgtggaga tgggggtgga aatggggcac catgctcctt gggatattga   6300
```

-continued

```
tgatctgtag tgctacagaa aaattgtggg tcacagtcta ttatggggta cctgtgtgga   6360
aggaagcaac caccactcta ttttgtgcat cagatgctaa agcatatgat acagaggtac   6420
ataatgtttg ggccacacat gcctgtgtac ccacagaccc caacccacaa gaagtagtat   6480
tggtaaatgt gacagaaaat tttaacatgt ggaaaaatga catggtagaa cagatgcatg   6540
aggatataat cagtttatgg gatcaaagcc taaagccatg tgtaaaatta accccactct   6600
gtgttagttt aaagtgcact gatttgaaga atgatactaa taccaatagt agtagcggga   6660
gaatgataat ggagaaagga gagataaaaa actgctcttt caatatcagc acaagcataa   6720
gagataaggt gcagaaagaa tatgcattct tttataaact tgatatagta ccaatagata   6780
ataccagcta taggttgata agttgtaaca cctcagtcat tacacaggcc tgtccaaagg   6840
tatcctttga gccaattccc atacattatt gtgccccggc tggttttgcg attctaaaat   6900
gtaataataa gacgttcaat ggaacaggac catgtacaaa tgtcagcaca gtacaatgta   6960
cacatggaat caggccagta gtatcaactc aactgctgtt aaatggcagt ctagcagaag   7020
aagatgtagt aattagatct gccaatttca cagacaatgc taaaaccata atagtacagc   7080
tgaacacatc tgtagaaatt aattgtacaa gacccaacaa caatacaaga aaaagtatcc   7140
gtatccagag gggaccaggg agagcatttg ttacaatagg aaaaatagga aatatgagac   7200
aagcacattg taacattagt agagcaaaat ggaatgccac tttaaaacag atagctagca   7260
aattaagaga acaatttgga aataataaaa caataatctt taagcaatcc tcaggagggg   7320
acccagaaat tgtaacgcac agttttaatt gtggagggga atttttctac tgtaattcaa   7380
cacaactgtt taatagtact tggtttaata gtacttggag tactgaaggg tcaaataaca   7440
ctgaaggaag tgacacaatc acactcccat gcagaataaa acaatttata aacatgtggc   7500
aggaagtagg aaaagcaatg tatgcccctc ccatcagtgg acaaattaga tgttcatcaa   7560
atattactgg gctgctatta acaagagatg gtggtaataa caacaatggg tccgagatct   7620
tcagacctgg aggaggcgat atgagggaca attggagaag tgaattatat aaatataaag   7680
tagtaaaaat tgaaccatta ggagtagcac ccaccaaggc aaagagaaga gtggtgcaga   7740
gagaaaaaag agcagtggga ataggagctt tgttccttgg gttcttggga gcagcaggaa   7800
gcactatggg cgcagcgtca atgacgctga cggtacaggc cagacaatta ttgtctgata   7860
tagtgcagca gcagaacaat ttgctgaggg ctattgaggc gcaacagcat ctgttgcaac   7920
tcacagtctg gggcatcaaa cagctccagg caagaatcct ggctgtggaa agatacctaa   7980
aggatcaaca gctcctgggg atttggggtt gctctggaaa actcatttgc accactgctg   8040
tgccttggaa tgctagttgg agtaataaat ctctggaaca gatttggaat aacatgacct   8100
ggatggagtg ggacagagaa attaacaatt acacaagctt aatacactcc ttaattgaag   8160
aatcgcaaaa ccagcaagaa aagaatgaac aagaattatt ggaattagat aaatgggcaa   8220
gtttgtggaa ttggtttaac ataacaaatt ggctgtggta tataaaatta ttcataatga   8280
tagtaggagg cttggtaggt ttaagaatag tttttgctgt actttctata gtgaatagag   8340
ttaggcaggg atattcacca ttatcgtttc agacccacct cccaatcccg aggggacccg   8400
acaggcccga aggaatagaa gaagaaggtg gagagagaga cagagacaga tccattcgat   8460
tagtgaacgg atccttagca cttatctggg acgatctgcg gagcctgtgc ctcttcagct   8520
accaccgctt gagagactta ctcttgattg taacgaggat tgtggaactt ctgggacgca   8580
gggggtggga agccctcaaa tattggtgga atctcctaca gtattggagt caggaactaa   8640
```

-continued agaatagtgc tgttaacttg ctcaatgcca cagccatagc agtagctgag gggacagata 8700
gggttataga agtattacaa gcagcttata gagctattcg ccacatacct agaagaataa 8760
gacagggctt ggaaaggatt ttgctataag atgggtggca agtggtcaaa aagtagtgtg 8820
attggatggc ctgctgtaag ggaaagaatg agacgagctg agccagcagc agatggggtg 8880
ggagcagtat ctcgagacct agaaaaacat ggagcaatca caagtagcaa tacagcagct 8940
aacaatgctg cttgtgcctg gctagaagca caagaggagg aagaggtggg ttttccagtc 9000
acacctcagg tacctttaag accaatgact tacaaggcag ctgtagatct tagccacttt 9060
ttaaaagaaa aggggggact ggaagggcta attcactccc aaagaaggca agatatcctt 9120
gatctgtgga tctaccacac acaaggctac ttccctgatt ggcagaacta cacaccaggg 9180
ccaggggtca gatatccact gacctttgga tggtgctaca agctagtacc agctgagcca 9240
gataaggtag aagaggccaa taaaggagag aacaccagct tgttacaccc tgtgagcctg 9300
catggaatgg atgaccctga gagagaagtg ttagagtgga ggtttgacag ccgcctagca 9360
tttcatcacg tggcccgaga gctgcatccg gagtacttca agaactgctg aacgcgtatt 9420
gcattactag ttattaatag taatcaatta cggggtcatt agttcatagc ccatatatgg 9480
agttccgcgt tacataactt acggtaaatg gcccgcctgg ctgaccgccc aacgaccccc 9540
gcccattgac gtcaataatg acgtatgttc ccatagtaac gccaataggg actttccatt 9600
gacgtcaatg ggtggagtat ttacggtaaa ctgcccactt ggcagtacat caagtgtatc 9660
atatgccaag tccgccccct attgacgtca atgacggtaa atggcccgcc tggcattatg 9720
cccagtacat gaccttacgg gactttccta cttggcagta catctacgta ttagtcatcg 9780
ctattaccat ggtgatgcgg ttttggcagt acaccaatgg gcgtggatag cggtttgact 9840
cacggggatt tccaagtctc caccccattg acgtcaatgg gagtttgttt tggcaccaaa 9900
atcaacggga ctttccaaaa tgtcgtaata accccgcccc gttgacgcaa atgggcggta 9960
ggcgtgtacg gtgggaggtc tatataagca gagctcgttt agtgaaccgt cagaattgtt 10020
tttatttta attttctttc aaatacttcc atcgaattca gatctggtac cacgcgtacc 10080
atggtgccca agaagaagag gaaagtctcc aacctgctga ctgtgcacca aaacctgcct 10140
gccctccctg tggatgccac ctctgatgaa gtcaggaaga acctgatgga catgttcagg 10200
gacaggcagg ccttctctga acacacctgg aagatgctcc tgtctgtgtg cagatcctgg 10260
gctgcctggt gcaagctgaa caacaggaaa tggttccctg ctgaacctga ggatgtgagg 10320
gactacctcc tgtacctgca agccagaggc ctggctgtga agaccatcca acagcacctg 10380
ggccagctca acatgctgca caggagatct ggcctgcctc gcccttctga ctccaatgct 10440
gtgtccctgg tgatgaggag aatcagaaag gagaatgtgg atgctgggga gagagccaag 10500
caggccctgg cctttgaacg cactgacttt gaccaagtca gatccctgat ggagaactct 10560
gacagatgcc aggacatcag gaacctggcc ttcctgggca ttgcctacaa caccctgctg 10620
cgcattgccg aaattgccag aatcagagtg aaggacatct cccgcaccga tggtgggaga 10680
atgctgatcc acattggcag gaccaagacc ctggtgtcca cagctggtgt ggagaaggcc 10740
ctgtccctgg gggttaccaa gctggtggag agatggatct ctgtgtctgg tgtggctgat 10800
gaccccaaca actacctgtt ctgccgggtc agaaagaatg gtgtggctgc cccttctgcc 10860
acctcccaac tgtccacccg ggccctggaa gggatctttg aggccaccca ccgcctgatc 10920
tatggtgcca aggatgactc tgggcagaga tacctggcct ggtctggcca ctctgccaga 10980
gtgggtgctg ccagggacat ggccagggct ggtgtgtcca tccctgaaat catgcaggct 11040

-continued

```
ggtggctgga ccaatgtgaa catagtgatg aactacatca gaaacctgga ctctgagact  11100
ggggccatgg tgaggctgct cgaggatggg gacggtggtg gtggcaagct ttgacgcatc  11160
ccgggtagcc actttttaaa agaaaagggg ggactggaag ggctaattca ctcccaaaga  11220
agacaagata tcccatccgg agtacttcaa gaactgctga catcgagctt gctacaaggg  11280
actttccgct ggggactttc cagggaggcg tggcctgggc gggactgggg agtggcgagc  11340
cctcagatgc tgcatataag cagctgcttt ttgcctgtac tgggtctctc tggttagacc  11400
agatctgagc ctgggagctc tctggctaac tagggaaccc actgcttaag cctcaataaa  11460
gcttgccttg agtgcttcaa gtagtgtgtg cccgtctgtt gtgtgactct ggtaactaga  11520
gatccctcag acccttttag tcagtgtgga aaatctctag cagttctaga gcggccgctc  11580
gcgaattctt gaagacgaaa gggcctcgtg atacgcctat ttttataggt taatgtcatg  11640
ataataatgg tttcttagac gtcaggtggc acttttcggg gaaatgtgcg cggaacccct  11700
atttgtttat ttttctaaat acattcaaat atgtatccgc tcatgagaca ataaccctga  11760
taaatgcttc aataatattg aaaaaggaag agtatgagta ttcaacattt ccgtgtcgcc  11820
cttattccct tttttgcggc attttgcctt cctgtttttg ctcacccaga aacgctggtg  11880
aaagtaaaag atgctgaaga tcagttgggt gcacgagtgg gttacatcga actggatctc  11940
aacagcggta agatccttga gagttttcgc cccgaagaac gttttccaat gatgagcact  12000
tttaaagttc tgctatgtgg cgcggtatta tcccgtgttg acgccgggca agagcaactc  12060
ggtcgccgca tacactattc tcagaatgac ttggttgagt actcaccagt cacagaaaag  12120
catcttacgg atggcatgac agtaagagaa ttatgcagtg ctgccataac catgagtgat  12180
aacactgcgg ccaacttact tctgacaacg atcggaggac cgaaggagct aaccgctttt  12240
ttgcacaaca tgggggatca tgtaactcgc cttgatcgtt gggaaccgga gctgaatgaa  12300
gccataccaa acgacgagcg tgacaccacg atgcctgcag caatggcaac aacgttgcgc  12360
aaactattaa ctggcgaact acttactcta gcttcccggc aacaattaat agactggatg  12420
gaggcggata aagttgcagg accacttctg cgctcggccc ttccggctgg ctggtttatt  12480
gctgataaat ctggagccgg tgagcgtggg tctcgcggta tcattgcagc actggggcca  12540
gatggtaagc cctcccgtat cgtagttatc tacacgacgg ggagtcaggc aactatggat  12600
gaacgaaata gacagatcgc tgagataggt gcctcactga ttaagcattg gtaactgtca  12660
gaccaagttt actcatatat actttagatt gatttaaaac ttcattttta atttaaaagg  12720
atctaggtga agatcctttt tgataatctc atgaccaaaa tcccttaacg tgagttttcg  12780
ttccactgag cgtcagaccc cgtagaaaag atcaaaggat cttcttgaga tccttttttt  12840
ctgcgcgtaa tctgctgctt gcaaacaaaa aaaccaccgc taccagcggt ggtttgtttg  12900
ccggatcaag agctaccaac tctttttccg aaggtaactg gcttcagcag agcgcagata  12960
ccaaatactg tccttctagt gtagccgtag ttaggccacc acttcaagaa ctctgtagca  13020
ccgcctacat acctcgctct gctaatcctg ttaccagtgg ctgctgccag tggcgataag  13080
tcgtgtctta ccgggttgga ctcaagacga tagttaccgg ataaggcgca gcggtcgggc  13140
tgaacggggg gttcgtgcac acagcccagc ttggagcgaa cgacctacac cgaactgaga  13200
tacctacagc gtgagctatg agaaagcgcc acgcttcccg aagggagaaa ggcggacagg  13260
tatccggtaa gcggcagggt cggaacagga gagcgcacga gggagcttcc agggggaaac  13320
gcctggtatc tttatagtcc tgtcgggttt cgccacctct gacttgagcg tcgatttttg  13380
```

-continued

```
tgatgctcgt caggggggcg gagcctatgg aaaaacgcca gcaacgcggc ctttttacgg  13440

ttcctggcct tttgctggcc ttttgctcac atgttctttc ctgcgttatc ccctgattct  13500

gtggataacc gtattaccgc ctttgagtga gctgataccg ctcgccgcag ccgaacgacc  13560

gagcgcagcg agtcagtgag cgaggaagcg gaagagcgcc tgatgcggta ttttctcctt  13620

acgcatctgt gcggtatttc acaccgcata tggtgcactc tcagtacaat ctgctctgat  13680

gccgcatagt taagccagta tacactccgc tatcgctacg tgactgggtc atggctgcgc  13740

cccgacaccc gccaacaccc gctgacgcgc cctgacgggc ttgtctgctc ccggcatccg  13800

cttacagaca agctgtgacc gtctccggga gctgcatgtg tcagaggttt tcaccgtcat  13860

caccgaaacg cgcgaggcag atcccgcaag aggcccggca gtaccggcat aaccaagcct  13920

atgcctacag catccagggt gacggtgccg aggatgacga tgagcgcatt gttagatttc  13980

atacacggtg cctgactgcg ttagcaattt aactgtgata aactaccgca ttaaagcttg  14040

tcgacagcgc tacgcgc                                                 14057


<210> SEQ ID NO 13
<211> LENGTH: 14517
<212> TYPE: DNA
<213> ORGANISM: Artificial Sequence
<220> FEATURE:
<223> OTHER INFORMATION: pBR-SIVmac239-Nef-IRES-Cre

<400> SEQUENCE: 13

tggaagggat ttattacagt gcaagaagac atagaatctt agacatatac ttagaaaagg     60

aagaaggcat cataccagat tggcaggatt acacctcagg accaggaatt agatacccaa    120

agacatttgg ctggctatgg aaattagtcc ctgtaaatgt atcagatgag gcacaggagg    180

atgaggagca ttatttaatg catccagctc aaacttccca gtgggatgac ccttggggag    240

aggttctagc atggaagttt gatccaactc tggcctacac ttatgaggca tatgttagat    300

acccagaaga gtttggaagc aagtcaggcc tgtcagagga agaggttaga agaaggctaa    360

ccgcaagagg ccttcttaac atggctgaca agaaggaaac tcgctgaaac agcagggact    420

ttccacaagg ggatgttacg gggaggtact ggggaggagc cggtcgggaa cgcccacttt    480

cttgatgtat aaatatcact gcatttcgct ctgtattcag tcgctctgcg gagaggctgg    540

cagattgagc cctgggaggt tctctccagc actagcaggt agagcctggg tgttccctgc    600

tagactctca ccagcacttg gccggtgctg ggcagagtga ctccacgctt gcttgcttaa    660

agccctcttc aataaagctg ccattttagg aagtaagcta gtgtgtgttc ccatctctcc    720

tagccgccgc ctggtcaact cggtacttca ataataagaa gactcctggt ctgttaggac    780

cctttctgct ttgggaaacc gaagcaggaa aatccctagc agattggcgc ctgaacaggg    840

acttgaagga gagtgagaga ctcctgagta cggctgagtg aaggcagtaa gggcggcagg    900

aaccaaccac gacggagtgc tcctataaag gcgcgggtcg gtaccagacg gcgtgaggag    960

cgggagagga agaggcctcc ggttgcaggt aagtgcaaca caaaaaagaa atagctgtct   1020

tttatccagg aaggggtaat aagatagagt gggagatggg cgtgagaaac tccgtcttgt   1080

cagggaagaa agcagatgaa ttagaaaaaa ttaggctacg acccaacgga aagaaaaagt   1140

acatgttgaa gcatgtagta tgggcagcaa atgaattaga tagatttgga ttagcagaaa   1200

gcctgttgga gaacaaagaa ggatgtcaaa aaatactttc ggtcttagct ccattagtgc   1260

caacaggctc agaaaattta aaaagccttt ataatactgt ctgcgtcatc tggtgcattc   1320

acgcagaaga gaaagtgaaa cacactgagg aagcaaaaca gatagtgcag agacacctag   1380
```

-continued

```
tggtggaaac aggaacaaca gaaactatgc caaaaacaag tagaccaaca gcaccatcta   1440
gcggcagagg aggaaattac ccagtacaac aaataggtgg taactatgtc cacctgccat   1500
taagcccgag aacattaaat gcctgggtaa aattgataga ggaaaagaaa tttggagcag   1560
aagtagtgcc aggatttcag gcactgtcag aaggttgcac cccctatgac attaatcaga   1620
tgttaaattg tgtgggagac catcaagcgg ctatgcagat tatcagagat attataaacg   1680
aggaggctgc agattgggac ttgcagcacc cacaaccagc tccacaacaa ggacaactta   1740
gggagccgtc aggatcagat attgcaggaa caactagttc agtagatgaa caaatccagt   1800
ggatgtacag acaacagaac cccataccag taggcaacat ttacaggaga tggatccaac   1860
tggggttgca aaaatgtgtc agaatgtata acccaacaaa cattctagat gtaaaacaag   1920
ggccaaaaga gccatttcag agctatgtag acaggttcta caaaagttta agagcagaac   1980
agacagatgc agcagtaaag aattggatga ctcaaacact gctgattcaa aatgctaacc   2040
cagattgcaa gctagtgctg aaggggctgg gtgtgaatcc caccctagaa gaaatgctga   2100
cggcttgtca aggagtaggg gggccgggac agaaggctag attaatggca gaagccctga   2160
aagaggccct cgcaccagtg ccaatccctt ttgcagcagc ccaacagagg ggaccaagaa   2220
agccaattaa gtgttggaat tgtgggaaag agggacactc tgcaaggcaa tgcagagccc   2280
caagaagaca gggatgctgg aaatgtggaa aaatggacca tgttatggcc aaatgcccag   2340
acagacaggc gggtttttta ggccttggtc catggggaaa gaagccccgc aatttcccca   2400
tggctcaagt gcatcagggg ctgatgccaa ctgctccccc agaggaccca gctgtggatc   2460
tgctaaagaa ctacatgcag ttgggcaagc agcagagaga aaagcagaga gaaagcagag   2520
agaagcctta caaggaggtg acagaggatt tgctgcacct caattctctc tttggaggag   2580
accagtagtc actgctcata ttgaaggaca gcctgtagaa gtattactgg atacaggggc   2640
tgatgattct attgtaacag gaatagagtt aggtccacat tataccccaa aaatagtagg   2700
aggaatagga ggttttatta atactaaaga atacaaaaat gtagaaatag aagttttagg   2760
caaaaggatt aaagggacaa tcatgacagg ggacaccccg attaacattt ttggtagaaa   2820
tttgctaaca gctctgggga tgtctctaaa ttttcccata gctaaagtag agcctgtaaa   2880
agtcgcctta aagccaggaa aggatggacc aaaattgaag cagtggccat tatcaaaaga   2940
aaagatagtt gcattaagag aaatctgtga aaagatggaa aaggatggtc agttggagga   3000
agctcccccg accaatccat acaacacccc cacatttgct ataaagaaaa aggataagaa   3060
caaatggaga atgctgatag attttaggga actaaatagg gtcactcagg actttacgga   3120
agtccaatta ggaataccac accctgcagg actagcaaaa aggaaaagaa ttacagtact   3180
ggatataggt gatgcatatt tctccatacc tctagatgaa gaatttaggc agtacactgc   3240
ctttacttta ccatcagtaa ataatgcaga gccaggaaaa cgatacattt ataaggttct   3300
gcctcaggga tggaaggggt caccagccat cttccaatac actatgagac atgtgctaga   3360
acccttcagg aaggcaaatc cagatgtgac cttagtccag tatatggatg acatcttaat   3420
agctagtgac aggacagacc tggaacatga cagggtagtt ttacagtcaa aggaactctt   3480
gaatagcata gggttttcta ccccagaaga gaaattccaa aaagatcccc catttcaatg   3540
gatggggtac gaattgtggc caacaaaatg gaagttgcaa aagatagagt tgccacaaag   3600
agagacctgg acagtgaatg atatacagaa gttagtagga gtattaaatt gggcagctca   3660
aatttatcca ggtataaaaa ccaaacatct ctgtaggtta attagaggaa aaatgactct   3720
```

-continued

```
aacagaggaa gttcagtgga ctgagatggc agaagcagaa tatgaggaaa ataaaataat   3780
tctcagtcag gaacaagaag gatgttatta ccaagaaggc aagccattag aagccacggt   3840
aataaagagt caggacaatc agtggtctta taaaattcac caagaagaca aaatactgaa   3900
agtaggaaaa tttgcaaaga taaagaatac acataccaat ggagtgagac tattagcaca   3960
tgtaatacag aaaataggaa aggaagcaat agtgatctgg ggacaggtcc caaaattcca   4020
cttaccagtt gagaaggatg tatgggaaca gtggtggaca gactattggc aggtaacctg   4080
gataccggaa tgggatttta tctcaacacc accgctagta agattagtct tcaatctagt   4140
gaaggaccct atagagggag aagaaaccta ttatacagat ggatcatgta ataaacagtc   4200
aaaagaaggg aaagcaggat atatcacaga taggggcaaa gacaaagtaa aagtgttaga   4260
acagactact aatcaacaag cagaattgga agcatttctc atggcattga cagactcagg   4320
gccaaaggca aatattatag tagattcaca atatgttatg ggaataataa caggatgccc   4380
tacagaatca gagagcaggc tagttaatca aataatagaa gaaatgatta aaaagtcaga   4440
aatttatgta gcatgggtac cagcacacaa aggtatagga ggaaaccaag aaatagacca   4500
cctagttagt caagggatta gacaagttct cttcttggaa aagatagagc cagcacaaga   4560
agaacatgat aaataccata gtaatgtaaa agaattggta ttcaaatttg gattacccag   4620
aatagtggcc agacagatag tagacacctg tgataaatgt catcagaaag gagaggctat   4680
acatgggcag gcaaattcag atctagggac ttggcaaatg gattgtaccc atctagaggg   4740
aaaaataatc atagttgcag tacatgtagc tagtggattc atagaagcag aggtaattcc   4800
acaagagaca ggaagacaga cagcactatt tctgttaaaa ttggcaggca gatggcctat   4860
tacacatcta cacacagata atggtgctaa ctttgcttcg caagaagtaa agatggttgc   4920
atggtgggca gggatagagc acacctttgg ggtaccatac aatccacaga gtcagggagt   4980
agtggaagca atgaatcacc acctgaaaaa tcaaatagat agaatcaggg aacaagcaaa   5040
ttcagtagaa accatagtat taatggcagt tcattgcatg aattttaaaa gaaggggagg   5100
aataggggat atgactccag cagaaagatt aattaacatg atcactacag aacaagagat   5160
acaatttcaa caatcaaaaa actcaaaatt taaaaatttt cgggtctatt acagagaagg   5220
cagagatcaa ctgtggaagg gacccggtga gctattgtgg aaaggggaag gagcagtcat   5280
cttaaaggta gggacagaca ttaaggtagt acccagaaga aaggctaaaa ttatcaaaga   5340
ttatggagga ggaaaagagg tggatagcag ttcccacatg gaggataccg gagaggctag   5400
agaggtggca tagcctcata aaatatctga aatataaaac taaagatcta caaaaggttt   5460
gctatgtgcc ccattttaag gtcggatggg catggtggac ctgcagcaga gtaatcttcc   5520
cactacagga aggaagccat ttagaagtac aagggtattg gcatttgaca ccagaaaaag   5580
ggtggctcag tacttatgca gtgaggataa cctggtactc aaagaacttt tggacagatg   5640
taacaccaaa ctatgcagac attttactgc atagcactta tttcccttgc tttacagcgg   5700
gagaagtgag aagggccatc aggggagaac aactgctgtc ttgctgcagg ttcccgagag   5760
ctcataagta ccaggtacca agcctacagt acttagcact gaaagtagta agcgatgtca   5820
gatcccaggg agagaatccc acctggaaac agtggagaag agacaatagg agaggccttc   5880
gaatggctaa acagaacagt agaggagata aacagagagg cggtaaacca cctaccaagg   5940
gagctaattt tccaggtttg gcaaaggtct tgggaatact ggcatgatga acaagggatg   6000
tcaccaagct atgtaaaata cagatacttg tgtttaatac aaaaggcttt atttatgcat   6060
tgcaagaaag gctgtagatg tctaggggaa ggacatgggg caggggggatg gagaccagga   6120
```

```
cctcctcctc ctccccctcc aggactagca taaatggaag aaagacctcc agaaaatgaa   6180
ggaccacaaa gggaaccatg ggatgaatgg gtagtggagg ttctggaaga actgaaagaa   6240
gaagctttaa aacattttga tcctcgcttg ctaactgcac ttggtaatca tatctataat   6300
agacatggag acacccttga gggagcagga gaactcatta gaatcctcca acgagcgctc   6360
ttcatgcatt tcagaggcgg atgcatccac tccagaatcg gccaacctgg gggaggaaat   6420
cctctctcag ctataccgcc ctctagaagc atgctataac acatgctatt gtaaaaagtg   6480
ttgctaccat tgccagtttt gttttcttaa aaaaggcttg gggatatgtt atgagcaatc   6540
acgaaagaga agaagaactc cgaaaaaggc taaggctaat acatcttctg catcaaacaa   6600
gtaagtatgg gatgtcttgg gaatcagctg cttatcgcca tcttgctttt aagtgtctat   6660
gggatctatt gtactctata tgtcacagtc ttttatggtg taccagcttg gaggaatgcg   6720
acaattcccc tcttttgtgc aaccaagaat agggatactt ggggaacaac tcagtgccta   6780
ccagataatg gtgattattc agaagtggcc cttaatgtta cagaaagctt tgatgcctgg   6840
aataatacag tcacagaaca ggcaatagag gatgtatggc aactctttga gacctcaata   6900
aagccttgtg taaaattatc cccattatgc attactatga gatgcaataa aagtgagaca   6960
gatagatggg gattgacaaa atcaataaca acaacagcat caacaacatc aacgacagca   7020
tcagcaaaag tagacatggt caatgagact agttcttgta tagcccagga taattgcaca   7080
ggcttggaac aagagcaaat gataagctgt aaattcaaca tgacagggtt aaaaagagac   7140
aagaaaaaag agtacaatga aacttggtac tctgcagatt tggtatgtga acaagggaat   7200
aacactggta atgaaagtag atgttacatg aaccactgta acacttctgt tatccaagag   7260
tcttgtgaca aacattattg ggatgctatt agatttaggt attgtgcacc tccaggttat   7320
gctttgctta gatgtaatga cacaaattat tcaggcttta tgcctaaatg ttctaaggtg   7380
gtggtctctt catgcacaag gatgatggag acacagactt ctacttggtt tggctttaat   7440
ggaactagag cagaaaatag aacttatatt tactggcatg gtagggataa taggactata   7500
attagtttaa ataagtatta taatctaaca atgaaatgta gaagaccagg aaataagaca   7560
gttttaccag tcaccattat gtctggattg gttttccact cacaaccaat caatgatagg   7620
ccaaagcagg catggtgttg gtttggagga aaatggaagg atgcaataaa agaggtgaag   7680
cagaccattg tcaaacatcc caggtatact ggaactaaca atactgataa aatcaatttg   7740
acggctcctg gaggaggaga tccggaagtt accttcatgt ggacaaattg cagaggagag   7800
ttcctctact gtaaaatgaa ttggtttcta aattgggtag aagataggaa tacagctaac   7860
cagaagccaa aggaacagca taaaaggaat tacgtgccat gtcatattag acaaataatc   7920
aacacttggc ataaagtagg caaaaatgtt tatttgcctc caagagaggg agacctcacg   7980
tgtaactcca cagtgaccag tctcatagca aacatagatt ggattgatgg aaaccaaact   8040
aatatcacca tgagtgcaga ggtggcagaa ctgtatcgat tggaattggg agattataaa   8100
ttagtagaga tcactccaat tggcttggcc cccacagatg tgaagaggta cactactggt   8160
ggcacctcaa gaaataaaag aggggtcttt gtgctagggt tcttgggttt tctcgcaacg   8220
gcaggttctg caatgggcgc ggcgtcgttg acgctgaccg ctcagtcccg aactttattg   8280
gctgggatag tgcagcaaca gcaacagctg ttggacgtgg tcaagagaca acaagaattg   8340
ttgcgactga ccgtctgggg aacaaagaac ctccagacta gggtcactgc catcgagaag   8400
tacttaaagg accaggcgca gctgaatgct tggggatgtg cgtttagaca agtctgccac   8460
```

-continued

```
actactgtac catggccaaa tgcaagtcta acaccaaagt ggaacaatga gacttggcaa   8520
gagtgggagc gaaaggttga cttcttggaa gaaaatataa cagccctcct agaggaggca   8580
caaattcaac aagagaagaa catgtatgaa ttacaaaagt tgaatagctg ggatgtgttt   8640
ggcaattggt ttgaccttgc ttcttggata aagtatatac aatatggagt ttatatagtt   8700
gtaggagtaa tactgttaag aatagtgatc tatatagtac aaatgctagc taagttaagg   8760
caggggtata ggccagtgtt ctcttcccca ccctcttatt tccagcagac ccatatccaa   8820
caggacccgg cactgccaac cagagaaggc aaagaaagag acggtggaga aggcggtggc   8880
aacagctcct ggccttggca gatagaatat attcatttcc tgatccgcca actgatacgc   8940
ctcttgactt ggctattcag caactgcaga accttgctat cgagagtata ccagatcctc   9000
caaccaatac tccagaggct ctctgcgacc ctacagagga ttcgagaagt cctcaggact   9060
gaactgacct acctacaata tgggtggagc tatttccatg aggcggtcca ggccgtctgg   9120
agatctgcga cagagactct tgcgggcgcg tggggagact tatgggagac tcttaggaga   9180
ggtggaagat ggatactcgc aatccccagg aggattagac aagggcttga gctcactctc   9240
ttgtgaggga cagaaataca atcagggaca gtatatgaat actccatgga gaaacccagc   9300
tgaagagaga gaaaaattag catacagaaa acaaaatatg gatgatatag atgaggaaga   9360
tgatgacttg gtaggggtat cagtgaggcc aaaagttccc ctaagaacaa tgagttacaa   9420
attggcaata gacatgtctc attttataaa agaaaagggg ggactggaag ggatttatta   9480
cagtgcaaga agacatagaa tcttagacat atacttagaa aaggaaggag gcatcatacc   9540
agattggcag gattacacct caggaccagg aattagatac ccaaagacat ttggctggct   9600
atggaaatta gtccctgtaa atgtatcaga tgaggcacag gaggatgagg agcattattt   9660
aatgcatcca gctcaaactt cccagtggga tgacccttgg ggagaggttc tagcatggaa   9720
gtttgatcca actctggcct acacttatga ggcatatgtt agatacccag aagagtttgg   9780
aagcaagtca ggcctgtcag aggaagaggt tagaagaagg ctaaccgcaa gaggccttct   9840
taacatggct gacaagaagg aaactcgctg aacgcgtcgg atcccggagt actacaaaga   9900
ctgctgacgc gaattccgcc cccccccccta acgttactgg ccgaagccgc ttggaataag   9960
gccggtgtgc gtttgtctat atgttatttt ccaccatatt gccgtctttt ggcaatgtga  10020
gggcccggaa acctggccct gtcttcttga cgagcattcc taggggtctt tcccctctcg  10080
ccaaaggaat gcaaggtctg ttgaatgtcg tgaaggaagc agttcctctg gaagcttctt  10140
gaagacaaac aacgtctgta gcgacccttt gcaggcagcg gaacccccca cctggcgaca  10200
ggtgcctctg cggccaaaag ccacgtgtat aagatacacc tgcaaaggcg gcacaacccc  10260
agtgccacgt tgtgagttgg atagttgtgg aaagagtcaa atggctctcc tcaagcgtat  10320
tcaacaaggg gctgaaggat gcccagaagg taccccattg tatgggatct gatctggggc  10380
ctcggtgcac atgctttaca tgtgtttagt cgaggttaaa aaacgtctag gccccccgaa  10440
ccacggggac gtggttttcc tttgaaaaac acgatgataa taccatggtg cccaagaaga  10500
agaggaaagt ctccaacctg ctgactgtgc accaaaacct gcctgccctc cctgtggatg  10560
ccacctctga tgaagtcagg aagaacctga tggacatgtt cagggacagg caggccttct  10620
ctgaacacac ctggaagatg ctcctgtctg tgtgcagatc ctgggctgcc tggtgcaagc  10680
tgaacaacag gaaatggttc cctgctgaac ctgaggatgt gagggactac ctcctgtacc  10740
tgcaagccag aggcctggct gtgaagacca tccaacagca cctgggccag ctcaacatgc  10800
tgcacaggag atctggcctg cctcgccctt ctgactccaa tgctgtgtcc ctggtgatga  10860
```

ggagaatcag aaaggagaat gtggatgctg gggagagagc caagcaggcc ctggcctttg 10920
aacgcactga ctttgaccaa gtcagatccc tgatggagaa ctctgacaga tgccaggaca 10980
tcaggaacct ggccttcctg ggcattgcct acaacaccct gctgcgcatt gccgaaattg 11040
ccagaatcag agtgaaggac atctcccgca ccgatggtgg gagaatgctg atccacattg 11100
gcaggaccaa gaccctggtg tccacagctg gtgtggagaa ggccctgtcc ctgggggtta 11160
ccaagctggt ggagagatgg atctctgtgt ctggtgtggc tgatgacccc aacaactacc 11220
tgttctgccg ggtcagaaag aatggtgtgg ctgccccttc tgccacctcc caactgtcca 11280
cccgggccct ggaagggatc tttgaggcca cccaccgcct gatctatggt gccaaggatg 11340
actctgggca gagatacctg gcctggtctg gccactctgc cagagtgggt gctgccaggg 11400
acatggccag ggctggtgtg tccatccctg aaatcatgca ggctggtggc tggaccaatg 11460
tgaacatagt gatgaactac atcagaaacc tggactctga gactggggcc atggtgaggc 11520
tgctcgagga tggggactga cccgggtctc attttataaa agaaaagggg ggactggaag 11580
ggatttatcc gcggttcact cgagactcgc tgaaacagca gggactttcc acaaggggat 11640
gttacgggga ggtactgggg aggagccggt cgggaacgcc cactttcttg atgtataaat 11700
atcactgcat ttcgctctgt attcagtcgc tctgcggaga ggctggcaga ttgagccctg 11760
ggaggttctc tccagcacta gcaggtagag cctgggtgtt ccctgctaga ctctcaccag 11820
cacttggccg gtgctgggca gagtgactcc acgcttgctt gcttaaagcc ctcttcaata 11880
aagctgccat tttagaagta agctagtgtg tgttcccatc tctcctagcc gccgcctggt 11940
caactcggta ctcaataata agaagaccct ggtctgttag gaccctttct gctttgggaa 12000
accgaagcag gaaaatccct agcagaattc ttgaagacga aagggcctcg tgatacgcct 12060
atttttatag gttaatgtca tgataataat ggtttcttag acgtcaggtg gcacttttcg 12120
gggaaatgtg cgcggaaccc ctatttgttt atttttctaa atacattcaa atatgtatcc 12180
gctcatgaga caataaccct gataaatgct tcaataatat tgaaaaagga agagtatgag 12240
tattcaacat ttccgtgtcg cccttattcc cttttttgcg gcattttgcc ttcctgtttt 12300
tgctcaccca gaaacgctgg tgaaagtaaa agatgctgaa gatcagttgg gtgcacgagt 12360
gggttacatc gaactggatc tcaacagcgg taagatcctt gagagttttc gccccgaaga 12420
acgttttcca atgatgagca cttttaaagt tctgctatgt ggcgcggtat tatcccgtgt 12480
tgacgccggg caagagcaac tcggtcgccg catacactat tctcagaatg acttggttga 12540
gtactcacca gtcacagaaa agcatcttac ggatggcatg acagtaagag aattatgcag 12600
tgctgccata accatgagtg ataacactgc ggccaactta cttctgacaa cgatcggagg 12660
accgaaggag ctaaccgctt ttttgcacaa catgggggat catgtaactc gccttgatcg 12720
ttgggaaccg gagctgaatg aagccatacc aaacgacgag cgtgacacca cgatgcctgc 12780
agcaatggca acaacgttgc gcaaactatt aactggcgaa ctacttactc tagcttcccg 12840
gcaacaatta atagactgga tggaggcgga taaagttgca ggaccacttc tgcgctcggc 12900
ccttccggct ggctggttta ttgctgataa atctggagcc ggtgagcgtg ggtctcgcgg 12960
tatcattgca gcactggggc cagatggtaa gccctcccgt atcgtagtta tctacacgac 13020
ggggagtcag gcaactatgg atgaacgaaa tagacagatc gctgagatag gtgcctcact 13080
gattaagcat tggtaactgt cagaccaagt ttactcatat atactttaga ttgatttaaa 13140
acttcatttt taatttaaaa ggatctaggt gaagatcctt tttgataatc tcatgaccaa 13200
aatcccttaa cgtgagtttt cgttccactg agcgtcagac cccgtagaaa agatcaaagg 13260
atcttcttga gatccttttt ttctgcgcgt aatctgctgc ttgcaaacaa aaaaaccacc 13320
gctaccagcg gtggtttgtt tgccggatca agagctacca actctttttc cgaaggtaac 13380
tggcttcagc agagcgcaga taccaaatac tgtccttcta gtgtagccgt agttaggcca 13440
ccacttcaag aactctgtag caccgcctac atacctcgct ctgctaatcc tgttaccagt 13500
ggctgctgcc agtggcgata agtcgtgtct taccgggttg gactcaagac gatagttacc 13560
ggataaggcg cagcggtcgg gctgaacggg gggttcgtgc acacagccca gcttggagcg 13620
aacgacctac accgaactga gatacctaca gcgtgagcta tgagaaagcg ccacgcttcc 13680
cgaagggaga aaggcggaca ggtatccggt aagcggcagg gtcggaacag gagagcgcac 13740
gagggagctt ccagggggaa acgcctggta tctttatagt cctgtcgggt ttcgccacct 13800
ctgacttgag cgtcgatttt tgtgatgctc gtcagggggg cggagcctat ggaaaaacgc 13860
cagcaacgcg gcctttttac ggttcctggc cttttgctgg ccttttgctc acatgttctt 13920
tcctgcgtta tcccctgatt ctgtggataa ccgtattacc gcctttgagt gagctgatac 13980
cgctcgccgc agccgaacga ccgagcgcag cgagtcagtg agcgaggaag cggaagagcg 14040
cctgatgcgg tattttctcc ttacgcatct gtgcggtatt tcacaccgca tatggtgcac 14100
tctcagtaca atctgctctg atgccgcata gttaagccag tatacactcc gctatcgcta 14160
cgtgactggg tcatggctgc gccccgacac ccgccaacac ccgctgacgc gccctgacgg 14220
gcttgtctgc tcccggcatc cgcttacaga caagctgtga ccgtctccgg gagctgcatg 14280
tgtcagaggt tttcaccgtc atcaccgaaa cgcgcgaggc agatcccgca agaggcccgg 14340
cagtaccggc ataaccaagc ctatgcctac agcatccagg gtgacggtgc cgaggatgac 14400
gatgagcgca ttgttagatt tcatacacgg tgcctgactg cgttagcaat ttaactgtga 14460
taaactaccg cattaaagct tactgtaaat ttactggctg tcttccttgc aggtttc 14517

<210> SEQ ID NO 14
<211> LENGTH: 14517
<212> TYPE: DNA
<213> ORGANISM: Artificial Sequence
<220> FEATURE:
<223> OTHER INFORMATION: pBR-SIVmac239-Nef IRES-Cre

<400> SEQUENCE: 14
tggaagggat ttattacagt gcaagaagac atagaatctt agacatatac ttagaaaagg 60
aagaaggcat cataccagat tggcaggatt acacctcagg accaggaatt agatacccaa 120
agacatttgg ctggctatgg aaattagtcc ctgtaaatgt atcagatgag gcacaggagg 180
atgaggagca ttatttaatg catccagctc aaacttccca gtgggatgac ccttggggag 240
aggttctagc atggaagttt gatccaactc tggcctacac ttatgaggca tatgttagat 300
acccagaaga gtttggaagc aagtcaggcc tgtcagagga agaggttaga agaaggctaa 360
ccgcaagagg ccttcttaac atggctgaca agaaggaaac tcgctgaaac agcagggact 420
ttccacaagg ggatgttacg gggaggtact ggggaggagc cggtcgggaa cgcccacttt 480
cttgatgtat aaatatcact gcatttcgct ctgtattcag tcgctctgcg gagaggctgg 540
cagattgagc cctgggaggt tctctccagc actagcaggt agagcctggg tgttccctgc 600
tagactctca ccagcacttg gccggtgctg ggcagagtga ctccacgctt gcttgcttaa 660
agccctcttc aataaagctg ccattttagg aagtaagcta gtgtgtgttc ccatctctcc 720
tagccgccgc ctggtcaact cggtacttca ataataagaa gactcctggt ctgttaggac 780

-continued

```
cctttctgct ttgggaaacc gaagcaggaa aatccctagc agattggcgc ctgaacaggg    840
acttgaagga gagtgagaga ctcctgagta cggctgagtg aaggcagtaa gggcggcagg    900
aaccaaccac gacggagtgc tcctataaag gcgcgggtcg gtaccagacg gcgtgaggag    960
cgggagagga agaggcctcc ggttgcaggt aagtgcaaca caaaaaagaa atagctgtct   1020
tttatccagg aaggggtaat aagatagagt gggagatggg cgtgagaaac tccgtcttgt   1080
cagggaagaa agcagatgaa ttagaaaaaa ttaggctacg acccaacgga aagaaaaagt   1140
acatgttgaa gcatgtagta tggcagcaa atgaattaga tagatttgga ttagcagaaa   1200
gcctgttgga gaacaaagaa ggatgtcaaa aaatactttc ggtcttagct ccattagtgc   1260
caacaggctc agaaaattta aaaagccttt ataatactgt ctgcgtcatc tggtgcattc   1320
acgcagaaga gaaagtgaaa cacactgagg aagcaaaaca gatagtgcag agacacctag   1380
tggtggaaac aggaacaaca gaaactatgc caaaaacaag tagaccaaca gcaccatcta   1440
gcggcagagg aggaaattac ccagtacaac aaataggtgg taactatgtc cacctgccat   1500
taagcccgag aacattaaat gcctgggtaa aattgataga ggaaaagaaa tttggagcag   1560
aagtagtgcc aggatttcag gcactgtcag aaggttgcac cccctatgac attaatcaga   1620
tgttaaattg tgtgggagac catcaagcgg ctatgcagat tatcagagat attataaacg   1680
aggaggctgc agattgggac ttgcagcacc cacaaccagc tccacaacaa ggacaactta   1740
gggagccgtc aggatcagat attgcaggaa caactagttc agtagatgaa caaatccagt   1800
ggatgtacag acaacagaac cccataccag taggcaacat ttacaggaga tggatccaac   1860
tggggttgca aaaatgtgtc agaatgtata acccaacaaa cattctagat gtaaaacaag   1920
ggccaaaaga gccatttcag agctatgtag acaggttcta caaaagttta agagcagaac   1980
agacagatgc agcagtaaag aattggatga ctcaaacact gctgattcaa aatgctaacc   2040
cagattgcaa gctagtgctg aaggggctgg gtgtgaatcc caccctagaa gaaatgctga   2100
cggcttgtca aggagtaggg gggccgggac agaaggctag attaatggca gaagccctga   2160
aagaggccct cgcaccagtg ccaatccctt ttgcagcagc ccaacagagg ggaccaagaa   2220
agccaattaa gtgttggaat tgtgggaaag agggacactc tgcaaggcaa tgcagagccc   2280
caagaagaca gggatgctgg aaatgtggaa aaatggacca tgttatggcc aaatgcccag   2340
acagacaggc gggtttttta ggccttggtc catggggaaa gaagccccgc aatttcccca   2400
tggctcaagt gcatcagggg ctgatgccaa ctgctccccc agaggaccca gctgtggatc   2460
tgctaaagaa ctacatgcag ttgggcaagc agcagagaga aaagcagaga gaaagcagag   2520
agaagcctta caaggaggtg acagaggatt tgctgcacct caattctctc tttggaggag   2580
accagtagtc actgctcata ttgaaggaca gcctgtagaa gtattactgg atacaggggc   2640
tgatgattct attgtaacag gaatagagtt aggtccacat tataccccaa aaatagtagg   2700
aggaatagga ggttttatta atactaaaga atacaaaaat gtagaaatag aagttttagg   2760
caaaaggatt aaagggacaa tcatgacagg ggacaccccg attaacattt ttggtagaaa   2820
tttgctaaca gctctgggga tgtctctaaa ttttcccata gctaaagtag agcctgtaaa   2880
agtcgcctta aagccaggaa aggatggacc aaaattgaag cagtggccat tatcaaaaga   2940
aaagatagtt gcattaagag aaatctgtga aaagatggaa aaggatggtc agttggagga   3000
agctcccccg accaatccat acaacacccc cacatttgct ataaagaaaa aggataagaa   3060
caaatggaga atgctgatag attttaggga actaaatagg gtcactcagg actttacgga   3120
```

agtccaatta ggaataccac accctgcagg actagcaaaa aggaaaagaa ttacagtact 3180
ggatataggt gatgcatatt tctccatacc tctagatgaa gaatttaggc agtacactgc 3240
ctttacttta ccatcagtaa ataatgcaga gccaggaaaa cgatacattt ataaggttct 3300
gcctcaggga tggaaggggt caccagccat cttccaatac actatgagac atgtgctaga 3360
acccttcagg aaggcaaatc cagatgtgac cttagtccag tatatggatg acatcttaat 3420
agctagtgac aggacagacc tggaacatga cagggtagtt ttacagtcaa aggaactctt 3480
gaatagcata gggttttcta ccccagaaga gaaattccaa aaagatcccc catttcaatg 3540
gatggggtac gaattgtggc caacaaaatg gaagttgcaa aagatagagt tgccacaaag 3600
agagacctgg acagtgaatg atatacagaa gttagtagga gtattaaatt gggcagctca 3660
aatttatcca ggtataaaaa ccaaacatct ctgtaggtta attagaggaa aaatgactct 3720
aacagaggaa gttcagtgga ctgagatggc agaagcagaa tatgaggaaa ataaaataat 3780
tctcagtcag gaacaagaag gatgttatta ccaagaaggc aagccattag aagccacggt 3840
aataaagagt caggacaatc agtggtctta taaaattcac caagaagaca aaatactgaa 3900
agtaggaaaa tttgcaaaga taaagaatac acataccaat ggagtgagac tattagcaca 3960
tgtaatacag aaaataggaa aggaagcaat agtgatctgg ggacaggtcc caaaattcca 4020
cttaccagtt gagaaggatg tatgggaaca gtggtggaca gactattggc aggtaacctg 4080
gataccggaa tgggatttta tctcaacacc accgctagta agattagtct tcaatctagt 4140
gaaggaccct atagagggag aagaaaccta ttatacagat ggatcatgta ataaacagtc 4200
aaaagaaggg aaagcaggat atatcacaga taggggcaaa gacaaagtaa aagtgttaga 4260
acagactact aatcaacaag cagaattgga agcatttctc atggcattga cagactcagg 4320
gccaaaggca aatattatag tagattcaca atatgttatg ggaataataa caggatgccc 4380
tacagaatca gagagcaggc tagttaatca aataatagaa gaaatgatta aaaagtcaga 4440
aatttatgta gcatgggtac cagcacacaa aggtatagga ggaaaccaag aaatagacca 4500
cctagttagt caagggatta gacaagttct cttcttggaa aagatagagc cagcacaaga 4560
agaacatgat aaataccata gtaatgtaaa agaattggta ttcaaatttg gattacccag 4620
aatagtggcc agacagatag tagacacctg tgataaatgt catcagaaag gagaggctat 4680
acatgggcag gcaaattcag atctagggac ttggcaaatg gattgtaccc atctagaggg 4740
aaaaataatc atagttgcag tacatgtagc tagtggattc atagaagcag aggtaattcc 4800
acaagagaca ggaagacaga cagcactatt tctgttaaaa ttggcaggca gatggcctat 4860
tacacatcta cacacagata atggtgctaa ctttgcttcg caagaagtaa agatggttgc 4920
atggtgggca gggatagagc acacctttgg ggtaccatac aatccacaga gtcagggagt 4980
agtggaagca atgaatcacc acctgaaaaa tcaaatagat agaatcaggg aacaagcaaa 5040
ttcagtagaa accatagtat taatggcagt tcattgcatg aattttaaaa gaaggggagg 5100
aataggggat atgactccag cagaaagatt aattaacatg atcactacag aacaagagat 5160
acaatttcaa caatcaaaaa actcaaaatt taaaaatttt cgggtctatt acagagaagg 5220
cagagatcaa ctgtggaagg gacccggtga gctattgtgg aaaggggaag gagcagtcat 5280
cttaaaggta gggacagaca ttaaggtagt acccagaaga aaggctaaaa ttatcaaaga 5340
ttatggagga ggaaaagagg tggatagcag ttcccacatg gaggataccg gagaggctag 5400
agaggtggca tagcctcata aaatatctga aatataaaac taaagatcta caaaaggttt 5460
gctatgtgcc ccattttaag gtcggatggg catggtggac ctgcagcaga gtaatcttcc 5520

-continued

```
cactacagga aggaagccat ttagaagtac aagggtattg gcatttgaca ccagaaaaag   5580
ggtggctcag tacttatgca gtgaggataa cctggtactc aaagaacttt tggacagatg   5640
taacaccaaa ctatgcagac attttactgc atagcactta tttcccttgc tttacagcgg   5700
gagaagtgag aagggccatc aggggagaac aactgctgtc ttgctgcagg ttcccgagag   5760
ctcataagta ccaggtacca agcctacagt acttagcact gaaagtagta agcgatgtca   5820
gatcccaggg agagaatccc acctggaaac agtggagaag agacaatagg agaggccttc   5880
gaatggctaa acagaacagt agaggagata aacagagagg cggtaaacca cctaccaagg   5940
gagctaattt tccaggtttg gcaaaggtct tgggaatact ggcatgatga acaagggatg   6000
tcaccaagct atgtaaaata cagatacttg tgtttaatac aaaaggcttt atttatgcat   6060
tgcaagaaag gctgtagatg tctaggggaa ggacatgggg caggggggatg gagaccagga   6120
cctcctcctc ctccccctcc aggactagca taaatggaag aaagacctcc agaaaatgaa   6180
ggaccacaaa gggaaccatg ggatgaatgg gtagtggagg ttctggaaga actgaaagaa   6240
gaagctttaa aacattttga tcctcgcttg ctaactgcac ttggtaatca tatctataat   6300
agacatggag acacccttga gggagcagga gaactcatta gaatcctcca acgagcgctc   6360
ttcatgcatt tcagaggcgg atgcatccac tccagaatcg gccaacctgg gggaggaaat   6420
cctctctcag ctataccgcc ctctagaagc atgctataac acatgctatt gtaaaaagtg   6480
ttgctaccat tgccagtttt gttttcttaa aaaaggcttg ggatatgtt atgagcaatc   6540
acgaaagaga agaagaactc cgaaaaaggc taaggctaat acatcttctg catcaaacaa   6600
gtaagtatgg gatgtcttgg gaatcagctg cttatcgcca tcttgctttt aagtgtctat   6660
gggatctatt gtactctata tgtcacagtc ttttatggtg taccagcttg gaggaatgcg   6720
acaattcccc tcttttgtgc aaccaagaat agggatactt ggggaacaac tcagtgccta   6780
ccagataatg gtgattattc agaagtggcc cttaatgtta cagaaagctt tgatgcctgg   6840
aataatacag tcacagaaca ggcaatagag gatgtatggc aactctttga gacctcaata   6900
aagccttgtg taaaattatc cccattatgc attactatga gatgcaataa aagtgagaca   6960
gatagatggg gattgacaaa atcaataaca acaacagcat caacaacatc aacgacagca   7020
tcagcaaaag tagacatggt caatgagact agttcttgta tagcccagga taattgcaca   7080
ggcttggaac aagagcaaat gataagctgt aaattcaaca tgacagggtt aaaaagagac   7140
aagaaaaaag agtacaatga aacttggtac tctgcagatt tggtatgtga acaagggaat   7200
aacactggta atgaaagtag atgttacatg aaccactgta acacttctgt tatccaagag   7260
tcttgtgaca aacattattg ggatgctatt agatttaggt attgtgcacc tccaggttat   7320
gctttgctta gatgtaatga cacaaattat tcaggcttta tgcctaaatg ttctaaggtg   7380
gtggtctctt catgcacaag gatgatggag acacagactt ctacttggtt tggctttaat   7440
ggaactagag cagaaaatag aacttatatt tactggcatg gtagggataa taggactata   7500
attagtttaa ataagtatta taatctaaca atgaaatgta gaagaccagg aaataagaca   7560
gttttaccag tcaccattat gtctggattg gttttccact cacaaccaat caatgatagg   7620
ccaaagcagg catggtgttg gtttggagga aaatggaagg atgcaataaa agaggtgaag   7680
cagaccattg tcaaacatcc caggtatact ggaactaaca atactgataa aatcaatttg   7740
acggctcctg gaggaggaga tccggaagtt accttcatgt ggacaaattg cagaggagag   7800
ttcctctact gtaaaatgaa ttggtttcta aattgggtag aagataggaa tacagctaac   7860
```

-continued

```
cagaagccaa aggaacagca taaaaggaat tacgtgccat gtcatattag acaaataatc   7920
aacacttggc ataaagtagg caaaaatgtt tatttgcctc caagagaggg agacctcacg   7980
tgtaactcca cagtgaccag tctcatagca aacatagatt ggattgatgg aaaccaaact   8040
aatatcacca tgagtgcaga ggtggcagaa ctgtatcgat tggaattggg agattataaa   8100
ttagtagaga tcactccaat tggcttggcc cccacagatg tgaagaggta cactactggt   8160
ggcacctcaa gaaataaaag aggggtcttt gtgctagggt tcttgggttt tctcgcaacg   8220
gcaggttctg caatgggcgc ggcgtcgttg acgctgaccg ctcagtcccg aactttattg   8280
gctgggatag tgcagcaaca gcaacagctg ttggacgtgg tcaagagaca acaagaattg   8340
ttgcgactga ccgtctgggg aacaaagaac ctccagacta gggtcactgc catcgagaag   8400
tacttaaagg accaggcgca gctgaatgct tggggatgtg cgtttagaca agtctgccac   8460
actactgtac catggccaaa tgcaagtcta acaccaaagt ggaacaatga gacttggcaa   8520
gagtgggagc gaaaggttga cttcttggaa gaaaatataa cagccctcct agaggaggca   8580
caaattcaac aagagaagaa catgtatgaa ttacaaaagt tgaatagctg ggatgtgttt   8640
ggcaattggt ttgaccttgc ttcttggata aagtatatac aatatggagt ttatatagtt   8700
gtaggagtaa tactgttaag aatagtgatc tatatagtac aaatgctagc taagttaagg   8760
caggggtata ggccagtgtt ctcttcccca ccctcttatt tccagcagac ccatatccaa   8820
caggacccgg cactgccaac cagagaaggc aaagaaagag acggtggaga aggcggtggc   8880
aacagctcct ggccttggca gatagaatat attcatttcc tgatccgcca actgatacgc   8940
ctcttgactt ggctattcag caactgcaga accttgctat cgagagtata ccagatcctc   9000
caaccaatac tccagaggct ctctgcgacc ctacagagga ttcgagaagt cctcaggact   9060
gaactgacct acctacaata tgggtggagc tatttccatg aggcggtcca ggccgtctgg   9120
agatctgcga cagagactct tgcgggcgcg tggggagact tatgggagac tcttaggaga   9180
ggtggaagat ggatactcgc aatccccagg aggattagac aagggcttga gctcactctc   9240
ttgtgaggga cagaaataca atcagggaca gtatatgaat actccatgga gaaacccagc   9300
tgaagagaga gaaaaattag catacagaaa acaaaatatg gatgatatag atgaggaaga   9360
tgatgacttg gtaggggtat cagtgaggcc aaaagttccc ctaagaacaa tgagttacaa   9420
attggcaatt gacatgtcac atttcattaa ggagaagggc ggactggagg ggatatacta   9480
ttctgccagg aggcatagaa tcttagacat atacttagaa aaggaaggag gcatcatacc   9540
agattggcag gattacacct caggaccagg aattagatac ccaaagacat ttggctggct   9600
atggaaatta gtccctgtaa atgtatcaga tgaggcacag gaggatgagg agcattattt   9660
aatgcatcca gctcaaactt cccagtggga tgacccttgg ggagaggttc tagcatggaa   9720
gtttgatcca actctggcct acacttatga ggcatatgtt agatacccag aagagtttgg   9780
aagcaagtca ggcctgtcag aggaagaggt tagaagaagg ctaaccgcaa gaggccttct   9840
taacatggct gacaagaagg aaactcgctg aacgcgtcgg atcccggagt actacaaaga   9900
ctgctgacgc gaattccgcc cccccccccta acgttactgg ccgaagccgc ttggaataag   9960
gccggtgtgc gtttgtctat atgttatttt ccaccatatt gccgtctttt ggcaatgtga  10020
gggcccggaa acctggccct gtcttcttga cgagcattcc taggggtctt tcccctctcg  10080
ccaaaggaat gcaaggtctg ttgaatgtcg tgaaggaagc agttcctctg gaagcttctt  10140
gaagacaaac aacgtctgta gcgacccttt gcaggcagcg gaacccccca cctggcgaca  10200
ggtgcctctg cggccaaaag ccacgtgtat aagatacacc tgcaaaggcg gcacaacccc  10260
```

-continued

```
agtgccacgt tgtgagttgg atagttgtgg aaagagtcaa atggctctcc tcaagcgtat  10320
tcaacaaggg gctgaaggat gcccagaagg taccccattg tatgggatct gatctggggc  10380
ctcggtgcac atgctttaca tgtgtttagt cgaggttaaa aaacgtctag gccccccgaa  10440
ccacggggac gtggttttcc tttgaaaaac acgatgataa taccatggtg cccaagaaga  10500
agaggaaagt ctccaacctg ctgactgtgc accaaaacct gcctgccctc cctgtggatg  10560
ccacctctga tgaagtcagg aagaacctga tggacatgtt cagggacagg caggccttct  10620
ctgaacacac ctggaagatg ctcctgtctg tgtgcagatc ctgggctgcc tggtgcaagc  10680
tgaacaacag gaaatggttc cctgctgaac ctgaggatgt gagggactac ctcctgtacc  10740
tgcaagccag aggcctggct gtgaagacca tccaacagca cctgggccag ctcaacatgc  10800
tgcacaggag atctggcctg cctcgccctt ctgactccaa tgctgtgtcc ctggtgatga  10860
ggagaatcag aaaggagaat gtggatgctg gggagagagc caagcaggcc ctggcctttg  10920
aacgcactga ctttgaccaa gtcagatccc tgatggagaa ctctgacaga tgccaggaca  10980
tcaggaacct ggccttcctg ggcattgcct acaacaccct gctgcgcatt gccgaaattg  11040
ccagaatcag agtgaaggac atctcccgca ccgatggtgg gagaatgctg atccacattg  11100
gcaggaccaa gaccctggtg tccacagctg gtgtggagaa ggccctgtcc ctgggggtta  11160
ccaagctggt ggagagatgg atctctgtgt ctggtgtggc tgatgacccc aacaactacc  11220
tgttctgccg ggtcagaaag aatggtgtgg ctgccccttc tgccacctcc caactgtcca  11280
cccgggccct ggaagggatc tttgaggcca cccaccgcct gatctatggt gccaaggatg  11340
actctgggca gagatacctg gcctggtctg gccactctgc cagagtgggt gctgccaggg  11400
acatggccag ggctggtgtg tccatccctg aaatcatgca ggctggtggc tggaccaatg  11460
tgaacatagt gatgaactac atcagaaacc tggactctga gactggggcc atggtgaggc  11520
tgctcgagga tggggactga cccgggtctc attttataaa agaaaagggg ggactggaag  11580
ggatttatcc gcggttcact cgagactcgc tgaaacagca gggactttcc acaaggggat  11640
gttacgggga ggtactgggg aggagccggt cgggaacgcc cactttcttg atgtataaat  11700
atcactgcat ttcgctctgt attcagtcgc tctgcggaga ggctggcaga ttgagccctg  11760
ggaggttctc tccagcacta gcaggtagag cctgggtgtt ccctgctaga ctctcaccag  11820
cacttggccg gtgctgggca gagtgactcc acgcttgctt gcttaaagcc ctcttcaata  11880
aagctgccat tttagaagta agctagtgtg tgttcccatc tctcctagcc gccgcctggt  11940
caactcggta ctcaataata agaagaccct ggtctgttag gaccctttct gctttgggaa  12000
accgaagcag gaaaatccct agcagaattc ttgaagacga aagggcctcg tgatacgcct  12060
atttttatag gttaatgtca tgataataat ggtttcttag acgtcaggtg gcacttttcg  12120
gggaaatgtg cgcggaaccc ctatttgttt atttttctaa atacattcaa atatgtatcc  12180
gctcatgaga caataaccct gataaatgct tcaataatat tgaaaaagga agagtatgag  12240
tattcaacat ttccgtgtcg cccttattcc cttttttgcg gcattttgcc ttcctgtttt  12300
tgctcaccca gaaacgctgg tgaaagtaaa agatgctgaa gatcagttgg gtgcacgagt  12360
gggttacatc gaactggatc tcaacagcgg taagatcctt gagagttttc gccccgaaga  12420
acgttttcca atgatgagca cttttaaagt tctgctatgt ggcgcggtat tatcccgtgt  12480
tgacgccggg caagagcaac tcggtcgccg catacactat tctcagaatg acttggttga  12540
gtactcacca gtcacagaaa agcatcttac ggatggcatg acagtaagag aattatgcag  12600
```

```
tgctgccata accatgagtg ataacactgc ggccaactta cttctgacaa cgatcggagg  12660

accgaaggag ctaaccgctt ttttgcacaa catgggggat catgtaactc gccttgatcg  12720

ttgggaaccg gagctgaatg aagccatacc aaacgacgag cgtgacacca cgatgcctgc  12780

agcaatggca acaacgttgc gcaaactatt aactggcgaa ctacttactc tagcttcccg  12840

gcaacaatta atagactgga tggaggcgga taaagttgca ggaccacttc tgcgctcggc  12900

ccttccggct ggctggttta ttgctgataa atctggagcc ggtgagcgtg ggtctcgcgg  12960

tatcattgca gcactggggc cagatggtaa gccctcccgt atcgtagtta tctacacgac  13020

ggggagtcag gcaactatgg atgaacgaaa tagacagatc gctgagatag gtgcctcact  13080

gattaagcat tggtaactgt cagaccaagt ttactcatat atactttaga ttgatttaaa  13140

acttcatttt taatttaaaa ggatctaggt gaagatcctt tttgataatc tcatgaccaa  13200

aatcccttaa cgtgagtttt cgttccactg agcgtcagac cccgtagaaa agatcaaagg  13260

atcttcttga gatccttttt ttctgcgcgt aatctgctgc ttgcaaacaa aaaaaccacc  13320

gctaccagcg gtggtttgtt tgccggatca agagctacca actctttttc cgaaggtaac  13380

tggcttcagc agagcgcaga taccaaatac tgtccttcta gtgtagccgt agttaggcca  13440

ccacttcaag aactctgtag caccgcctac atacctcgct ctgctaatcc tgttaccagt  13500

ggctgctgcc agtggcgata agtcgtgtct taccgggttg gactcaagac gatagttacc  13560

ggataaggcg cagcggtcgg gctgaacggg gggttcgtgc acacagccca gcttggagcg  13620

aacgacctac accgaactga gatacctaca gcgtgagcta tgagaaagcg ccacgcttcc  13680

cgaagggaga aaggcggaca ggtatccggt aagcggcagg gtcggaacag gagagcgcac  13740

gagggagctt ccagggggaa acgcctggta tctttatagt cctgtcgggt ttcgccacct  13800

ctgacttgag cgtcgatttt tgtgatgctc gtcagggggg cggagcctat ggaaaaacgc  13860

cagcaacgcg gcctttttac ggttcctggc cttttgctgg ccttttgctc acatgttctt  13920

tcctgcgtta tcccctgatt ctgtggataa ccgtattacc gcctttgagt gagctgatac  13980

cgctcgccgc agccgaacga ccgagcgcag cgagtcagtg agcgaggaag cggaagagcg  14040

cctgatgcgg tattttctcc ttacgcatct gtgcggtatt tcacaccgca tatggtgcac  14100

tctcagtaca atctgctctg atgccgcata gttaagccag tatacactcc gctatcgcta  14160

cgtgactggg tcatggctgc gccccgacac ccgccaacac ccgctgacgc gccctgacgg  14220

gcttgtctgc tcccggcatc cgcttacaga caagctgtga ccgtctccgg gagctgcatg  14280

tgtcagaggt tttcaccgtc atcaccgaaa cgcgcgaggc agatcccgca agaggcccgg  14340

cagtaccggc ataaccaagc ctatgcctac agcatccagg gtgacggtgc cgaggatgac  14400

gatgagcgca ttgttagatt tcatacacgg tgcctgactg cgttagcaat ttaactgtga  14460

taaactaccg cattaaagct tactgtaaat ttactggctg tcttccttgc aggtttc     14517
```

```
<210> SEQ ID NO 15
<211> LENGTH: 14596
<212> TYPE: DNA
<213> ORGANISM: Artificial Sequence
<220> FEATURE:
<223> OTHER INFORMATION: pBR-SIVmac239-Nef-CMV-Cre :

<400> SEQUENCE: 15

tggaagggat ttattacagt gcaagaagac atagaatctt agacatatac ttagaaaagg     60

aagaaggcat cataccagat tggcaggatt acacctcagg accaggaatt agatacccaa    120

agacatttgg ctggctatgg aaattagtcc ctgtaaatgt atcagatgag gcacaggagg    180
```

-continued

```
atgaggagca ttatttaatg catccagctc aaacttccca gtgggatgac ccttggggag    240
aggttctagc atggaagttt gatccaactc tggcctacac ttatgaggca tatgttagat    300
acccagaaga gtttggaagc aagtcaggcc tgtcagagga agaggttaga agaaggctaa    360
ccgcaagagg ccttcttaac atggctgaca agaaggaaac tcgctgaaac agcagggact    420
ttccacaagg ggatgttacg gggaggtact ggggaggagc cggtcgggaa cgcccacttt    480
cttgatgtat aaatatcact gcatttcgct ctgtattcag tcgctctgcg gagaggctgg    540
cagattgagc cctgggaggt tctctccagc actagcaggt agagcctggg tgttccctgc    600
tagactctca ccagcacttg gccggtgctg ggcagagtga ctccacgctt gcttgcttaa    660
agccctcttc aataaagctg ccattttagg aagtaagcta gtgtgtgttc ccatctctcc    720
tagccgccgc ctggtcaact cggtacttca ataataagaa gactcctggt ctgttaggac    780
cctttctgct ttgggaaacc gaagcaggaa aatccctagc agattggcgc ctgaacaggg    840
acttgaagga gagtgagaga ctcctgagta cggctgagtg aaggcagtaa gggcggcagg    900
aaccaaccac gacggagtgc tcctataaag gcgcgggtcg gtaccagacg gcgtgaggag    960
cgggagagga agaggcctcc ggttgcaggt aagtgcaaca caaaaaagaa atagctgtct   1020
tttatccagg aaggggtaat aagatagagt gggagatggg cgtgagaaac tccgtcttgt   1080
cagggaagaa agcagatgaa ttagaaaaaa ttaggctacg acccaacgga aagaaaaagt   1140
acatgttgaa gcatgtagta tggcagcaa atgaattaga tagatttgga ttagcagaaa   1200
gcctgttgga gaacaaagaa ggatgtcaaa aaatactttc ggtcttagct ccattagtgc   1260
caacaggctc agaaaattta aaaagccttt ataatactgt ctgcgtcatc tggtgcattc   1320
acgcagaaga gaaagtgaaa cacactgagg aagcaaaaca gatagtgcag agacacctag   1380
tggtggaaac aggaacaaca gaaactatgc caaaaacaag tagaccaaca gcaccatcta   1440
gcggcagagg aggaaattac ccagtacaac aaataggtgg taactatgtc cacctgccat   1500
taagcccgag aacattaaat gcctgggtaa aattgataga ggaaaagaaa tttggagcag   1560
aagtagtgcc aggatttcag gcactgtcag aaggttgcac cccctatgac attaatcaga   1620
tgttaaattg tgtgggagac catcaagcgg ctatgcagat tatcagagat attataaacg   1680
aggaggctgc agattgggac ttgcagcacc cacaaccagc tccacaacaa ggacaactta   1740
gggagccgtc aggatcagat attgcaggaa caactagttc agtagatgaa caaatccagt   1800
ggatgtacag acaacagaac cccataccag taggcaacat ttacaggaga tggatccaac   1860
tggggttgca aaaatgtgtc agaatgtata acccaacaaa cattctagat gtaaaacaag   1920
ggccaaaaga gccatttcag agctatgtag acaggttcta caaaagttta agagcagaac   1980
agacagatgc agcagtaaag aattggatga ctcaaacact gctgattcaa aatgctaacc   2040
cagattgcaa gctagtgctg aaggggctgg gtgtgaatcc caccctagaa gaaatgctga   2100
cggcttgtca aggagtaggg ggccgggac agaaggctag attaatggca gaagccctga   2160
aagaggccct cgcaccagtg ccaatccctt ttgcagcagc ccaacagagg ggaccaagaa   2220
agccaattaa gtgttggaat tgtgggaaag agggacactc tgcaaggcaa tgcagagccc   2280
caagaagaca gggatgctgg aaatgtggaa aaatggacca tgttatggcc aaatgcccag   2340
acagacaggc gggtttttta ggccttggtc catggggaaa gaagccccgc aatttcccca   2400
tggctcaagt gcatcagggg ctgatgccaa ctgctccccc agaggaccca gctgtggatc   2460
tgctaaagaa ctacatgcag ttgggcaagc agcagagaga aaagcagaga gaaagcagag   2520
```

-continued

```
agaagcctta caaggaggtg acagaggatt tgctgcacct caattctctc tttggaggag   2580
accagtagtc actgctcata ttgaaggaca gcctgtagaa gtattactgg atacaggggc   2640
tgatgattct attgtaacag gaatagagtt aggtccacat tataccccaa aaatagtagg   2700
aggaatagga ggttttatta atactaaaga atacaaaaat gtagaaatag aagttttagg   2760
caaaaggatt aaagggacaa tcatgacagg ggacaccccg attaacattt ttggtagaaa   2820
tttgctaaca gctctgggga tgtctctaaa ttttcccata gctaaagtag agcctgtaaa   2880
agtcgcctta aagccaggaa aggatggacc aaaattgaag cagtggccat tatcaaaaga   2940
aaagatagtt gcattaagag aaatctgtga aaagatggaa aaggatggtc agttggagga   3000
agctccccg accaatccat acaacacccc cacatttgct ataaagaaaa aggataagaa   3060
caaatggaga atgctgatag attttaggga actaaatagg gtcactcagg actttacgga   3120
agtccaatta ggaataccac accctgcagg actagcaaaa aggaaaagaa ttacagtact   3180
ggatataggt gatgcatatt tctccatacc tctagatgaa gaatttaggc agtacactgc   3240
ctttacttta ccatcagtaa ataatgcaga gccaggaaaa cgatacattt ataaggttct   3300
gcctcaggga tggaaggggt caccagccat cttccaatac actatgagac atgtgctaga   3360
acccttcagg aaggcaaatc cagatgtgac cttagtccag tatatggatg acatcttaat   3420
agctagtgac aggacagacc tggaacatga cagggtagtt ttacagtcaa aggaactctt   3480
gaatagcata gggttttcta ccccagaaga gaaattccaa aaagatcccc catttcaatg   3540
gatggggtac gaattgtggc caacaaaatg gaagttgcaa aagatagagt tgccacaaag   3600
agagacctgg acagtgaatg atatacagaa gttagtagga gtattaaatt gggcagctca   3660
aatttatcca ggtataaaaa ccaaacatct ctgtaggtta attagaggaa aaatgactct   3720
aacagaggaa gttcagtgga ctgagatggc agaagcagaa tatgaggaaa ataaaataat   3780
tctcagtcag gaacaagaag gatgttatta ccaagaaggc aagccattag aagccacggt   3840
aataaagagt caggacaatc agtggtctta taaaattcac caagaagaca aaatactgaa   3900
agtaggaaaa tttgcaaaga taaagaatac acataccaat ggagtgagac tattagcaca   3960
tgtaatacag aaaataggaa aggaagcaat agtgatctgg ggacaggtcc caaaattcca   4020
cttaccagtt gagaaggatg tatgggaaca gtggtggaca gactattggc aggtaacctg   4080
gataccggaa tgggatttta tctcaacacc accgctagta agattagtct tcaatctagt   4140
gaaggaccct atagagggag aagaaaccta ttatacagat ggatcatgta ataaacagtc   4200
aaaagaaggg aaagcaggat atatcacaga taggggcaaa gacaaagtaa aagtgttaga   4260
acagactact aatcaacaag cagaattgga agcatttctc atggcattga cagactcagg   4320
gccaaaggca aatattatag tagattcaca atatgttatg ggaataataa caggatgccc   4380
tacagaatca gagagcaggc tagttaatca aataatagaa gaaatgatta aaaagtcaga   4440
aatttatgta gcatgggtac cagcacacaa aggtatagga ggaaaccaag aaatagacca   4500
cctagttagt caagggatta gacaagttct cttcttggaa aagatagagc cagcacaaga   4560
agaacatgat aaataccata gtaatgtaaa agaattggta ttcaaatttg gattacccag   4620
aatagtggcc agacagatag tagacacctg tgataaatgt catcagaaag gagaggctat   4680
acatgggcag gcaaattcag atctagggac ttggcaaatg gattgtaccc atctagaggg   4740
aaaaataatc atagttgcag tacatgtagc tagtggattc atagaagcag aggtaattcc   4800
acaagagaca ggaagacaga cagcactatt tctgttaaaa ttggcaggca gatggcctat   4860
tacacatcta cacacagata atggtgctaa ctttgcttcg caagaagtaa agatggttgc   4920
```

atggtgggca gggatagagc acacctttgg ggtaccatac aatccacaga gtcagggagt 4980
agtggaagca atgaatcacc acctgaaaaa tcaaatagat agaatcaggg aacaagcaaa 5040
ttcagtagaa accatagtat taatggcagt tcattgcatg aattttaaaa gaaggggagg 5100
aataggggat atgactccag cagaaagatt aattaacatg atcactacag aacaagagat 5160
acaatttcaa caatcaaaaa actcaaaatt taaaaatttt cgggtctatt acagagaagg 5220
cagagatcaa ctgtggaagg gacccggtga gctattgtgg aaaggggaag gagcagtcat 5280
cttaaaggta gggacagaca ttaaggtagt acccagaaga aaggctaaaa ttatcaaaga 5340
ttatggagga ggaaaagagg tggatagcag ttcccacatg gaggataccg gagaggctag 5400
agaggtggca tagcctcata aaatatctga aatataaaac taaagatcta caaaaggttt 5460
gctatgtgcc ccattttaag gtcggatggg catggtggac ctgcagcaga gtaatcttcc 5520
cactacagga aggaagccat ttagaagtac aagggtattg gcatttgaca ccagaaaaag 5580
ggtggctcag tacttatgca gtgaggataa cctggtactc aaagaacttt tggacagatg 5640
taacaccaaa ctatgcagac attttactgc atagcactta tttcccttgc tttacagcgg 5700
gagaagtgag aagggccatc aggggagaac aactgctgtc ttgctgcagg ttcccgagag 5760
ctcataagta ccaggtacca agcctacagt acttagcact gaaagtagta agcgatgtca 5820
gatcccaggg agagaatccc acctggaaac agtggagaag agacaatagg agaggccttc 5880
gaatggctaa acagaacagt agaggagata aacagagagg cggtaaacca cctaccaagg 5940
gagctaattt tccaggtttg gcaaaggtct tgggaatact ggcatgatga acaagggatg 6000
tcaccaagct atgtaaaata cagatacttg tgtttaatac aaaaggcttt atttatgcat 6060
tgcaagaaag gctgtagatg tctaggggaa ggacatgggg caggggggatg gagaccagga 6120
cctcctcctc ctccccctcc aggactagca taaatggaag aaagacctcc agaaaatgaa 6180
ggaccacaaa gggaaccatg ggatgaatgg gtagtggagg ttctggaaga actgaaagaa 6240
gaagctttaa aacattttga tcctcgcttg ctaactgcac ttggtaatca tatctataat 6300
agacatggag acacccttga gggagcagga gaactcatta gaatcctcca acgagcgctc 6360
ttcatgcatt tcagaggcgg atgcatccac tccagaatcg gccaacctgg gggaggaaat 6420
cctctctcag ctataccgcc ctctagaagc atgctataac acatgctatt gtaaaaagtg 6480
ttgctaccat tgccagtttt gttttcttaa aaaaggcttg gggatatgtt atgagcaatc 6540
acgaaagaga agaagaactc cgaaaaaggc taaggctaat acatcttctg catcaaacaa 6600
gtaagtatgg gatgtcttgg gaatcagctg cttatcgcca tcttgctttt aagtgtctat 6660
gggatctatt gtactctata tgtcacagtc ttttatggtg taccagcttg gaggaatgcg 6720
acaattcccc tcttttgtgc aaccaagaat agggatactt ggggaacaac tcagtgccta 6780
ccagataatg gtgattattc agaagtggcc cttaatgtta cagaaagctt tgatgcctgg 6840
aataatacag tcacagaaca ggcaatagag gatgtatggc aactctttga gacctcaata 6900
aagccttgtg taaaattatc cccattatgc attactatga gatgcaataa aagtgagaca 6960
gatagatggg gattgacaaa atcaataaca acaacagcat caacaacatc aacgacagca 7020
tcagcaaaag tagacatggt caatgagact agttcttgta tagcccagga taattgcaca 7080
ggcttggaac aagagcaaat gataagctgt aaattcaaca tgacagggtt aaaaagagac 7140
aagaaaaaag agtacaatga aacttggtac tctgcagatt tggtatgtga acaagggaat 7200
aacactggta atgaaagtag atgttacatg aaccactgta acacttctgt tatccaagag 7260

-continued

```
tcttgtgaca aacattattg ggatgctatt agatttaggt attgtgcacc tccaggttat   7320

gctttgctta gatgtaatga cacaaattat tcaggcttta tgcctaaatg ttctaaggtg   7380

gtggtctctt catgcacaag gatgatggag acacagactt ctacttggtt tggctttaat   7440

ggaactagag cagaaaatag aacttatatt tactggcatg gtagggataa taggactata   7500

attagtttaa ataagtatta taatctaaca atgaaatgta gaagaccagg aaataagaca   7560

gttttaccag tcaccattat gtctggattg gttttccact cacaaccaat caatgatagg   7620

ccaaagcagg catggtgttg gtttggagga aaatggaagg atgcaataaa agaggtgaag   7680

cagaccattg tcaaacatcc caggtatact ggaactaaca atactgataa aatcaatttg   7740

acggctcctg gaggaggaga tccggaagtt accttcatgt ggacaaattg cagaggagag   7800

ttcctctact gtaaaatgaa ttggtttcta aattgggtag aagataggaa tacagctaac   7860

cagaagccaa aggaacagca taaaaggaat tacgtgccat gtcatattag acaaataatc   7920

aacacttggc ataaagtagg caaaaatgtt tatttgcctc caagagaggg agacctcacg   7980

tgtaactcca cagtgaccag tctcatagca aacatagatt ggattgatgg aaaccaaact   8040

aatatcacca tgagtgcaga ggtggcagaa ctgtatcgat tggaattggg agattataaa   8100

ttagtagaga tcactccaat tggcttggcc cccacagatg tgaagaggta cactactggt   8160

ggcacctcaa gaaataaaag aggggtcttt gtgctagggt tcttgggttt tctcgcaacg   8220

gcaggttctg caatgggcgc ggcgtcgttg acgctgaccg ctcagtcccg aactttattg   8280

gctgggatag tgcagcaaca gcaacagctg ttggacgtgg tcaagagaca acaagaattg   8340

ttgcgactga ccgtctgggg aacaaagaac ctccagacta gggtcactgc catcgagaag   8400

tacttaaagg accaggcgca gctgaatgct tggggatgtg cgtttagaca agtctgccac   8460

actactgtac catggccaaa tgcaagtcta acaccaaagt ggaacaatga gacttggcaa   8520

gagtgggagc gaaaggttga cttcttggaa gaaaatataa cagccctcct agaggaggca   8580

caaattcaac aagagaagaa catgtatgaa ttacaaaagt tgaatagctg ggatgtgttt   8640

ggcaattggt ttgaccttgc ttcttggata aagtatatac aatatggagt ttatatagtt   8700

gtaggagtaa tactgttaag aatagtgatc tatatagtac aaatgctagc taagttaagg   8760

caggggtata ggccagtgtt ctcttcccca ccctcttatt tccagcagac ccatatccaa   8820

caggacccgg cactgccaac cagagaaggc aaagaaagag acggtggaga aggcggtggc   8880

aacagctcct ggccttggca gatagaatat attcatttcc tgatccgcca actgatacgc   8940

ctcttgactt ggctattcag caactgcaga accttgctat cgagagtata ccagatcctc   9000

caaccaatac tccagaggct ctctgcgacc ctacagagga ttcgagaagt cctcaggact   9060

gaactgacct acctacaata tgggtggagc tatttccatg aggcggtcca ggccgtctgg   9120

agatctgcga cagagactct tgcgggcgcg tggggagact tatgggagac tcttaggaga   9180

ggtggaagat ggatactcgc aatccccagg aggattagac aagggcttga gctcactctc   9240

ttgtgaggga cagaaataca atcagggaca gtatatgaat actccatgga gaaacccagc   9300

tgaagagaga gaaaaattag catacagaaa acaaaatatg gatgatatag atgaggaaga   9360

tgatgacttg gtaggggtat cagtgaggcc aaaagttccc ctaagaacaa tgagttacaa   9420

attggcaata gacatgtctc attttataaa agaaaagggg ggactggaag ggatttatta   9480

cagtgcaaga agacatagaa tcttagacat atacttagaa aaggaaggag gcatcatacc   9540

agattggcag gattacacct caggaccagg aattagatac ccaaagacat ttggctggct   9600

atggaaatta gtccctgtaa atgtatcaga tgaggcacag gaggatgagg agcattattt   9660
```

```
aatgcatcca gctcaaactt cccagtggga tgacccttgg ggagaggttc tagcatggaa   9720
gtttgatcca actctggcct acacttatga ggcatatgtt agatacccag aagagtttgg   9780
aagcaagtca ggcctgtcag aggaagaggt tagaagaagg ctaaccgcaa gaggccttct   9840
taacatggct gacaagaagg aaactcgctg aacgcgtatt gcattactag ttattaatag   9900
taatcaatta cggggtcatt agttcatagc ccatatatgg agttccgcgt tacataactt   9960
acggtaaatg gcccgcctgg ctgaccgccc aacgaccccc gcccattgac gtcaataatg  10020
acgtatgttc ccatagtaac gccaataggg actttccatt gacgtcaatg ggtggagtat  10080
ttacggtaaa ctgcccactt ggcagtacat caagtgtatc atatgccaag tccgccccct  10140
attgacgtca atgacggtaa atggcccgcc tggcattatg cccagtacat gaccttacgg  10200
gactttccta cttggcagta catctacgta ttagtcatcg ctattaccat ggtgatgcgg  10260
ttttggcagt acaccaatgg gcgtggatag cggtttgact cacggggatt tccaagtctc  10320
caccccattg acgtcaatgg gagtttgttt tggcaccaaa atcaacggga ctttccaaaa  10380
tgtcgtaata accccgcccc gttgacgcaa atgggcggta ggcgtgtacg gtgggaggtc  10440
tatataagca gagctcgttt agtgaaccgt cagaattgtt tttattttta attttctttc  10500
aaatacttcc atcgaattca gatctggtac cacgcgtacc atggtgccca agaagaagag  10560
gaaagtctcc aacctgctga ctgtgcacca aaacctgcct gccctccctg tggatgccac  10620
ctctgatgaa gtcaggaaga acctgatgga catgttcagg gacaggcagg ccttctctga  10680
acacacctgg aagatgctcc tgtctgtgtg cagatcctgg gctgcctggt gcaagctgaa  10740
caacaggaaa tggttccctg ctgaacctga ggatgtgagg gactacctcc tgtacctgca  10800
agccagaggc ctggctgtga agaccatcca acagcacctg ggccagctca acatgctgca  10860
caggagatct ggcctgcctc gcccttctga ctccaatgct gtgtccctgg tgatgaggag  10920
aatcagaaag gagaatgtgg atgctgggga gagagccaag caggccctgg cctttgaacg  10980
cactgacttt gaccaagtca gatccctgat ggagaactct gacagatgcc aggacatcag  11040
gaacctggcc ttcctgggca ttgcctacaa caccctgctg cgcattgccg aaattgccag  11100
aatcagagtg aaggacatct cccgcaccga tggtgggaga atgctgatcc acattggcag  11160
gaccaagacc ctggtgtcca cagctggtgt ggagaaggcc ctgtccctgg gggttaccaa  11220
gctggtggag agatggatct ctgtgtctgg tgtggctgat gaccccaaca actacctgtt  11280
ctgccgggtc agaaagaatg gtgtggctgc cccttctgcc acctcccaac tgtccacccg  11340
ggccctggaa gggatctttg aggccaccca ccgcctgatc tatggtgcca aggatgactc  11400
tgggcagaga tacctggcct ggtctggcca ctctgccaga gtgggtgctg ccagggacat  11460
ggccagggct ggtgtgtcca tccctgaaat catgcaggct ggtggctgga ccaatgtgaa  11520
catagtgatg aactacatca gaaacctgga ctctgagact ggggccatgg tgaggctgct  11580
cgaggatggg gacggtggtg gtggcaagct ttgacgcatc ccgggtctca ttttataaaa  11640
gaaaaggggg gactggaagg gatttatccg cggttcactc gagactcgct gaaacagcag  11700
ggactttcca caaggggatg ttacggggag gtactgggga ggagccggtc gggaacgccc  11760
actttcttga tgtataaata tcactgcatt tcgctctgta ttcagtcgct ctgcggagag  11820
gctggcagat tgagccctgg gaggttctct ccagcactag caggtagagc ctgggtgttc  11880
cctgctagac tctcaccagc acttggccgg tgctgggcag agtgactcca cgcttgcttg  11940
cttaaagccc tcttcaataa agctgccatt ttagaagtaa gctagtgtgt gttcccatct  12000
```

```
ctcctagccg ccgcctggtc aactcggtac tcaataataa gaagaccctg gtctgttagg  12060
accctttctg ctttgggaaa ccgaagcagg aaaatcccta gcagaattct tgaagacgaa  12120
agggcctcgt gatacgccta tttttatagg ttaatgtcat gataataatg gtttcttaga  12180
cgtcaggtgg cacttttcgg ggaaatgtgc gcggaacccc tatttgttta tttttctaaa  12240
tacattcaaa tatgtatccg ctcatgagac aataaccctg ataaatgctt caataatatt  12300
gaaaaaggaa gagtatgagt attcaacatt tccgtgtcgc ccttattccc ttttttgcgg  12360
cattttgcct tcctgttttt gctcacccag aaacgctggt gaaagtaaaa gatgctgaag  12420
atcagttggg tgcacgagtg ggttacatcg aactggatct caacagcggt aagatccttg  12480
agagttttcg ccccgaagaa cgttttccaa tgatgagcac ttttaaagtt ctgctatgtg  12540
gcgcggtatt atcccgtgtt gacgccgggc aagagcaact cggtcgccgc atacactatt  12600
ctcagaatga cttggttgag tactcaccag tcacagaaaa gcatcttacg gatggcatga  12660
cagtaagaga attatgcagt gctgccataa ccatgagtga taacactgcg gccaacttac  12720
ttctgacaac gatcggagga ccgaaggagc taaccgcttt tttgcacaac atgggggatc  12780
atgtaactcg ccttgatcgt tgggaaccgg agctgaatga agccatacca aacgacgagc  12840
gtgacaccac gatgcctgca gcaatggcaa caacgttgcg caaactatta actggcgaac  12900
tacttactct agcttcccgg caacaattaa tagactggat ggaggcggat aaagttgcag  12960
gaccacttct gcgctcggcc cttccggctg gctggtttat tgctgataaa tctggagccg  13020
gtgagcgtgg gtctcgcggt atcattgcag cactggggcc agatggtaag ccctcccgta  13080
tcgtagttat ctacacgacg gggagtcagg caactatgga tgaacgaaat agacagatcg  13140
ctgagatagg tgcctcactg attaagcatt ggtaactgtc agaccaagtt tactcatata  13200
tactttagat tgatttaaaa cttcattttt aatttaaaag gatctaggtg aagatccttt  13260
ttgataatct catgaccaaa atcccttaac gtgagttttc gttccactga gcgtcagacc  13320
ccgtagaaaa gatcaaagga tcttcttgag atcctttttt tctgcgcgta atctgctgct  13380
tgcaaacaaa aaaaccaccg ctaccagcgg tggtttgttt gccggatcaa gagctaccaa  13440
ctctttttcc gaaggtaact ggcttcagca gagcgcagat accaaatact gtccttctag  13500
tgtagccgta gttaggccac cacttcaaga actctgtagc accgcctaca tacctcgctc  13560
tgctaatcct gttaccagtg gctgctgcca gtggcgataa gtcgtgtctt accgggttgg  13620
actcaagacg atagttaccg gataaggcgc agcggtcggg ctgaacgggg ggttcgtgca  13680
cacagcccag cttggagcga acgacctaca ccgaactgag atacctacag cgtgagctat  13740
gagaaagcgc cacgcttccc gaagggagaa aggcggacag gtatccggta agcggcaggg  13800
tcggaacagg agagcgcacg agggagcttc caggggggaaa cgcctggtat ctttatagtc  13860
ctgtcgggtt tcgccacctc tgacttgagc gtcgattttt gtgatgctcg tcaggggggc  13920
ggagcctatg gaaaaacgcc agcaacgcgg cctttttacg gttcctggcc ttttgctggc  13980
cttttgctca catgttcttt cctgcgttat cccctgattc tgtggataac cgtattaccg  14040
cctttgagtg agctgatacc gctcgccgca gccgaacgac cgagcgcagc gagtcagtga  14100
gcgaggaagc ggaagagcgc ctgatgcggt attttctcct tacgcatctg tgcggtattt  14160
cacaccgcat atggtgcact ctcagtacaa tctgctctga tgccgcatag ttaagccagt  14220
atacactccg ctatcgctac gtgactgggt catggctgcg ccccgacacc cgccaacacc  14280
cgctgacgcg ccctgacggg cttgtctgct cccggcatcc gcttacagac aagctgtgac  14340
cgtctccggg agctgcatgt gtcagaggtt ttcaccgtca tcaccgaaac gcgcgaggca  14400
```

```
gatcccgcaa gaggcccggc agtaccggca taaccaagcc tatgcctaca gcatccaggg  14460
tgacggtgcc gaggatgacg atgagcgcat tgttagattt catacacggt gcctgactgc  14520
gttagcaatt taactgtgat aaactaccgc attaaagctt actgtaaatt tactggctgt  14580
cttccttgca ggtttc                                                  14596
```

<210> SEQ ID NO 16
<211> LENGTH: 14596
<212> TYPE: DNA
<213> ORGANISM: Artificial Sequence
<220> FEATURE:
<223> OTHER INFORMATION: pBR-SIVmac239-Nef (codon opt)-CMV-Cre :

<400> SEQUENCE: 16

```
tggaagggat ttattacagt gcaagaagac atagaatctt agacatatac ttagaaaagg     60
aagaaggcat cataccagat tggcaggatt acacctcagg accaggaatt agatacccaa    120
agacatttgg ctggctatgg aaattagtcc ctgtaaatgt atcagatgag gcacaggagg    180
atgaggagca ttatttaatg catccagctc aaacttccca gtgggatgac ccttggggag    240
aggttctagc atggaagttt gatccaactc tggcctacac ttatgaggca tatgttagat    300
acccagaaga gtttggaagc aagtcaggcc tgtcagagga agaggttaga agaaggctaa    360
ccgcaagagg ccttcttaac atggctgaca agaaggaaac tcgctgaaac agcagggact    420
ttccacaagg ggatgttacg gggaggtact ggggaggagc cggtcgggaa cgcccacttt    480
cttgatgtat aaatatcact gcatttcgct ctgtattcag tcgctctgcg gagaggctgg    540
cagattgagc cctgggaggt tctctccagc actagcaggt agagcctggg tgttccctgc    600
tagactctca ccagcacttg gccggtgctg ggcagagtga ctccacgctt gcttgcttaa    660
agccctcttc aataaagctg ccattttagg aagtaagcta gtgtgtgttc ccatctctcc    720
tagccgccgc ctggtcaact cggtacttca ataataagaa gactcctggt ctgttaggac    780
cctttctgct tgggaaaccc gaagcaggaa aatccctagc agattggcgc ctgaacaggg    840
acttgaagga gagtgagaga ctcctgagta cggctgagtg aaggcagtaa gggcggcagg    900
aaccaaccac gacggagtgc tcctataaag gcgcgggtcg gtaccagacg gcgtgaggag    960
cgggagagga agaggcctcc ggttgcaggt aagtgcaaca caaaaaagaa atagctgtct   1020
tttatccagg aaggggtaat aagatagagt gggagatggg cgtgagaaac tccgtcttgt   1080
cagggaagaa agcagatgaa ttagaaaaaa ttaggctacg acccaacgga aagaaaaagt   1140
acatgttgaa gcatgtagta tgggcagcaa atgaattaga tagatttgga ttagcagaaa   1200
gcctgttgga gaacaaagaa ggatgtcaaa aaatactttc ggtcttagct ccattagtgc   1260
caacaggctc agaaaattta aaaagccttt ataatactgt ctgcgtcatc tggtgcattc   1320
acgcagaaga gaaagtgaaa cacactgagg aagcaaaaca gatagtgcag agacacctag   1380
tggtggaaac aggaacaaca gaaactatgc caaaaacaag tagaccaaca gcaccatcta   1440
gcggcagagg aggaaattac ccagtacaac aaataggtgg taactatgtc cacctgccat   1500
taagcccgag aacattaaat gcctgggtaa aattgataga ggaaaagaaa tttggagcag   1560
aagtagtgcc aggatttcag gcactgtcag aaggttgcac cccctatgac attaatcaga   1620
tgttaaattg tgtgggagac catcaagcgg ctatgcagat tatcagagat attataaacg   1680
aggaggctgc agattgggac ttgcagcacc cacaaccagc tccacaacaa ggacaactta   1740
gggagccgtc aggatcagat attgcaggaa caactagttc agtagatgaa caaatccagt   1800
```

-continued

```
ggatgtacag acaacagaac cccataccag taggcaacat ttacaggaga tggatccaac   1860
tggggttgca aaaatgtgtc agaatgtata acccaacaaa cattctagat gtaaaacaag   1920
ggccaaaaga gccatttcag agctatgtag acaggttcta caaaagttta agagcagaac   1980
agacagatgc agcagtaaag aattggatga ctcaaacact gctgattcaa aatgctaacc   2040
cagattgcaa gctagtgctg aaggggctgg gtgtgaatcc caccctagaa gaaatgctga   2100
cggcttgtca aggagtaggg gggccgggac agaaggctag attaatggca gaagccctga   2160
aagaggccct cgcaccagtg ccaatccctt ttgcagcagc ccaacagagg ggaccaagaa   2220
agccaattaa gtgttggaat tgtgggaaag agggacactc tgcaaggcaa tgcagagccc   2280
caagaagaca gggatgctgg aaatgtggaa aaatggacca tgttatggcc aaatgcccag   2340
acagacaggc gggtttttta ggccttggtc catggggaaa gaagccccgc aatttcccca   2400
tggctcaagt gcatcagggg ctgatgccaa ctgctccccc agaggaccca gctgtggatc   2460
tgctaaagaa ctacatgcag ttgggcaagc agcagagaga aaagcagaga gaaagcagag   2520
agaagcctta caaggaggtg acagaggatt tgctgcacct caattctctc tttggaggag   2580
accagtagtc actgctcata ttgaaggaca gcctgtagaa gtattactgg atacaggggc   2640
tgatgattct attgtaacag gaatagagtt aggtccacat tataccccaa aaatagtagg   2700
aggaatagga ggttttatta atactaaaga atacaaaaat gtagaaatag aagttttagg   2760
caaaaggatt aaagggacaa tcatgacagg ggacaccccg attaacattt ttggtagaaa   2820
tttgctaaca gctctgggga tgtctctaaa ttttcccata gctaaagtag agcctgtaaa   2880
agtcgcctta aagccaggaa aggatggacc aaaattgaag cagtggccat tatcaaaaga   2940
aaagatagtt gcattaagag aaatctgtga aaagatggaa aaggatggtc agttggagga   3000
agctcccccg accaatccat acaacacccc cacatttgct ataaagaaaa aggataagaa   3060
caaatggaga atgctgatag attttaggga actaaatagg gtcactcagg actttacgga   3120
agtccaatta ggaataccac accctgcagg actagcaaaa aggaaaagaa ttacagtact   3180
ggatataggt gatgcatatt tctccatacc tctagatgaa gaatttaggc agtacactgc   3240
ctttacttta ccatcagtaa ataatgcaga gccaggaaaa cgatacattt ataaggttct   3300
gcctcaggga tggaaggggt caccagccat cttccaatac actatgagac atgtgctaga   3360
acccttcagg aaggcaaatc cagatgtgac cttagtccag tatatggatg acatcttaat   3420
agctagtgac aggacagacc tggaacatga cagggtagtt ttacagtcaa aggaactctt   3480
gaatagcata gggttttcta ccccagaaga gaaattccaa aaagatcccc catttcaatg   3540
gatggggtac gaattgtggc caacaaaatg gaagttgcaa aagatagagt tgccacaaag   3600
agagacctgg acagtgaatg atatacagaa gttagtagga gtattaaatt gggcagctca   3660
aatttatcca ggtataaaaa ccaaacatct ctgtaggtta attagaggaa aaatgactct   3720
aacagaggaa gttcagtgga ctgagatggc agaagcagaa tatgaggaaa ataaaataat   3780
tctcagtcag gaacaagaag gatgttatta ccaagaaggc aagccattag aagccacggt   3840
aataaagagt caggacaatc agtggtctta taaaattcac caagaagaca aaatactgaa   3900
agtaggaaaa tttgcaaaga taaagaatac acataccaat ggagtgagac tattagcaca   3960
tgtaatacag aaaataggaa aggaagcaat agtgatctgg ggacaggtcc caaaattcca   4020
cttaccagtt gagaaggatg tatgggaaca gtggtggaca gactattggc aggtaacctg   4080
gataccggaa tgggatttta tctcaacacc accgctagta agattagtct tcaatctagt   4140
gaaggaccct atagagggag aagaaaccta ttatacagat ggatcatgta ataaacagtc   4200
```

-continued aaaagaaggg aaagcaggat atatcacaga taggggcaaa gacaaagtaa aagtgttaga 4260
acagactact aatcaacaag cagaattgga agcatttctc atggcattga cagactcagg 4320
gccaaaggca aatattatag tagattcaca atatgttatg ggaataataa caggatgccc 4380
tacagaatca gagagcaggc tagttaatca aataatagaa gaaatgatta aaaagtcaga 4440
aatttatgta gcatgggtac cagcacacaa aggtatagga ggaaaccaag aaatagacca 4500
cctagttagt caagggatta gacaagttct cttcttggaa aagatagagc cagcacaaga 4560
agaacatgat aaataccata gtaatgtaaa agaattggta ttcaaatttg gattacccag 4620
aatagtggcc agacagatag tagacacctg tgataaatgt catcagaaag gagaggctat 4680
acatgggcag gcaaattcag atctagggac ttggcaaatg gattgtaccc atctagaggg 4740
aaaaataatc atagttgcag tacatgtagc tagtggattc atagaagcag aggtaattcc 4800
acaagagaca ggaagacaga cagcactatt tctgttaaaa ttggcaggca gatggcctat 4860
tacacatcta cacacagata atggtgctaa ctttgcttcg caagaagtaa agatggttgc 4920
atggtgggca gggatagagc acacctttgg ggtaccatac aatccacaga gtcagggagt 4980
agtggaagca atgaatcacc acctgaaaaa tcaaatagat agaatcaggg aacaagcaaa 5040
ttcagtagaa accatagtat taatggcagt tcattgcatg aattttaaaa gaaggggagg 5100
aataggggat atgactccag cagaaagatt aattaacatg atcactacag aacaagagat 5160
acaatttcaa caatcaaaaa actcaaaatt taaaaatttt cgggtctatt acagagaagg 5220
cagagatcaa ctgtggaagg gacccggtga gctattgtgg aaaggggaag gagcagtcat 5280
cttaaaggta gggacagaca ttaaggtagt acccagaaga aaggctaaaa ttatcaaaga 5340
ttatggagga ggaaaagagg tggatagcag ttcccacatg gaggataccg gagaggctag 5400
agaggtggca tagcctcata aaatatctga aatataaaac taaagatcta caaaaggttt 5460
gctatgtgcc ccattttaag gtcggatggg catggtggac ctgcagcaga gtaatcttcc 5520
cactacagga aggaagccat ttagaagtac aagggtattg gcatttgaca ccagaaaaag 5580
ggtggctcag tacttatgca gtgaggataa cctggtactc aaagaacttt tggacagatg 5640
taacaccaaa ctatgcagac attttactgc atagcactta tttcccttgc tttacagcgg 5700
gagaagtgag aagggccatc aggggagaac aactgctgtc ttgctgcagg ttcccgagag 5760
ctcataagta ccaggtacca agcctacagt acttagcact gaaagtagta agcgatgtca 5820
gatcccaggg agagaatccc acctggaaac agtggagaag agacaatagg agaggccttc 5880
gaatggctaa acagaacagt agaggagata aacagagagg cggtaaacca cctaccaagg 5940
gagctaattt tccaggtttg gcaaaggtct tgggaatact ggcatgatga acaagggatg 6000
tcaccaagct atgtaaaata cagatacttg tgtttaatac aaaaggcttt atttatgcat 6060
tgcaagaaag gctgtagatg tctaggggaa ggacatgggg caggggggatg gagaccagga 6120
cctcctcctc ctccccctcc aggactagca taaatggaag aaagacctcc agaaaatgaa 6180
ggaccacaaa gggaaccatg ggatgaatgg gtagtggagg ttctggaaga actgaaagaa 6240
gaagctttaa aacattttga tcctcgcttg ctaactgcac ttggtaatca tatctataat 6300
agacatggag acacccttga gggagcagga gaactcatta gaatcctcca acgagcgctc 6360
ttcatgcatt tcagaggcgg atgcatccac tccagaatcg gccaacctgg gggaggaaat 6420
cctctctcag ctataccgcc ctctagaagc atgctataac acatgctatt gtaaaaagtg 6480
ttgctaccat tgccagtttt gttttcttaa aaaaggcttg ggatatgtt atgagcaatc 6540

-continued

```
acgaaagaga agaagaactc cgaaaaaggc taaggctaat acatcttctg catcaaacaa   6600
gtaagtatgg gatgtcttgg gaatcagctg cttatcgcca tcttgctttt aagtgtctat   6660
gggatctatt gtactctata tgtcacagtc ttttatggtg taccagcttg gaggaatgcg   6720
acaattcccc tcttttgtgc aaccaagaat agggatactt ggggaacaac tcagtgccta   6780
ccagataatg gtgattattc agaagtggcc cttaatgtta cagaaagctt tgatgcctgg   6840
aataatacag tcacagaaca ggcaatagag gatgtatggc aactctttga gacctcaata   6900
aagccttgtg taaaattatc cccattatgc attactatga gatgcaataa aagtgagaca   6960
gatagatggg gattgacaaa atcaataaca acaacagcat caacaacatc aacgacagca   7020
tcagcaaaag tagacatggt caatgagact agttcttgta tagcccagga taattgcaca   7080
ggcttggaac aagagcaaat gataagctgt aaattcaaca tgacagggtt aaaaagagac   7140
aagaaaaaag agtacaatga aacttggtac tctgcagatt tggtatgtga acaagggaat   7200
aacactggta atgaaagtag atgttacatg aaccactgta acacttctgt tatccaagag   7260
tcttgtgaca aacattattg ggatgctatt agatttaggt attgtgcacc tccaggttat   7320
gctttgctta gatgtaatga cacaaattat tcaggcttta tgcctaaatg ttctaaggtg   7380
gtggtctctt catgcacaag gatgatggag acacagactt ctacttggtt tggctttaat   7440
ggaactagag cagaaaatag aacttatatt tactggcatg gtagggataa taggactata   7500
attagtttaa ataagtatta taatctaaca atgaaatgta gaagaccagg aaataagaca   7560
gttttaccag tcaccattat gtctggattg gttttccact cacaaccaat caatgatagg   7620
ccaaagcagg catggtgttg gtttggagga aaatggaagg atgcaataaa agaggtgaag   7680
cagaccattg tcaaacatcc caggtatact ggaactaaca atactgataa aatcaatttg   7740
acggctcctg gaggaggaga tccggaagtt accttcatgt ggacaaattg cagaggagag   7800
ttcctctact gtaaaatgaa ttggtttcta aattgggtag aagataggaa tacagctaac   7860
cagaagccaa aggaacagca taaaaggaat tacgtgccat gtcatattag acaaataatc   7920
aacacttggc ataaagtagg caaaaatgtt tatttgcctc caagagaggg agacctcacg   7980
tgtaactcca cagtgaccag tctcatagca aacatagatt ggattgatgg aaaccaaact   8040
aatatcacca tgagtgcaga ggtggcagaa ctgtatcgat tggaattggg agattataaa   8100
ttagtagaga tcactccaat tggcttggcc cccacagatg tgaagaggta cactactggt   8160
ggcacctcaa gaaataaaag aggggtcttt gtgctagggt tcttgggttt tctcgcaacg   8220
gcaggttctg caatgggcgc ggcgtcgttg acgctgaccg ctcagtcccg aactttattg   8280
gctgggatag tgcagcaaca gcaacagctg ttggacgtgg tcaagagaca acaagaattg   8340
ttgcgactga ccgtctgggg aacaaagaac ctccagacta gggtcactgc catcgagaag   8400
tacttaaagg accaggcgca gctgaatgct tggggatgtg cgtttagaca agtctgccac   8460
actactgtac catggccaaa tgcaagtcta acaccaaagt ggaacaatga gacttggcaa   8520
gagtgggagc gaaaggttga cttcttggaa gaaaatataa cagccctcct agaggaggca   8580
caaattcaac aagagaagaa catgtatgaa ttacaaaagt tgaatagctg ggatgtgttt   8640
ggcaattggt ttgaccttgc ttcttggata aagtatatac aatatggagt ttatatagtt   8700
gtaggagtaa tactgttaag aatagtgatc tatatagtac aaatgctagc taagttaagg   8760
caggggtata ggccagtgtt ctcttcccca ccctcttatt tccagcagac ccatatccaa   8820
caggacccgg cactgccaac cagagaaggc aaagaaagag acggtggaga aggcggtggc   8880
aacagctcct ggccttggca gatagaatat attcatttcc tgatccgcca actgatacgc   8940
```

-continued

```
ctcttgactt ggctattcag caactgcaga accttgctat cgagagtata ccagatcctc   9000
caaccaatac tccagaggct ctctgcgacc ctacagagga ttcgagaagt cctcaggact   9060
gaactgacct acctacaata tgggtggagc tatttccatg aggcggtcca ggccgtctgg   9120
agatctgcga cagagactct tgcgggcgcg tggggagact tatgggagac tcttaggaga   9180
ggtggaagat ggatactcgc aatcccccagg aggattagac aagggcttga gctcactctc   9240
ttgtgaggga cagaaataca atcagggaca gtatatgaat actccatgga gaaacccagc   9300
tgaagagaga gaaaaattag catacagaaa acaaaatatg gatgatatag atgaggaaga   9360
tgatgacttg gtaggggtat cagtgaggcc aaaagttccc ctaagaacaa tgagttacaa   9420
attggcaatt gacatgtcac atttcattaa ggagaagggc ggactggagg ggatatacta   9480
ttctgccagg aggcatagaa tcttagacat atacttagaa aaggaaggag gcatcatacc   9540
agattggcag gattacacct caggaccagg aattagatac ccaaagacat ttggctggct   9600
atggaaatta gtccctgtaa atgtatcaga tgaggcacag gaggatgagg agcattattt   9660
aatgcatcca gctcaaactt cccagtggga tgacccttgg ggagaggttc tagcatggaa   9720
gtttgatcca actctggcct acacttatga ggcatatgtt agatacccag aagagtttgg   9780
aagcaagtca ggcctgtcag aggaagaggt tagaagaagg ctaaccgcaa gaggccttct   9840
taacatggct gacaagaagg aaactcgctg aacgcgtatt gcattactag ttattaatag   9900
taatcaatta cggggtcatt agttcatagc ccatatatgg agttccgcgt tacataactt   9960
acggtaaatg gcccgcctgg ctgaccgccc aacgaccccc gcccattgac gtcaataatg  10020
acgtatgttc ccatagtaac gccaataggg actttccatt gacgtcaatg ggtggagtat  10080
ttacggtaaa ctgcccactt ggcagtacat caagtgtatc atatgccaag tccgccccct  10140
attgacgtca atgacggtaa atggcccgcc tggcattatg cccagtacat gaccttacgg  10200
gactttccta cttggcagta catctacgta ttagtcatcg ctattaccat ggtgatgcgg  10260
ttttggcagt acaccaatgg gcgtggatag cggtttgact cacggggatt tccaagtctc  10320
caccccattg acgtcaatgg gagtttgttt tggcaccaaa atcaacggga ctttccaaaa  10380
tgtcgtaata accccgcccc gttgacgcaa atgggcggta ggcgtgtacg gtgggaggtc  10440
tatataagca gagctcgttt agtgaaccgt cagaattgtt tttattttta attttctttc  10500
aaatacttcc atcgaattca gatctggtac cacgcgtacc atggtgccca agaagaagag  10560
gaaagtctcc aacctgctga ctgtgcacca aaacctgcct gccctccctg tggatgccac  10620
ctctgatgaa gtcaggaaga acctgatgga catgttcagg gacaggcagg ccttctctga  10680
acacacctgg aagatgctcc tgtctgtgtg cagatcctgg gctgcctggt gcaagctgaa  10740
caacaggaaa tggttccctg ctgaacctga ggatgtgagg gactacctcc tgtacctgca  10800
agccagaggc ctggctgtga agaccatcca acagcacctg ggccagctca acatgctgca  10860
caggagatct ggcctgcctc gcccttctga ctccaatgct gtgtccctgg tgatgaggag  10920
aatcagaaag gagaatgtgg atgctgggga gagagccaag caggccctgg cctttgaacg  10980
cactgacttt gaccaagtca gatccctgat ggagaactct gacagatgcc aggacatcag  11040
gaacctggcc ttcctgggca ttgcctacaa caccctgctg cgcattgccg aaattgccag  11100
aatcagagtg aaggacatct cccgcaccga tggtgggaga atgctgatcc acattggcag  11160
gaccaagacc ctggtgtcca cagctggtgt ggagaaggcc ctgtccctgg gggttaccaa  11220
gctggtggag agatggatct ctgtgtctgg tgtggctgat gaccccaaca actacctgtt  11280
```

-continued

```
ctgccgggtc agaaagaatg gtgtggctgc cccttctgcc acctcccaac tgtccacccg  11340
ggccctggaa gggatctttg aggccaccca ccgcctgatc tatggtgcca aggatgactc  11400
tgggcagaga tacctggcct ggtctggcca ctctgccaga gtgggtgctg ccagggacat  11460
ggccagggct ggtgtgtcca tccctgaaat catgcaggct ggtggctgga ccaatgtgaa  11520
catagtgatg aactacatca gaaacctgga ctctgagact ggggccatgg tgaggctgct  11580
cgaggatggg gacggtggtg gtggcaagct ttgacgcatc ccgggtctca ttttataaaa  11640
gaaaaggggg gactggaagg gatttatccg cggttcactc gagactcgct gaaacagcag  11700
ggactttcca caaggggatg ttacggggag gtactgggga ggagccggtc gggaacgccc  11760
actttcttga tgtataaata tcactgcatt tcgctctgta ttcagtcgct ctgcggagag  11820
gctggcagat tgagccctgg gaggttctct ccagcactag caggtagagc ctgggtgttc  11880
cctgctagac tctcaccagc acttggccgg tgctgggcag agtgactcca cgcttgcttg  11940
cttaaagccc tcttcaataa agctgccatt ttagaagtaa gctagtgtgt gttcccatct  12000
ctcctagccg ccgcctggtc aactcggtac tcaataataa gaagaccctg gtctgttagg  12060
accctttctg ctttgggaaa ccgaagcagg aaaatcccta gcagaattct tgaagacgaa  12120
agggcctcgt gatacgccta tttttatagg ttaatgtcat gataataatg gtttcttaga  12180
cgtcaggtgg cacttttcgg ggaaatgtgc gcggaacccc tatttgttta tttttctaaa  12240
tacattcaaa tatgtatccg ctcatgagac aataaccctg ataaatgctt caataatatt  12300
gaaaaaggaa gagtatgagt attcaacatt tccgtgtcgc ccttattccc ttttttgcgg  12360
cattttgcct tcctgttttt gctcacccag aaacgctggt gaaagtaaaa gatgctgaag  12420
atcagttggg tgcacgagtg ggttacatcg aactggatct caacagcggt aagatccttg  12480
agagttttcg ccccgaagaa cgttttccaa tgatgagcac ttttaaagtt ctgctatgtg  12540
gcgcggtatt atcccgtgtt gacgccgggc aagagcaact cggtcgccgc atacactatt  12600
ctcagaatga cttggttgag tactcaccag tcacagaaaa gcatcttacg gatggcatga  12660
cagtaagaga attatgcagt gctgccataa ccatgagtga taacactgcg gccaacttac  12720
ttctgacaac gatcggagga ccgaaggagc taaccgcttt tttgcacaac atgggggatc  12780
atgtaactcg ccttgatcgt tgggaaccgg agctgaatga agccatacca aacgacgagc  12840
gtgacaccac gatgcctgca gcaatggcaa caacgttgcg caaactatta actggcgaac  12900
tacttactct agcttcccgg caacaattaa tagactggat ggaggcggat aaagttgcag  12960
gaccacttct gcgctcggcc cttccggctg gctggtttat tgctgataaa tctggagccg  13020
gtgagcgtgg gtctcgcggt atcattgcag cactggggcc agatggtaag ccctcccgta  13080
tcgtagttat ctacacgacg gggagtcagg caactatgga tgaacgaaat agacagatcg  13140
ctgagatagg tgcctcactg attaagcatt ggtaactgtc agaccaagtt tactcatata  13200
tactttagat tgatttaaaa cttcattttt aatttaaaag gatctaggtg aagatccttt  13260
ttgataatct catgaccaaa atcccttaac gtgagttttc gttccactga gcgtcagacc  13320
ccgtagaaaa gatcaaagga tcttcttgag atcctttttt tctgcgcgta atctgctgct  13380
tgcaaacaaa aaaaccaccg ctaccagcgg tggtttgttt gccggatcaa gagctaccaa  13440
ctctttttcc gaaggtaact ggcttcagca gagcgcagat accaaatact gtccttctag  13500
tgtagccgta gttaggccac cacttcaaga actctgtagc accgcctaca tacctcgctc  13560
tgctaatcct gttaccagtg gctgctgcca gtggcgataa gtcgtgtctt accgggttgg  13620
actcaagacg atagttaccg gataaggcgc agcggtcggg ctgaacgggg ggttcgtgca  13680
```

```
cacagcccag cttggagcga acgacctaca ccgaactgag atacctacag cgtgagctat  13740

gagaaagcgc cacgcttccc gaagggagaa aggcggacag gtatccggta agcggcaggg  13800

tcggaacagg agagcgcacg agggagcttc caggggggaaa cgcctggtat ctttatagtc  13860

ctgtcgggtt tcgccacctc tgacttgagc gtcgattttt gtgatgctcg tcaggggggc  13920

ggagcctatg gaaaaacgcc agcaacgcgg cctttttacg gttcctggcc ttttgctggc  13980

cttttgctca catgttcttt cctgcgttat cccctgattc tgtggataac cgtattaccg  14040

cctttgagtg agctgatacc gctcgccgca gccgaacgac cgagcgcagc gagtcagtga  14100

gcgaggaagc ggaagagcgc ctgatgcggt attttctcct tacgcatctg tgcggtattt  14160

cacaccgcat atggtgcact ctcagtacaa tctgctctga tgccgcatag ttaagccagt  14220

atacactccg ctatcgctac gtgactgggt catggctgcg ccccgacacc cgccaacacc  14280

cgctgacgcg ccctgacggg cttgtctgct cccggcatcc gcttacagac aagctgtgac  14340

cgtctccggg agctgcatgt gtcagaggtt ttcaccgtca tcaccgaaac gcgcgaggca  14400

gatcccgcaa gaggcccggc agtaccggca taaccaagcc tatgcctaca gcatccaggg  14460

tgacggtgcc gaggatgacg atgagcgcat tgttagattt catacacggt gcctgactgc  14520

gttagcaatt taactgtgat aaactaccgc attaaagctt actgtaaatt tactggctgt  14580

cttccttgca ggtttc                                                  14596


<210> SEQ ID NO 17
<211> LENGTH: 1056
<212> TYPE: DNA
<213> ORGANISM: Bacteriophage P1
<220> FEATURE:
<221> NAME/KEY: CDS
<222> LOCATION: (1)..(1056)

<400> SEQUENCE: 17

atg gtg ccc aag aag aag agg aaa gtc tcc aac ctg ctg act gtg cac       48
Met Val Pro Lys Lys Lys Arg Lys Val Ser Asn Leu Leu Thr Val His
1               5                   10                  15

caa aac ctg cct gcc ctc cct gtg gat gcc acc tct gat gaa gtc agg       96
Gln Asn Leu Pro Ala Leu Pro Val Asp Ala Thr Ser Asp Glu Val Arg
            20                  25                  30

aag aac ctg atg gac atg ttc agg gac agg cag gcc ttc tct gaa cac      144
Lys Asn Leu Met Asp Met Phe Arg Asp Arg Gln Ala Phe Ser Glu His
        35                  40                  45

acc tgg aag atg ctc ctg tct gtg tgc aga tcc tgg gct gcc tgg tgc      192
Thr Trp Lys Met Leu Leu Ser Val Cys Arg Ser Trp Ala Ala Trp Cys
    50                  55                  60

aag ctg aac aac agg aaa tgg ttc cct gct gaa cct gag gat gtg agg      240
Lys Leu Asn Asn Arg Lys Trp Phe Pro Ala Glu Pro Glu Asp Val Arg
65                  70                  75                  80

gac tac ctc ctg tac ctg caa gcc aga ggc ctg gct gtg aag acc atc      288
Asp Tyr Leu Leu Tyr Leu Gln Ala Arg Gly Leu Ala Val Lys Thr Ile
                85                  90                  95

caa cag cac ctg ggc cag ctc aac atg ctg cac agg aga tct ggc ctg      336
Gln Gln His Leu Gly Gln Leu Asn Met Leu His Arg Arg Ser Gly Leu
            100                 105                 110

cct cgc cct tct gac tcc aat gct gtg tcc ctg gtg atg agg aga atc      384
Pro Arg Pro Ser Asp Ser Asn Ala Val Ser Leu Val Met Arg Arg Ile
        115                 120                 125

aga aag gag aat gtg gat gct ggg gag aga gcc aag cag gcc ctg gcc      432
Arg Lys Glu Asn Val Asp Ala Gly Glu Arg Ala Lys Gln Ala Leu Ala
    130                 135                 140
```

```
ttt gaa cgc act gac ttt gac caa gtc aga tcc ctg atg gag aac tct      480
Phe Glu Arg Thr Asp Phe Asp Gln Val Arg Ser Leu Met Glu Asn Ser
145                 150                 155                 160

gac aga tgc cag gac atc agg aac ctg gcc ttc ctg ggc att gcc tac      528
Asp Arg Cys Gln Asp Ile Arg Asn Leu Ala Phe Leu Gly Ile Ala Tyr
                165                 170                 175

aac acc ctg ctg cgc att gcc gaa att gcc aga atc aga gtg aag gac      576
Asn Thr Leu Leu Arg Ile Ala Glu Ile Ala Arg Ile Arg Val Lys Asp
            180                 185                 190

atc tcc cgc acc gat ggt ggg aga atg ctg atc cac att ggc agg acc      624
Ile Ser Arg Thr Asp Gly Gly Arg Met Leu Ile His Ile Gly Arg Thr
        195                 200                 205

aag acc ctg gtg tcc aca gct ggt gtg gag aag gcc ctg tcc ctg ggg      672
Lys Thr Leu Val Ser Thr Ala Gly Val Glu Lys Ala Leu Ser Leu Gly
    210                 215                 220

gtt acc aag ctg gtg gag aga tgg atc tct gtg tct ggt gtg gct gat      720
Val Thr Lys Leu Val Glu Arg Trp Ile Ser Val Ser Gly Val Ala Asp
225                 230                 235                 240

gac ccc aac aac tac ctg ttc tgc cgg gtc aga aag aat ggt gtg gct      768
Asp Pro Asn Asn Tyr Leu Phe Cys Arg Val Arg Lys Asn Gly Val Ala
                245                 250                 255

gcc cct tct gcc acc tcc caa ctg tcc acc cgg gcc ctg gaa ggg atc      816
Ala Pro Ser Ala Thr Ser Gln Leu Ser Thr Arg Ala Leu Glu Gly Ile
            260                 265                 270

ttt gag gcc acc cac cgc ctg atc tat ggt gcc aag gat gac tct ggg      864
Phe Glu Ala Thr His Arg Leu Ile Tyr Gly Ala Lys Asp Asp Ser Gly
        275                 280                 285

cag aga tac ctg gcc tgg tct ggc cac tct gcc aga gtg ggt gct gcc      912
Gln Arg Tyr Leu Ala Trp Ser Gly His Ser Ala Arg Val Gly Ala Ala
    290                 295                 300

agg gac atg gcc agg gct ggt gtg tcc atc cct gaa atc atg cag gct      960
Arg Asp Met Ala Arg Ala Gly Val Ser Ile Pro Glu Ile Met Gln Ala
305                 310                 315                 320

ggt ggc tgg acc aat gtg aac ata gtg atg aac tac atc aga aac ctg     1008
Gly Gly Trp Thr Asn Val Asn Ile Val Met Asn Tyr Ile Arg Asn Leu
                325                 330                 335

gac tct gag act ggg gcc atg gtg agg ctg ctc gag gat ggg gac tga     1056
Asp Ser Glu Thr Gly Ala Met Val Arg Leu Leu Glu Asp Gly Asp
            340                 345                 350


<210> SEQ ID NO 18
<211> LENGTH: 351
<212> TYPE: PRT
<213> ORGANISM: Bacteriophage P1

<400> SEQUENCE: 18

Met Val Pro Lys Lys Lys Arg Lys Val Ser Asn Leu Leu Thr Val His
1               5                   10                  15

Gln Asn Leu Pro Ala Leu Pro Val Asp Ala Thr Ser Asp Glu Val Arg
            20                  25                  30

Lys Asn Leu Met Asp Met Phe Arg Asp Arg Gln Ala Phe Ser Glu His
        35                  40                  45

Thr Trp Lys Met Leu Leu Ser Val Cys Arg Ser Trp Ala Ala Trp Cys
    50                  55                  60

Lys Leu Asn Asn Arg Lys Trp Phe Pro Ala Glu Pro Glu Asp Val Arg
65                  70                  75                  80

Asp Tyr Leu Leu Tyr Leu Gln Ala Arg Gly Leu Ala Val Lys Thr Ile
                85                  90                  95
```

```
Gln Gln His Leu Gly Gln Leu Asn Met Leu His Arg Arg Ser Gly Leu
            100                 105                 110

Pro Arg Pro Ser Asp Ser Asn Ala Val Ser Leu Val Met Arg Arg Ile
        115                 120                 125

Arg Lys Glu Asn Val Asp Ala Gly Glu Arg Ala Lys Gln Ala Leu Ala
    130                 135                 140

Phe Glu Arg Thr Asp Phe Asp Gln Val Arg Ser Leu Met Glu Asn Ser
145                 150                 155                 160

Asp Arg Cys Gln Asp Ile Arg Asn Leu Ala Phe Leu Gly Ile Ala Tyr
                165                 170                 175

Asn Thr Leu Leu Arg Ile Ala Glu Ile Ala Arg Ile Arg Val Lys Asp
            180                 185                 190

Ile Ser Arg Thr Asp Gly Gly Arg Met Leu Ile His Ile Gly Arg Thr
        195                 200                 205

Lys Thr Leu Val Ser Thr Ala Gly Val Glu Lys Ala Leu Ser Leu Gly
    210                 215                 220

Val Thr Lys Leu Val Glu Arg Trp Ile Ser Val Ser Gly Val Ala Asp
225                 230                 235                 240

Asp Pro Asn Asn Tyr Leu Phe Cys Arg Val Arg Lys Asn Gly Val Ala
                245                 250                 255

Ala Pro Ser Ala Thr Ser Gln Leu Ser Thr Arg Ala Leu Glu Gly Ile
            260                 265                 270

Phe Glu Ala Thr His Arg Leu Ile Tyr Gly Ala Lys Asp Asp Ser Gly
        275                 280                 285

Gln Arg Tyr Leu Ala Trp Ser Gly His Ser Ala Arg Val Gly Ala Ala
    290                 295                 300

Arg Asp Met Ala Arg Ala Gly Val Ser Ile Pro Glu Ile Met Gln Ala
305                 310                 315                 320

Gly Gly Trp Thr Asn Val Asn Ile Val Met Asn Tyr Ile Arg Asn Leu
                325                 330                 335

Asp Ser Glu Thr Gly Ala Met Val Arg Leu Leu Glu Asp Gly Asp
            340                 345                 350


<210> SEQ ID NO 19
<211> LENGTH: 1074
<212> TYPE: DNA
<213> ORGANISM: Bacteriophage P1
<220> FEATURE:
<221> NAME/KEY: CDS
<222> LOCATION: (1)..(1074)

<400> SEQUENCE: 19

atg gtg ccc aag aag aag agg aaa gtc tcc aac ctg ctg act gtg cac       48
Met Val Pro Lys Lys Lys Arg Lys Val Ser Asn Leu Leu Thr Val His
1               5                   10                  15

caa aac ctg cct gcc ctc cct gtg gat gcc acc tct gat gaa gtc agg       96
Gln Asn Leu Pro Ala Leu Pro Val Asp Ala Thr Ser Asp Glu Val Arg
            20                  25                  30

aag aac ctg atg gac atg ttc agg gac agg cag gcc ttc tct gaa cac      144
Lys Asn Leu Met Asp Met Phe Arg Asp Arg Gln Ala Phe Ser Glu His
        35                  40                  45

acc tgg aag atg ctc ctg tct gtg tgc aga tcc tgg gct gcc tgg tgc      192
Thr Trp Lys Met Leu Leu Ser Val Cys Arg Ser Trp Ala Ala Trp Cys
    50                  55                  60

aag ctg aac aac agg aaa tgg ttc cct gct gaa cct gag gat gtg agg      240
Lys Leu Asn Asn Arg Lys Trp Phe Pro Ala Glu Pro Glu Asp Val Arg
65                  70                  75                  80
```

```
gac tac ctc ctg tac ctg caa gcc aga ggc ctg gct gtg aag acc atc      288
Asp Tyr Leu Leu Tyr Leu Gln Ala Arg Gly Leu Ala Val Lys Thr Ile
                85                  90                  95

caa cag cac ctg ggc cag ctc aac atg ctg cac agg aga tct ggc ctg      336
Gln Gln His Leu Gly Gln Leu Asn Met Leu His Arg Arg Ser Gly Leu
            100                 105                 110

cct cgc cct tct gac tcc aat gct gtg tcc ctg gtg atg agg aga atc      384
Pro Arg Pro Ser Asp Ser Asn Ala Val Ser Leu Val Met Arg Arg Ile
        115                 120                 125

aga aag gag aat gtg gat gct ggg gag aga gcc aag cag gcc ctg gcc      432
Arg Lys Glu Asn Val Asp Ala Gly Glu Arg Ala Lys Gln Ala Leu Ala
    130                 135                 140

ttt gaa cgc act gac ttt gac caa gtc aga tcc ctg atg gag aac tct      480
Phe Glu Arg Thr Asp Phe Asp Gln Val Arg Ser Leu Met Glu Asn Ser
145                 150                 155                 160

gac aga tgc cag gac atc agg aac ctg gcc ttc ctg ggc att gcc tac      528
Asp Arg Cys Gln Asp Ile Arg Asn Leu Ala Phe Leu Gly Ile Ala Tyr
                165                 170                 175

aac acc ctg ctg cgc att gcc gaa att gcc aga atc aga gtg aag gac      576
Asn Thr Leu Leu Arg Ile Ala Glu Ile Ala Arg Ile Arg Val Lys Asp
            180                 185                 190

atc tcc cgc acc gat ggt ggg aga atg ctg atc cac att ggc agg acc      624
Ile Ser Arg Thr Asp Gly Gly Arg Met Leu Ile His Ile Gly Arg Thr
        195                 200                 205

aag acc ctg gtg tcc aca gct ggt gtg gag aag gcc ctg tcc ctg ggg      672
Lys Thr Leu Val Ser Thr Ala Gly Val Glu Lys Ala Leu Ser Leu Gly
    210                 215                 220

gtt acc aag ctg gtg gag aga tgg atc tct gtg tct ggt gtg gct gat      720
Val Thr Lys Leu Val Glu Arg Trp Ile Ser Val Ser Gly Val Ala Asp
225                 230                 235                 240

gac ccc aac aac tac ctg ttc tgc cgg gtc aga aag aat ggt gtg gct      768
Asp Pro Asn Asn Tyr Leu Phe Cys Arg Val Arg Lys Asn Gly Val Ala
                245                 250                 255

gcc cct tct gcc acc tcc caa ctg tcc acc cgg gcc ctg gaa ggg atc      816
Ala Pro Ser Ala Thr Ser Gln Leu Ser Thr Arg Ala Leu Glu Gly Ile
            260                 265                 270

ttt gag gcc acc cac cgc ctg atc tat ggt gcc aag gat gac tct ggg      864
Phe Glu Ala Thr His Arg Leu Ile Tyr Gly Ala Lys Asp Asp Ser Gly
        275                 280                 285

cag aga tac ctg gcc tgg tct ggc cac tct gcc aga gtg ggt gct gcc      912
Gln Arg Tyr Leu Ala Trp Ser Gly His Ser Ala Arg Val Gly Ala Ala
    290                 295                 300

agg gac atg gcc agg gct ggt gtg tcc atc cct gaa atc atg cag gct      960
Arg Asp Met Ala Arg Ala Gly Val Ser Ile Pro Glu Ile Met Gln Ala
305                 310                 315                 320

ggt ggc tgg acc aat gtg aac ata gtg atg aac tac atc aga aac ctg     1008
Gly Gly Trp Thr Asn Val Asn Ile Val Met Asn Tyr Ile Arg Asn Leu
                325                 330                 335

gac tct gag act ggg gcc atg gtg agg ctg ctc gag gat ggg gac ggt     1056
Asp Ser Glu Thr Gly Ala Met Val Arg Leu Leu Glu Asp Gly Asp Gly
            340                 345                 350

ggt ggt ggc aag ctt tga                                             1074
Gly Gly Gly Lys Leu
        355
```

<210> SEQ ID NO 20
<211> LENGTH: 357
<212> TYPE: PRT
<213> ORGANISM: Bacteriophage P1

<400> SEQUENCE: 20

```
Met Val Pro Lys Lys Lys Arg Lys Val Ser Asn Leu Leu Thr Val His
1               5                   10                  15

Gln Asn Leu Pro Ala Leu Pro Val Asp Ala Thr Ser Asp Glu Val Arg
            20                  25                  30

Lys Asn Leu Met Asp Met Phe Arg Asp Arg Gln Ala Phe Ser Glu His
        35                  40                  45

Thr Trp Lys Met Leu Leu Ser Val Cys Arg Ser Trp Ala Ala Trp Cys
    50                  55                  60

Lys Leu Asn Asn Arg Lys Trp Phe Pro Ala Glu Pro Glu Asp Val Arg
65                  70                  75                  80

Asp Tyr Leu Leu Tyr Leu Gln Ala Arg Gly Leu Ala Val Lys Thr Ile
                85                  90                  95

Gln Gln His Leu Gly Gln Leu Asn Met Leu His Arg Arg Ser Gly Leu
            100                 105                 110

Pro Arg Pro Ser Asp Ser Asn Ala Val Ser Leu Val Met Arg Arg Ile
        115                 120                 125

Arg Lys Glu Asn Val Asp Ala Gly Glu Arg Ala Lys Gln Ala Leu Ala
    130                 135                 140

Phe Glu Arg Thr Asp Phe Asp Gln Val Arg Ser Leu Met Glu Asn Ser
145                 150                 155                 160

Asp Arg Cys Gln Asp Ile Arg Asn Leu Ala Phe Leu Gly Ile Ala Tyr
                165                 170                 175

Asn Thr Leu Leu Arg Ile Ala Glu Ile Ala Arg Ile Arg Val Lys Asp
            180                 185                 190

Ile Ser Arg Thr Asp Gly Gly Arg Met Leu Ile His Ile Gly Arg Thr
        195                 200                 205

Lys Thr Leu Val Ser Thr Ala Gly Val Glu Lys Ala Leu Ser Leu Gly
    210                 215                 220

Val Thr Lys Leu Val Glu Arg Trp Ile Ser Val Ser Gly Val Ala Asp
225                 230                 235                 240

Asp Pro Asn Asn Tyr Leu Phe Cys Arg Val Arg Lys Asn Gly Val Ala
                245                 250                 255

Ala Pro Ser Ala Thr Ser Gln Leu Ser Thr Arg Ala Leu Glu Gly Ile
            260                 265                 270

Phe Glu Ala Thr His Arg Leu Ile Tyr Gly Ala Lys Asp Asp Ser Gly
        275                 280                 285

Gln Arg Tyr Leu Ala Trp Ser Gly His Ser Ala Arg Val Gly Ala Ala
    290                 295                 300

Arg Asp Met Ala Arg Ala Gly Val Ser Ile Pro Glu Ile Met Gln Ala
305                 310                 315                 320

Gly Gly Trp Thr Asn Val Asn Ile Val Met Asn Tyr Ile Arg Asn Leu
                325                 330                 335

Asp Ser Glu Thr Gly Ala Met Val Arg Leu Leu Glu Asp Gly Asp Gly
            340                 345                 350

Gly Gly Gly Lys Leu
        355
```

<210> SEQ ID NO 21
<211> LENGTH: 11503
<212> TYPE: DNA
<213> ORGANISM: Artificial Sequence
<220> FEATURE:
<223> OTHER INFORMATION: HIV 1 strain NL4-3 Nef-IRES Cre

<400> SEQUENCE: 21

-continued

```
gcgttggaag ggctaattca ctcccaaaga agacaagata tccttgatct gtggatctac     60
cacacacaag gctacttccc tgattggcag aactacacac cagggccagg ggtcagatat    120
ccactgacct ttggatggtg ctacaagcta gtaccagttg agccagataa ggtagaagag    180
gccaataaag gagagaacac cagcttgtta caccctgtga gcctgcatgg aatggatgac    240
cctgagagag aagtgttaga gtggaggttt gacagccgcc tagcatttca tcacgtggcc    300
cgagagctgc atccggagta ctacaaagac tgctgacatc gagctttcta caagggactt    360
tccgctgggg actttccagg gaggtgtggc ctgggcggga ctggggagtg gcgagccctc    420
agatgctaca tataagcagc tgctttttgc ctgtactggg tctctctggt tagaccagat    480
ctgagcctgg gagctctctg gctaactagg gaacccactg cttaagcctc aataaagctt    540
gccttgagtg ctcaaagtag tgtgtgcccg tctgttgtgt gactctggta actagagatc    600
cctcagaccc ttttagtcag tgtggaaaat ctctagcagt ggcgcccgaa cagggacttg    660
aaagcgaaag taaagccaga ggagatctct cgacgcagga ctcggcttgc tgaagcgcgc    720
acggcaagag gcgagggggcg gcgactggtg agtacgccaa aaattttgac tagcggaggc    780
tagaaggaga gagatgggtg cgagagcgtc ggtattaagc gggggagaat tagataaatg    840
ggaaaaaatt cggttaaggc cagggggaaa gaaacaatat aaactaaaac atatagtatg    900
ggcaagcagg gagctagaac gattcgcagt taatcctggc cttttagaga catcagaagg    960
ctgtagacaa atactgggac agctacaacc atcccttcag acaggatcag aagaacttag   1020
atcattatat aatacaatag cagtcctcta ttgtgtgcat caaaggatag atgtaaaaga   1080
caccaaggaa gccttagata agatagagga agagcaaaac aaaagtaaga aaaaggcaca   1140
gcaagcagca gctgacacag gaaacaacag ccaggtcagc caaaattacc ctatagtgca   1200
gaacctccag gggcaaatgg tacatcaggc catatcacct agaactttaa atgcatgggt   1260
aaaagtagta gaagagaagg ctttcagccc agaagtaata cccatgtttt cagcattatc   1320
agaaggagcc accccacaag atttaaatac catgctaaac acagtggggg gacatcaagc   1380
agccatgcaa atgttaaaag agaccatcaa tgaggaagct gcagaatggg atagattgca   1440
tccagtgcat gcagggccta ttgcaccagg ccagatgaga gaaccaaggg gaagtgacat   1500
agcaggaact actagtaccc ttcaggaaca aataggatgg atgacacata atccacctat   1560
cccagtagga gaaatctata aaagatggat aatcctggga ttaaataaaa tagtaagaat   1620
gtatagccct accagcattc tggacataag acaaggacca aaggaaccct ttagagacta   1680
tgtagaccga ttctataaaa ctctaagagc cgagcaagct tcacaagagg taaaaaattg   1740
gatgacagaa accttgttgg tccaaaatgc gaacccagat tgtaagacta ttttaaaagc   1800
attgggacca ggagcgacac tagaagaaat gatgacagca tgtcagggag tgggggggacc   1860
cggccataaa gcaagagttt tggctgaagc aatgagccaa gtaacaaatc cagctaccat   1920
aatgatacag aaaggcaatt ttaggaacca aagaaagact gttaagtgtt tcaattgtgg   1980
caaagaaggg cacatagcca aaaattgcag ggcccctagg aaaaagggct gttggaaatg   2040
tggaaaggaa ggacaccaaa tgaaagattg tactgagaga caggctaatt ttttagggaa   2100
gatctggcct tcccacaagg gaaggccagg gaattttctt cagagcagac cagagccaac   2160
agccccacca gaagagagct tcaggtttgg ggaagagaca acaactccct ctcagaagca   2220
ggagccgata gacaaggaac tgtatccttt agcttccctc agatcactct ttggcagcga   2280
cccctcgtca caataaagat aggggggcaa ttaaaggaag ctctattaga tacaggagca   2340
```

-continued

```
gatgatacag tattagaaga aatgaatttg ccaggaagat ggaaaccaaa aatgataggg   2400
ggaattggag gttttatcaa agtaggacag tatgatcaga tactcataga aatctgcgga   2460
cataaagcta taggtacagt attagtagga cctacacctg tcaacataat tggaagaaat   2520
ctgttgactc agattggctg cactttaaat tttcccatta gtcctattga gactgtacca   2580
gtaaaattaa agccaggaat ggatggccca aaagttaaac aatggccatt gacagaagaa   2640
aaaataaaag cattagtaga aatttgtaca gaaatggaaa aggaaggaaa aatttcaaaa   2700
attgggcctg aaaatccata caatactcca gtatttgcca taaagaaaaa agacagtact   2760
aaatggagaa aattagtaga tttcagagaa cttaataaga gaactcaaga tttctgggaa   2820
gttcaattag gaataccaca tcctgcaggg ttaaaacaga aaaaatcagt aacagtactg   2880
gatgtgggcg atgcatattt ttcagttccc ttagataaag acttcaggaa gtatactgca   2940
tttaccatac ctagtataaa caatgagaca ccagggatta gatatcagta caatgtgctt   3000
ccacagggat ggaaaggatc accagcaata ttccagtgta gcatgacaaa aatcttagag   3060
ccttttagaa aacaaaatcc agacatagtc atctatcaat acatggatga tttgtatgta   3120
ggatctgact tagaaatagg gcagcataga acaaaaatag aggaactgag acaacatctg   3180
ttgaggtggg gatttaccac accagacaaa aaacatcaga aagaacctcc attcctttgg   3240
atgggttatg aactccatcc tgataaatgg acagtacagc ctatagtgct gccagaaaag   3300
gacagctgga ctgtcaatga catacagaaa ttagtgggaa aattgaattg ggcaagtcag   3360
atttatgcag ggattaaagt aaggcaatta tgtaaacttc ttaggggaac caaagcacta   3420
acagaagtag taccactaac agaagaagca gagctagaac tggcagaaaa cagggagatt   3480
ctaaaagaac cggtacatgg agtgtattat gacccatcaa aagacttaat agcagaaata   3540
cagaagcagg ggcaaggcca atggacatat caaatttatc aagagccatt taaaaatctg   3600
aaaacaggaa aatatgcaag aatgaagggt gcccacacta atgatgtgaa acaattaaca   3660
gaggcagtac aaaaaatagc cacagaaagc atagtaatat ggggaaagac tcctaaattt   3720
aaattaccca tacaaaagga aacatgggaa gcatggtgga cagagtattg gcaagccacc   3780
tggattcctg agtgggagtt tgtcaatacc cctcccttag tgaagttatg gtaccagtta   3840
gagaaagaac ccataatagg agcagaaact ttctatgtag atggggcagc caatagggaa   3900
actaaattag gaaaagcagg atatgtaact gacagaggaa gacaaaaagt tgtcccccta   3960
acggacacaa caaatcagaa gactgagtta caagcaattc atctagcttt gcaggattcg   4020
ggattagaag taaacatagt gacagactca caatatgcat tgggaatcat tcaagcacaa   4080
ccagataaga gtgaatcaga gttagtcagt caaataatag agcagttaat aaaaaaggaa   4140
aaagtctacc tggcatgggt accagcacac aaaggaattg gaggaaatga acaagtagat   4200
aaattggtca gtgctggaat caggaaagta ctatttttag atggaataga taaggcccaa   4260
gaagaacatg agaaatatca cagtaattgg agagcaatgg ctagtgattt taacctacca   4320
cctgtagtag caaaagaaat agtagccagc tgtgataaat gtcagctaaa aggggaagcc   4380
atgcatggac aagtagactg tagcccagga atatggcagc tagattgtac acatttagaa   4440
ggaaaagtta tcttggtagc agttcatgta gccagtggat atatagaagc agaagtaatt   4500
ccagcagaga cagggcaaga aacagcatac ttcctcttaa aattagcagg aagatggcca   4560
gtaaaaacag tacatacaga caatggcagc aatttcacca gtactacagt taaggccgcc   4620
tgttggtggg cggggatcaa gcaggaattt ggcattccct acaatcccca aagtcaagga   4680
gtaatagaat ctatgaataa agaattaaag aaaattatag gacaggtaag agatcaggct   4740
```

```
gaacatctta agacagcagt acaaatggca gtattcatcc acaattttaa aagaaaaggg   4800
gggattgggg ggtacagtgc aggggaaaga atagtagaca taatagcaac agacatacaa   4860
actaaagaat tacaaaaaca aattacaaaa attcaaaatt ttcgggttta ttacagggac   4920
agcagagatc cagtttggaa aggaccagca aagctcctct ggaaaggtga aggggcagta   4980
gtaatacaag ataatagtga cataaaagta gtgccaagaa gaaaagcaaa gatcatcagg   5040
gattatggaa aacagatggc aggtgatgat tgtgtggcaa gtagacagga tgaggattaa   5100
cacatggaaa agattagtaa aacaccatat gtatatttca aggaaagcta aggactggtt   5160
ttatagacat cactatgaaa gtactaatcc aaaaataagt tcagaagtac acatcccact   5220
aggggatgct aaattagtaa taacaacata ttggggtctg catacaggag aaagagactg   5280
gcatttgggt cagggagtct ccatagaatg gaggaaaaag agatatagca cacaagtaga   5340
ccctgaccta gcagaccaac taattcatct gcactatttt gattgttttt cagaatctgc   5400
tataagaaat accatattag gacgtatagt tagtcctagg tgtgaatatc aagcaggaca   5460
taacaaggta ggatctctac agtacttggc actagcagca ttaataaaac caaaacagat   5520
aaagccacct ttgcctagtg ttaggaaact gacagaggac agatggaaca agccccagaa   5580
gaccaagggc cacagaggga gccatacaat gaatggacac tagagctttt agaggaactt   5640
aagagtgaag ctgttagaca ttttcctagg atatggctcc ataacttagg acaacatatc   5700
tatgaaactt acggggatac ttgggcagga gtggaagcca taataagaat tctgcaacaa   5760
ctgctgttta tccatttcag aattgggtgt cgacatagca gaataggcgt tactcgacag   5820
aggagagcaa gaaatggagc cagtagatcc tagactagag ccctggaagc atccaggaag   5880
tcagcctaaa actgcttgta ccaattgcta ttgtaaaaag tgttgctttc attgccaagt   5940
ttgtttcatg acaaaagcct taggcatctc ctatggcagg aagaagcgga gacagcgacg   6000
aagagctcat cagaacagtc agactcatca agcttctcta tcaaagcagt aagtagtaca   6060
tgtaatgcaa cctataatag tagcaatagt agcattagta gtagcaataa taatagcaat   6120
agttgtgtgg tccatagtaa tcatagaata taggaaaata ttaagacaaa gaaaaataga   6180
caggttaatt gatagactaa tagaaagagc agaagacagt ggcaatgaga gtgaaggaga   6240
agtatcagca cttgtggaga tgggggtgga aatggggcac catgctcctt gggatattga   6300
tgatctgtag tgctacagaa aaattgtggg tcacagtcta ttatggggta cctgtgtgga   6360
aggaagcaac caccactcta ttttgtgcat cagatgctaa agcatatgat acagaggtac   6420
ataatgtttg ggccacacat gcctgtgtac ccacagaccc caacccacaa gaagtagtat   6480
tggtaaatgt gacagaaaat tttaacatgt ggaaaaatga catggtagaa cagatgcatg   6540
aggatataat cagtttatgg gatcaaagcc taaagccatg tgtaaaatta accccactct   6600
gtgttagttt aaagtgcact gatttgaaga atgatactaa taccaatagt agtagcggga   6660
gaatgataat ggagaaagga gagataaaaa actgctcttt caatatcagc acaagcataa   6720
gagataaggt gcagaaagaa tatgcattct tttataaact tgatatagta ccaatagata   6780
ataccagcta taggttgata agttgtaaca cctcagtcat tacacaggcc tgtccaaagg   6840
tatcctttga gccaattccc atacattatt gtgccccggc tggttttgcg attctaaaat   6900
gtaataataa gacgttcaat ggaacaggac catgtacaaa tgtcagcaca gtacaatgta   6960
cacatggaat caggccagta gtatcaactc aactgctgtt aaatggcagt ctagcagaag   7020
aagatgtagt aattagatct gccaatttca cagacaatgc taaaaccata atagtacagc   7080
```

-continued

```
tgaacacatc tgtagaaatt aattgtacaa gacccaacaa caatacaaga aaaagtatcc   7140
gtatccagag ggaccaggg agagcatttg ttacaatagg aaaaatagga aatatgagac    7200
aagcacattg taacattagt agagcaaaat ggaatgccac tttaaaacag atagctagca   7260
aattaagaga acaatttgga aataataaaa caataatctt taagcaatcc tcaggagggg   7320
acccagaaat tgtaacgcac agttttaatt gtggagggga atttttctac tgtaattcaa   7380
cacaactgtt taatagtact tggtttaata gtacttggag tactgaaggg tcaaataaca   7440
ctgaaggaag tgacacaatc acactcccat gcagaataaa acaatttata aacatgtggc   7500
aggaagtagg aaaagcaatg tatgcccctc ccatcagtgg acaaattaga tgttcatcaa   7560
atattactgg gctgctatta acaagagatg gtggtaataa caacaatggg tccgagatct   7620
tcagacctgg aggaggcgat atgagggaca attggagaag tgaattatat aaatataaag   7680
tagtaaaaat tgaaccatta ggagtagcac ccaccaaggc aaagagaaga gtggtgcaga   7740
gagaaaaaag agcagtggga ataggagctt tgttccttgg gttcttggga gcagcaggaa   7800
gcactatggg cgcagcgtca atgacgctga cggtacaggc cagacaatta ttgtctgata   7860
tagtgcagca gcagaacaat ttgctgaggg ctattgaggc gcaacagcat ctgttgcaac   7920
tcacagtctg gggcatcaaa cagctccagg caagaatcct ggctgtggaa agatacctaa   7980
aggatcaaca gctcctgggg atttggggtt gctctggaaa actcatttgc accactgctg   8040
tgccttggaa tgctagttgg agtaataaat ctctggaaca gatttggaat aacatgacct   8100
ggatggagtg ggacagagaa attaacaatt acacaagctt aatacactcc ttaattgaag   8160
aatcgcaaaa ccagcaagaa aagaatgaac aagaattatt ggaattagat aaatgggcaa   8220
gtttgtggaa ttggtttaac ataacaaatt ggctgtggta tataaaatta ttcataatga   8280
tagtaggagg cttggtaggt ttaagaatag tttttgctgt actttctata gtgaatagag   8340
ttaggcaggg atattcacca ttatcgtttc agacccacct cccaatcccg aggggacccg   8400
acaggcccga aggaatagaa gaagaaggtg gagagagaga cagagacaga tccattcgat   8460
tagtgaacgg atccttagca cttatctggg acgatctgcg gagcctgtgc ctcttcagct   8520
accaccgctt gagagactta ctcttgattg taacgaggat tgtggaactt ctgggacgca   8580
gggggtggga agccctcaaa tattggtgga atctcctaca gtattggagt caggaactaa   8640
agaatagtgc tgttaacttg ctcaatgcca cagccatagc agtagctgag gggacagata   8700
gggttataga agtattacaa gcagcttata gagctattcg ccacatacct agaagaataa   8760
gacagggctt ggaaaggatt ttgctataag atgggtggca agtggtcaaa aagtagtgtg   8820
attggatggc ctgctgtaag ggaaagaatg agacgagctg agccagcagc agatggggtg   8880
ggagcagtat ctcgagacct agaaaaacat ggagcaatca caagtagcaa tacagcagct   8940
aacaatgctg cttgtgcctg gctagaagca caagaggagg aagaggtggg ttttccagtc   9000
acacctcagg tacctttaag accaatgact tacaaggcag ctgtagatct tagccacttt   9060
ttaaaagaaa aggggggact ggaagggcta attcactccc aaagaaggca agatatcctt   9120
gatctgtgga tctaccacac acaaggctac ttccctgatt ggcagaacta cacaccaggg   9180
ccaggggtca gatatccact gacctttgga tggtgctaca agctagtacc agctgagcca   9240
gataaggtag aagaggccaa taaaggagag aacaccagct tgttacaccc tgtgagcctg   9300
catggaatgg atgaccctga gagagaagtg ttagagtgga ggtttgacag ccgcctagca   9360
tttcatcacg tggcccgaga gctgcatccg gagtacttca agaactgctg aacgcgtcgg   9420
atcccggagt actacaaaga ctgctgacgc gaattccgcc cccccccta acgttactgg    9480
```

```
ccgaagccgc ttggaataag gccggtgtgc gtttgtctat atgttatttt ccaccatatt   9540

gccgtctttt ggcaatgtga gggcccggaa acctggccct gtcttcttga cgagcattcc   9600

taggggtctt tcccctctcg ccaaaggaat gcaaggtctg ttgaatgtcg tgaaggaagc   9660

agttcctctg gaagcttctt gaagacaaac aacgtctgta gcgacccttt gcaggcagcg   9720

gaacccccca cctggcgaca ggtgcctctg cggccaaaag ccacgtgtat aagatacacc   9780

tgcaaaggcg gcacaacccc agtgccacgt tgtgagttgg atagttgtgg aaagagtcaa   9840

atggctctcc tcaagcgtat tcaacaaggg gctgaaggat gcccagaagg taccccattg   9900

tatgggatct gatctggggc ctcggtgcac atgctttaca tgtgtttagt cgaggttaaa   9960

aaacgtctag gccccccgaa ccacggggac gtggttttcc tttgaaaaac acgatgataa  10020

taccatggtg cccaagaaga agaggaaagt ctccaacctg ctgactgtgc accaaaacct  10080

gcctgccctc cctgtggatg ccacctctga tgaagtcagg aagaacctga tggacatgtt  10140

cagggacagg caggccttct ctgaacacac ctggaagatg ctcctgtctg tgtgcagatc  10200

ctgggctgcc tggtgcaagc tgaacaacag gaaatggttc cctgctgaac ctgaggatgt  10260

gagggactac ctcctgtacc tgcaagccag aggcctggct gtgaagacca tccaacagca  10320

cctgggccag ctcaacatgc tgcacaggag atctggcctg cctcgccctt ctgactccaa  10380

tgctgtgtcc ctggtgatga ggagaatcag aaaggagaat gtggatgctg gggagagagc  10440

caagcaggcc ctggcctttg aacgcactga ctttgaccaa gtcagatccc tgatggagaa  10500

ctctgacaga tgccaggaca tcaggaacct ggccttcctg ggcattgcct acaacaccct  10560

gctgcgcatt gccgaaattg ccagaatcag agtgaaggac atctcccgca ccgatggtgg  10620

gagaatgctg atccacattg gcaggaccaa gaccctggtg tccacagctg gtgtggagaa  10680

ggccctgtcc ctgggggtta ccaagctggt ggagagatgg atctctgtgt ctggtgtggc  10740

tgatgacccc aacaactacc tgttctgccg ggtcagaaag aatggtgtgg ctgccccttc  10800

tgccacctcc caactgtcca cccgggccct ggaagggatc tttgaggcca cccaccgcct  10860

gatctatggt gccaaggatg actctgggca gagatacctg gcctggtctg gccactctgc  10920

cagagtgggt gctgccaggg acatggccag ggctggtgtg tccatccctg aaatcatgca  10980

ggctggtggc tggaccaatg tgaacattgt gatgaactac atcagaaacc tggactctga  11040

gactggggcc atggtgaggc tgctcgagga tggggactga cccgggtagc cactttttaa  11100

aagaaaaggg gggactggaa gggctaattc actcccaaag aagacaagat atccatccg  11160

gagtacttca agaactgctg acatcgagct tgctacaagg gactttccgc tggggacttt  11220

ccagggaggc gtggcctggg cgggactggg gagtggcgag ccctcagatg ctgcatataa  11280

gcagctgctt tttgcctgta ctgggtctct ctggttagac cagatctgag cctgggagct  11340

ctctggctaa ctagggaacc cactgcttaa gcctcaataa agcttgcctt gagtgcttca  11400

agtagtgtgt gcccgtctgt tgtgtgactc tggtaactag agatccctca gaccctttta  11460

gtcagtgtgg aaaatctcta gcagttctag agcggccgct cgc                    11503
```

<210> SEQ ID NO 22
<211> LENGTH: 11503
<212> TYPE: DNA
<213> ORGANISM: Artificial Sequence
<220> FEATURE:
<223> OTHER INFORMATION: HIV strain NL4-3 Nef IRES Cre with optimized codon

<400> SEQUENCE: 22

```
gcgttggaag ggctaattca ctcccaaaga agacaagata tccttgatct gtggatctac      60
cacacacaag gctacttccc tgattggcag aactacacac cagggccagg ggtcagatat     120
ccactgacct ttggatggtg ctacaagcta gtaccagttg agccagataa ggtagaagag     180
gccaataaag gagagaacac cagcttgtta caccctgtga gcctgcatgg aatggatgac     240
cctgagagag aagtgttaga gtggaggttt gacagccgcc tagcatttca tcacgtggcc     300
cgagagctgc atccggagta ctacaaagac tgctgacatc gagctttcta caagggactt     360
tccgctgggg actttccagg gaggtgtggc ctgggcggga ctggggagtg gcgagccctc     420
agatgctaca tataagcagc tgctttttgc ctgtactggg tctctctggt tagaccagat     480
ctgagcctgg gagctctctg gctaactagg gaacccactg cttaagcctc aataaagctt     540
gccttgagtg ctcaaagtag tgtgtgcccg tctgttgtgt gactctggta actagagatc     600
cctcagaccc ttttagtcag tgtggaaaat ctctagcagt ggcgcccgaa cagggacttg     660
aaagcgaaag taaagccaga ggagatctct cgacgcagga ctcggcttgc tgaagcgcgc     720
acggcaagag gcgagggggcg gcgactggtg agtacgccaa aaattttgac tagcggaggc     780
tagaaggaga gagatgggtg cgagagcgtc ggtattaagc gggggagaat tagataaatg     840
ggaaaaaatt cggttaaggc cagggggaaa gaaacaatat aaactaaaac atatagtatg     900
ggcaagcagg gagctagaac gattcgcagt taatcctggc cttttagaga catcagaagg     960
ctgtagacaa atactgggac agctacaacc atcccttcag acaggatcag aagaacttag    1020
atcattatat aatacaatag cagtcctcta ttgtgtgcat caaaggatag atgtaaaaga    1080
caccaaggaa gccttagata agatagagga agagcaaaac aaaagtaaga aaaaggcaca    1140
gcaagcagca gctgacacag gaaacaacag ccaggtcagc caaaattacc ctatagtgca    1200
gaacctccag gggcaaatgg tacatcaggc catatcacct agaactttaa atgcatgggt    1260
aaaagtagta gaagagaagg ctttcagccc agaagtaata cccatgtttt cagcattatc    1320
agaaggagcc accccacaag atttaaatac catgctaaac acagtggggg gacatcaagc    1380
agccatgcaa atgttaaaag agaccatcaa tgaggaagct gcagaatggg atagattgca    1440
tccagtgcat gcagggccta ttgcaccagg ccagatgaga gaaccaaggg gaagtgacat    1500
agcaggaact actagtaccc ttcaggaaca aataggatgg atgacacata atccacctat    1560
cccagtagga gaaatctata aaagatggat aatcctggga ttaaataaaa tagtaagaat    1620
gtatagccct accagcattc tggacataag acaaggacca aaggaaccct ttagagacta    1680
tgtagaccga ttctataaaa ctctaagagc cgagcaagct tcacaagagg taaaaaattg    1740
gatgacagaa accttgttgg tccaaaatgc gaacccagat tgtaagacta ttttaaaagc    1800
attgggacca ggagcgacac tagaagaaat gatgacagca tgtcagggag tgggggggacc    1860
cggccataaa gcaagagttt tggctgaagc aatgagccaa gtaacaaatc cagctaccat    1920
aatgatacag aaaggcaatt ttaggaacca aagaaagact gttaagtgtt tcaattgtgg    1980
caaagaaggg cacatagcca aaaattgcag ggcccctagg aaaaagggct gttggaaatg    2040
tggaaaggaa ggacaccaaa tgaaagattg tactgagaga caggctaatt ttttagggaa    2100
gatctggcct tcccacaagg gaaggccagg gaattttctt cagagcagac cagagccaac    2160
agccccacca gaagagagct tcaggtttgg ggaagagaca acaactccct ctcagaagca    2220
ggagccgata gacaaggaac tgtatccttt agcttccctc agatcactct ttggcagcga    2280
cccctcgtca caataaagat agggggcaa ttaaaggaag ctctattaga tacaggagca    2340
```

```
gatgatacag tattagaaga aatgaatttg ccaggaagat ggaaaccaaa aatgataggg   2400
ggaattggag gttttatcaa agtaggacag tatgatcaga tactcataga aatctgcgga   2460
cataaagcta taggtacagt attagtagga cctacacctg tcaacataat tggaagaaat   2520
ctgttgactc agattggctg cactttaaat tttcccatta gtcctattga gactgtacca   2580
gtaaaattaa agccaggaat ggatggccca aaagttaaac aatggccatt gacagaagaa   2640
aaaataaaag cattagtaga aatttgtaca gaaatggaaa aggaaggaaa aatttcaaaa   2700
attgggcctg aaaatccata caatactcca gtatttgcca taaagaaaaa agacagtact   2760
aaatggagaa aattagtaga tttcagagaa cttaataaga gaactcaaga tttctgggaa   2820
gttcaattag gaataccaca tcctgcaggg ttaaaacaga aaaaatcagt aacagtactg   2880
gatgtgggcg atgcatattt ttcagttccc ttagataaag acttcaggaa gtatactgca   2940
tttaccatac ctagtataaa caatgagaca ccagggatta gatatcagta caatgtgctt   3000
ccacagggat ggaaaggatc accagcaata ttccagtgta gcatgacaaa aatcttagag   3060
ccttttagaa aacaaaatcc agacatagtc atctatcaat acatggatga tttgtatgta   3120
ggatctgact tagaaatagg gcagcataga acaaaaatag aggaactgag acaacatctg   3180
ttgaggtggg gatttaccac accagacaaa aaacatcaga aagaacctcc attcctttgg   3240
atgggttatg aactccatcc tgataaatgg acagtacagc ctatagtgct gccagaaaag   3300
gacagctgga ctgtcaatga catacagaaa ttagtgggaa aattgaattg ggcaagtcag   3360
atttatgcag ggattaaagt aaggcaatta tgtaaacttc ttaggggaac caaagcacta   3420
acagaagtag taccactaac agaagaagca gagctagaac tggcagaaaa cagggagatt   3480
ctaaaagaac cggtacatgg agtgtattat gacccatcaa aagacttaat agcagaaata   3540
cagaagcagg ggcaaggcca atggacatat caaatttatc aagagccatt taaaaatctg   3600
aaaacaggaa aatatgcaag aatgaagggt gcccacacta atgatgtgaa acaattaaca   3660
gaggcagtac aaaaaatagc cacagaaagc atagtaatat ggggaaagac tcctaaattt   3720
aaattaccca tacaaaagga aacatgggaa gcatggtgga cagagtattg gcaagccacc   3780
tggattcctg agtgggagtt tgtcaatacc cctcccttag tgaagttatg gtaccagtta   3840
gagaaagaac ccataatagg agcagaaact ttctatgtag atggggcagc caatagggaa   3900
actaaattag gaaaagcagg atatgtaact gacagaggaa gacaaaaagt tgtcccccta   3960
acggacacaa caaatcagaa gactgagtta caagcaattc atctagcttt gcaggattcg   4020
ggattagaag taaacatagt gacagactca caatatgcat tgggaatcat tcaagcacaa   4080
ccagataaga gtgaatcaga gttagtcagt caaataatag agcagttaat aaaaaaggaa   4140
aaagtctacc tggcatgggt accagcacac aaaggaattg gaggaaatga acaagtagat   4200
aaattggtca gtgctggaat caggaaagta ctatttttag atggaataga taaggcccaa   4260
gaagaacatg agaaatatca cagtaattgg agagcaatgg ctagtgattt taacctacca   4320
cctgtagtag caaaagaaat agtagccagc tgtgataaat gtcagctaaa aggggaagcc   4380
atgcatggac aagtagactg tagcccagga atatggcagc tagattgtac acatttagaa   4440
ggaaaagtta tcttggtagc agttcatgta gccagtggat atatagaagc agaagtaatt   4500
ccagcagaga cagggcaaga aacagcatac ttcctcttaa aattagcagg aagatggcca   4560
gtaaaaacag tacatacaga caatggcagc aatttcacca gtactacagt taaggccgcc   4620
tgttggtggg cggggatcaa gcaggaattt ggcattccct acaatcccca aagtcaagga   4680
gtaatagaat ctatgaataa agaattaaag aaaattatag gacaggtaag agatcaggct   4740
```

```
gaacatctta agacagcagt acaaatggca gtattcatcc acaattttaa aagaaaaggg   4800
gggattgggg ggtacagtgc aggggaaaga atagtagaca taatagcaac agacatacaa   4860
actaaagaat tacaaaaaca aattacaaaa attcaaaatt ttcgggttta ttacagggac   4920
agcagagatc cagtttggaa aggaccagca aagctcctct ggaaaggtga aggggcagta   4980
gtaatacaag ataatagtga cataaaagta gtgccaagaa gaaaagcaaa gatcatcagg   5040
gattatggaa aacagatggc aggtgatgat tgtgtggcaa gtagacagga tgaggattaa   5100
cacatggaaa agattagtaa aacaccatat gtatatttca aggaaagcta aggactggtt   5160
ttatagacat cactatgaaa gtactaatcc aaaaataagt tcagaagtac acatcccact   5220
aggggatgct aaattagtaa taacaacata ttggggtctg catacaggag aaagagactg   5280
gcatttgggt cagggagtct ccatagaatg gaggaaaaag agatatagca cacaagtaga   5340
ccctgaccta gcagaccaac taattcatct gcactatttt gattgttttt cagaatctgc   5400
tataagaaat accatattag gacgtatagt tagtcctagg tgtgaatatc aagcaggaca   5460
taacaaggta ggatctctac agtacttggc actagcagca ttaataaaac caaaacagat   5520
aaagccacct ttgcctagtg ttaggaaact gacagaggac agatggaaca agccccagaa   5580
gaccaagggc cacagaggga gccatacaat gaatggacac tagagctttt agaggaactt   5640
aagagtgaag ctgttagaca ttttcctagg atatggctcc ataacttagg acaacatatc   5700
tatgaaactt acggggatac ttgggcagga gtggaagcca taataagaat tctgcaacaa   5760
ctgctgttta tccatttcag aattgggtgt cgacatagca gaataggcgt tactcgacag   5820
aggagagcaa gaaatggagc cagtagatcc tagactagag ccctggaagc atccaggaag   5880
tcagcctaaa actgcttgta ccaattgcta ttgtaaaaag tgttgctttc attgccaagt   5940
ttgtttcatg acaaaagcct taggcatctc ctatggcagg aagaagcgga gacagcgacg   6000
aagagctcat cagaacagtc agactcatca agcttctcta tcaaagcagt aagtagtaca   6060
tgtaatgcaa cctataatag tagcaatagt agcattagta gtagcaataa taatagcaat   6120
agttgtgtgg tccatagtaa tcatagaata taggaaaata ttaagacaaa gaaaaataga   6180
caggttaatt gatagactaa tagaaagagc agaagacagt ggcaatgaga gtgaaggaga   6240
agtatcagca cttgtggaga tgggggtgga aatggggcac catgctcctt gggatattga   6300
tgatctgtag tgctacagaa aaattgtggg tcacagtcta ttatggggta cctgtgtgga   6360
aggaagcaac caccactcta ttttgtgcat cagatgctaa agcatatgat acagaggtac   6420
ataatgtttg ggccacacat gcctgtgtac ccacagaccc caacccacaa gaagtagtat   6480
tggtaaatgt gacagaaaat tttaacatgt ggaaaaatga catggtagaa cagatgcatg   6540
aggatataat cagtttatgg gatcaaagcc taaagccatg tgtaaaatta accccactct   6600
gtgttagttt aaagtgcact gatttgaaga atgatactaa taccaatagt agtagcggga   6660
gaatgataat ggagaaagga gagataaaaa actgctcttt caatatcagc acaagcataa   6720
gagataaggt gcagaaagaa tatgcattct tttataaact tgatatagta ccaatagata   6780
ataccagcta taggttgata agttgtaaca cctcagtcat tacacaggcc tgtccaaagg   6840
tatcctttga gccaattccc atacattatt gtgccccggc tggttttgcg attctaaaat   6900
gtaataataa gacgttcaat ggaacaggac catgtacaaa tgtcagcaca gtacaatgta   6960
cacatggaat caggccagta gtatcaactc aactgctgtt aaatggcagt ctagcagaag   7020
aagatgtagt aattagatct gccaatttca cagacaatgc taaaaccata atagtacagc   7080
```

```
tgaacacatc tgtagaaatt aattgtacaa gacccaacaa caatacaaga aaaagtatcc   7140
gtatccagag ggaccagggg agagcatttg ttacaatagg aaaaatagga aatatgagac   7200
aagcacattg taacattagt agagcaaaat ggaatgccac tttaaaacag atagctagca   7260
aattaagaga acaatttgga aataataaaa caataatctt taagcaatcc tcaggagggg   7320
acccagaaat tgtaacgcac agttttaatt gtggaggggga atttttctac tgtaattcaa   7380
cacaactgtt taatagtact tggtttaata gtacttggag tactgaaggg tcaaataaca   7440
ctgaaggaag tgacacaatc acactcccat gcagaataaa acaatttata aacatgtggc   7500
aggaagtagg aaaagcaatg tatgcccctc ccatcagtgg acaaattaga tgttcatcaa   7560
atattactgg gctgctatta acaagagatg gtggtaataa caacaatggg tccgagatct   7620
tcagacctgg aggaggcgat atgagggaca attggagaag tgaattatat aaatataaag   7680
tagtaaaaat tgaaccatta ggagtagcac ccaccaaggc aaagagaaga gtggtgcaga   7740
gagaaaaaag agcagtggga ataggagctt tgttccttgg gttcttggga gcagcaggaa   7800
gcactatggg cgcagcgtca atgacgctga cggtacaggc cagacaatta ttgtctgata   7860
tagtgcagca gcagaacaat ttgctgaggg ctattgaggc gcaacagcat ctgttgcaac   7920
tcacagtctg gggcatcaaa cagctccagg caagaatcct ggctgtggaa agatacctaa   7980
aggatcaaca gctcctgggg atttggggtt gctctggaaa actcatttgc accactgctg   8040
tgccttggaa tgctagttgg agtaataaat ctctggaaca gatttggaat aacatgacct   8100
ggatggagtg ggacagagaa attaacaatt acacaagctt aatacactcc ttaattgaag   8160
aatcgcaaaa ccagcaagaa aagaatgaac aagaattatt ggaattagat aaatgggcaa   8220
gtttgtggaa ttggtttaac ataacaaatt ggctgtggta tataaaatta ttcataatga   8280
tagtaggagg cttggtaggt ttaagaatag tttttgctgt actttctata gtgaatagag   8340
ttaggcaggg atattcacca ttatcgtttc agacccacct cccaatcccg aggggacccg   8400
acaggcccga aggaatagaa gaagaaggtg gagagagaga cagagacaga tccattcgat   8460
tagtgaacgg atccttagca cttatctggg acgatctgcg gagcctgtgc ctcttcagct   8520
accaccgctt gagagactta ctcttgattg taacgaggat tgtggaactt ctgggacgca   8580
gggggtggga agccctcaaa tattggtgga atctcctaca gtattggagt caggaactaa   8640
agaatagtgc tgttaacttg ctcaatgcca cagccatagc agtagctgag gggacagata   8700
gggttataga agtattacaa gcagcttata gagctattcg ccacatacct agaagaataa   8760
gacagggctt ggaaaggatt ttgctataag atgggtggca agtggtcaaa aagtagtgtg   8820
attggatggc ctgctgtaag ggaaagaatg agacgagctg agccagcagc agatggggtg   8880
ggagcagtat ctcgagacct agaaaaacat ggagcaatca caagtagcaa tacagcagct   8940
aacaatgctg cttgtgcctg gctagaagca caagaggagg aagaggtggg ttttccagtc   9000
acacctcagg tacctttaag accaatgact tacaaggcag ctgtagatct gagccatttc   9060
ctgaaggaga agggaggcct tgagggcctg attcacagcc agcggcgcca agacatcctt   9120
gacttgtgga tttaccatac acaggggtac ttccccgact ggcagaacta tacaccagga   9180
cccggagtga gataccccct gaccttcgga tggtgttaca aactggttcc agtggagcct   9240
gataaggtcg aagaggcaaa caaaggcgag aatacatctt tgctgcatcc tgtgtcactg   9300
cacgggatgg acgaccctga gcgggaggtg cttgagtgga ggttcgactc tcgactggcc   9360
tttcaccacg tagcaaggga gctgcaccct gagtatttta aaaattgttg aacgcgtcgg   9420
atcccggagt actacaaaga ctgctgacgc gaattccgcc cccccccta acgttactgg   9480
```

ccgaagccgc ttggaataag gccggtgtgc gtttgtctat atgttatttt ccaccatatt 9540
gccgtctttt ggcaatgtga gggcccggaa acctggccct gtcttcttga cgagcattcc 9600
taggggtctt tcccctctcg ccaaaggaat gcaaggtctg ttgaatgtcg tgaaggaagc 9660
agttcctctg gaagcttctt gaagacaaac aacgtctgta gcgacccttt gcaggcagcg 9720
gaacccccca cctggcgaca ggtgcctctg cggccaaaag ccacgtgtat aagatacacc 9780
tgcaaaggcg gcacaacccc agtgccacgt tgtgagttgg atagttgtgg aaagagtcaa 9840
atggctctcc tcaagcgtat tcaacaaggg gctgaaggat gcccagaagg taccccattg 9900
tatgggatct gatctggggc ctcggtgcac atgctttaca tgtgtttagt cgaggttaaa 9960
aaacgtctag gccccccgaa ccacggggac gtggttttcc tttgaaaaac acgatgataa 10020
taccatggtg cccaagaaga agaggaaagt ctccaacctg ctgactgtgc accaaaacct 10080
gcctgccctc cctgtggatg ccacctctga tgaagtcagg aagaacctga tggacatgtt 10140
cagggacagg caggccttct ctgaacacac ctggaagatg ctcctgtctg tgtgcagatc 10200
ctgggctgcc tggtgcaagc tgaacaacag gaaatggttc cctgctgaac ctgaggatgt 10260
gagggactac ctcctgtacc tgcaagccag aggcctggct gtgaagacca tccaacagca 10320
cctgggccag ctcaacatgc tgcacaggag atctggcctg cctcgccctt ctgactccaa 10380
tgctgtgtcc ctggtgatga ggagaatcag aaaggagaat gtggatgctg gggagagagc 10440
caagcaggcc ctggcctttg aacgcactga ctttgaccaa gtcagatccc tgatggagaa 10500
ctctgacaga tgccaggaca tcaggaacct ggccttcctg ggcattgcct acaacaccct 10560
gctgcgcatt gccgaaattg ccagaatcag agtgaaggac atctcccgca ccgatggtgg 10620
gagaatgctg atccacattg gcaggaccaa gaccctggtg tccacagctg gtgtggagaa 10680
ggccctgtcc ctgggggtta ccaagctggt ggagagatgg atctctgtgt ctggtgtggc 10740
tgatgacccc aacaactacc tgttctgccg ggtcagaaag aatggtgtgg ctgccccttc 10800
tgccacctcc caactgtcca cccgggccct ggaagggatc tttgaggcca cccaccgcct 10860
gatctatggt gccaaggatg actctgggca gagatacctg gcctggtctg gccactctgc 10920
cagagtgggt gctgccaggg acatggccag ggctggtgtg tccatccctg aaatcatgca 10980
ggctggtggc tggaccaatg tgaacattgt gatgaactac atcagaaacc tggactctga 11040
gactggggcc atggtgaggc tgctcgagga tggggactga cccgggtagc cactttttaa 11100
aagaaaaggg gggactggaa gggctaattc actcccaaag aagacaagat atccatccg 11160 gagtacttca agaactgctg acatcgagct tgctacaagg gactttccgc tggggacttt 11220
ccagggaggc gtggcctggg cgggactggg gagtggcgag ccctcagatg ctgcatataa 11280
gcagctgctt tttgcctgta ctgggtctct ctggttagac cagatctgag cctgggagct 11340
ctctggctaa ctagggaacc cactgcttaa gcctcaataa agcttgcctt gagtgcttca 11400
agtagtgtgt gcccgtctgt tgtgtgactc tggtaactag agatccctca gacccttta 11460 gtcagtgtgg aaaatctcta gcagttctag agcggccgct cgc 11503

<210> SEQ ID NO 23
<211> LENGTH: 11582
<212> TYPE: DNA
<213> ORGANISM: Artificial Sequence
<220> FEATURE:
<223> OTHER INFORMATION: HIV strain NL4-3 CMV Cre

<400> SEQUENCE: 23

-continued

```
gcgttggaag ggctaattca ctcccaaaga agacaagata tccttgatct gtggatctac     60
cacacacaag gctacttccc tgattggcag aactacacac cagggccagg ggtcagatat    120
ccactgacct ttggatggtg ctacaagcta gtaccagttg agccagataa ggtagaagag    180
gccaataaag gagagaacac cagcttgtta caccctgtga gcctgcatgg aatggatgac    240
cctgagagag aagtgttaga gtggaggttt gacagccgcc tagcatttca tcacgtggcc    300
cgagagctgc atccggagta ctacaaagac tgctgacatc gagctttcta caagggactt    360
tccgctgggg actttccagg gaggtgtggc ctgggcggga ctggggagtg gcgagccctc    420
agatgctaca tataagcagc tgctttttgc ctgtactggg tctctctggt tagaccagat    480
ctgagcctgg gagctctctg gctaactagg gaacccactg cttaagcctc aataaagctt    540
gccttgagtg ctcaaagtag tgtgtgcccg tctgttgtgt gactctggta actagagatc    600
cctcagaccc ttttagtcag tgtggaaaat ctctagcagt ggcgcccgaa cagggacttg    660
aaagcgaaag taaagccaga ggagatctct cgacgcagga ctcggcttgc tgaagcgcgc    720
acggcaagag gcgaggggcg gcgactggtg agtacgccaa aaattttgac tagcggaggc    780
tagaaggaga gagatgggtg cgagagcgtc ggtattaagc gggggagaat tagataaatg    840
ggaaaaaatt cggttaaggc caggggggaaa gaaacaatat aaactaaaac atatagtatg    900
ggcaagcagg gagctagaac gattcgcagt taatcctggc cttttagaga catcagaagg    960
ctgtagacaa atactgggac agctacaacc atcccttcag acaggatcag aagaacttag   1020
atcattatat aatacaatag cagtcctcta ttgtgtgcat caaaggatag atgtaaaaga   1080
caccaaggaa gccttagata agatagagga agagcaaaac aaaagtaaga aaaaggcaca   1140
gcaagcagca gctgacacag gaaacaacag ccaggtcagc caaaattacc ctatagtgca   1200
gaacctccag gggcaaatgg tacatcaggc catatcacct agaactttaa atgcatgggt   1260
aaaagtagta gaagagaagg ctttcagccc agaagtaata cccatgtttt cagcattatc   1320
agaaggagcc accccacaag atttaaatac catgctaaac acagtggggg gacatcaagc   1380
agccatgcaa atgttaaaag agaccatcaa tgaggaagct gcagaatggg atagattgca   1440
tccagtgcat gcagggccta ttgcaccagg ccagatgaga gaaccaaggg gaagtgacat   1500
agcaggaact actagtaccc ttcaggaaca aataggatgg atgacacata atccacctat   1560
cccagtagga gaaatctata aaagatggat aatcctggga ttaaataaaa tagtaagaat   1620
gtatagccct accagcattc tggacataag acaaggacca aaggaaccct ttagagacta   1680
tgtagaccga ttctataaaa ctctaagagc cgagcaagct tcacaagagg taaaaaattg   1740
gatgacagaa accttgttgg tccaaaatgc gaacccagat tgtaagacta ttttaaaagc   1800
attgggacca ggagcgacac tagaagaaat gatgacagca tgtcagggag tggggggacc   1860
cggccataaa gcaagagttt tggctgaagc aatgagccaa gtaacaaatc cagctaccat   1920
aatgatacag aaaggcaatt ttaggaacca aagaaagact gttaagtgtt tcaattgtgg   1980
caaagaaggg cacatagcca aaaattgcag ggcccctagg aaaaagggct gttggaaatg   2040
tggaaaggaa ggacaccaaa tgaaagattg tactgagaga caggctaatt ttttagggaa   2100
gatctggcct tcccacaagg gaaggccagg gaattttctt cagagcagac cagagccaac   2160
agccccacca gaagagagct tcaggtttgg ggaagagaca acaactccct ctcagaagca   2220
ggagccgata gacaaggaac tgtatccttt agcttccctc agatcactct ttggcagcga   2280
cccctcgtca caataaagat aggggggcaa ttaaaggaag ctctattaga tacaggagca   2340
gatgatacag tattagaaga aatgaatttg ccaggaagat ggaaaccaaa aatgataggg   2400
```

```
ggaattggag gttttatcaa agtaggacag tatgatcaga tactcataga aatctgcgga   2460
cataaagcta taggtacagt attagtagga cctacacctg tcaacataat tggaagaaat   2520
ctgttgactc agattggctg cactttaaat ttcccatta gtcctattga gactgtacca   2580
gtaaaattaa agccaggaat ggatggccca aaagttaaac aatggccatt gacagaagaa   2640
aaaataaaag cattagtaga aatttgtaca gaaatggaaa aggaaggaaa aatttcaaaa   2700
attgggcctg aaaatccata caatactcca gtatttgcca taaagaaaaa agacagtact   2760
aaatggagaa aattagtaga tttcagagaa cttaataaga gaactcaaga tttctgggaa   2820
gttcaattag gaataccaca tcctgcaggg ttaaaacaga aaaaatcagt aacagtactg   2880
gatgtgggcg atgcatattt ttcagttccc ttagataaag acttcaggaa gtatactgca   2940
tttaccatac ctagtataaa caatgagaca ccagggatta gatatcagta caatgtgctt   3000
ccacagggat ggaaaggatc accagcaata ttccagtgta gcatgacaaa aatcttagag   3060
ccttttagaa aacaaaatcc agacatagtc atctatcaat acatggatga tttgtatgta   3120
ggatctgact tagaaatagg gcagcataga acaaaaatag aggaactgag acaacatctg   3180
ttgaggtggg gatttaccac accagacaaa aaacatcaga aagaacctcc attcctttgg   3240
atgggttatg aactccatcc tgataaatgg acagtacagc ctatagtgct gccagaaaag   3300
gacagctgga ctgtcaatga catacagaaa ttagtgggaa aattgaattg ggcaagtcag   3360
atttatgcag ggattaaagt aaggcaatta tgtaaacttc ttaggggaac caaagcacta   3420
acagaagtag taccactaac agaagaagca gagctagaac tggcagaaaa cagggagatt   3480
ctaaaagaac cggtacatgg agtgtattat gacccatcaa aagacttaat agcagaaata   3540
cagaagcagg ggcaaggcca atggacatat caaatttatc aagagccatt taaaaatctg   3600
aaaacaggaa aatatgcaag aatgaagggt gcccacacta atgatgtgaa acaattaaca   3660
gaggcagtac aaaaaatagc cacagaaagc atagtaatat ggggaaagac tcctaaattt   3720
aaattaccca tacaaaagga aacatgggaa gcatggtgga cagagtattg gcaagccacc   3780
tggattcctg agtgggagtt tgtcaatacc cctcccttag tgaagttatg gtaccagtta   3840
gagaaagaac ccataatagg agcagaaact ttctatgtag atggggcagc caatagggaa   3900
actaaattag gaaaagcagg atatgtaact gacagaggaa gacaaaaagt tgtcccccta   3960
acggacacaa caaatcagaa gactgagtta caagcaattc atctagcttt gcaggattcg   4020
ggattagaag taaacatagt gacagactca caatatgcat tgggaatcat tcaagcacaa   4080
ccagataaga gtgaatcaga gttagtcagt caaataatag agcagttaat aaaaaaggaa   4140
aaagtctacc tggcatgggt accagcacac aaaggaattg gaggaaatga acaagtagat   4200
aaattggtca gtgctggaat caggaaagta ctatttttag atggaataga taaggcccaa   4260
gaagaacatg agaaatatca cagtaattgg agagcaatgg ctagtgattt taacctacca   4320
cctgtagtag caaaagaaat agtagccagc tgtgataaat gtcagctaaa aggggaagcc   4380
atgcatggac aagtagactg tagcccagga atatggcagc tagattgtac acatttagaa   4440
ggaaaagtta tcttggtagc agttcatgta gccagtggat atatagaagc agaagtaatt   4500
ccagcagaga cagggcaaga aacagcatac ttcctcttaa aattagcagg aagatggcca   4560
gtaaaaacag tacatacaga caatggcagc aatttcacca gtactacagt taaggccgcc   4620
tgttggtggg cggggatcaa gcaggaattt ggcattccct acaatcccca aagtcaagga   4680
gtaatagaat ctatgaataa agaattaaag aaaattatag gacaggtaag agatcaggct   4740
```

-continued

```
gaacatctta agacagcagt acaaatggca gtattcatcc acaattttaa aagaaaaggg   4800
gggattgggg ggtacagtgc aggggaaaga atagtagaca taatagcaac agacatacaa   4860
actaaagaat tacaaaaaca aattacaaaa attcaaaatt ttcgggttta ttacagggac   4920
agcagagatc cagtttggaa aggaccagca aagctcctct ggaaaggtga aggggcagta   4980
gtaatacaag ataatagtga cataaaagta gtgccaagaa gaaaagcaaa gatcatcagg   5040
gattatggaa aacagatggc aggtgatgat tgtgtggcaa gtagacagga tgaggattaa   5100
cacatggaaa agattagtaa aacaccatat gtatatttca aggaaagcta aggactggtt   5160
ttatagacat cactatgaaa gtactaatcc aaaaataagt tcagaagtac acatcccact   5220
aggggatgct aaattagtaa taacaacata ttggggtctg catacaggag aaagagactg   5280
gcatttgggt cagggagtct ccatagaatg gaggaaaaag agatatagca cacaagtaga   5340
ccctgaccta gcagaccaac taattcatct gcactatttt gattgttttt cagaatctgc   5400
tataagaaat accatattag gacgtatagt tagtcctagg tgtgaatatc aagcaggaca   5460
taacaaggta ggatctctac agtacttggc actagcagca ttaataaaac caaaacagat   5520
aaagccacct ttgcctagtg ttaggaaact gacagaggac agatggaaca agccccagaa   5580
gaccaagggc cacagaggga gccatacaat gaatggacac tagagctttt agaggaactt   5640
aagagtgaag ctgttagaca ttttcctagg atatggctcc ataacttagg acaacatatc   5700
tatgaaactt acggggatac ttgggcagga gtggaagcca taataagaat tctgcaacaa   5760
ctgctgttta tccatttcag aattgggtgt cgacatagca gaataggcgt tactcgacag   5820
aggagagcaa gaaatggagc cagtagatcc tagactagag ccctggaagc atccaggaag   5880
tcagcctaaa actgcttgta ccaattgcta ttgtaaaaag tgttgctttc attgccaagt   5940
ttgtttcatg acaaaagcct taggcatctc ctatggcagg aagaagcgga gacagcgacg   6000
aagagctcat cagaacagtc agactcatca agcttctcta tcaaagcagt aagtagtaca   6060
tgtaatgcaa cctataatag tagcaatagt agcattagta gtagcaataa taatagcaat   6120
agttgtgtgg tccatagtaa tcatagaata taggaaaata ttaagacaaa gaaaaataga   6180
caggttaatt gatagactaa tagaaagagc agaagacagt ggcaatgaga gtgaaggaga   6240
agtatcagca cttgtggaga tgggggtgga aatggggcac catgctcctt gggatattga   6300
tgatctgtag tgctacagaa aaattgtggg tcacagtcta ttatggggta cctgtgtgga   6360
aggaagcaac caccactcta ttttgtgcat cagatgctaa agcatatgat acagaggtac   6420
ataatgtttg ggccacacat gcctgtgtac ccacagaccc caacccacaa gaagtagtat   6480
tggtaaatgt gacagaaaat tttaacatgt ggaaaaatga catggtagaa cagatgcatg   6540
aggatataat cagtttatgg gatcaaagcc taaagccatg tgtaaaatta accccactct   6600
gtgttagttt aaagtgcact gatttgaaga atgatactaa taccaatagt agtagcggga   6660
gaatgataat ggagaaagga gagataaaaa actgctcttt caatatcagc acaagcataa   6720
gagataaggt gcagaaagaa tatgcattct tttataaact tgatatagta ccaatagata   6780
ataccagcta taggttgata agttgtaaca cctcagtcat tacacaggcc tgtccaaagg   6840
tatcctttga gccaattccc atacattatt gtgccccggc tggttttgcg attctaaaat   6900
gtaataataa gacgttcaat ggaacaggac catgtacaaa tgtcagcaca gtacaatgta   6960
cacatggaat caggccagta gtatcaactc aactgctgtt aaatggcagt ctagcagaag   7020
aagatgtagt aattagatct gccaatttca cagacaatgc taaaaccata atagtacagc   7080
tgaacacatc tgtagaaatt aattgtacaa gacccaacaa caatacaaga aaaagtatcc   7140
```

-continued

```
gtatccagag gggaccaggg agagcatttg ttacaatagg aaaaatagga aatatgagac   7200
aagcacattg taacattagt agagcaaaat ggaatgccac tttaaaacag atagctagca   7260
aattaagaga acaatttgga aataataaaa caataatctt taagcaatcc tcaggagggg   7320
acccagaaat tgtaacgcac agttttaatt gtggagggga atttttctac tgtaattcaa   7380
cacaactgtt taatagtact tggtttaata gtacttggag tactgaaggg tcaaataaca   7440
ctgaaggaag tgacacaatc acactcccat gcagaataaa acaatttata aacatgtggc   7500
aggaagtagg aaaagcaatg tatgcccctc ccatcagtgg acaaattaga tgttcatcaa   7560
atattactgg gctgctatta acaagagatg gtggtaataa caacaatggg tccgagatct   7620
tcagacctgg aggaggcgat atgagggaca attggagaag tgaattatat aaatataaag   7680
tagtaaaaat tgaaccatta ggagtagcac ccaccaaggc aaagagaaga gtggtgcaga   7740
gagaaaaaag agcagtggga ataggagctt tgttccttgg gttcttggga gcagcaggaa   7800
gcactatggg cgcagcgtca atgacgctga cggtacaggc cagacaatta ttgtctgata   7860
tagtgcagca gcagaacaat ttgctgaggg ctattgaggc gcaacagcat ctgttgcaac   7920
tcacagtctg gggcatcaaa cagctccagg caagaatcct ggctgtggaa agatacctaa   7980
aggatcaaca gctcctgggg atttggggtt gctctggaaa actcatttgc accactgctg   8040
tgccttggaa tgctagttgg agtaataaat ctctggaaca gatttggaat aacatgacct   8100
ggatggagtg ggacagagaa attaacaatt acacaagctt aatacactcc ttaattgaag   8160
aatcgcaaaa ccagcaagaa aagaatgaac aagaattatt ggaattagat aaatgggcaa   8220
gtttgtggaa ttggtttaac ataacaaatt ggctgtggta tataaaatta ttcataatga   8280
tagtaggagg cttggtaggt ttaagaatag tttttgctgt actttctata gtgaatagag   8340
ttaggcaggg atattcacca ttatcgtttc agacccacct cccaatcccg aggggacccg   8400
acaggcccga aggaatagaa gaagaaggtg gagagagaga cagagacaga tccattcgat   8460
tagtgaacgg atccttagca cttatctggg acgatctgcg gagcctgtgc ctcttcagct   8520
accaccgctt gagagactta ctcttgattg taacgaggat tgtggaactt ctgggacgca   8580
gggggtggga agccctcaaa tattggtgga atctcctaca gtattggagt caggaactaa   8640
agaatagtgc tgttaacttg ctcaatgcca cagccatagc agtagctgag gggacagata   8700
gggttataga agtattacaa gcagcttata gagctattcg ccacatacct agaagaataa   8760
gacagggctt ggaaaggatt ttgctataag atgggtggca agtggtcaaa aagtagtgtg   8820
attggatggc ctgctgtaag ggaaagaatg agacgagctg agccagcagc agatggggtg   8880
ggagcagtat ctcgagacct agaaaaacat ggagcaatca caagtagcaa tacagcagct   8940
aacaatgctg cttgtgcctg gctagaagca caagaggagg aagaggtggg ttttccagtc   9000
acacctcagg tacctttaag accaatgact tacaaggcag ctgtagatct tagccacttt   9060
ttaaaagaaa aggggggact ggaagggcta attcactccc aaagaaggca agatatcctt   9120
gatctgtgga tctaccacac acaaggctac ttccctgatt ggcagaacta cacaccaggg   9180
ccaggggtca gatatccact gacctttgga tggtgctaca agctagtacc agctgagcca   9240
gataaggtag aagaggccaa taaaggagag aacaccagct tgttacaccc tgtgagcctg   9300
catggaatgg atgaccctga gagagaagtg ttagagtgga ggtttgacag ccgcctagca   9360
tttcatcacg tggcccgaga gctgcatccg gagtacttca agaactgctg aacgcgtatt   9420
gcattactag ttattaatag taatcaatta cggggtcatt agttcatagc ccatatatgg   9480
```

-continued

```
agttccgcgt tacataactt acggtaaatg gcccgcctgg ctgaccgccc aacgaccccc   9540
gcccattgac gtcaataatg acgtatgttc ccatagtaac gccaataggg actttccatt   9600
gacgtcaatg ggtggagtat ttacggtaaa ctgcccactt ggcagtacat caagtgtatc   9660
atatgccaag tccgccccct attgacgtca atgacggtaa atggcccgcc tggcattatg   9720
cccagtacat gaccttacgg gactttccta cttggcagta catctacgta ttagtcatcg   9780
ctattaccat ggtgatgcgg ttttggcagt acaccaatgg gcgtggatag cggtttgact   9840
cacggggatt tccaagtctc caccccattg acgtcaatgg gagtttgttt tggcaccaaa   9900
atcaacggga ctttccaaaa tgtcgtaata accccgcccc gttgacgcaa atgggcggta   9960
ggcgtgtacg gtgggaggtc tatataagca gagctcgttt agtgaaccgt cagaattgtt  10020
tttatttta  atttcttc  aaatacttcc atcgaattca gatctggtac cacgcgtacc  10080
atggtgccca agaagaagag gaaagtctcc aacctgctga ctgtgcacca aaacctgcct  10140
gccctccctg tggatgccac ctctgatgaa gtcaggaaga acctgatgga catgttcagg  10200
gacaggcagg ccttctctga acacacctgg aagatgctcc tgtctgtgtg cagatcctgg  10260
gctgcctggt gcaagctgaa caacaggaaa tggttccctg ctgaacctga ggatgtgagg  10320
gactacctcc tgtacctgca agccagaggc ctggctgtga agaccatcca acagcacctg  10380
ggccagctca acatgctgca caggagatct ggcctgcctc gcccttctga ctccaatgct  10440
gtgtccctgg tgatgaggag aatcagaaag gagaatgtgg atgctgggga gagagccaag  10500
caggccctgg cctttgaacg cactgacttt gaccaagtca gatccctgat ggagaactct  10560
gacagatgcc aggacatcag gaacctggcc ttcctgggca ttgcctacaa caccctgctg  10620
cgcattgccg aaattgccag aatcagagtg aaggacatct cccgcaccga tggtgggaga  10680
atgctgatcc acattggcag gaccaagacc ctggtgtcca cagctggtgt ggagaaggcc  10740
ctgtccctgg gggttaccaa gctggtggag agatggatct ctgtgtctgg tgtggctgat  10800
gaccccaaca actacctgtt ctgccgggtc agaaagaatg gtgtggctgc cccttctgcc  10860
acctcccaac tgtccacccg ggccctggaa gggatctttg aggccaccca ccgcctgatc  10920
tatggtgcca aggatgactc tgggcagaga tacctggcct ggtctggcca ctctgccaga  10980
gtgggtgctg ccagggacat ggccagggct ggtgtgtcca tccctgaaat catgcaggct  11040
ggtggctgga ccaatgtgaa catagtgatg aactacatca gaaacctgga ctctgagact  11100
ggggccatgg tgaggctgct cgaggatggg gacggtggtg gtggcaagct ttgacgcatc  11160
ccgggtagcc actttttaaa agaaaagggg ggactggaag ggctaattca ctcccaaaga  11220
agacaagata tcccatccgg agtacttcaa gaactgctga catcgagctt gctacaaggg  11280
actttccgct ggggactttc cagggaggcg tggcctgggc gggactgggg agtggcgagc  11340
cctcagatgc tgcatataag cagctgcttt ttgcctgtac tgggtctctc tggttagacc  11400
agatctgagc ctgggagctc tctggctaac tagggaaccc actgcttaag cctcaataaa  11460
gcttgccttg agtgcttcaa gtagtgtgtg cccgtctgtt gtgtgactct ggtaactaga  11520
gatccctcag acccttttag tcagtgtgga aaatctctag cagttctaga gcggccgctc  11580
gc                                                                 11582
```

<210> SEQ ID NO 24
<211> LENGTH: 11582
<212> TYPE: DNA
<213> ORGANISM: Artificial Sequence
<220> FEATURE:
<223> OTHER INFORMATION: HIV strain NL4-3 CMV Cre optimized codon

<400> SEQUENCE: 24

```
gcgttggaag ggctaattca ctcccaaaga agacaagata tccttgatct gtggatctac     60
cacacacaag gctacttccc tgattggcag aactacacac cagggccagg ggtcagatat    120
ccactgacct ttggatggtg ctacaagcta gtaccagttg agccagataa ggtagaagag    180
gccaataaag gagagaacac cagcttgtta caccctgtga gcctgcatgg aatggatgac    240
cctgagagag aagtgttaga gtggaggttt gacagccgcc tagcatttca tcacgtggcc    300
cgagagctgc atccggagta ctacaaagac tgctgacatc gagctttcta caagggactt    360
tccgctgggg actttccagg gaggtgtggc ctgggcggga ctggggagtg gcgagccctc    420
agatgctaca tataagcagc tgctttttgc ctgtactggg tctctctggt tagaccagat    480
ctgagcctgg gagctctctg gctaactagg gaacccactg cttaagcctc aataaagctt    540
gccttgagtg ctcaaagtag tgtgtgcccg tctgttgtgt gactctggta actagagatc    600
cctcagaccc ttttagtcag tgtggaaaat ctctagcagt ggcgcccgaa cagggacttg    660
aaagcgaaag taaagccaga ggagatctct cgacgcagga ctcggcttgc tgaagcgcgc    720
acggcaagag gcgaggggcg gcgactggtg agtacgccaa aaattttgac tagcggaggc    780
tagaaggaga gagatgggtg cgagagcgtc ggtattaagc gggggagaat tagataaatg    840
ggaaaaaatt cggttaaggc cagggggaaa gaaacaatat aaactaaaac atatagtatg    900
ggcaagcagg gagctagaac gattcgcagt taatcctggc cttttagaga catcagaagg    960
ctgtagacaa atactgggac agctacaacc atcccttcag acaggatcag aagaacttag   1020
atcattatat aatacaatag cagtcctcta ttgtgtgcat caaaggatag atgtaaaaga   1080
caccaaggaa gccttagata agatagagga agagcaaaac aaaagtaaga aaaaggcaca   1140
gcaagcagca gctgacacag gaaacaacag ccaggtcagc caaaattacc ctatagtgca   1200
gaacctccag gggcaaatgg tacatcaggc catatcacct agaactttaa atgcatgggt   1260
aaaagtagta gaagagaagg ctttcagccc agaagtaata cccatgtttt cagcattatc   1320
agaaggagcc accccacaag atttaaatac catgctaaac acagtggggg gacatcaagc   1380
agccatgcaa atgttaaaag agaccatcaa tgaggaagct gcagaatggg atagattgca   1440
tccagtgcat gcagggccta ttgcaccagg ccagatgaga gaaccaaggg gaagtgacat   1500
agcaggaact actagtaccc ttcaggaaca aataggatgg atgacacata atccacctat   1560
cccagtagga gaaatctata aaagatggat aatcctggga ttaaataaaa tagtaagaat   1620
gtatagccct accagcattc tggacataag acaaggacca aaggaaccct ttagagacta   1680
tgtagaccga ttctataaaa ctctaagagc cgagcaagct tcacaagagg taaaaaattg   1740
gatgacagaa accttgttgg tccaaaatgc gaacccagat tgtaagacta ttttaaaagc   1800
attgggacca ggagcgacac tagaagaaat gatgacagca tgtcagggag tggggggacc   1860
cggccataaa gcaagagttt tggctgaagc aatgagccaa gtaacaaatc cagctaccat   1920
aatgatacag aaaggcaatt ttaggaacca aagaaagact gttaagtgtt tcaattgtgg   1980
caaagaaggg cacatagcca aaaattgcag ggcccctagg aaaaagggct gttggaaatg   2040
tggaaaggaa ggacaccaaa tgaaagattg tactgagaga caggctaatt ttttagggaa   2100
gatctggcct tcccacaagg gaaggccagg gaattttctt cagagcagac cagagccaac   2160
agccccacca gaagagagct tcaggtttgg ggaagagaca acaactccct ctcagaagca   2220
ggagccgata gacaaggaac tgtatccttt agcttccctc agatcactct ttggcagcga   2280
```

```
ccccctcgtca caataaagat aggggggcaa ttaaaggaag ctctattaga tacaggagca   2340

gatgatacag tattagaaga aatgaatttg ccaggaagat ggaaaccaaa aatgataggg   2400

ggaattggag gttttatcaa agtaggacag tatgatcaga tactcataga aatctgcgga   2460

cataaagcta taggtacagt attagtagga cctacacctg tcaacataat tggaagaaat   2520

ctgttgactc agattggctg cactttaaat tttcccatta gtcctattga gactgtacca   2580

gtaaaattaa agccaggaat ggatggccca aaagttaaac aatggccatt gacagaagaa   2640

aaaataaaag cattagtaga aatttgtaca gaaatggaaa aggaaggaaa aatttcaaaa   2700

attgggcctg aaaatccata caatactcca gtatttgcca taaagaaaaa agacagtact   2760

aaatggagaa aattagtaga tttcagagaa cttaataaga gaactcaaga tttctgggaa   2820

gttcaattag gaataccaca tcctgcaggg ttaaaacaga aaaaatcagt aacagtactg   2880

gatgtgggcg atgcatattt ttcagttccc ttagataaag acttcaggaa gtatactgca   2940

tttaccatac ctagtataaa caatgagaca ccagggatta gatatcagta caatgtgctt   3000

ccacagggat ggaaaggatc accagcaata ttccagtgta gcatgacaaa aatcttagag   3060

ccttttagaa aacaaaatcc agacatagtc atctatcaat acatggatga tttgtatgta   3120

ggatctgact tagaaatagg gcagcataga acaaaaatag aggaactgag acaacatctg   3180

ttgaggtggg gatttaccac accagacaaa aaacatcaga aagaacctcc attcctttgg   3240

atgggttatg aactccatcc tgataaatgg acagtacagc ctatagtgct gccagaaaag   3300

gacagctgga ctgtcaatga catacagaaa ttagtgggaa aattgaattg ggcaagtcag   3360

atttatgcag ggattaaagt aaggcaatta tgtaaacttc ttaggggaac caaagcacta   3420

acagaagtag taccactaac agaagaagca gagctagaac tggcagaaaa cagggagatt   3480

ctaaaagaac cggtacatgg agtgtattat gacccatcaa aagacttaat agcagaaata   3540

cagaagcagg ggcaaggcca atggacatat caaatttatc aagagccatt taaaaatctg   3600

aaaacaggaa aatatgcaag aatgaagggt gcccacacta atgatgtgaa acaattaaca   3660

gaggcagtac aaaaaatagc cacagaaagc atagtaatat ggggaaagac tcctaaattt   3720

aaattaccca tacaaaagga aacatgggaa gcatggtgga cagagtattg gcaagccacc   3780

tggattcctg agtgggagtt tgtcaatacc cctcccttag tgaagttatg gtaccagtta   3840

gagaaagaac ccataatagg agcagaaact ttctatgtag atggggcagc caatagggaa   3900

actaaattag gaaaagcagg atatgtaact gacagaggaa gacaaaaagt tgtcccccta   3960

acggacacaa caaatcagaa gactgagtta caagcaattc atctagcttt gcaggattcg   4020

ggattagaag taaacatagt gacagactca caatatgcat tgggaatcat tcaagcacaa   4080

ccagataaga gtgaatcaga gttagtcagt caaataatag agcagttaat aaaaaaggaa   4140

aaagtctacc tggcatgggt accagcacac aaaggaattg gaggaaatga acaagtagat   4200

aaattggtca gtgctggaat caggaaagta ctatttttag atggaataga taaggcccaa   4260

gaagaacatg agaaatatca cagtaattgg agagcaatgg ctagtgattt taacctacca   4320

cctgtagtag caaaagaaat agtagccagc tgtgataaat gtcagctaaa aggggaagcc   4380

atgcatggac aagtagactg tagcccagga atatggcagc tagattgtac acatttagaa   4440

ggaaaagtta tcttggtagc agttcatgta gccagtggat atatagaagc agaagtaatt   4500

ccagcagaga cagggcaaga aacagcatac ttcctcttaa aattagcagg aagatggcca   4560

gtaaaaacag tacatacaga caatggcagc aatttcacca gtactacagt taaggccgcc   4620

tgttggtggg cggggatcaa gcaggaattt ggcattccct acaatcccca aagtcaagga   4680
```

-continued

```
gtaatagaat ctatgaataa agaattaaag aaaattatag gacaggtaag agatcaggct   4740
gaacatctta agacagcagt acaaatggca gtattcatcc acaattttaa aagaaaaggg   4800
gggattgggg ggtacagtgc aggggaaaga atagtagaca taatagcaac agacatacaa   4860
actaaagaat tacaaaaaca aattacaaaa attcaaaatt ttcgggttta ttacagggac   4920
agcagagatc cagtttggaa aggaccagca aagctcctct ggaaaggtga aggggcagta   4980
gtaatacaag ataatagtga cataaaagta gtgccaagaa gaaaagcaaa gatcatcagg   5040
gattatggaa aacagatggc aggtgatgat tgtgtggcaa gtagacagga tgaggattaa   5100
cacatggaaa agattagtaa aacaccatat gtatatttca aggaaagcta aggactggtt   5160
ttatagacat cactatgaaa gtactaatcc aaaaataagt tcagaagtac acatcccact   5220
aggggatgct aaattagtaa taacaacata ttggggtctg catacaggag aaagagactg   5280
gcatttgggt cagggagtct ccatagaatg gaggaaaaag agatatagca cacaagtaga   5340
ccctgaccta gcagaccaac taattcatct gcactatttt gattgttttt cagaatctgc   5400
tataagaaat accatattag gacgtatagt tagtcctagg tgtgaatatc aagcaggaca   5460
taacaaggta ggatctctac agtacttggc actagcagca ttaataaaac caaaacagat   5520
aaagccacct ttgcctagtg ttaggaaact gacagaggac agatggaaca agccccagaa   5580
gaccaagggc cacagaggga gccatacaat gaatggacac tagagctttt agaggaactt   5640
aagagtgaag ctgttagaca ttttcctagg atatggctcc ataacttagg acaacatatc   5700
tatgaaactt acggggatac ttgggcagga gtggaagcca taataagaat tctgcaacaa   5760
ctgctgttta tccatttcag aattgggtgt cgacatagca gaataggcgt tactcgacag   5820
aggagagcaa gaaatggagc cagtagatcc tagactagag ccctggaagc atccaggaag   5880
tcagcctaaa actgcttgta ccaattgcta ttgtaaaaag tgttgctttc attgccaagt   5940
ttgtttcatg acaaaagcct taggcatctc ctatggcagg aagaagcgga gacagcgacg   6000
aagagctcat cagaacagtc agactcatca agcttctcta tcaaagcagt aagtagtaca   6060
tgtaatgcaa cctataatag tagcaatagt agcattagta gtagcaataa taatagcaat   6120
agttgtgtgg tccatagtaa tcatagaata taggaaaata ttaagacaaa gaaaaataga   6180
caggttaatt gatagactaa tagaaagagc agaagacagt ggcaatgaga gtgaaggaga   6240
agtatcagca cttgtggaga tgggggtgga aatggggcac catgctcctt gggatattga   6300
tgatctgtag tgctacagaa aaattgtggg tcacagtcta ttatggggta cctgtgtgga   6360
aggaagcaac caccactcta ttttgtgcat cagatgctaa agcatatgat acagaggtac   6420
ataatgtttg ggccacacat gcctgtgtac ccacagaccc caacccacaa gaagtagtat   6480
tggtaaatgt gacagaaaat tttaacatgt ggaaaaatga catggtagaa cagatgcatg   6540
aggatataat cagtttatgg gatcaaagcc taaagccatg tgtaaaatta accccactct   6600
gtgttagttt aaagtgcact gatttgaaga atgatactaa taccaatagt agtagcggga   6660
gaatgataat ggagaaagga gagataaaaa actgctcttt caatatcagc acaagcataa   6720
gagataaggt gcagaaagaa tatgcattct tttataaact tgatatagta ccaatagata   6780
ataccagcta taggttgata agttgtaaca cctcagtcat tacacaggcc tgtccaaagg   6840
tatcctttga gccaattccc atacattatt gtgccccggc tggttttgcg attctaaaat   6900
gtaataataa gacgttcaat ggaacaggac catgtacaaa tgtcagcaca gtacaatgta   6960
cacatggaat caggccagta gtatcaactc aactgctgtt aaatggcagt ctagcagaag   7020
```

```
aagatgtagt aattagatct gccaatttca cagacaatgc taaaaccata atagtacagc   7080
tgaacacatc tgtagaaatt aattgtacaa gacccaacaa caatacaaga aaaagtatcc   7140
gtatccagag ggaccaggg agagcatttg ttacaatagg aaaaatagga aatatgagac   7200
aagcacattg taacattagt agagcaaaat ggaatgccac tttaaaacag atagctagca   7260
aattaagaga acaatttgga aataataaaa caataatctt taagcaatcc tcaggagggg   7320
acccagaaat tgtaacgcac agttttaatt gtggaggga atttttctac tgtaattcaa   7380
cacaactgtt taatagtact tggtttaata gtacttggag tactgaaggg tcaaataaca   7440
ctgaaggaag tgacacaatc acactcccat gcagaataaa acaatttata aacatgtggc   7500
aggaagtagg aaaagcaatg tatgcccctc ccatcagtgg acaaattaga tgttcatcaa   7560
atattactgg gctgctatta acaagagatg gtggtaataa caacaatggg tccgagatct   7620
tcagacctgg aggaggcgat atgagggaca attggagaag tgaattatat aaatataaag   7680
tagtaaaaat tgaaccatta ggagtagcac ccaccaaggc aaagagaaga gtggtgcaga   7740
gagaaaaaag agcagtggga ataggagctt tgttccttgg gttcttggga gcagcaggaa   7800
gcactatggg cgcagcgtca atgacgctga cggtacaggc cagacaatta ttgtctgata   7860
tagtgcagca gcagaacaat ttgctgaggg ctattgaggc gcaacagcat ctgttgcaac   7920
tcacagtctg gggcatcaaa cagctccagg caagaatcct ggctgtggaa agatacctaa   7980
aggatcaaca gctcctgggg atttggggtt gctctggaaa actcatttgc accactgctg   8040
tgccttggaa tgctagttgg agtaataaat ctctggaaca gatttggaat aacatgacct   8100
ggatggagtg ggacagagaa attaacaatt acacaagctt aatacactcc ttaattgaag   8160
aatcgcaaaa ccagcaagaa aagaatgaac aagaattatt ggaattagat aaatgggcaa   8220
gtttgtggaa ttggtttaac ataacaaatt ggctgtggta tataaaatta ttcataatga   8280
tagtaggagg cttggtaggt ttaagaatag tttttgctgt actttctata gtgaatagag   8340
ttaggcaggg atattcacca ttatcgtttc agacccacct cccaatcccg aggggacccg   8400
acaggcccga aggaatagaa gaagaaggtg gagagagaga cagagacaga tccattcgat   8460
tagtgaacgg atccttagca cttatctggg acgatctgcg gagcctgtgc ctcttcagct   8520
accaccgctt gagagactta ctcttgattg taacgaggat tgtggaactt ctgggacgca   8580
gggggtggga agccctcaaa tattggtgga atctcctaca gtattggagt caggaactaa   8640
agaatagtgc tgttaacttg ctcaatgcca cagccatagc agtagctgag gggacagata   8700
gggttataga agtattacaa gcagcttata gagctattcg ccacatacct agaagaataa   8760
gacagggctt ggaaaggatt ttgctataag atgggtggca agtggtcaaa aagtagtgtg   8820
attggatggc ctgctgtaag ggaaagaatg agacgagctg agccagcagc agatggggtg   8880
ggagcagtat ctcgagacct agaaaaacat ggagcaatca caagtagcaa tacagcagct   8940
aacaatgctg cttgtgcctg gctagaagca caagaggagg aagaggtggg ttttccagtc   9000
acacctcagg tacctttaag accaatgact tacaaggcag ctgtagatct gagccatttc   9060
ctgaaggaga agggaggcct tgagggcctg attcacagcc agcggcgcca agacatcctt   9120
gacttgtgga tttaccatac acaggggtac ttccccgact ggcagaacta tacaccagga   9180
cccggagtga gatacccccct gaccttcgga tggtgttaca aactggttcc agtggagcct   9240
gataaggtcg aagaggcaaa caaaggcgag aatacatctt tgctgcatcc tgtgtcactg   9300
cacgggatgg acgaccctga gcgggaggtg cttgagtgga ggttcgactc tcgactggcc   9360
tttcaccacg tagcaaggga gctgcaccct gagtatttta aaaattgttg aacgcgtatt   9420
```

```
gcattactag ttattaatag taatcaatta cggggtcatt agttcatagc ccatatatgg   9480
agttccgcgt tacataactt acggtaaatg gcccgcctgg ctgaccgccc aacgaccccc   9540
gcccattgac gtcaataatg acgtatgttc ccatagtaac gccaataggg actttccatt   9600
gacgtcaatg ggtggagtat ttacggtaaa ctgcccactt ggcagtacat caagtgtatc   9660
atatgccaag tccgccccct attgacgtca atgacggtaa atggcccgcc tggcattatg   9720
cccagtacat gaccttacgg gactttccta cttggcagta catctacgta ttagtcatcg   9780
ctattaccat ggtgatgcgg ttttggcagt acaccaatgg gcgtggatag cggtttgact   9840
cacggggatt tccaagtctc caccccattg acgtcaatgg gagtttgttt tggcaccaaa   9900
atcaacggga ctttccaaaa tgtcgtaata accccgcccc gttgacgcaa atgggcggta   9960
ggcgtgtacg gtgggaggtc tatataagca gagctcgttt agtgaaccgt cagaattgtt  10020
tttatttta atttcttc aaatacttcc atcgaattca gatctggtac cacgcgtacc  10080
atggtgccca agaagaagag gaaagtctcc aacctgctga ctgtgcacca aaacctgcct  10140
gccctccctg tggatgccac ctctgatgaa gtcaggaaga acctgatgga catgttcagg  10200
gacaggcagg ccttctctga acacacctgg aagatgctcc tgtctgtgtg cagatcctgg  10260
gctgcctggt gcaagctgaa caacaggaaa tggttccctg ctgaacctga ggatgtgagg  10320
gactacctcc tgtacctgca agccagaggc ctggctgtga agaccatcca acagcacctg  10380
ggccagctca acatgctgca caggagatct ggcctgcctc gcccttctga ctccaatgct  10440
gtgtccctgg tgatgaggag aatcagaaag gagaatgtgg atgctgggga gagagccaag  10500
caggccctgg cctttgaacg cactgacttt gaccaagtca gatccctgat ggagaactct  10560
gacagatgcc aggacatcag gaacctggcc ttcctgggca ttgcctacaa caccctgctg  10620
cgcattgccg aaattgccag aatcagagtg aaggacatct cccgcaccga tggtgggaga  10680
atgctgatcc acattggcag gaccaagacc ctggtgtcca cagctggtgt ggagaaggcc  10740
ctgtccctgg gggttaccaa gctggtggag agatggatct ctgtgtctgg tgtggctgat  10800
gaccccaaca actacctgtt ctgccgggtc agaaagaatg gtgtggctgc cccttctgcc  10860
acctcccaac tgtccacccg ggccctggaa gggatctttg aggccaccca ccgcctgatc  10920
tatggtgcca aggatgactc tgggcagaga tacctggcct ggtctggcca ctctgccaga  10980
gtgggtgctg ccagggacat ggccagggct ggtgtgtcca tccctgaaat catgcaggct  11040
ggtggctgga ccaatgtgaa catagtgatg aactacatca gaaacctgga ctctgagact  11100
ggggccatgg tgaggctgct cgaggatggg gacggtggtg gtggcaagct ttgacgcatc  11160
ccgggtagcc actttttaaa agaaaagggg ggactggaag ggctaattca ctcccaaaga  11220
agacaagata tcccatccgg agtacttcaa gaactgctga catcgagctt gctacaaggg  11280
actttccgct ggggactttc cagggaggcg tggcctgggc gggactgggg agtggcgagc  11340
cctcagatgc tgcatataag cagctgcttt ttgcctgtac tgggtctctc tggttagacc  11400
agatctgagc ctgggagctc tctggctaac tagggaaccc actgcttaag cctcaataaa  11460
gcttgccttg agtgcttcaa gtagtgtgtg cccgtctgtt gtgtgactct ggtaactaga  11520
gatccctcag acccttttag tcagtgtgga aaatctctag cagttctaga gcggccgctc  11580
gc                                                                 11582
```

<210> SEQ ID NO 25
<211> LENGTH: 12024
<212> TYPE: DNA

<213> ORGANISM: Artificial Sequence
<220> FEATURE:
<223> OTHER INFORMATION: SIVmac239-Nef-IRES-Cre

<400> SEQUENCE: 25
tggaagggat ttattacagt gcaagaagac atagaatctt agacatatac ttagaaaagg 60
aagaaggcat cataccagat tggcaggatt acacctcagg accaggaatt agatacccaa 120
agacatttgg ctggctatgg aaattagtcc ctgtaaatgt atcagatgag gcacaggagg 180
atgaggagca ttatttaatg catccagctc aaacttccca gtgggatgac ccttggggag 240
aggttctagc atggaagttt gatccaactc tggcctacac ttatgaggca tatgttagat 300
acccagaaga gtttggaagc aagtcaggcc tgtcagagga agaggttaga agaaggctaa 360
ccgcaagagg ccttcttaac atggctgaca agaaggaaac tcgctgaaac agcagggact 420
ttccacaagg ggatgttacg gggaggtact ggggaggagc cggtcgggaa cgcccacttt 480
cttgatgtat aaatatcact gcatttcgct ctgtattcag tcgctctgcg gagaggctgg 540
cagattgagc cctgggaggt tctctccagc actagcaggt agagcctggg tgttccctgc 600
tagactctca ccagcacttg gccggtgctg ggcagagtga ctccacgctt gcttgcttaa 660
agccctcttc aataaagctg ccattttagg aagtaagcta gtgtgtgttc ccatctctcc 720
tagccgccgc ctggtcaact cggtacttca ataataagaa gactcctggt ctgttaggac 780
cctttctgct ttgggaaacc gaagcaggaa aatccctagc agattggcgc ctgaacaggg 840
acttgaagga gagtgagaga ctcctgagta cggctgagtg aaggcagtaa gggcggcagg 900
aaccaaccac gacggagtgc tcctataaag gcgcgggtcg gtaccagacg gcgtgaggag 960
cgggagagga agaggcctcc ggttgcaggt aagtgcaaca caaaaaagaa atagctgtct 1020
tttatccagg aaggggtaat aagatagagt gggagatggg cgtgagaaac tccgtcttgt 1080
cagggaagaa agcagatgaa ttagaaaaaa ttaggctacg acccaacgga aagaaaaagt 1140
acatgttgaa gcatgtagta tgggcagcaa atgaattaga tagatttgga ttagcagaaa 1200
gcctgttgga gaacaaagaa ggatgtcaaa aaatactttc ggtcttagct ccattagtgc 1260
caacaggctc agaaaattta aaaagccttt ataatactgt ctgcgtcatc tggtgcattc 1320
acgcagaaga gaaagtgaaa cacactgagg aagcaaaaca gatagtgcag agacacctag 1380
tggtggaaac aggaacaaca gaaactatgc caaaaacaag tagaccaaca gcaccatcta 1440
gcggcagagg aggaaattac ccagtacaac aaataggtgg taactatgtc cacctgccat 1500
taagcccgag aacattaaat gcctgggtaa aattgataga ggaaaagaaa tttggagcag 1560
aagtagtgcc aggatttcag gcactgtcag aaggttgcac cccctatgac attaatcaga 1620
tgttaaattg tgtgggagac catcaagcgg ctatgcagat tatcagagat attataaacg 1680
aggaggctgc agattgggac ttgcagcacc cacaaccagc tccacaacaa ggacaactta 1740
gggagccgtc aggatcagat attgcaggaa caactagttc agtagatgaa caaatccagt 1800
ggatgtacag acaacagaac cccataccag taggcaacat ttacaggaga tggatccaac 1860
tggggttgca aaaatgtgtc agaatgtata acccaacaaa cattctagat gtaaaacaag 1920
ggccaaaaga gccatttcag agctatgtag acaggttcta caaaagttta agagcagaac 1980
agacagatgc agcagtaaag aattggatga ctcaaacact gctgattcaa aatgctaacc 2040
cagattgcaa gctagtgctg aaggggctgg gtgtgaatcc caccctagaa gaaatgctga 2100
cggcttgtca aggagtaggg gggccgggac agaaggctag attaatggca gaagccctga 2160
aagaggccct cgcaccagtg ccaatccctt ttgcagcagc ccaacagagg ggaccaagaa 2220

```
agccaattaa gtgttggaat tgtgggaaag agggacactc tgcaaggcaa tgcagagccc   2280
caagaagaca gggatgctgg aaatgtggaa aaatggacca tgttatggcc aaatgcccag   2340
acagacaggc gggtttttta ggccttggtc catggggaaa gaagccccgc aatttcccca   2400
tggctcaagt gcatcagggg ctgatgccaa ctgctccccc agaggaccca gctgtggatc   2460
tgctaaagaa ctacatgcag ttgggcaagc agcagagaga aaagcagaga gaaagcagag   2520
agaagcctta caaggaggtg acagaggatt tgctgcacct caattctctc tttggaggag   2580
accagtagtc actgctcata ttgaaggaca gcctgtagaa gtattactgg atacaggggc   2640
tgatgattct attgtaacag gaatagagtt aggtccacat tataccccaa aaatagtagg   2700
aggaatagga ggttttatta atactaaaga atacaaaaat gtagaaatag aagttttagg   2760
caaaaggatt aaagggacaa tcatgacagg ggacaccccg attaacattt ttggtagaaa   2820
tttgctaaca gctctgggga tgtctctaaa ttttcccata gctaaagtag agcctgtaaa   2880
agtcgcctta aagccaggaa aggatggacc aaaattgaag cagtggccat tatcaaaaga   2940
aaagatagtt gcattaagag aaatctgtga aaagatggaa aaggatggtc agttggagga   3000
agctcccccg accaatccat acaacacccc cacatttgct ataaagaaaa aggataagaa   3060
caaatggaga atgctgatag attttaggga actaaatagg gtcactcagg actttacgga   3120
agtccaatta ggaataccac accctgcagg actagcaaaa aggaaaagaa ttacagtact   3180
ggatataggt gatgcatatt tctccatacc tctagatgaa gaatttaggc agtacactgc   3240
ctttacttta ccatcagtaa ataatgcaga gccaggaaaa cgatacattt ataaggttct   3300
gcctcaggga tggaaggggt caccagccat cttccaatac actatgagac atgtgctaga   3360
acccttcagg aaggcaaatc cagatgtgac cttagtccag tatatggatg acatcttaat   3420
agctagtgac aggacagacc tggaacatga cagggtagtt ttacagtcaa aggaactctt   3480
gaatagcata gggttttcta ccccagaaga gaaattccaa aaagatcccc catttcaatg   3540
gatggggtac gaattgtggc caacaaaatg gaagttgcaa aagatagagt tgccacaaag   3600
agagacctgg acagtgaatg atatacagaa gttagtagga gtattaaatt gggcagctca   3660
aatttatcca ggtataaaaa ccaaacatct ctgtaggtta attagaggaa aaatgactct   3720
aacagaggaa gttcagtgga ctgagatggc agaagcagaa tatgaggaaa ataaaataat   3780
tctcagtcag gaacaagaag gatgttatta ccaagaaggc aagccattag aagccacggt   3840
aataaagagt caggacaatc agtggtctta taaaattcac caagaagaca aaatactgaa   3900
agtaggaaaa tttgcaaaga taaagaatac acataccaat ggagtgagac tattagcaca   3960
tgtaatacag aaaataggaa aggaagcaat agtgatctgg ggacaggtcc caaaattcca   4020
cttaccagtt gagaaggatg tatgggaaca gtggtggaca gactattggc aggtaacctg   4080
gataccggaa tgggatttta tctcaacacc accgctagta agattagtct tcaatctagt   4140
gaaggaccct atagagggag aagaaaccta ttatacagat ggatcatgta ataaacagtc   4200
aaaagaaggg aaagcaggat atatcacaga taggggcaaa gacaaagtaa aagtgttaga   4260
acagactact aatcaacaag cagaattgga agcatttctc atggcattga cagactcagg   4320
gccaaaggca aatattatag tagattcaca atatgttatg ggaataataa caggatgccc   4380
tacagaatca gagagcaggc tagttaatca aataatagaa gaaatgatta aaaagtcaga   4440
aatttatgta gcatgggtac cagcacacaa aggtatagga ggaaaccaag aaatagacca   4500
cctagttagt caagggatta gacaagttct cttcttggaa aagatagagc cagcacaaga   4560
```

-continued agaacatgat aaataccata gtaatgtaaa agaattggta ttcaaatttg gattacccag 4620
aatagtggcc agacagatag tagacacctg tgataaatgt catcagaaag gagaggctat 4680
acatgggcag gcaaattcag atctagggac ttggcaaatg gattgtaccc atctagaggg 4740
aaaaataatc atagttgcag tacatgtagc tagtggattc atagaagcag aggtaattcc 4800
acaagagaca ggaagacaga cagcactatt tctgttaaaa ttggcaggca gatggcctat 4860
tacacatcta cacacagata atggtgctaa ctttgcttcg caagaagtaa agatggttgc 4920
atggtgggca gggatagagc acacctttgg ggtaccatac aatccacaga gtcagggagt 4980
agtggaagca atgaatcacc acctgaaaaa tcaaatagat agaatcaggg aacaagcaaa 5040
ttcagtagaa accatagtat taatggcagt tcattgcatg aattttaaaa gaaggggagg 5100
aataggggat atgactccag cagaaagatt aattaacatg atcactacag aacaagagat 5160
acaatttcaa caatcaaaaa actcaaaatt taaaaatttt cgggtctatt acagagaagg 5220
cagagatcaa ctgtggaagg gacccggtga gctattgtgg aaaggggaag gagcagtcat 5280
cttaaaggta gggacagaca ttaaggtagt acccagaaga aaggctaaaa ttatcaaaga 5340
ttatggagga ggaaaagagg tggatagcag ttcccacatg gaggataccg gagaggctag 5400
agaggtggca tagcctcata aaatatctga aatataaaac taaagatcta caaaaggttt 5460
gctatgtgcc ccattttaag gtcggatggg catggtggac ctgcagcaga gtaatcttcc 5520
cactacagga aggaagccat ttagaagtac aagggtattg gcatttgaca ccagaaaaag 5580
ggtggctcag tacttatgca gtgaggataa cctggtactc aaagaacttt tggacagatg 5640
taacaccaaa ctatgcagac attttactgc atagcactta tttcccttgc tttacagcgg 5700
gagaagtgag aagggccatc aggggagaac aactgctgtc ttgctgcagg ttcccgagag 5760
ctcataagta ccaggtacca agcctacagt acttagcact gaaagtagta agcgatgtca 5820
gatcccaggg agagaatccc acctggaaac agtggagaag agacaatagg agaggccttc 5880
gaatggctaa acagaacagt agaggagata aacagagagg cggtaaacca cctaccaagg 5940
gagctaattt tccaggtttg gcaaaggtct tgggaatact ggcatgatga acaagggatg 6000
tcaccaagct atgtaaaata cagatacttg tgtttaatac aaaaggcttt atttatgcat 6060
tgcaagaaag gctgtagatg tctaggggaa ggacatgggg caggggggatg gagaccagga 6120 cctcctcctc ctccccctcc aggactagca taaatggaag aaagacctcc agaaaatgaa 6180
ggaccacaaa gggaaccatg ggatgaatgg gtagtggagg ttctggaaga actgaaagaa 6240
gaagctttaa aacattttga tcctcgcttg ctaactgcac ttggtaatca tatctataat 6300
agacatggag acacccttga gggagcagga gaactcatta gaatcctcca acgagcgctc 6360
ttcatgcatt tcagaggcgg atgcatccac tccagaatcg gccaacctgg gggaggaaat 6420
cctctctcag ctataccgcc ctctagaagc atgctataac acatgctatt gtaaaaagtg 6480
ttgctaccat tgccagtttt gttttcttaa aaaaggcttg ggatatgtt atgagcaatc 6540 acgaaagaga agaagaactc cgaaaaaggc taaggctaat acatcttctg catcaaacaa 6600
gtaagtatgg gatgtcttgg gaatcagctg cttatcgcca tcttgctttt aagtgtctat 6660
gggatctatt gtactctata tgtcacagtc ttttatggtg taccagcttg gaggaatgcg 6720
acaattcccc tcttttgtgc aaccaagaat agggatactt ggggaacaac tcagtgccta 6780
ccagataatg gtgattattc agaagtggcc cttaatgtta cagaaagctt tgatgcctgg 6840
aataatacag tcacagaaca ggcaatagag gatgtatggc aactctttga gacctcaata 6900
aagccttgtg taaaattatc cccattatgc attactatga gatgcaataa aagtgagaca 6960
gatagatggg gattgacaaa atcaataaca acaacagcat caacaacatc aacgacagca 7020
tcagcaaaag tagacatggt caatgagact agttcttgta tagcccagga taattgcaca 7080
ggcttggaac aagagcaaat gataagctgt aaattcaaca tgacagggtt aaaaagagac 7140
aagaaaaaag agtacaatga aacttggtac tctgcagatt tggtatgtga acaagggaat 7200
aacactggta atgaaagtag atgttacatg aaccactgta acacttctgt tatccaagag 7260
tcttgtgaca aacattattg ggatgctatt agatttaggt attgtgcacc tccaggttat 7320
gctttgctta gatgtaatga cacaaattat tcaggcttta tgcctaaatg ttctaaggtg 7380
gtggtctctt catgcacaag gatgatggag acacagactt ctacttggtt tggctttaat 7440
ggaactagag cagaaaatag aacttatatt tactggcatg gtagggataa taggactata 7500
attagtttaa ataagtatta taatctaaca atgaaatgta gaagaccagg aaataagaca 7560
gttttaccag tcaccattat gtctggattg gttttccact cacaaccaat caatgatagg 7620
ccaaagcagg catggtgttg gtttggagga aaatggaagg atgcaataaa agaggtgaag 7680
cagaccattg tcaaacatcc caggtatact ggaactaaca atactgataa aatcaatttg 7740
acggctcctg gaggaggaga tccggaagtt accttcatgt ggacaaattg cagaggagag 7800
ttcctctact gtaaaatgaa ttggtttcta aattgggtag aagataggaa tacagctaac 7860
cagaagccaa aggaacagca taaaaggaat tacgtgccat gtcatattag acaaataatc 7920
aacacttggc ataaagtagg caaaaatgtt tatttgcctc caagagaggg agacctcacg 7980
tgtaactcca cagtgaccag tctcatagca aacatagatt ggattgatgg aaaccaaact 8040
aatatcacca tgagtgcaga ggtggcagaa ctgtatcgat tggaattggg agattataaa 8100
ttagtagaga tcactccaat tggcttggcc cccacagatg tgaagaggta cactactggt 8160
ggcacctcaa gaaataaaag aggggtcttt gtgctagggt tcttgggttt tctcgcaacg 8220
gcaggttctg caatgggcgc ggcgtcgttg acgctgaccg ctcagtcccg aactttattg 8280
gctgggatag tgcagcaaca gcaacagctg ttggacgtgg tcaagagaca acaagaattg 8340
ttgcgactga ccgtctgggg aacaaagaac ctccagacta gggtcactgc catcgagaag 8400
tacttaaagg accaggcgca gctgaatgct tggggatgtg cgtttagaca agtctgccac 8460
actactgtac catggccaaa tgcaagtcta acaccaaagt ggaacaatga gacttggcaa 8520
gagtgggagc gaaaggttga cttcttggaa gaaaatataa cagccctcct agaggaggca 8580
caaattcaac aagagaagaa catgtatgaa ttacaaaagt tgaatagctg ggatgtgttt 8640
ggcaattggt ttgaccttgc ttcttggata aagtatatac aatatggagt ttatatagtt 8700
gtaggagtaa tactgttaag aatagtgatc tatatagtac aaatgctagc taagttaagg 8760
caggggtata ggccagtgtt ctcttcccca ccctcttatt tccagcagac ccatatccaa 8820
caggacccgg cactgccaac cagagaaggc aaagaaagag acggtggaga aggcggtggc 8880
aacagctcct ggccttggca gatagaatat attcatttcc tgatccgcca actgatacgc 8940
ctcttgactt ggctattcag caactgcaga accttgctat cgagagtata ccagatcctc 9000
caaccaatac tccagaggct ctctgcgacc ctacagagga ttcgagaagt cctcaggact 9060
gaactgacct acctacaata tgggtggagc tatttccatg aggcggtcca ggccgtctgg 9120
agatctgcga cagagactct tgcgggcgcg tggggagact tatgggagac tcttaggaga 9180
ggtggaagat ggatactcgc aatccccagg aggattagac aagggcttga gctcactctc 9240
ttgtgaggga cagaaataca atcagggaca gtatatgaat actccatgga gaaacccagc 9300
tgaagagaga gaaaaattag catacagaaa acaaaatatg gatgatatag atgaggaaga 9360
tgatgacttg gtaggggtat cagtgaggcc aaaagttccc ctaagaacaa tgagttacaa 9420
attggcaata gacatgtctc attttataaa agaaaagggg ggactggaag ggatttatta 9480
cagtgcaaga agacatagaa tcttagacat atacttagaa aaggaaggag gcatcatacc 9540
agattggcag gattacacct caggaccagg aattagatac ccaaagacat ttggctggct 9600
atggaaatta gtccctgtaa atgtatcaga tgaggcacag gaggatgagg agcattattt 9660
aatgcatcca gctcaaactt cccagtggga tgacccttgg ggagaggttc tagcatggaa 9720
gtttgatcca actctggcct acacttatga ggcatatgtt agatacccag aagagtttgg 9780
aagcaagtca ggcctgtcag aggaagaggt tagaagaagg ctaaccgcaa gaggccttct 9840
taacatggct gacaagaagg aaactcgctg aacgcgtcgg atcccggagt actacaaaga 9900
ctgctgacgc gaattccgcc cccccccta acgttactgg ccgaagccgc ttggaataag 9960
gccggtgtgc gtttgtctat atgttatttt ccaccatatt gccgtctttt ggcaatgtga 10020
gggcccggaa acctggccct gtcttcttga cgagcattcc taggggtctt tcccctctcg 10080
ccaaaggaat gcaaggtctg ttgaatgtcg tgaaggaagc agttcctctg gaagcttctt 10140
gaagacaaac aacgtctgta gcgacccttt gcaggcagcg gaacccccca cctggcgaca 10200
ggtgcctctg cggccaaaag ccacgtgtat aagatacacc tgcaaaggcg gcacaacccc 10260
agtgccacgt tgtgagttgg atagttgtgg aaagagtcaa atggctctcc tcaagcgtat 10320
tcaacaaggg gctgaaggat gcccagaagg taccccattg tatgggatct gatctggggc 10380
ctcggtgcac atgctttaca tgtgtttagt cgaggttaaa aaacgtctag gccccccgaa 10440
ccacggggac gtggttttcc tttgaaaaac acgatgataa taccatggtg cccaagaaga 10500
agaggaaagt ctccaacctg ctgactgtgc accaaaacct gcctgccctc cctgtggatg 10560
ccacctctga tgaagtcagg aagaacctga tggacatgtt cagggacagg caggccttct 10620
ctgaacacac ctggaagatg ctcctgtctg tgtgcagatc ctgggctgcc tggtgcaagc 10680
tgaacaacag gaaatggttc cctgctgaac ctgaggatgt gagggactac ctcctgtacc 10740
tgcaagccag aggcctggct gtgaagacca tccaacagca cctgggccag ctcaacatgc 10800
tgcacaggag atctggcctg cctcgccctt ctgactccaa tgctgtgtcc ctggtgatga 10860
ggagaatcag aaaggagaat gtggatgctg gggagagagc caagcaggcc ctggcctttg 10920
aacgcactga ctttgaccaa gtcagatccc tgatggagaa ctctgacaga tgccaggaca 10980
tcaggaacct ggccttcctg ggcattgcct acaacaccct gctgcgcatt gccgaaattg 11040
ccagaatcag agtgaaggac atctcccgca ccgatggtgg gagaatgctg atccacattg 11100
gcaggaccaa gaccctggtg tccacagctg gtgtggagaa ggccctgtcc ctgggggtta 11160
ccaagctggt ggagagatgg atctctgtgt ctggtgtggc tgatgacccc aacaactacc 11220
tgttctgccg ggtcagaaag aatggtgtgg ctgccccttc tgccacctcc caactgtcca 11280
cccgggccct ggaagggatc tttgaggcca cccaccgcct gatctatggt gccaaggatg 11340
actctgggca gagatacctg gcctggtctg gccactctgc cagagtgggt gctgccaggg 11400
acatggccag ggctggtgtg tccatccctg aaatcatgca ggctggtggc tggaccaatg 11460
tgaacatagt gatgaactac atcagaaacc tggactctga gactggggcc atggtgaggc 11520
tgctcgagga tggggactga cccgggtctc attttataaa agaaaagggg ggactggaag 11580
ggatttatcc gcggttcact cgagactcgc tgaaacagca gggactttcc acaaggggat 11640
gttacgggga ggtactgggg aggagccggt cgggaacgcc cactttcttg atgtataaat 11700
atcactgcat ttcgctctgt attcagtcgc tctgcggaga ggctggcaga ttgagccctg 11760
ggaggttctc tccagcacta gcaggtagag cctgggtgtt ccctgctaga ctctcaccag 11820
cacttggccg gtgctgggca gagtgactcc acgcttgctt gcttaaagcc ctcttcaata 11880
aagctgccat tttagaagta agctagtgtg tgttcccatc tctcctagcc gccgcctggt 11940
caactcggta ctcaataata agaagaccct ggtctgttag gaccctttct gctttgggaa 12000
accgaagcag gaaaatccct agca 12024

<210> SEQ ID NO 26
<211> LENGTH: 12024
<212> TYPE: DNA
<213> ORGANISM: Artificial Sequence
<220> FEATURE:
<223> OTHER INFORMATION: SIVmac239-Nef-IRES-Cre optimized codon

<400> SEQUENCE: 26
tggaagggat ttattacagt gcaagaagac atagaatctt agacatatac ttagaaaagg 60
aagaaggcat cataccagat tggcaggatt acacctcagg accaggaatt agatacccaa 120
agacatttgg ctggctatgg aaattagtcc ctgtaaatgt atcagatgag gcacaggagg 180
atgaggagca ttatttaatg catccagctc aaacttccca gtgggatgac ccttggggag 240
aggttctagc atggaagttt gatccaactc tggcctacac ttatgaggca tatgttagat 300
acccagaaga gtttggaagc aagtcaggcc tgtcagagga agaggttaga agaaggctaa 360
ccgcaagagg ccttcttaac atggctgaca agaaggaaac tcgctgaaac agcagggact 420
ttccacaagg ggatgttacg gggaggtact ggggaggagc cggtcgggaa cgcccacttt 480
cttgatgtat aaatatcact gcatttcgct ctgtattcag tcgctctgcg gagaggctgg 540
cagattgagc cctgggaggt tctctccagc actagcaggt agagcctggg tgttccctgc 600
tagactctca ccagcacttg gccggtgctg ggcagagtga ctccacgctt gcttgcttaa 660
agccctcttc aataaagctg ccattttagg aagtaagcta gtgtgtgttc ccatctctcc 720
tagccgccgc ctggtcaact cggtacttca ataataagaa gactcctggt ctgttaggac 780
cctttctgct ttgggaaacc gaagcaggaa aatccctagc agattggcgc ctgaacaggg 840
acttgaagga gagtgagaga ctcctgagta cggctgagtg aaggcagtaa gggcggcagg 900
aaccaaccac gacggagtgc tcctataaag gcgcgggtcg gtaccagacg gcgtgaggag 960
cgggagagga agaggcctcc ggttgcaggt aagtgcaaca caaaaaagaa atagctgtct 1020
tttatccagg aaggggtaat aagatagagt gggagatggg cgtgagaaac tccgtcttgt 1080
cagggaagaa agcagatgaa ttagaaaaaa ttaggctacg acccaacgga aagaaaaagt 1140
acatgttgaa gcatgtagta tgggcagcaa atgaattaga tagatttgga ttagcagaaa 1200
gcctgttgga gaacaaagaa ggatgtcaaa aaatactttc ggtcttagct ccattagtgc 1260
caacaggctc agaaaattta aaaagccttt ataatactgt ctgcgtcatc tggtgcattc 1320
acgcagaaga gaaagtgaaa cacactgagg aagcaaaaca gatagtgcag agacacctag 1380
tggtggaaac aggaacaaca gaaactatgc caaaaacaag tagaccaaca gcaccatcta 1440
gcggcagagg aggaaattac ccagtacaac aaataggtgg taactatgtc cacctgccat 1500
taagcccgag aacattaaat gcctgggtaa aattgataga ggaaaagaaa tttggagcag 1560
aagtagtgcc aggatttcag gcactgtcag aaggttgcac cccctatgac attaatcaga 1620
tgttaaattg tgtgggagac catcaagcgg ctatgcagat tatcagagat attataaacg 1680

-continued

```
aggaggctgc agattgggac ttgcagcacc cacaaccagc tccacaacaa ggacaactta   1740
gggagccgtc aggatcagat attgcaggaa caactagttc agtagatgaa caaatccagt   1800
ggatgtacag acaacagaac cccataccag taggcaacat ttacaggaga tggatccaac   1860
tggggttgca aaaatgtgtc agaatgtata acccaacaaa cattctagat gtaaaacaag   1920
ggccaaaaga gccatttcag agctatgtag acaggttcta caaaagttta agagcagaac   1980
agacagatgc agcagtaaag aattggatga ctcaaacact gctgattcaa aatgctaacc   2040
cagattgcaa gctagtgctg aaggggctgg gtgtgaatcc caccctagaa gaaatgctga   2100
cggcttgtca aggagtaggg ggcccgggac agaaggctag attaatggca gaagccctga   2160
aagaggccct cgcaccagtg ccaatccctt ttgcagcagc ccaacagagg ggaccaagaa   2220
agccaattaa gtgttggaat tgtgggaaag agggacactc tgcaaggcaa tgcagagccc   2280
caagaagaca gggatgctgg aaatgtggaa aaatggacca tgttatggcc aaatgcccag   2340
acagacaggc gggtttttta ggccttggtc catggggaaa gaagccccgc aatttcccca   2400
tggctcaagt gcatcagggg ctgatgccaa ctgctccccc agaggaccca gctgtggatc   2460
tgctaaagaa ctacatgcag ttgggcaagc agcagagaga aaagcagaga gaaagcagag   2520
agaagcctta caaggaggtg acagaggatt tgctgcacct caattctctc tttggaggag   2580
accagtagtc actgctcata ttgaaggaca gcctgtagaa gtattactgg atacaggggc   2640
tgatgattct attgtaacag gaatagagtt aggtccacat tataccccaa aaatagtagg   2700
aggaatagga ggttttatta atactaaaga atacaaaaat gtagaaatag aagttttagg   2760
caaaaggatt aaagggacaa tcatgacagg ggacaccccg attaacattt ttggtagaaa   2820
tttgctaaca gctctgggga tgtctctaaa ttttcccata gctaaagtag agcctgtaaa   2880
agtcgcctta aagccaggaa aggatggacc aaaattgaag cagtggccat tatcaaaaga   2940
aaagatagtt gcattaagag aaatctgtga aaagatggaa aaggatggtc agttggagga   3000
agctcccccg accaatccat acaacacccc cacatttgct ataaagaaaa aggataagaa   3060
caaatggaga atgctgatag attttaggga actaaatagg gtcactcagg actttacgga   3120
agtccaatta ggaataccac accctgcagg actagcaaaa aggaaaagaa ttacagtact   3180
ggatataggt gatgcatatt tctccatacc tctagatgaa gaatttaggc agtacactgc   3240
ctttacttta ccatcagtaa ataatgcaga gccaggaaaa cgatacattt ataaggttct   3300
gcctcaggga tggaaggggt caccagccat cttccaatac actatgagac atgtgctaga   3360
acccttcagg aaggcaaatc cagatgtgac cttagtccag tatatggatg acatcttaat   3420
agctagtgac aggacagacc tggaacatga cagggtagtt ttacagtcaa aggaactctt   3480
gaatagcata gggttttcta ccccagaaga gaaattccaa aaagatcccc catttcaatg   3540
gatggggtac gaattgtggc caacaaaatg gaagttgcaa aagatagagt tgccacaaag   3600
agagacctgg acagtgaatg atatacagaa gttagtagga gtattaaatt gggcagctca   3660
aatttatcca ggtataaaaa ccaaacatct ctgtaggtta attagaggaa aaatgactct   3720
aacagaggaa gttcagtgga ctgagatggc agaagcagaa tatgaggaaa ataaaataat   3780
tctcagtcag gaacaagaag gatgttatta ccaagaaggc aagccattag aagccacggt   3840
aataaagagt caggacaatc agtggtctta taaaattcac caagaagaca aaatactgaa   3900
agtaggaaaa tttgcaaaga taaagaatac acataccaat ggagtgagac tattagcaca   3960
tgtaatacag aaaataggaa aggaagcaat agtgatctgg ggacaggtcc caaaattcca   4020
cttaccagtt gagaaggatg tatgggaaca gtggtggaca gactattggc aggtaacctg   4080
```

gataccggaa tgggatttta tctcaacacc accgctagta agattagtct tcaatctagt 4140
gaaggaccct atagagggag aagaaaccta ttatacagat ggatcatgta ataaacagtc 4200
aaaagaaggg aaagcaggat atatcacaga taggggcaaa gacaaagtaa aagtgttaga 4260
acagactact aatcaacaag cagaattgga agcatttctc atggcattga cagactcagg 4320
gccaaaggca aatattatag tagattcaca atatgttatg ggaataataa caggatgccc 4380
tacagaatca gagagcaggc tagttaatca aataatagaa gaaatgatta aaaagtcaga 4440
aatttatgta gcatgggtac cagcacacaa aggtatagga ggaaaccaag aaatagacca 4500
cctagttagt caagggatta gacaagttct cttcttggaa aagatagagc cagcacaaga 4560
agaacatgat aaataccata gtaatgtaaa agaattggta ttcaaatttg gattacccag 4620
aatagtggcc agacagatag tagacacctg tgataaatgt catcagaaag gagaggctat 4680
acatgggcag gcaaattcag atctagggac ttggcaaatg gattgtaccc atctagaggg 4740
aaaaataatc atagttgcag tacatgtagc tagtggattc atagaagcag aggtaattcc 4800
acaagagaca ggaagacaga cagcactatt tctgttaaaa ttggcaggca gatggcctat 4860
tacacatcta cacacagata atggtgctaa ctttgcttcg caagaagtaa agatggttgc 4920
atggtgggca gggatagagc acacctttgg ggtaccatac aatccacaga gtcagggagt 4980
agtggaagca atgaatcacc acctgaaaaa tcaaatagat agaatcaggg aacaagcaaa 5040
ttcagtagaa accatagtat taatggcagt tcattgcatg aattttaaaa gaaggggagg 5100
aataggggat atgactccag cagaaagatt aattaacatg atcactacag aacaagagat 5160
acaatttcaa caatcaaaaa actcaaaatt taaaaatttt cgggtctatt acagagaagg 5220
cagagatcaa ctgtggaagg gacccggtga gctattgtgg aaaggggaag gagcagtcat 5280
cttaaaggta gggacagaca ttaaggtagt acccagaaga aaggctaaaa ttatcaaaga 5340
ttatggagga ggaaaagagg tggatagcag ttcccacatg gaggataccg gagaggctag 5400
agaggtggca tagcctcata aaatatctga aatataaaac taaagatcta caaaaggttt 5460
gctatgtgcc ccattttaag gtcggatggg catggtggac ctgcagcaga gtaatcttcc 5520
cactacagga aggaagccat ttagaagtac aagggtattg gcatttgaca ccagaaaaag 5580
ggtggctcag tacttatgca gtgaggataa cctggtactc aaagaacttt tggacagatg 5640
taacaccaaa ctatgcagac attttactgc atagcactta tttcccttgc tttacagcgg 5700
gagaagtgag aagggccatc aggggagaac aactgctgtc ttgctgcagg ttcccgagag 5760
ctcataagta ccaggtacca agcctacagt acttagcact gaaagtagta agcgatgtca 5820
gatcccaggg agagaatccc acctggaaac agtggagaag agacaatagg agaggccttc 5880
gaatggctaa acagaacagt agaggagata aacagagagg cggtaaacca cctaccaagg 5940
gagctaattt tccaggtttg gcaaaggtct tgggaatact ggcatgatga acaagggatg 6000
tcaccaagct atgtaaaata cagatacttg tgtttaatac aaaaggcttt atttatgcat 6060
tgcaagaaag gctgtagatg tctaggggaa ggacatgggg caggggggatg gagaccagga 6120 cctcctcctc ctcccctcc aggactagca taaatggaag aaagacctcc agaaaatgaa 6180
ggaccacaaa gggaaccatg ggatgaatgg gtagtggagg ttctggaaga actgaaagaa 6240
gaagctttaa aacattttga tcctcgcttg ctaactgcac ttggtaatca tatctataat 6300
agacatggag acaccccttga gggagcagga gaactcatta gaatcctcca acgagcgctc 6360
ttcatgcatt tcagaggcgg atgcatccac tccagaatcg gccaacctgg gggaggaaat 6420

-continued

```
cctctctcag ctataccgcc ctctagaagc atgctataac acatgctatt gtaaaaagtg   6480
ttgctaccat tgccagtttt gttttcttaa aaaaggcttg gggatatgtt atgagcaatc   6540
acgaaagaga agaagaactc cgaaaaaggc taaggctaat acatcttctg catcaaacaa   6600
gtaagtatgg gatgtcttgg gaatcagctg cttatcgcca tcttgctttt aagtgtctat   6660
gggatctatt gtactctata tgtcacagtc ttttatggtg taccagcttg gaggaatgcg   6720
acaattcccc tcttttgtgc aaccaagaat agggatactt ggggaacaac tcagtgccta   6780
ccagataatg gtgattattc agaagtggcc cttaatgtta cagaaagctt tgatgcctgg   6840
aataatacag tcacagaaca ggcaatagag gatgtatggc aactctttga gacctcaata   6900
aagccttgtg taaaattatc cccattatgc attactatga gatgcaataa aagtgagaca   6960
gatagatggg gattgacaaa atcaataaca acaacagcat caacaacatc aacgacagca   7020
tcagcaaaag tagacatggt caatgagact agttcttgta tagcccagga taattgcaca   7080
ggcttggaac aagagcaaat gataagctgt aaattcaaca tgacagggtt aaaaagagac   7140
aagaaaaaag agtacaatga aacttggtac tctgcagatt tggtatgtga acaagggaat   7200
aacactggta atgaaagtag atgttacatg aaccactgta acacttctgt tatccaagag   7260
tcttgtgaca aacattattg ggatgctatt agatttaggt attgtgcacc tccaggttat   7320
gctttgctta gatgtaatga cacaaattat tcaggcttta tgcctaaatg ttctaaggtg   7380
gtggtctctt catgcacaag gatgatggag acacagactt ctacttggtt tggctttaat   7440
ggaactagag cagaaaatag aacttatatt tactggcatg gtagggataa taggactata   7500
attagtttaa ataagtatta taatctaaca atgaaatgta gaagaccagg aaataagaca   7560
gttttaccag tcaccattat gtctggattg gttttccact cacaaccaat caatgatagg   7620
ccaaagcagg catggtgttg gtttggagga aaatggaagg atgcaataaa agaggtgaag   7680
cagaccattg tcaaacatcc caggtatact ggaactaaca atactgataa aatcaatttg   7740
acggctcctg gaggaggaga tccggaagtt accttcatgt ggacaaattg cagaggagag   7800
ttcctctact gtaaaatgaa ttggtttcta aattgggtag aagataggaa tacagctaac   7860
cagaagccaa aggaacagca taaaaggaat tacgtgccat gtcatattag acaaataatc   7920
aacacttggc ataaagtagg caaaaatgtt tatttgcctc caagagaggg agacctcacg   7980
tgtaactcca cagtgaccag tctcatagca aacatagatt ggattgatgg aaaccaaact   8040
aatatcacca tgagtgcaga ggtggcagaa ctgtatcgat tggaattggg agattataaa   8100
ttagtagaga tcactccaat tggcttggcc cccacagatg tgaagaggta cactactggt   8160
ggcacctcaa gaaataaaag aggggtcttt gtgctagggt tcttgggttt tctcgcaacg   8220
gcaggttctg caatgggcgc ggcgtcgttg acgctgaccg ctcagtcccg aactttattg   8280
gctgggatag tgcagcaaca gcaacagctg ttggacgtgg tcaagagaca acaagaattg   8340
ttgcgactga ccgtctgggg aacaaagaac ctccagacta gggtcactgc catcgagaag   8400
tacttaaagg accaggcgca gctgaatgct tggggatgtg cgtttagaca agtctgccac   8460
actactgtac catggccaaa tgcaagtcta acaccaaagt ggaacaatga gacttggcaa   8520
gagtgggagc gaaaggttga cttcttggaa gaaaatataa cagccctcct agaggaggca   8580
caaattcaac aagagaagaa catgtatgaa ttacaaaagt tgaatagctg ggatgtgttt   8640
ggcaattggt ttgaccttgc ttcttggata aagtatatac aatatggagt ttatatagtt   8700
gtaggagtaa tactgttaag aatagtgatc tatatagtac aaatgctagc taagttaagg   8760
caggggtata ggccagtgtt ctcttcccca ccctcttatt tccagcagac ccatatccaa   8820
```

```
caggacccgg cactgccaac cagagaaggc aaagaaagag acggtggaga aggcggtggc   8880
aacagctcct ggccttggca gatagaatat attcatttcc tgatccgcca actgatacgc   8940
ctcttgactt ggctattcag caactgcaga accttgctat cgagagtata ccagatcctc   9000
caaccaatac tccagaggct ctctgcgacc ctacagagga ttcgagaagt cctcaggact   9060
gaactgacct acctacaata tgggtggagc tatttccatg aggcggtcca ggccgtctgg   9120
agatctgcga cagagactct tgcgggcgcg tggggagact tatgggagac tcttaggaga   9180
ggtggaagat ggatactcgc aatccccagg aggattagac aagggcttga gctcactctc   9240
ttgtgaggga cagaaataca atcagggaca gtatatgaat actccatgga gaaacccagc   9300
tgaagagaga gaaaaattag catacagaaa acaaaatatg gatgatatag atgaggaaga   9360
tgatgacttg gtaggggtat cagtgaggcc aaaagttccc ctaagaacaa tgagttacaa   9420
attggcaatt gacatgtcac atttcattaa ggagaagggc ggactggagg ggatatacta   9480
ttctgccagg aggcatagaa tcttagacat atacttagaa aaggaaggag gcatcatacc   9540
agattggcag gattacacct caggaccagg aattagatac ccaaagacat ttggctggct   9600
atggaaatta gtccctgtaa atgtatcaga tgaggcacag gaggatgagg agcattattt   9660
aatgcatcca gctcaaactt cccagtggga tgacccttgg ggagaggttc tagcatggaa   9720
gtttgatcca actctggcct acacttatga ggcatatgtt agatacccag aagagtttgg   9780
aagcaagtca ggcctgtcag aggaagaggt tagaagaagg ctaaccgcaa gaggccttct   9840
taacatggct gacaagaagg aaactcgctg aacgcgtcgg atcccggagt actacaaaga   9900
ctgctgacgc gaattccgcc cccccccta acgttactgg ccgaagccgc ttggaataag   9960
gccggtgtgc gtttgtctat atgttatttt ccaccatatt gccgtctttt ggcaatgtga  10020
gggcccggaa acctggccct gtcttcttga cgagcattcc taggggtctt tcccctctcg  10080
ccaaaggaat gcaaggtctg ttgaatgtcg tgaaggaagc agttcctctg gaagcttctt  10140
gaagacaaac aacgtctgta gcgacccttt gcaggcagcg gaacccccca cctggcgaca  10200
ggtgcctctg cggccaaaag ccacgtgtat aagatacacc tgcaaaggcg gcacaacccc  10260
agtgccacgt tgtgagttgg atagttgtgg aaagagtcaa atggctctcc tcaagcgtat  10320
tcaacaaggg gctgaaggat gcccagaagg taccccattg tatgggatct gatctggggc  10380
ctcggtgcac atgctttaca tgtgtttagt cgaggttaaa aaacgtctag gccccccgaa  10440
ccacggggac gtggttttcc tttgaaaaac acgatgataa taccatggtg cccaagaaga  10500
agaggaaagt ctccaacctg ctgactgtgc accaaaacct gcctgccctc cctgtggatg  10560
ccacctctga tgaagtcagg aagaacctga tggacatgtt cagggacagg caggccttct  10620
ctgaacacac ctggaagatg ctcctgtctg tgtgcagatc ctgggctgcc tggtgcaagc  10680
tgaacaacag gaaatggttc cctgctgaac ctgaggatgt gagggactac ctcctgtacc  10740
tgcaagccag aggcctggct gtgaagacca tccaacagca cctgggccag ctcaacatgc  10800
tgcacaggag atctggcctg cctcgccctt ctgactccaa tgctgtgtcc ctggtgatga  10860
ggagaatcag aaaggagaat gtggatgctg gggagagagc caagcaggcc ctggcctttg  10920
aacgcactga ctttgaccaa gtcagatccc tgatggagaa ctctgacaga tgccaggaca  10980
tcaggaacct ggccttcctg ggcattgcct acaacaccct gctgcgcatt gccgaaattg  11040
ccagaatcag agtgaaggac atctcccgca ccgatggtgg gagaatgctg atccacattg  11100
gcaggaccaa gaccctggtg tccacagctg gtgtggagaa ggccctgtcc ctggggggta  11160
```

-continued

```
ccaagctggt ggagagatgg atctctgtgt ctggtgtggc tgatgacccc aacaactacc  11220

tgttctgccg ggtcagaaag aatggtgtgg ctgccccttc tgccacctcc caactgtcca  11280

cccgggccct ggaagggatc tttgaggcca cccaccgcct gatctatggt gccaaggatg  11340

actctgggca gagatacctg gcctggtctg gccactctgc cagagtgggt gctgccaggg  11400

acatggccag ggctggtgtg tccatccctg aaatcatgca ggctggtggc tggaccaatg  11460

tgaacatagt gatgaactac atcagaaacc tggactctga gactggggcc atggtgaggc  11520

tgctcgagga tggggactga cccgggtctc attttataaa agaaaagggg ggactggaag  11580

ggatttatcc gcggttcact cgagactcgc tgaaacagca gggactttcc acaaggggat  11640

gttacgggga ggtactgggg aggagccggt cgggaacgcc cactttcttg atgtataaat  11700

atcactgcat ttcgctctgt attcagtcgc tctgcggaga ggctggcaga ttgagccctg  11760

ggaggttctc tccagcacta gcaggtagag cctgggtgtt ccctgctaga ctctcaccag  11820

cacttggccg gtgctgggca gagtgactcc acgcttgctt gcttaaagcc ctcttcaata  11880

aagctgccat tttagaagta agctagtgtg tgttcccatc tctcctagcc gccgcctggt  11940

caactcggta ctcaataata agaagaccct ggtctgttag gaccctttct gctttgggaa  12000

accgaagcag gaaaatccct agca                                         12024
```

```
<210> SEQ ID NO 27
<211> LENGTH: 12103
<212> TYPE: DNA
<213> ORGANISM: Artificial Sequence
<220> FEATURE:
<223> OTHER INFORMATION: SIVmac239-Nef-CMV-Cre

<400> SEQUENCE: 27

tggaagggat ttattacagt gcaagaagac atagaatctt agacatatac ttagaaaagg     60

aagaaggcat cataccagat tggcaggatt acacctcagg accaggaatt agatacccaa    120

agacatttgg ctggctatgg aaattagtcc ctgtaaatgt atcagatgag gcacaggagg    180

atgaggagca ttatttaatg catccagctc aaacttccca gtgggatgac ccttggggag    240

aggttctagc atggaagttt gatccaactc tggcctacac ttatgaggca tatgttagat    300

acccagaaga gtttggaagc aagtcaggcc tgtcagagga agaggttaga agaaggctaa    360

ccgcaagagg ccttcttaac atggctgaca agaaggaaac tcgctgaaac agcagggact    420

ttccacaagg ggatgttacg gggaggtact ggggaggagc cggtcgggaa cgcccacttt    480

cttgatgtat aaatatcact gcatttcgct ctgtattcag tcgctctgcg gagaggctgg    540

cagattgagc cctgggaggt tctctccagc actagcaggt agagcctggg tgttccctgc    600

tagactctca ccagcacttg gccggtgctg ggcagagtga ctccacgctt gcttgcttaa    660

agccctcttc aataaagctg ccattttagg aagtaagcta gtgtgtgttc ccatctctcc    720

tagccgccgc ctggtcaact cggtacttca ataataagaa gactcctggt ctgttaggac    780

cctttctgct ttgggaaacc gaagcaggaa aatccctagc agattggcgc ctgaacaggg    840

acttgaagga gagtgagaga ctcctgagta cggctgagtg aaggcagtaa gggcggcagg    900

aaccaaccac gacggagtgc tcctataaag gcgcgggtcg gtaccagacg gcgtgaggag    960

cgggagagga agaggcctcc ggttgcaggt aagtgcaaca caaaaaagaa atagctgtct   1020

tttatccagg aaggggtaat aagatagagt gggagatggg cgtgagaaac tccgtcttgt   1080

cagggaagaa agcagatgaa ttagaaaaaa ttaggctacg acccaacgga aagaaaaagt   1140

acatgttgaa gcatgtagta tgggcagcaa atgaattaga tagatttgga ttagcagaaa   1200
```

```
gcctgttgga gaacaaagaa ggatgtcaaa aaatactttc ggtcttagct ccattagtgc   1260
caacaggctc agaaaattta aaaagccttt ataatactgt ctgcgtcatc tggtgcattc   1320
acgcagaaga gaaagtgaaa cacactgagg aagcaaaaca gatagtgcag agacacctag   1380
tggtggaaac aggaacaaca gaaactatgc caaaaacaag tagaccaaca gcaccatcta   1440
gcggcagagg aggaaattac ccagtacaac aaataggtgg taactatgtc cacctgccat   1500
taagcccgag aacattaaat gcctgggtaa aattgataga ggaaaagaaa tttggagcag   1560
aagtagtgcc aggatttcag gcactgtcag aaggttgcac cccctatgac attaatcaga   1620
tgttaaattg tgtgggagac catcaagcgg ctatgcagat tatcagagat attataaacg   1680
aggaggctgc agattgggac ttgcagcacc cacaaccagc tccacaacaa ggacaactta   1740
gggagccgtc aggatcagat attgcaggaa caactagttc agtagatgaa caaatccagt   1800
ggatgtacag acaacagaac cccataccag taggcaacat ttacaggaga tggatccaac   1860
tggggttgca aaaatgtgtc agaatgtata acccaacaaa cattctagat gtaaaacaag   1920
ggccaaaaga gccatttcag agctatgtag acaggttcta caaaagttta agagcagaac   1980
agacagatgc agcagtaaag aattggatga ctcaaacact gctgattcaa aatgctaacc   2040
cagattgcaa gctagtgctg aaggggctgg gtgtgaatcc caccctagaa gaaatgctga   2100
cggcttgtca aggagtaggg gggccgggac agaaggctag attaatggca gaagccctga   2160
aagaggccct cgcaccagtg ccaatccctt ttgcagcagc ccaacagagg ggaccaagaa   2220
agccaattaa gtgttggaat tgtgggaaag agggacactc tgcaaggcaa tgcagagccc   2280
caagaagaca gggatgctgg aaatgtggaa aaatggacca tgttatggcc aaatgcccag   2340
acagacaggc gggtttttta ggccttggtc catggggaaa gaagccccgc aatttcccca   2400
tggctcaagt gcatcagggg ctgatgccaa ctgctccccc agaggaccca gctgtggatc   2460
tgctaaagaa ctacatgcag ttgggcaagc agcagagaga aaagcagaga gaaagcagag   2520
agaagcctta caaggaggtg acagaggatt tgctgcacct caattctctc tttggaggag   2580
accagtagtc actgctcata ttgaaggaca gcctgtagaa gtattactgg atacaggggc   2640
tgatgattct attgtaacag gaatagagtt aggtccacat tataccccaa aaatagtagg   2700
aggaatagga ggttttatta atactaaaga atacaaaaat gtagaaatag aagttttagg   2760
caaaaggatt aaagggacaa tcatgacagg ggacaccccg attaacattt ttggtagaaa   2820
tttgctaaca gctctgggga tgtctctaaa ttttcccata gctaaagtag agcctgtaaa   2880
agtcgcctta aagccaggaa aggatggacc aaaattgaag cagtggccat tatcaaaaga   2940
aaagatagtt gcattaagag aaatctgtga aaagatggaa aaggatggtc agttggagga   3000
agctcccccg accaatccat acaacacccc cacatttgct ataaagaaaa aggataagaa   3060
caaatggaga atgctgatag attttaggga actaaatagg gtcactcagg actttacgga   3120
agtccaatta ggaataccac accctgcagg actagcaaaa aggaaaagaa ttacagtact   3180
ggatataggt gatgcatatt tctccatacc tctagatgaa gaatttaggc agtacactgc   3240
ctttacttta ccatcagtaa ataatgcaga gccaggaaaa cgatacattt ataaggttct   3300
gcctcaggga tggaaggggt caccagccat cttccaatac actatgagac atgtgctaga   3360
acccttcagg aaggcaaatc cagatgtgac cttagtccag tatatggatg acatcttaat   3420
agctagtgac aggacagacc tggaacatga cagggtagtt ttacagtcaa aggaactctt   3480
gaatagcata gggttttcta ccccagaaga gaaattccaa aaagatcccc catttcaatg   3540
```

gatggggtac gaattgtggc caacaaaatg gaagttgcaa aagatagagt tgccacaaag 3600
agagacctgg acagtgaatg atatacagaa gttagtagga gtattaaatt gggcagctca 3660
aatttatcca ggtataaaaa ccaaacatct ctgtaggtta attagaggaa aaatgactct 3720
aacagaggaa gttcagtgga ctgagatggc agaagcagaa tatgaggaaa ataaaataat 3780
tctcagtcag gaacaagaag gatgttatta ccaagaaggc aagccattag aagccacggt 3840
aataaagagt caggacaatc agtggtctta taaaattcac caagaagaca aaatactgaa 3900
agtaggaaaa tttgcaaaga taaagaatac acataccaat ggagtgagac tattagcaca 3960
tgtaatacag aaaataggaa aggaagcaat agtgatctgg ggacaggtcc caaaattcca 4020
cttaccagtt gagaaggatg tatgggaaca gtggtggaca gactattggc aggtaacctg 4080
gataccggaa tgggatttta tctcaacacc accgctagta agattagtct tcaatctagt 4140
gaaggaccct atagagggag aagaaaccta ttatacagat ggatcatgta ataaacagtc 4200
aaaagaaggg aaagcaggat atatcacaga taggggcaaa gacaaagtaa aagtgttaga 4260
acagactact aatcaacaag cagaattgga agcatttctc atggcattga cagactcagg 4320
gccaaaggca aatattatag tagattcaca atatgttatg ggaataataa caggatgccc 4380
tacagaatca gagagcaggc tagttaatca aataatagaa gaaatgatta aaaagtcaga 4440
aatttatgta gcatgggtac cagcacacaa aggtatagga ggaaaccaag aaatagacca 4500
cctagttagt caagggatta gacaagttct cttcttggaa aagatagagc cagcacaaga 4560
agaacatgat aaataccata gtaatgtaaa agaattggta ttcaaatttg gattacccag 4620
aatagtggcc agacagatag tagacacctg tgataaatgt catcagaaag gagaggctat 4680
acatgggcag gcaaattcag atctagggac ttggcaaatg gattgtaccc atctagaggg 4740
aaaaataatc atagttgcag tacatgtagc tagtggattc atagaagcag aggtaattcc 4800
acaagagaca ggaagacaga cagcactatt tctgttaaaa ttggcaggca gatggcctat 4860
tacacatcta cacacagata atggtgctaa ctttgcttcg caagaagtaa agatggttgc 4920
atggtgggca gggatagagc acacctttgg ggtaccatac aatccacaga gtcagggagt 4980
agtggaagca atgaatcacc acctgaaaaa tcaaatagat agaatcaggg aacaagcaaa 5040
ttcagtagaa accatagtat taatggcagt tcattgcatg aattttaaaa gaaggggagg 5100
aataggggat atgactccag cagaaagatt aattaacatg atcactacag aacaagagat 5160
acaatttcaa caatcaaaaa actcaaaatt taaaaatttt cgggtctatt acagagaagg 5220
cagagatcaa ctgtggaagg gacccggtga gctattgtgg aaaggggaag gagcagtcat 5280
cttaaaggta gggacagaca ttaaggtagt acccagaaga aaggctaaaa ttatcaaaga 5340
ttatggagga ggaaaagagg tggatagcag ttcccacatg gaggataccg gagaggctag 5400
agaggtggca tagcctcata aaatatctga aatataaaac taaagatcta caaaaggttt 5460
gctatgtgcc ccattttaag gtcggatggg catggtggac ctgcagcaga gtaatcttcc 5520
cactacagga aggaagccat ttagaagtac aagggtattg gcatttgaca ccagaaaaag 5580
ggtggctcag tacttatgca gtgaggataa cctggtactc aaagaacttt tggacagatg 5640
taacaccaaa ctatgcagac attttactgc atagcactta tttcccttgc tttacagcgg 5700
gagaagtgag aagggccatc aggggagaac aactgctgtc ttgctgcagg ttcccgagag 5760
ctcataagta ccaggtacca agcctacagt acttagcact gaaagtagta agcgatgtca 5820
gatcccaggg agagaatccc acctggaaac agtggagaag agacaatagg agaggccttc 5880
gaatggctaa acagaacagt agaggagata aacagagagg cggtaaacca cctaccaagg 5940
gagctaattt tccaggtttg gcaaaggtct tgggaatact ggcatgatga acaagggatg 6000
tcaccaagct atgtaaaata cagatacttg tgtttaatac aaaaggcttt atttatgcat 6060
tgcaagaaag gctgtagatg tctaggggaa ggacatgggg caggggggatg gagaccagga 6120
cctcctcctc ctccccctcc aggactagca taaatggaag aaagacctcc agaaaatgaa 6180
ggaccacaaa gggaaccatg ggatgaatgg gtagtggagg ttctggaaga actgaaagaa 6240
gaagctttaa aacattttga tcctcgcttg ctaactgcac ttggtaatca tatctataat 6300
agacatggag acacccttga gggagcagga gaactcatta gaatcctcca acgagcgctc 6360
ttcatgcatt tcagaggcgg atgcatccac tccagaatcg gccaacctgg gggaggaaat 6420
cctctctcag ctataccgcc ctctagaagc atgctataac acatgctatt gtaaaaagtg 6480
ttgctaccat tgccagtttt gttttcttaa aaaaggcttg gggatatgtt atgagcaatc 6540
acgaaagaga agaagaactc cgaaaaaggc taaggctaat acatcttctg catcaaacaa 6600
gtaagtatgg gatgtcttgg gaatcagctg cttatcgcca tcttgctttt aagtgtctat 6660
gggatctatt gtactctata tgtcacagtc ttttatggtg taccagcttg gaggaatgcg 6720
acaattcccc tcttttgtgc aaccaagaat agggatactt ggggaacaac tcagtgccta 6780
ccagataatg gtgattattc agaagtggcc cttaatgtta cagaaagctt tgatgcctgg 6840
aataatacag tcacagaaca ggcaatagag gatgtatggc aactctttga gacctcaata 6900
aagccttgtg taaaattatc cccattatgc attactatga gatgcaataa aagtgagaca 6960
gatagatggg gattgacaaa atcaataaca acaacagcat caacaacatc aacgacagca 7020
tcagcaaaag tagacatggt caatgagact agttcttgta tagcccagga taattgcaca 7080
ggcttggaac aagagcaaat gataagctgt aaattcaaca tgacagggtt aaaaagagac 7140
aagaaaaaag agtacaatga aacttggtac tctgcagatt tggtatgtga acaagggaat 7200
aacactggta atgaaagtag atgttacatg aaccactgta acacttctgt tatccaagag 7260
tcttgtgaca aacattattg ggatgctatt agatttaggt attgtgcacc tccaggttat 7320
gctttgctta gatgtaatga cacaaattat tcaggcttta tgcctaaatg ttctaaggtg 7380
gtggtctctt catgcacaag gatgatggag acacagactt ctacttggtt tggctttaat 7440
ggaactagag cagaaaatag aacttatatt tactggcatg gtagggataa taggactata 7500
attagtttaa ataagtatta taatctaaca atgaaatgta gaagaccagg aaataagaca 7560
gttttaccag tcaccattat gtctggattg gttttccact cacaaccaat caatgatagg 7620
ccaaagcagg catggtgttg gtttggagga aaatggaagg atgcaataaa agaggtgaag 7680
cagaccattg tcaaacatcc caggtatact ggaactaaca atactgataa aatcaatttg 7740
acggctcctg gaggaggaga tccggaagtt accttcatgt ggacaaattg cagaggagag 7800
ttcctctact gtaaaatgaa ttggtttcta aattgggtag aagataggaa tacagctaac 7860
cagaagccaa aggaacagca taaaaggaat tacgtgccat gtcatattag acaaataatc 7920
aacacttggc ataaagtagg caaaaatgtt tatttgcctc caagagaggg agacctcacg 7980
tgtaactcca cagtgaccag tctcatagca aacatagatt ggattgatgg aaaccaaact 8040
aatatcacca tgagtgcaga ggtggcagaa ctgtatcgat tggaattggg agattataaa 8100
ttagtagaga tcactccaat tggcttggcc cccacagatg tgaagaggta cactactggt 8160
ggcacctcaa gaaataaaag aggggtcttt gtgctagggt tcttgggttt tctcgcaacg 8220
gcaggttctg caatgggcgc ggcgtcgttg acgctgaccg ctcagtcccg aactttattg 8280

-continued

```
gctgggatag tgcagcaaca gcaacagctg ttggacgtgg tcaagagaca acaagaattg   8340
ttgcgactga ccgtctgggg aacaaagaac ctccagacta gggtcactgc catcgagaag   8400
tacttaaagg accaggcgca gctgaatgct tggggatgtg cgtttagaca agtctgccac   8460
actactgtac catggccaaa tgcaagtcta acaccaaagt ggaacaatga gacttggcaa   8520
gagtgggagc gaaaggttga cttcttggaa gaaaatataa cagccctcct agaggaggca   8580
caaattcaac aagagaagaa catgtatgaa ttacaaaagt tgaatagctg ggatgtgttt   8640
ggcaattggt ttgaccttgc ttcttggata aagtatatac aatatggagt ttatatagtt   8700
gtaggagtaa tactgttaag aatagtgatc tatatagtac aaatgctagc taagttaagg   8760
caggggtata ggccagtgtt ctcttcccca ccctcttatt tccagcagac ccatatccaa   8820
caggacccgg cactgccaac cagagaaggc aaagaaagag acggtggaga aggcggtggc   8880
aacagctcct ggccttggca gatagaatat attcatttcc tgatccgcca actgatacgc   8940
ctcttgactt ggctattcag caactgcaga accttgctat cgagagtata ccagatcctc   9000
caaccaatac tccagaggct ctctgcgacc ctacagagga ttcgagaagt cctcaggact   9060
gaactgacct acctacaata tgggtggagc tatttccatg aggcggtcca ggccgtctgg   9120
agatctgcga cagagactct tgcgggcgcg tggggagact tatgggagac tcttaggaga   9180
ggtggaagat ggatactcgc aatccccagg aggattagac aagggcttga gctcactctc   9240
ttgtgaggga cagaaataca atcagggaca gtatatgaat actccatgga gaaacccagc   9300
tgaagagaga gaaaaattag catacagaaa acaaaatatg gatgatatag atgaggaaga   9360
tgatgacttg gtaggggtat cagtgaggcc aaaagttccc ctaagaacaa tgagttacaa   9420
attggcaata gacatgtctc attttataaa agaaaagggg ggactggaag ggatttatta   9480
cagtgcaaga agacatagaa tcttagacat atacttagaa aaggaaggag gcatcatacc   9540
agattggcag gattacacct caggaccagg aattagatac ccaaagacat ttggctggct   9600
atggaaatta gtccctgtaa atgtatcaga tgaggcacag gaggatgagg agcattattt   9660
aatgcatcca gctcaaactt cccagtggga tgacccttgg ggagaggttc tagcatggaa   9720
gtttgatcca actctggcct acacttatga ggcatatgtt agatacccag aagagtttgg   9780
aagcaagtca ggcctgtcag aggaagaggt tagaagaagg ctaaccgcaa gaggccttct   9840
taacatggct gacaagaagg aaactcgctg aacgcgtatt gcattactag ttattaatag   9900
taatcaatta cggggtcatt agttcatagc ccatatatgg agttccgcgt tacataactt   9960
acggtaaatg gcccgcctgg ctgaccgccc aacgaccccc gcccattgac gtcaataatg  10020
acgtatgttc ccatagtaac gccaataggg actttccatt gacgtcaatg ggtggagtat  10080
ttacggtaaa ctgcccactt ggcagtacat caagtgtatc atatgccaag tccgccccct  10140
attgacgtca atgacggtaa atggcccgcc tggcattatg cccagtacat gaccttacgg  10200
gactttccta cttggcagta catctacgta ttagtcatcg ctattaccat ggtgatgcgg  10260
ttttggcagt acaccaatgg gcgtggatag cggtttgact cacggggatt tccaagtctc  10320
caccccattg acgtcaatgg gagtttgttt tggcaccaaa atcaacggga ctttccaaaa  10380
tgtcgtaata accccgcccc gttgacgcaa atgggcggta ggcgtgtacg gtgggaggtc  10440
tatataagca gagctcgttt agtgaaccgt cagaattgtt tttatttttta attttctttc  10500
aaatacttcc atcgaattca gatctggtac cacgcgtacc atggtgccca agaagaagag  10560
gaaagtctcc aacctgctga ctgtgcacca aaacctgcct gccctccctg tggatgccac  10620
ctctgatgaa gtcaggaaga acctgatgga catgttcagg gacaggcagg ccttctctga  10680
```

-continued

```
acacacctgg aagatgctcc tgtctgtgtg cagatcctgg gctgcctggt gcaagctgaa  10740
caacaggaaa tggttccctg ctgaacctga ggatgtgagg gactacctcc tgtacctgca  10800
agccagaggc ctggctgtga agaccatcca acagcacctg ggccagctca acatgctgca  10860
caggagatct ggcctgcctc gcccttctga ctccaatgct gtgtccctgg tgatgaggag  10920
aatcagaaag gagaatgtgg atgctgggga gagagccaag caggccctgg cctttgaacg  10980
cactgacttt gaccaagtca gatccctgat ggagaactct gacagatgcc aggacatcag  11040
gaacctggcc ttcctgggca ttgcctacaa caccctgctg cgcattgccg aaattgccag  11100
aatcagagtg aaggacatct cccgcaccga tggtgggaga atgctgatcc acattggcag  11160
gaccaagacc ctggtgtcca cagctggtgt ggagaaggcc ctgtccctgg gggttaccaa  11220
gctggtggag agatggatct ctgtgtctgg tgtggctgat gaccccaaca actacctgtt  11280
ctgccgggtc agaaagaatg gtgtggctgc cccttctgcc acctcccaac tgtccacccg  11340
ggccctggaa gggatctttg aggccaccca ccgcctgatc tatggtgcca aggatgactc  11400
tgggcagaga tacctggcct ggtctggcca ctctgccaga gtgggtgctg ccagggacat  11460
ggccagggct ggtgtgtcca tccctgaaat catgcaggct ggtggctgga ccaatgtgaa  11520
catagtgatg aactacatca gaaacctgga ctctgagact ggggccatgg tgaggctgct  11580
cgaggatggg gacggtggtg gtggcaagct ttgacgcatc ccgggtctca ttttataaaa  11640
gaaaaggggg gactggaagg gatttatccg cggttcactc gagactcgct gaaacagcag  11700
ggactttcca caaggggatg ttacggggag gtactgggga ggagccggtc gggaacgccc  11760
actttcttga tgtataaata tcactgcatt tcgctctgta ttcagtcgct ctgcggagag  11820
gctggcagat tgagccctgg gaggttctct ccagcactag caggtagagc ctgggtgttc  11880
cctgctagac tctcaccagc acttggccgg tgctgggcag agtgactcca cgcttgcttg  11940
cttaaagccc tcttcaataa agctgccatt ttagaagtaa gctagtgtgt gttcccatct  12000
ctcctagccg ccgcctggtc aactcggtac tcaataataa gaagaccctg gtctgttagg  12060
accctttctg ctttgggaaa ccgaagcagg aaaatcccta gca                    12103
```

<210> SEQ ID NO 28
<211> LENGTH: 12103
<212> TYPE: DNA
<213> ORGANISM: Artificial Sequence
<220> FEATURE:
<223> OTHER INFORMATION: SIVmac239-Nef-CMV-Cre optimized codon

<400> SEQUENCE: 28

```
tggaagggat ttattacagt gcaagaagac atagaatctt agacatatac ttagaaaagg     60
aagaaggcat cataccagat tggcaggatt acacctcagg accaggaatt agatacccaa    120
agacatttgg ctggctatgg aaattagtcc ctgtaaatgt atcagatgag gcacaggagg    180
atgaggagca ttatttaatg catccagctc aaacttccca gtgggatgac ccttggggag    240
aggttctagc atggaagttt gatccaactc tggcctacac ttatgaggca tatgttagat    300
acccagaaga gtttggaagc aagtcaggcc tgtcagagga agaggttaga agaaggctaa    360
ccgcaagagg ccttcttaac atggctgaca agaaggaaac tcgctgaaac agcagggact    420
ttccacaagg ggatgttacg gggaggtact ggggaggagc cggtcgggaa cgcccacttt    480
cttgatgtat aaatatcact gcatttcgct ctgtattcag tcgctctgcg gagaggctgg    540
cagattgagc cctgggaggt tctctccagc actagcaggt agagcctggg tgttccctgc    600
```

```
tagactctca ccagcacttg gccggtgctg ggcagagtga ctccacgctt gcttgcttaa    660
agccctcttc aataaagctg ccattttagg aagtaagcta gtgtgtgttc ccatctctcc    720
tagccgccgc ctggtcaact cggtacttca ataataagaa gactcctggt ctgttaggac    780
cctttctgct ttgggaaacc gaagcaggaa aatccctagc agattggcgc ctgaacaggg    840
acttgaagga gagtgagaga ctcctgagta cggctgagtg aaggcagtaa gggcggcagg    900
aaccaaccac gacggagtgc tcctataaag gcgcgggtcg gtaccagacg gcgtgaggag    960
cgggagagga agaggcctcc ggttgcaggt aagtgcaaca caaaaaagaa atagctgtct   1020
tttatccagg aaggggtaat aagatagagt gggagatggg cgtgagaaac tccgtcttgt   1080
cagggaagaa agcagatgaa ttagaaaaaa ttaggctacg acccaacgga aagaaaaagt   1140
acatgttgaa gcatgtagta tggcagcaa atgaattaga tagatttgga ttagcagaaa   1200
gcctgttgga gaacaaagaa ggatgtcaaa aaatactttc ggtcttagct ccattagtgc   1260
caacaggctc agaaaattta aaaagccttt ataatactgt ctgcgtcatc tggtgcattc   1320
acgcagaaga gaaagtgaaa cacactgagg aagcaaaaca gatagtgcag agacacctag   1380
tggtggaaac aggaacaaca gaaactatgc caaaaacaag tagaccaaca gcaccatcta   1440
gcggcagagg aggaaattac ccagtacaac aaataggtgg taactatgtc cacctgccat   1500
taagcccgag aacattaaat gcctgggtaa aattgataga ggaaaagaaa tttggagcag   1560
aagtagtgcc aggatttcag gcactgtcag aaggttgcac cccctatgac attaatcaga   1620
tgttaaattg tgtgggagac catcaagcgg ctatgcagat tatcagagat attataaacg   1680
aggaggctgc agattgggac ttgcagcacc cacaaccagc tccacaacaa ggacaactta   1740
gggagccgtc aggatcagat attgcaggaa caactagttc agtagatgaa caaatccagt   1800
ggatgtacag acaacagaac cccataccag taggcaacat ttacaggaga tggatccaac   1860
tggggttgca aaaatgtgtc agaatgtata acccaacaaa cattctagat gtaaaacaag   1920
ggccaaaaga gccatttcag agctatgtag acaggttcta caaaagttta agagcagaac   1980
agacagatgc agcagtaaag aattggatga ctcaaacact gctgattcaa aatgctaacc   2040
cagattgcaa gctagtgctg aaggggctgg gtgtgaatcc caccctagaa gaaatgctga   2100
cggcttgtca aggagtaggg gggccgggac agaaggctag attaatggca gaagccctga   2160
aagaggccct cgcaccagtg ccaatccctt ttgcagcagc ccaacagagg ggaccaagaa   2220
agccaattaa gtgttggaat tgtgggaaag agggacactc tgcaaggcaa tgcagagccc   2280
caagaagaca gggatgctgg aaatgtggaa aaatggacca tgttatggcc aaatgcccag   2340
acagacaggc gggtttttta ggccttggtc catggggaaa gaagccccgc aatttcccca   2400
tggctcaagt gcatcagggg ctgatgccaa ctgctccccc agaggaccca gctgtggatc   2460
tgctaaagaa ctacatgcag ttgggcaagc agcagagaga aaagcagaga gaaagcagag   2520
agaagcctta caaggaggtg acagaggatt tgctgcacct caattctctc tttggaggag   2580
accagtagtc actgctcata ttgaaggaca gcctgtagaa gtattactgg atacaggggc   2640
tgatgattct attgtaacag gaatagagtt aggtccacat tataccccaa aaatagtagg   2700
aggaatagga ggttttatta atactaaaga atacaaaaat gtagaaatag aagttttagg   2760
caaaaggatt aaagggacaa tcatgacagg ggacaccccg attaacattt ttggtagaaa   2820
tttgctaaca gctctgggga tgtctctaaa ttttcccata gctaaagtag agcctgtaaa   2880
agtcgcctta aagccaggaa aggatggacc aaaattgaag cagtggccat tatcaaaaga   2940
aaagatagtt gcattaagag aaatctgtga aaagatggaa aaggatggtc agttggagga   3000
```

agctcccccg accaatccat acaacacccc cacatttgct ataaagaaaa aggataagaa 3060
caaatggaga atgctgatag attttaggga actaaatagg gtcactcagg actttacgga 3120
agtccaatta ggaataccac accctgcagg actagcaaaa aggaaaagaa ttacagtact 3180
ggatataggt gatgcatatt tctccatacc tctagatgaa gaatttaggc agtacactgc 3240
ctttacttta ccatcagtaa ataatgcaga gccaggaaaa cgatacattt ataaggttct 3300
gcctcaggga tggaaggggt caccagccat cttccaatac actatgagac atgtgctaga 3360
acccttcagg aaggcaaatc cagatgtgac cttagtccag tatatggatg acatcttaat 3420
agctagtgac aggacagacc tggaacatga cagggtagtt ttacagtcaa aggaactctt 3480
gaatagcata gggttttcta ccccagaaga gaaattccaa aaagatcccc catttcaatg 3540
gatggggtac gaattgtggc caacaaaatg gaagttgcaa aagatagagt tgccacaaag 3600
agagacctgg acagtgaatg atatacagaa gttagtagga gtattaaatt gggcagctca 3660
aatttatcca ggtataaaaa ccaaacatct ctgtaggtta attagaggaa aaatgactct 3720
aacagaggaa gttcagtgga ctgagatggc agaagcagaa tatgaggaaa ataaaataat 3780
tctcagtcag gaacaagaag gatgttatta ccaagaaggc aagccattag aagccacggt 3840
aataaagagt caggacaatc agtggtctta taaaattcac caagaagaca aaatactgaa 3900
agtaggaaaa tttgcaaaga taaagaatac acataccaat ggagtgagac tattagcaca 3960
tgtaatacag aaaataggaa aggaagcaat agtgatctgg ggacaggtcc caaaattcca 4020
cttaccagtt gagaaggatg tatgggaaca gtggtggaca gactattggc aggtaacctg 4080
gataccggaa tgggatttta tctcaacacc accgctagta agattagtct tcaatctagt 4140
gaaggaccct atagagggag aagaaaccta ttatacagat ggatcatgta ataaacagtc 4200
aaaagaaggg aaagcaggat atatcacaga taggggcaaa gacaaagtaa aagtgttaga 4260
acagactact aatcaacaag cagaattgga agcatttctc atggcattga cagactcagg 4320
gccaaaggca aatattatag tagattcaca atatgttatg ggaataataa caggatgccc 4380
tacagaatca gagagcaggc tagttaatca aataatagaa gaaatgatta aaaagtcaga 4440
aatttatgta gcatgggtac cagcacacaa aggtatagga ggaaaccaag aaatagacca 4500
cctagttagt caagggatta gacaagttct cttcttggaa aagatagagc cagcacaaga 4560
agaacatgat aaataccata gtaatgtaaa agaattggta ttcaaatttg gattacccag 4620
aatagtggcc agacagatag tagacacctg tgataaatgt catcagaaag gagaggctat 4680
acatgggcag gcaaattcag atctagggac ttggcaaatg gattgtaccc atctagaggg 4740
aaaaataatc atagttgcag tacatgtagc tagtggattc atagaagcag aggtaattcc 4800
acaagagaca ggaagacaga cagcactatt tctgttaaaa ttggcaggca gatggcctat 4860
tacacatcta cacacagata atggtgctaa ctttgcttcg caagaagtaa agatggttgc 4920
atggtgggca gggatagagc acacctttgg ggtaccatac aatccacaga gtcagggagt 4980
agtggaagca atgaatcacc acctgaaaaa tcaaatagat agaatcaggg aacaagcaaa 5040
ttcagtagaa accatagtat taatggcagt tcattgcatg aattttaaaa gaaggggagg 5100
aataggggat atgactccag cagaaagatt aattaacatg atcactacag aacaagagat 5160
acaatttcaa caatcaaaaa actcaaaatt taaaaatttt cgggtctatt acagagaagg 5220
cagagatcaa ctgtggaagg gacccggtga gctattgtgg aaaggggaag gagcagtcat 5280
cttaaaggta gggacagaca ttaaggtagt acccagaaga aaggctaaaa ttatcaaaga 5340

```
ttatggagga ggaaaagagg tggatagcag ttcccacatg gaggataccg gagaggctag   5400
agaggtggca tagcctcata aaatatctga aatataaaac taaagatcta caaaaggttt   5460
gctatgtgcc ccattttaag gtcggatggg catggtggac ctgcagcaga gtaatcttcc   5520
cactacagga aggaagccat ttagaagtac aagggtattg gcatttgaca ccagaaaaag   5580
ggtggctcag tacttatgca gtgaggataa cctggtactc aaagaacttt tggacagatg   5640
taacaccaaa ctatgcagac attttactgc atagcactta tttcccttgc tttacagcgg   5700
gagaagtgag aagggccatc aggggagaac aactgctgtc ttgctgcagg ttcccgagag   5760
ctcataagta ccaggtacca agcctacagt acttagcact gaaagtagta agcgatgtca   5820
gatcccaggg agagaatccc acctggaaac agtggagaag agacaatagg agaggccttc   5880
gaatggctaa acagaacagt agaggagata aacagagagg cggtaaacca cctaccaagg   5940
gagctaattt tccaggtttg gcaaaggtct tgggaatact ggcatgatga acaagggatg   6000
tcaccaagct atgtaaaata cagatacttg tgtttaatac aaaaggcttt atttatgcat   6060
tgcaagaaag gctgtagatg tctaggggaa ggacatgggg caggggggatg gagaccagga   6120
cctcctcctc ctccccctcc aggactagca taaatggaag aaagacctcc agaaaatgaa   6180
ggaccacaaa gggaaccatg ggatgaatgg gtagtggagg ttctggaaga actgaaagaa   6240
gaagctttaa aacattttga tcctcgcttg ctaactgcac ttggtaatca tatctataat   6300
agacatggag acacccttga gggagcagga gaactcatta gaatcctcca acgagcgctc   6360
ttcatgcatt tcagaggcgg atgcatccac tccagaatcg gccaacctgg gggaggaaat   6420
cctctctcag ctataccgcc ctctagaagc atgctataac acatgctatt gtaaaaagtg   6480
ttgctaccat tgccagtttt gttttcttaa aaaaggcttg ggatatgtt atgagcaatc    6540
acgaaagaga agaagaactc cgaaaaaggc taaggctaat acatcttctg catcaaacaa   6600
gtaagtatgg gatgtcttgg gaatcagctg cttatcgcca tcttgctttt aagtgtctat   6660
gggatctatt gtactctata tgtcacagtc ttttatggtg taccagcttg gaggaatgcg   6720
acaattcccc tcttttgtgc aaccaagaat agggatactt ggggaacaac tcagtgccta   6780
ccagataatg gtgattattc agaagtggcc cttaatgtta cagaaagctt tgatgcctgg   6840
aataatacag tcacagaaca ggcaatagag gatgtatggc aactctttga gacctcaata   6900
aagccttgtg taaaattatc cccattatgc attactatga gatgcaataa aagtgagaca   6960
gatagatggg gattgacaaa atcaataaca acaacagcat caacaacatc aacgacagca   7020
tcagcaaaag tagacatggt caatgagact agttcttgta tagcccagga taattgcaca   7080
ggcttggaac aagagcaaat gataagctgt aaattcaaca tgacagggtt aaaaagagac   7140
aagaaaaaag agtacaatga aacttggtac tctgcagatt tggtatgtga acaagggaat   7200
aacactggta atgaaagtag atgttacatg aaccactgta acacttctgt tatccaagag   7260
tcttgtgaca aacattattg ggatgctatt agatttaggt attgtgcacc tccaggttat   7320
gctttgctta gatgtaatga cacaaattat tcaggcttta tgcctaaatg ttctaaggtg   7380
gtggtctctt catgcacaag gatgatggag acacagactt ctacttggtt tggctttaat   7440
ggaactagag cagaaaatag aacttatatt tactggcatg gtagggataa taggactata   7500
attagtttaa ataagtatta taatctaaca atgaaatgta gaagaccagg aaataagaca   7560
gttttaccag tcaccattat gtctggattg gttttccact cacaaccaat caatgatagg   7620
ccaaagcagg catggtgttg gtttggagga aaatggaagg atgcaataaa agaggtgaag   7680
cagaccattg tcaaacatcc caggtatact ggaactaaca atactgataa aatcaatttg   7740
```

```
acggctcctg gaggaggaga tccggaagtt accttcatgt ggacaaattg cagaggagag   7800
ttcctctact gtaaaatgaa ttggtttcta aattgggtag aagataggaa tacagctaac   7860
cagaagccaa aggaacagca taaaaggaat tacgtgccat gtcatattag acaaataatc   7920
aacacttggc ataaagtagg caaaaatgtt tatttgcctc caagagaggg agacctcacg   7980
tgtaactcca cagtgaccag tctcatagca aacatagatt ggattgatgg aaaccaaact   8040
aatatcacca tgagtgcaga ggtggcagaa ctgtatcgat tggaattggg agattataaa   8100
ttagtagaga tcactccaat tggcttggcc cccacagatg tgaagaggta cactactggt   8160
ggcacctcaa gaaataaaag aggggtcttt gtgctagggt tcttgggttt tctcgcaacg   8220
gcaggttctg caatgggcgc ggcgtcgttg acgctgaccg ctcagtcccg aactttattg   8280
gctgggatag tgcagcaaca gcaacagctg ttggacgtgg tcaagagaca acaagaattg   8340
ttgcgactga ccgtctgggg aacaaagaac ctccagacta gggtcactgc catcgagaag   8400
tacttaaagg accaggcgca gctgaatgct tggggatgtg cgtttagaca agtctgccac   8460
actactgtac catggccaaa tgcaagtcta acaccaaagt ggaacaatga gacttggcaa   8520
gagtgggagc gaaaggttga cttcttggaa gaaaatataa cagccctcct agaggaggca   8580
caaattcaac aagagaagaa catgtatgaa ttacaaaagt tgaatagctg ggatgtgttt   8640
ggcaattggt ttgaccttgc ttcttggata aagtatatac aatatggagt ttatatagtt   8700
gtaggagtaa tactgttaag aatagtgatc tatatagtac aaatgctagc taagttaagg   8760
caggggtata ggccagtgtt ctcttcccca ccctcttatt tccagcagac ccatatccaa   8820
caggacccgg cactgccaac cagagaaggc aaagaaagag acggtggaga aggcggtggc   8880
aacagctcct ggccttggca gatagaatat attcatttcc tgatccgcca actgatacgc   8940
ctcttgactt ggctattcag caactgcaga accttgctat cgagagtata ccagatcctc   9000
caaccaatac tccagaggct ctctgcgacc ctacagagga ttcgagaagt cctcaggact   9060
gaactgacct acctacaata tgggtggagc tatttccatg aggcggtcca ggccgtctgg   9120
agatctgcga cagagactct tgcgggcgcg tggggagact tatgggagac tcttaggaga   9180
ggtggaagat ggatactcgc aatccccagg aggattagac aagggcttga gctcactctc   9240
ttgtgaggga cagaaataca atcagggaca gtatatgaat actccatgga gaaacccagc   9300
tgaagagaga gaaaaattag catacagaaa acaaaatatg gatgatatag atgaggaaga   9360
tgatgacttg gtaggggtat cagtgaggcc aaaagttccc ctaagaacaa tgagttacaa   9420
attggcaatt gacatgtcac atttcattaa ggagaagggc ggactggagg ggatatacta   9480
ttctgccagg aggcatagaa tcttagacat atacttagaa aaggaaggag gcatcatacc   9540
agattggcag gattacacct caggaccagg aattagatac ccaaagacat ttggctggct   9600
atggaaatta gtccctgtaa atgtatcaga tgaggcacag gaggatgagg agcattattt   9660
aatgcatcca gctcaaactt cccagtggga tgacccttgg ggagaggttc tagcatggaa   9720
gtttgatcca actctggcct acacttatga ggcatatgtt agatacccag aagagtttgg   9780
aagcaagtca ggcctgtcag aggaagaggt tagaagaagg ctaaccgcaa gaggccttct   9840
taacatggct gacaagaagg aaactcgctg aacgcgtatt gcattactag ttattaatag   9900
taatcaatta cggggtcatt agttcatagc ccatatatgg agttccgcgt tacataactt   9960
acggtaaatg gcccgcctgg ctgaccgccc aacgaccccc gcccattgac gtcaataatg  10020
acgtatgttc ccatagtaac gccaataggg actttccatt gacgtcaatg ggtggagtat  10080
```

-continued

```
ttacggtaaa ctgcccactt ggcagtacat caagtgtatc atatgccaag tccgccccct  10140
attgacgtca atgacggtaa atggcccgcc tggcattatg cccagtacat gaccttacgg  10200
gactttccta cttggcagta catctacgta ttagtcatcg ctattaccat ggtgatgcgg  10260
ttttggcagt acaccaatgg gcgtggatag cggtttgact cacggggatt tccaagtctc  10320
caccccattg acgtcaatgg gagtttgttt tggcaccaaa atcaacggga ctttccaaaa  10380
tgtcgtaata accccgcccc gttgacgcaa atgggcggta ggcgtgtacg gtgggaggtc  10440
tatataagca gagctcgttt agtgaaccgt cagaattgtt tttatttta attttctttc  10500
aaatacttcc atcgaattca gatctggtac cacgcgtacc atggtgccca agaagaagag  10560
gaaagtctcc aacctgctga ctgtgcacca aaacctgcct gccctccctg tggatgccac  10620
ctctgatgaa gtcaggaaga acctgatgga catgttcagg gacaggcagg ccttctctga  10680
acacacctgg aagatgctcc tgtctgtgtg cagatcctgg gctgcctggt gcaagctgaa  10740
caacaggaaa tggttccctg ctgaacctga ggatgtgagg gactacctcc tgtacctgca  10800
agccagaggc ctggctgtga agaccatcca acagcacctg ggccagctca acatgctgca  10860
caggagatct ggcctgcctc gcccttctga ctccaatgct gtgtccctgg tgatgaggag  10920
aatcagaaag gagaatgtgg atgctgggga gagagccaag caggccctgg cctttgaacg  10980
cactgacttt gaccaagtca gatccctgat ggagaactct gacagatgcc aggacatcag  11040
gaacctggcc ttcctgggca ttgcctacaa caccctgctg cgcattgccg aaattgccag  11100
aatcagagtg aaggacatct cccgcaccga tggtgggaga atgctgatcc acattggcag  11160
gaccaagacc ctggtgtcca cagctggtgt ggagaaggcc ctgtccctgg gggttaccaa  11220
gctggtggag agatggatct ctgtgtctgg tgtggctgat gaccccaaca actacctgtt  11280
ctgccgggtc agaaagaatg gtgtggctgc cccttctgcc acctcccaac tgtccacccg  11340
ggccctggaa gggatctttg aggccaccca ccgcctgatc tatggtgcca aggatgactc  11400
tgggcagaga tacctggcct ggtctggcca ctctgccaga gtgggtgctg ccagggacat  11460
ggccagggct ggtgtgtcca tccctgaaat catgcaggct ggtggctgga ccaatgtgaa  11520
catagtgatg aactacatca gaaacctgga ctctgagact ggggccatgg tgaggctgct  11580
cgaggatggg gacggtggtg gtggcaagct ttgacgcatc ccgggtctca ttttataaaa  11640
gaaaaggggg gactggaagg gatttatccg cggttcactc gagactcgct gaaacagcag  11700
ggactttcca caaggggatg ttacggggag gtactgggga ggagccggtc gggaacgccc  11760
actttcttga tgtataaata tcactgcatt tcgctctgta ttcagtcgct ctgcggagag  11820
gctggcagat tgagccctgg gaggttctct ccagcactag caggtagagc ctgggtgttc  11880
cctgctagac tctcaccagc acttggccgg tgctgggcag agtgactcca cgcttgcttg  11940
cttaaagccc tcttcaataa agctgccatt ttagaagtaa gctagtgtgt gttcccatct  12000
ctcctagccg ccgcctggtc aactcggtac tcaataataa gaagaccctg gtctgttagg  12060
accctttctg ctttgggaaa ccgaagcagg aaaatcccta gca                    12103
```

<210> SEQ ID NO 29
<211> LENGTH: 11151
<212> TYPE: DNA
<213> ORGANISM: Artificial Sequence
<220> FEATURE:
<223> OTHER INFORMATION: pHR-4lox-RFP/GFP flox

<400> SEQUENCE: 29

```
ttaattccgt gtattctata gtgtcaccta aatcgtatgt gtatgataca taaggttatg     60
```

```
tattaattgt agccgcgttc taacgacaat atgtacaagc ctaattgtgt agcatctggc    120
ttactgaagc agaccctatc atctctctcg taaactgccg tcagagtcgg tttggttgga    180
cgaaccttct gagtttctgg taacgccgtc ccgcacccgg aaatggtcag cgaaccaatc    240
agcagggtca tcgctagcca gatcctctac gccggacgca tcgtggccgg catcaccggc    300
gccacaggtg cggttgctgg cgcctatatc gccgacatca ccgatgggga agatcgggct    360
cgccacttcg ggctcatgag cgcttgtttc ggcgtgggta tggtggcagg ccccgtggcc    420
gggggactgt tgggcgccat ctccttgcat gcaccattcc ttgcggcggc ggtgctcaac    480
ggcctcaacc tactactggg ctgcttccta atgcaggagt cgcataaggg agagcgtcga    540
atggtgcact ctcagtacaa tctgctctga tgccgcatag ttaagccagc cccgacaccc    600
gccaacaccc gctgacgcgc cctgacgggc ttgtctgctc ccggcatccg cttacagaca    660
agctgtgacc gtctccggga gctgcatgtg tcagaggttt tcaccgtcat caccgaaacg    720
cgcgagacga aagggcctcg tgatacgcct atttttatag gttaatgtca tgataataat    780
ggtttcttag acgtcaggtg gcacttttcg gggaaatgtg cgcggaaccc ctatttgttt    840
atttttctaa atacattcaa atatgtatcc gctcatgaga caataaccct gataaatgct    900
tcaataatat tgaaaaagga agagtatgag tattcaacat ttccgtgtcg cccttattcc    960
cttttttgcg gcattttgcc ttcctgtttt tgctcaccca gaaacgctgg tgaaagtaaa   1020
agatgctgaa gatcagttgg gtgcacgagt gggttacatc gaactggatc tcaacagcgg   1080
taagatcctt gagagttttc gccccgaaga acgttttcca atgatgagca cttttaaagt   1140
tctgctatgt ggcgcggtat tatcccgtat tgacgccggg caagagcaac tcggtcgccg   1200
catacactat tctcagaatg acttggttga gtactcacca gtcacagaaa agcatcttac   1260
ggatggcatg acagtaagag aattatgcag tgctgccata accatgagtg ataacactgc   1320
ggccaactta cttctgacaa cgatcggagg accgaaggag ctaaccgctt ttttgcacaa   1380
catgggggat catgtaactc gccttgatcg ttgggaaccg gagctgaatg aagccatacc   1440
aaacgacgag cgtgacacca cgatgcctgt agcaatggca acaacgttgc gcaaactatt   1500
aactggcgaa ctacttactc tagcttcccg gcaacaatta atagactgga tggaggcgga   1560
taaagttgca ggaccacttc tgcgctcggc ccttccggct ggctggttta ttgctgataa   1620
atctggagcc ggtgagcgtg ggtctcgcgg tatcattgca gcactggggc cagatggtaa   1680
gccctcccgt atcgtagtta tctacacgac ggggagtcag gcaactatgg atgaacgaaa   1740
tagacagatc gctgagatag gtgcctcact gattaagcat tggtaactgt cagaccaagt   1800
ttactcatat atactttaga ttgatttaaa acttcatttt taatttaaaa ggatctaggt   1860
gaagatcctt tttgataatc tcatgaccaa aatcccttaa cgtgagtttt cgttccactg   1920
agcgtcagac cccgtagaaa agatcaaagg atcttcttga gatccttttt ttctgcgcgt   1980
aatctgctgc ttgcaaacaa aaaaaccacc gctaccagcg gtggtttgtt tgccggatca   2040
agagctacca actctttttc cgaaggtaac tggcttcagc agagcgcaga taccaaatac   2100
tgtccttcta gtgtagccgt agttaggcca ccacttcaag aactctgtag caccgcctac   2160
atacctcgct ctgctaatcc tgttaccagt ggctgctgcc agtggcgata agtcgtgtct   2220
taccgggttg gactcaagac gatagttacc ggataaggcg cagcggtcgg gctgaacggg   2280
gggttcgtgc acacagccca gcttggagcg aacgacctac accgaactga gatacctaca   2340
gcgtgagcat tgagaaagcg ccacgcttcc cgaagggaga aaggcggaca ggtatccggt   2400
```

-continued

```
aagcggcagg gtcggaacag gagagcgcac gagggagctt ccagggggaa acgcctggta   2460
tctttatagt cctgtcgggt ttcgccacct ctgacttgag cgtcgatttt tgtgatgctc   2520
gtcagggggg cggagcctat ggaaaaacgc cagcaacgcg gcctttttac ggttcctggc   2580
cttttgctgg ccttttgctc acatgttctt tcctgcgtta tcccctgatt ctgtggataa   2640
ccgtattacc gcctttgagt gagctgatac cgctcgccgc agccgaacga ccgagcgcag   2700
cgagtcagtg agcgaggaag cggaagagcg cccaatacgc aaaccgcctc tccccgcgcg   2760
ttggccgatt cattaatgca gctgtggaat gtgtgtcagt tagggtgtgg aaagtcccca   2820
ggctccccag caggcagaag tatgcaaagc atgcatctca attagtcagc aaccaggtgt   2880
ggaaagtccc caggctcccc agcaggcaga agtatgcaaa gcatgcatct caattagtca   2940
gcaaccatag tcccgcccct aactccgccc atcccgcccc taactccgcc cagttccgcc   3000
cattctccgc cccatggctg actaattttt tttatttatg cagaggccga ggccgcctcg   3060
gcctctgagc tattccagaa gtagtgagga ggcttttttg gaggcctagg cttttgcaaa   3120
aagcttggac acaagacagg cttgcgagat atgtttgaga ataccacttt atcccgcgtc   3180
agggagaggc agtgcgtaaa aagacgcgga ctcatgtgaa atactggttt ttagtgcgcc   3240
agatctctat aatctcgcgc aacctatttt cccctcgaac acttttttaag ccgtagataa   3300
acaggctggg acacttcaca tgagcgaaaa atacatcgtc acctgggaca tgttgcagat   3360
ccatgcacgt aaactcgcaa gccgactgat gccttctgaa caatggaaag gcattattgc   3420
cgtaagccgt ggcggtctgt accgggtgcg ttactggcgc gtgaactggg tattcgtcat   3480
gtcgataccg tttgtatttc cagctacgat cacgacaacc agcgcgagct taaagtgctg   3540
aaacgcgcag aaggcgatgg cgaaggcttc atcgttattg atgacctggt ggataccggt   3600
ggtactgcgg ttgcgattcg tgaaatgtat ccaaaagcgc actttgtcac catcttcgca   3660
aaaccggctg gtcgtccgct ggttgatgac tatgttgttg atatcccgca agatacctgg   3720
attgaacagc cgtgggatat gggcgtcgta ttcgtcccgc caatctccgg tcgctaatct   3780
tttcaacgcc tggcactgcc gggcgttgtt ctttttaact tcaggcgggt tacaatagtt   3840
tccagtaagt attctggagg ctgcatccat gacacaggca aacctgagcg aaaccctgtt   3900
caaaccccgc tttaaacatc ctgaaacctc gacgctagtc cgccgcttta atcacggcgc   3960
acaaccgcct gtgcagtcgg cccttgatgg taaaaccatc cctcactggt atcgcatgat   4020
taaccgtctg atgtggatct ggcgcggcat tgacccacgc gaaatcctcg acgtccaggc   4080
acgtattgtg atgagcgatg ccgaacgtac cgacgatgat ttatacgata cggtgattgg   4140
ctaccgtggc ggcaactgga tttatgagtg ggccccggat ctttgtgaag gaaccttact   4200
tctgtggtgt gacataattg gacaaactac ctacagagat ttaaagctct aaggtaaata   4260
taaaattttt aagtgtataa tgtgttaaac tactgattct aattgtttgt gtattttaga   4320
ttccaaccta tggaactgat gaatgggagc agtggtggaa tgcctttaat gaggaaaacc   4380
tgttttgctc agaagaaatg ccatctagtg atgatgaggc tactgctgac tctcaacatt   4440
ctactcctcc aaaaaagaag agaaaggtag aagaccccaa ggactttcct tcagaattgc   4500
taagtttttt gagtcatgct gtgtttagta atagaactct tgcttgcttt gctatttaca   4560
ccacaaagga aaaagctgca ctgctataca agaaaattat ggaaaaatat tctgtaacct   4620
ttataagtag gcataacagt tataatcata acatactgtt ttttcttact ccacacaggc   4680
atagagtgtc tgctattaat aactatgctc aaaaattgtg tacctttagc tttttaattt   4740
gtaaaggggt taataaggaa tatttgatgt atagtgcctt gactagagat cataatcagc   4800
```

-continued

```
cataccacat ttgtagaggt tttacttgct ttaaaaaacc tcccacacct ccccctgaac   4860
ctgaaacata aaatgaatgc aattgttgtt gttaacttgt ttattgcagc ttataatggt   4920
tacaaataaa gcaatagcat cacaaatttc acaaataaag catttttttc actgcattct   4980
agttgtggtt tgtccaaact catcaatgta tcttatcatg tctggatcaa ctggataact   5040
caagctaacc aaaatcatcc caaacttccc accccatacc ctattaccac tgccaattac   5100
ctagtggttt catttactct aaacctgtga ttcctctgaa ttattttcat tttaaagaaa   5160
ttgtatttgt taaatatgta ctacaaactt agtagttgga agggctaatt cactcccaaa   5220
gaagacaaga tatccttgat ctgtggatct accacacaca aggctacttc cctgattagc   5280
agaactacac accagggcca ggggtcagat atccactgac ctttggatgg tgctacaagc   5340
tagtaccagt tgagccagat aaggtagaag aggccaataa aggagagaac accagcttgt   5400
tacaccctgt gagcctgcat gggatggatg acccggagag agaagtgtta gagtggaggt   5460
ttgacagccg cctagcattt catcacgtgg cccgagagct gcatccggag tacttcaaga   5520
actgctgata tcgagcttgc tacaagggac tttccgctgg ggactttcca gggaggcgtg   5580
gcctgggcgg gactggggag tggcgagccc tcagatcctg catataagca gctgcttttt   5640
gcctgtactg ggtctctctg gttagaccag atctgagcct gggagctctc tggctaacta   5700
gggaacccac tgcttaagcc tcaataaagc ttgccttgag tgcttcaagt agtgtgtgcc   5760
cgtctgttgt gtgactctgg taactagaga tccctcagac ccttttagtc agtgtggaaa   5820
atctctagca gtggcgcccg aacagggact tgaaagcgaa agggaaacca gaggagctct   5880
ctcgacgcag gactcggctt gctgaagcgc gcacggcaag aggcgagggg cggcgactgg   5940
tgagtacgcc aaaaattttg actagcggag gctagaagga gagagatggg tgcgagagcg   6000
tcagtattaa gcgggggaga attagatcgc gatgggaaaa aattcggtta aggccagggg   6060
gaaagaaaaa atataaatta aaacatatag tatgggcaag cagggagcta gaacgattcg   6120
cagttaatcc tggcctgtta gaaacatcag aaggctgtag acaaatactg ggacagctac   6180
aaccatccct tcagacagga tcagaagaac ttagatcatt atataataca gtagcaaccc   6240
tctattgtgt gcatcaaagg atagagataa aagacaccaa ggaagcttta gacaagatag   6300
aggaagagca aaacaaaagt aagaccaccg cacagcaagc ggccgctgat cttcagacct   6360
ggaggaggag atatgaggga caattggaga agtgaattat ataaatataa agtagtaaaa   6420
attgaaccat taggagtagc acccaccaag gcaaagagaa gagtggtgca gagagaaaaa   6480
agagcagtgg gaataggagc tttgttcctt gggttcttgg gagcagcagg aagcactatg   6540
ggcgcagcgt caatgacgct gacggtacag gccagacaat tattgtctgg tatagtgcag   6600
cagcagaaca atttgctgag ggctattgag gcgcaacagc atctgttgca actcacagtc   6660
tggggcatca agcagctcca ggcaagaatc ctggctgtgg aaagatacct aaaggatcaa   6720
cagctcctgg ggatttgggg ttgctctgga aaactcattt gcaccactgc tgtgccttgg   6780
aatgctagtt ggagtaataa atctctggaa cagatttgga atcacacgac ctggatggag   6840
tgggacagag aaattaacaa ttacacaagc ttaatacact ccttaattga agaatcgcaa   6900
aaccagcaag aaaagaatga acaagaatta ttggaattag ataaatgggc aagtttgtgg   6960
aattggttta acataacaaa ttggctgtgg tatataaaat tattcataat gatagtagga   7020
ggcttggtag gtttaagaat agtttttgct gtactttcta tagtgaatag agttaggcag   7080
ggatattcac cattatcgtt tcagacccac ctcccaaccc cgaggggacc cgacaggccc   7140
```

-continued

```
gaaggaatag aagaagaagg tggagagaga gacagagaca gatccattcg attagtgaac   7200
ggatctcgac ggtatcgccg aattcacaaa tggcagtatt catccacaat tttaaaagaa   7260
aaggggggat tggggggtac agtgcagggg aaagaatagt agacataata gcaacagaca   7320
tacaaactaa agaattacaa aaacaaatta caaaaattca aaattttcgg gtttattaca   7380
gggacagcag agatccactt tatcgataag cttgggagtt ccgcgttaca taacttacgg   7440
taaatggccc gcctggctga ccgcccaacg acccccgccc attgacgtca ataatgacgt   7500
atgttcccat agtaacgcca atagggactt tccattgacg tcaatgggtg gagtatttac   7560
ggtaaactgc ccacttggca gtacatcaag tgtatcatat gccaagtacg ccccctattg   7620
acgtcaatga cggtaaatgg cccgcctggc attatgccca gtacatgacc ttacgggact   7680
ttcctacttg gcagtacatc tacgtattag tcatcgctat taccatggtg atgcggtttt   7740
ggcagtacac caatgggcgt ggatagcggt ttgactcacg gggatttcca agtctccacc   7800
ccattgacgt caatgggagt ttgttttggc accaaaatca acgggacttt ccaaaatgtc   7860
gtaacaactc cgccccattg acgcaaatgg gcggtaggcg tgtacggtgg gaggtctata   7920
taagcagagc tcgtttagtg aaccgtcaga tcgcctggag acgccatcca cgctgttttg   7980
acctccatag aagacaccga ctctagctag aggatccgga ctagtaactc gaggatgggg   8040
actgacccgg gctgcaggaa ttcataactt cgtataatgt atgctatacg aagttatcat   8100
atgccaccat gagcgagctg atcaaggaga acatgcacat gaagctgtac atggagggca   8160
ccgtgaacaa ccaccacttc aagtgcacat ccgagggcga aggcaagccc tacgagggca   8220
cccagaccat gaagatcaag gtggtcgagg gcggccctct ccccttcgcc ttcgacatcc   8280
tggctaccag cttcatgtac ggcagcaaag ccttcatcaa ccacacccag ggcatccccg   8340
acttctttaa gcagtccttc cctgagggct tcacatggga gagaatcacc acatacgaag   8400
acgggggcgt gctgaccgct acccaggaca ccagcttcca gaacggctgc atcatctaca   8460
acgtcaagat caacggggtg aacttcccat ccaacggccc tgtgatgcag aagaaaacac   8520
gcggctggga ggccaacacc gagatgctgt accccgctga cggcggcctg agaggccaca   8580
gccagatggc cctgaagctc gtgggcgggg gctacctgca ctgctccttc aagaccacat   8640
acagatccaa gaaacccgct aagaacctca agatgcccgg cttccacttc gtggaccaca   8700
gactggaaag aatcaaggag gccgacaaag agacctacgt cgagcagcac gagatggctg   8760
tggccaagta ctgcgacctc cctagcaaac tggggcacag ataaataact tcgtataaag   8820
tatcctatac gaagttatac tttggccgcg gctcgagggg gttggggttg cgccttttcc   8880
aaggcagccc tgggtttgcg cagggacgcg gctgctctgg gcgtggttcc gggaaacgca   8940
gcggcgccga ccctgggtct cgcacattct tcacgtccgt tcgcagcgtc acccggatct   9000
tcgccgctac ccttgtgggc cccccggcga cgcttcctgc tccgccccta agtcgggaag   9060
gttccttgcg gttcgcggcg tgccggacgt gacaaacgga agccgcacgt ctcactagta   9120
ccctcgcaga cggacagcgc cagggagcaa tggcagcgcg ccgaccgcga tgggctgtgg   9180
ccaatagcgg ctgctcagca gggcgcgccg agagcagcgg ccgggaaggg gcggtgcggg   9240
aggcggggtg tggggcggta gtgtgggccc tgttcctgcc cgcgcggtgt tccgcattct   9300
gcaagcctcc ggagcgcacg tcggcagtcg gctccctcgt tgaccgaatc accgacctct   9360
ctccccaggg ggatccaccg gtcgccacca tggtgagcaa gggcgaggag ctgttcaccg   9420
gggtggtgcc catcctggtc gagctggacg gcgacgtaaa cggccacaag ttcagcgtgt   9480
ccggcgaggg cgagggcgat gccacctacg gcaagctgac cctgaagttc atctgcacca   9540
```

```
ccggcaagct gcccgtgccc tggcccaccc tcgtgaccac cctgacctac ggcgtgcagt   9600

gcttcagccg ctaccccgac cacatgaagc agcacgactt cttcaagtcc gccatgcccg   9660

aaggctacgt ccaggagcgc accatcttct tcaaggacga cggcaactac aagacccgcg   9720

ccgaggtgaa gttcgagggc gacaccctgg tgaaccgcat cgagctgaag ggcatcgact   9780

tcaaggagga cggcaacatc ctggggcaca agctggagta caactacaac agccacaacg   9840

tctatatcat ggccgacaag cagaagaacg gcatcaaggt gaacttcaag atccgccaca   9900

acatcgagga cggcagcgtg cagctcgccg accactacca gcagaacacc cccatcggcg   9960

acggccccgt gctgctgccc gacaaccact acctgagcac ccagtccgcc ctgagcaaag  10020

accccaacga gaagcgcgat cacatggtcc tgctggagtt cgtgaccgcc gccgggatca  10080

ctctcggcat ggacgagctg tacaagtaag atatcaagct tatcgataat caacctctgg  10140

attacaaaat ttgtgaaaga ttgactggta ttcttaacta tgttgctcct tttacgctat  10200

gtggatacgc tgctttaatg cctttgtatc atgctattgc ttcccgtatg gctttcattt  10260

tctcctcctt gtataaatcc tggttgctgt ctctttatga ggagttgtgg cccgttgtca  10320

ggcaacgtgg cgtggtgtgc actgtgtttg ctgacgcaac ccccactggt tggggcattg  10380

ccaccacctg tcagctcctt tccgggactt tcgctttccc cctccctatt gccacggcgg  10440

aactcatcgc cgcctgcctt gcccgctgct ggacaggggc tcggctgttg ggcactgaca  10500

attccgtggt gttgtcgggg aaatcatcgt cctttccttg gctgctcgcc tgtgttgcca  10560

cctggattct gcgcgggacg tccttctgct acgtcccttc ggccctcaat ccagcggacc  10620

ttccttcccg cggcctgctg ccggctctgc ggcctcttcc gcgtcttcgc cttcgccctc  10680

agacgagtcg gatctccctt tgggccgcct ccccgcatcg ataccgtcga cctcgagaac  10740

ctagaaaaac atggagcaat cacaagtagc aatacagcag ctaccaatgc tgattgtgcc  10800

tggctagaag cacaagagga ggaggaggtg ggttttccag tcacacctca ggtaccttta  10860

agaccaatga cttacaaggc agctgtagat cttagccact tttaaaaga aaaggggga  10920

ctggaagggc taattcactc ccaacgaaga caagatcttt ttgcttgtac tgggtctctc  10980

tggttagacc agatctgagc ctgggagctc tctggctaac tagggaaccc actgcttaag  11040

cctcaataaa gcttgccttg agtgcttcaa gtagtgtgtg cccgtctgtt gtgtgactct  11100

ggtaactaga gatccctcag acccttttag tcagtgtgga aaatctctag a           11151
```

<210> SEQ ID NO 30
<211> LENGTH: 9118
<212> TYPE: DNA
<213> ORGANISM: Artificial Sequence
<220> FEATURE:
<223> OTHER INFORMATION: pSDT-4lox-RFP/GFP-WPRE-flox

<400> SEQUENCE: 30

```
ggaaattgta aacgttaata ttttgttaaa attcgcgtta aatttttgtt aaatcagctc     60

atttttaac caataggccg aaatcggcaa aatcccttat aaatcaaaag aatagaccga    120

gatagggttg agtgttgttc cagtttggaa caagagtcca ctattaaaga acgtggactc    180

caacgtcaaa gggcgaaaaa ccgtctatca gggcgatggc ccactacgtg aaccatcacc    240

ctaatcaagt tttttggggt cgaggtgccg taaagcacta aatcggaacc ctaaagggag    300

cccccgattt agagcttgac ggggaaagcc ggcgaacgtg gcgagaaagg aagggaagaa    360

agcgaaagga gcgggcgcta gggcgctggc aagtgtagcg gtcacgctgc gcgtaaccac    420
```

-continued

```
cacacccgcc gcgcttaatg cgccgctaca gggcgcgtcg cgccattcgc cattcaggct    480
gcgcaactgt tgggaagggc gatcggtgcg ggcctcttcg ctattacgcc agctggcgaa    540
agggggatgt gctgcaaggc gattaagttg ggtaacgcca gggttttccc agtcacgacg    600
ttgtaaaacg acggccagtg aattgtaata cgactcacta tagggcgaat tggagctcca    660
ccgcggtggc ggccgctcta gaattcccat tgcatacgtt gtatccatat cataatatgt    720
acatttatat tggctcatgt ccaacattac cgccatgttg acattgatta ttgactagtt    780
attaatagta atcaattacg gggtcattag ttcatagccc atatatggag ttccgcgtta    840
cataacttac ggtaaatggc ccgcctggct gaccgcccaa cgacccccgc ccattgacgt    900
caataatgac gtatgttccc atagtaacgc caatagggac tttccattga cgtcaatggg    960
tggagtattt acggtaaact gcccacttgg cagtacatca agtgtatcat atgccaagta   1020
cgccccctat tgacgtcaat gacggtaaat ggcccgcctg gcattatgcc cagtacatga   1080
ccttatggga ctttcctact tggcagtaca tctacgtatt agtcatcgct attaccatgg   1140
tgatgcggtt ttggcagtac atcaatgggc gtggatagcg gtttgactca cggggatttc   1200
caagtctcca ccccattgac gtcaatggga gtttgttttg gcaccaaaat caacgggact   1260
ttccaaaatg tcgtaacaac tccgccccat tgacgcaaat gggcggtagg cgtgtacggt   1320
gggaggtcta tataagcaga gctcgtttag tgaaccgcag tcgctctgcg gagaggctgg   1380
cagattgagc cctgggaggt tctctccagc actagcaggt agagcctggg tgttccctgc   1440
tagactctca ccagcacttg gccagtgctg ggcagagtgg ctccacgctt gcttgcttaa   1500
agacctcttc aataaagctg ccattttaga agtaagccag tgtgtgttcc catctctcct   1560
agtcgccgcc tggtcaactc ggtactcggt aataagaaga ccctggtctg ttaggaccct   1620
ttctgctttg agaaaccgaa gcaggaaaat ccctagcaga ttggcgcccg aacagggact   1680
tgaaggagag tgagagactc ctgagtacgg ctgagtgaag gcagtaaggg cggcaggaac   1740
caaccacgac ggagtgctcc tataaaggcg cgggtcggta ccagacggcg tgaggagcgg   1800
gagaggagga ggcctccggt tgcagtaagt gcaacacaaa aaagaaatag ctgtcttgtt   1860
atccaggaag ggataataag atagagtggg agatgggcgc gagaaactcc gtcttgtcag   1920
ggaagaaagc agatgaattg aaaaaattat taatcgcatg aattttaaaa gaaggggagg   1980
aatagggat atgactccag cagaaagatt aattaacatg atcactacag aacaagaaat   2040
acaatttcaa caatcaaaaa actcaaaatt taaaaatttt cgggtctatt acagagctca   2100
cgcgtgattg gagttgggag attataaatt agtagagatc actccgattg gcttggcccc   2160
cacagatgtg aagaggtaca ctactggtgg cacctcaaga aataaaagag ggtctttgt   2220
gctagggttc ttgggttttc tcgcaacggc aggttctgca atgggcgcgg cgtcgttgac   2280
gctgaccgct cagtcccgga ctttattggc tgggatagtg cagcaacagc aacagctgtt   2340
ggacgtggtc aagagacaac aagaattgtt gcgactgacc gtctggggaa caaagaacct   2400
ccagactagg gtcactgcca tcgagaagta cttaaaggac caggcgcagc taaatgcttg   2460
ggatgtgcg tttagacaag tctgccacac tactgtacca tggccaaatg caagtctaac   2520
accagactgg aacaatgata cttggcaaga gtgggagcga aaggttgact tcttggagga   2580
aaatataaca gccctcctag aagaggcaca aattcaacaa gagaagaaca tgtatgaatt   2640
acaaaagttg aatagctggg atgtgtttgg caattggttt gaccttgctt cttggataaa   2700
gtatatacaa tatggaattt atgtagttgt aggagtaata ctgttaagaa tagtgatcta   2760
tatagtacaa atgctagcta agttaaggca ggggtatagg ccagtgttct cttccccacc   2820
```

```
ctcttatttc cagtagactc atacccaaca ggacccggca ctgccaacca gagaaggcaa   2880
agaaggagac ggtggagaag gcggtggatc ctattatcga attcctgcag ccccgataaa   2940
ataaaagatt ttatttagtc tccagaaaaa ggggggaatg aaagacccca cctgtaggtt   3000
tggcaagcta gctgcagtaa cgccattttg caaggcatgg aaaaatacca aaccaagaat   3060
agagaagttc agatcaaggg cgggtacatg aaaatagcta acgttgggcc aaacaggata   3120
tctgcggtga gcagtttcgg ccccggcccg gggccaagaa cagatggtca ccgcagtttc   3180
ggccccggcc cgaggccaag aacagatggt ccccagatat ggcccaaccc tcagcagttt   3240
cttaagaccc atcagatgtt tccaggctcc cccaaggacc tgaaatgacc ctgcgcctta   3300
tttgaattaa ccaatcagcc tgcttctcgc ttctgttcgc gcgcttctgc ttcccgagct   3360
ctataaaaga gctcacaacc cctcactcgg cgcgccagtc ctccgacaga ctgagtcgcc   3420
cggggggat ccaccgggct gcaggaattc gatatcaagc ttatcgatga ttctagacat   3480
gcatatctag cgtcccgggc tgcaggaatt cataacttcg tataatgtat gctatacgaa   3540
gttatcatat gccaccatga gcgagctgat caaggagaac atgcacatga agctgtacat   3600
ggagggcacc gtgaacaacc accacttcaa gtgcacatcc gagggcgaag gcaagcccta   3660
cgagggcacc cagaccatga agatcaaggt ggtcgagggc ggccctctcc ccttcgcctt   3720
cgacatcctg gctaccagct tcatgtacgg cagcaaagcc ttcatcaacc acacccaggg   3780
catccccgac ttctttaagc agtccttccc tgagggcttc acatgggaga gaatcaccac   3840
atacgaagac gggggcgtgc tgaccgctac ccaggacacc agcttccaga acggctgcat   3900
catctacaac gtcaagatca acggggtgaa cttcccatcc aacggccctg tgatgcagaa   3960
gaaaacacgc ggctgggagg ccaacaccga gatgctgtac cccgctgacg gcggcctgag   4020
aggccacagc cagatggccc tgaagctcgt gggcgggggc tacctgcact gctccttcaa   4080
gaccacatac agatccaaga aacccgctaa gaacctcaag atgcccggct tccacttcgt   4140
ggaccacaga ctggaaagaa tcaaggaggc cgacaaagag acctacgtcg agcagcacga   4200
gatggctgtg gccaagtact gcgacctccc tagcaaactg ggcacagat aaataacttc   4260
gtataaagta tcctatacga agttatactt tggccgcggc tcgagggggt tggggttgcg   4320
ccttttccaa ggcagccctg ggtttgcgca gggacgcggc tgctctgggc gtggttccgg   4380
gaaacgcagc ggcgccgacc ctgggtctcg cacattcttc acgtccgttc gcagcgtcac   4440
ccggatcttc gccgctaccc ttgtgggccc cccggcgacg cttcctgctc cgcccctaag   4500
tcgggaaggt tccttgcggt tcgcggcgtg ccggacgtga caaacggaag ccgcacgtct   4560
cactagtacc ctcgcagacg gacagcgcca gggagcaatg gcagcgcgcc gaccgcgatg   4620
ggctgtggcc aatagcggct gctcagcagg gcgcgccgag agcagcggcc gggaaggggc   4680
ggtgcgggag gcggggtgtg gggcggtagt gtgggccctg ttcctgcccg cgcggtgttc   4740
cgcattctgc aagcctccgg agcgcacgtc ggcagtcggc tccctcgttg accgaatcac   4800
cgacctctct ccccaggggg atccaccggt cgccaccatg gtgagcaagg gcgaggagct   4860
gttcaccggg gtggtgccca tcctggtcga gctggacggc gacgtaaacg gccacaagtt   4920
cagcgtgtcc ggcgagggcg agggcgatgc cacctacggc aagctgaccc tgaagttcat   4980
ctgcaccacc ggcaagctgc ccgtgccctg gcccaccctc gtgaccaccc tgacctacgg   5040
cgtgcagtgc ttcagccgct accccgacca catgaagcag cacgacttct tcaagtccgc   5100
catgcccgaa ggctacgtcc aggagcgcac catcttcttc aaggacgacg gcaactacaa   5160
```

-continued

```
gacccgcgcc gaggtgaagt tcgagggcga caccctggtg aaccgcatcg agctgaaggg   5220
catcgacttc aaggaggacg gcaacatcct ggggcacaag ctggagtaca actacaacag   5280
ccacaacgtc tatatcatgg ccgacaagca gaagaacggc atcaaggtga acttcaagat   5340
ccgccacaac atcgaggacg gcagcgtgca gctcgccgac cactaccagc agaacacccc   5400
catcggcgac ggccccgtgc tgctgcccga caaccactac ctgagcaccc agtccgccct   5460
gagcaaagac cccaacgaga agcgcgatca catggtcctg ctggagttcg tgaccgccgc   5520
cgggatcact ctcggcatgg acgagctgta caagtaaagc ggccgcgact ctagagtcga   5580
cctgcaggca tgcaagcttg atatcaagct tatcgataat caacctctgg attacaaaat   5640
ttgtgaaaga ttgactggta ttcttaacta tgttgctcct tttacgctat gtggatacgc   5700
tgctttaatg cctttgtatc atgctattgc ttcccgtatg gctttcattt tctcctcctt   5760
gtataaatcc tggttgctgt ctctttatga ggagttgtgg cccgttgtca ggcaacgtgg   5820
cgtggtgtgc actgtgtttg ctgacgcaac ccccactggt tggggcattg ccaccacctg   5880
tcagctcctt tccgggactt tcgctttccc cctccctatt gccacggcgg aactcatcgc   5940
cgcctgcctt gcccgctgct ggacaggggc tcggctgttg ggcactgaca attccgtggt   6000
gttgtcgggg aaatcatcgt cctttccttg gctgctcgcc tgtgttgcca cctggattct   6060
gcgcgggacg tccttctgct acgtcccttc ggccctcaat ccagcggacc ttccttcccg   6120
cggcctgctg ccggctctgc ggcctcttcc gcgtcttcgc cttcgccctc agacgagtcg   6180
gatctccctt tgggccgcct ccccgcatcg ataccgtcga cctcgagttt tataaaagaa   6240
aagggggggac tggaagggat ttattacagt gcaagaagac atagaatctt agacatgtac   6300
ttagaaaagg aagaaggcat cataccagat tggcaggatt acacctcagg accaggaatt   6360
agatacccaa agacatttgg ctggctatgg aaattagtcc ctgtaaatgt atcagatgag   6420
gcacaggagg atgagaggca ttatttaatg cagccagctc aaacttccaa gtgggatgac   6480
ccttggggag aggttctagc gtggaagttt gatccaactc tagcctacac ttatgaggca   6540
tatgctagat acccagaaga gttggaagca agtcaggcct gtcagaactg catttcgctc   6600
tgtattcagt cgctctgcgg agaggctggc agattgagcc ctgggaggtt ctctccagca   6660
ctagcaggta gagcctgggt gttccctgct agactctcac cagcacttgg ccagtgctgg   6720
gcagagtggc tccacgcttg cttgcttaaa gacctcttca ataaagctgc cattttagaa   6780
gtaagccagt gtgtgttccc atctctccta gtcgccgcct ggtcaactcg gtactcggta   6840
ataagaagac cctggtctgt taggaccctt tctgctttga gaaaccgaag caggaaaatc   6900
cctagcatgg tacccagctt ttgttccctt tagtgagggt taattccgag cttggcgtaa   6960
tcatggtcat agctgtttcc tgtgtgaaat tgttatccgc tcacaattcc acacaacata   7020
cgagccggaa gcataaagtg taaagcctgg ggtgcctaat gagtgagcta actcacatta   7080
attgcgttgc gctcactgcc cgctttccag tcgggaaacc tgtcgtgcca gctgcattaa   7140
tgaatcggcc aacgcgcggg gagaggcggt ttgcgtattg ggcgctcttc cgcttcctcg   7200
ctcactgact cgctgcgctc ggtcgttcgg ctgcggcgag cggtatcagc tcactcaaag   7260
gcggtaatac ggttatccac agaatcaggg gataacgcag gaaagaacat gtgagcaaaa   7320
ggccagcaaa aggccaggaa ccgtaaaaag gccgcgttgc tggcgttttt ccataggctc   7380
cgcccccctg acgagcatca caaaaatcga cgctcaagtc agaggtggcg aaacccgaca   7440
ggactataaa gataccaggc gtttccccct ggaagctccc tcgtgcgctc tcctgttccg   7500
accctgccgc ttaccggata cctgtccgcc tttctccctt cgggaagcgt ggcgctttct   7560
```

```
catagctcac gctgtaggta tctcagttcg gtgtaggtcg ttcgctccaa gctgggctgt   7620
gtgcacgaac cccccgttca gcccgaccgc tgcgccttat ccggtaacta tcgtcttgag   7680
tccaacccgg taagacacga cttatcgcca ctggcagcag ccactggtaa caggattagc   7740
agagcgaggt atgtaggcgg tgctacagag ttcttgaagt ggtggcctaa ctacggctac   7800
actagaagga cagtatttgg tatctgcgct ctgctgaagc cagttacctt cggaaaaaga   7860
gttggtagct cttgatccgg caaacaaacc accgctggta gcggtggttt ttttgtttgc   7920
aagcagcaga ttacgcgcag aaaaaaagga tctcaagaag atcctttgat cttttctacg   7980
gggtctgacg ctcagtggaa cgaaaactca cgttaaggga ttttggtcat gagattatca   8040
aaaaggatct tcacctagat ccttttaaat taaaaatgaa gttttaaatc aatctaaagt   8100
atatatgagt aaacttggtc tgacagttac caatgcttaa tcagtgaggc acctatctca   8160
gcgatctgtc tatttcgttc atccatagtt gcctgactcc ccgtcgtgta gataactacg   8220
atacgggagg gcttaccatc tggccccagt gctgcaatga taccgcgaga cccacgctca   8280
ccggctccag atttatcagc aataaaccag ccagccggaa gggccgagcg cagaagtggt   8340
cctgcaactt tatccgcctc catccagtct attaattgtt gccgggaagc tagagtaagt   8400
agttcgccag ttaatagttt gcgcaacgtt gttgccattg ctacaggcat cgtggtgtca   8460
cgctcgtcgt ttggtatggc ttcattcagc tccggttccc aacgatcaag gcgagttaca   8520
tgatccccca tgttgtgcaa aaaagcggtt agctccttcg gtcctccgat cgttgtcaga   8580
agtaagttgg ccgcagtgtt atcactcatg gttatggcag cactgcataa ttctcttact   8640
gtcatgccat ccgtaagatg cttttctgtg actggtgagt actcaaccaa gtcattctga   8700
gaatagtgta tgcggcgacc gagttgctct tgcccggcgt caatacggga taataccgcg   8760
ccacatagca gaactttaaa agtgctcatc attggaaaac gttcttcggg gcgaaaactc   8820
tcaaggatct taccgctgtt gagatccagt tcgatgtaac ccactcgtgc acccaactga   8880
tcttcagcat cttttacttt caccagcgtt tctgggtgag caaaaacagg aaggcaaaat   8940
gccgcaaaaa agggaataag ggcgacacgg aaatgttgaa tactcatact cttccttttt   9000
caatattatt gaagcattta tcagggttat tgtctcatga gcggatacat atttgaatgt   9060
atttagaaaa ataaacaaat aggggttccg cgcacatttc cccgaaaagt gccacctg     9118
```

<210> SEQ ID NO 31
<211> LENGTH: 1653
<212> TYPE: DNA
<213> ORGANISM: Artificial Sequence
<220> FEATURE:
<223> OTHER INFORMATION: reverse luciferase

<400> SEQUENCE: 31

```
ttacacggcg atctttccgc ccttcttggc ctttatgagg atctctctga tttttcttgc     60
gtcgagtttt ccggtaagac ctttcggtac ttcgtccaca aacacaactc ctccgcgcaa    120
ctttttcgcg gttgttactt gactggcgac gtaatccacg atctcttttt ccgtcatcgt    180
ctttccgtgc tccaaaacaa caacggcggc gggaagttca ccggcgtcat cgtcgggaag    240
acctgcgaca cctgcgtcga agatgttggg gtgttggagc aagatggatt ccaattcagc    300
gggagccacc tgatagcctt tgtacttaat cagagacttc aggcggtcaa cgatgaagaa    360
gtgttcgtct tcgtcccagt aagctatgtc tccagaatgt agccatccat ccttgtcaat    420
caaggcgttg gtcgcttccg gattgtttac ataaccggac ataatcatag gacctctcac    480
```

acacagttcg cctctttgat taacgcccag cgttttcccg gtatccagat ccacaacctt 540
cgcttcaaaa aatggaacaa ctttaccgac cgcgcccggt ttatcatccc cctcgggtgt 600
aatcagaata gctgatgtag tctcagtgag cccatatcct tgcctgatac ctggcagatg 660
gaacctcttg gcaaccgctt ccccgacttc cttagagagg ggagcgccac cagaagcaat 720
ttcgtgtaaa ttagataaat cgtatttgtc aatcagagtg cttttggcga agaaggagaa 780
tagggttggc accagcagcg cactttgaat cttgtaatcc tgaaggctcc tcagaaacag 840
ctcttcttca aatctataca ttaagacgac tcgaaatcca catatcaaat atccgagtgt 900
agtaaacatt ccaaaaccgt gatggaatgg aacaacactt aaaatcgcag tatccggaat 960
gatttgattg ccaaaaatag gatctctggc atgcgagaat ctcacgcagg cagttctatg 1020
aggcagagcg acacctttag gcagaccagt agatccagag gagttcatga tcagtgcaat 1080
tgtcttgtcc ctatcgaagg actctggcac aaaatcgtat tcattaaaac cgggaggtag 1140
atgagatgtg acgaacgtgt acatcgactg aaatccctgg taatccgttt tagaatccat 1200
gataataatt ttttggatga ttgggagctt tttttgcacg ttcaaaattt tttgcaaccc 1260
ctttttggaa acgaacacca cggtaggctg cgaaatgccc atactgttga gcaattcacg 1320
ttcattataa atgtcgttcg cgggcgcaac tgcaactccg ataaataacg cgcccaacac 1380
cggcataaag aattgaagag agttttcact gcatacgacg attctgtgat ttgtattcag 1440
cccatatcgt ttcatagctt ctgccaaccg aacggacatt tcgaagtact cagcgtaagt 1500
gatgtccacc tcgatatgtg catctgtaaa agcaattgtt ccaggaacca gggcgtatct 1560
cttcatagcc ttatgcagtt gctctccagc ggttccatct tccagcggat agaatggcgc 1620
cgggcctttc tttatgtttt tggcgtcttc cat 1653

<210> SEQ ID NO 32
<211> LENGTH: 11336
<212> TYPE: DNA
<213> ORGANISM: Artificial Sequence
<220> FEATURE:
<223> OTHER INFORMATION: sequence for screening human cells

<400> SEQUENCE: 32
ttaattccgt gtattctata gtgtcaccta aatcgtatgt gtatgataca taaggttatg 60
tattaattgt agccgcgttc taacgacaat atgtacaagc ctaattgtgt agcatctggc 120
ttactgaagc agaccctatc atctctctcg taaactgccg tcagagtcgg tttggttgga 180
cgaaccttct gagtttctgg taacgccgtc ccgcacccgg aaatggtcag cgaaccaatc 240
agcagggtca tcgctagcca gatcctctac gccggacgca tcgtggccgg catcaccggc 300
gccacaggtg cggttgctgg cgcctatatc gccgacatca ccgatgggga agatcgggct 360
cgccacttcg ggctcatgag cgcttgtttc ggcgtgggta tggtggcagg ccccgtggcc 420
gggggactgt tgggcgccat ctccttgcat gcaccattcc ttgcggcggc ggtgctcaac 480
ggcctcaacc tactactggg ctgcttccta atgcaggagt cgcataaggg agagcgtcga 540
atggtgcact ctcagtacaa tctgctctga tgccgcatag ttaagccagc cccgacaccc 600
gccaacaccc gctgacgcgc cctgacgggc ttgtctgctc ccggcatccg cttacagaca 660
agctgtgacc gtctccggga gctgcatgtg tcagaggttt tcaccgtcat caccgaaacg 720
cgcgagacga aagggcctcg tgatacgcct atttttatag gttaatgtca tgataataat 780
ggtttcttag acgtcaggtg gcacttttcg gggaaatgtg cgcggaaccc ctatttgttt 840
atttttctaa atacattcaa atatgtatcc gctcatgaga caataaccct gataaatgct 900

```
tcaataatat tgaaaaagga agagtatgag tattcaacat ttccgtgtcg cccttattcc    960
ctttttgcg gcattttgcc ttcctgtttt tgctcaccca gaaacgctgg tgaaagtaaa   1020
agatgctgaa gatcagttgg gtgcacgagt gggttacatc gaactggatc tcaacagcgg   1080
taagatcctt gagagttttc gccccgaaga acgttttcca atgatgagca cttttaaagt   1140
tctgctatgt ggcgcggtat tatcccgtat tgacgccggg caagagcaac tcggtcgccg   1200
catacactat tctcagaatg acttggttga gtactcacca gtcacagaaa agcatcttac   1260
ggatggcatg acagtaagag aattatgcag tgctgccata accatgagtg ataacactgc   1320
ggccaactta cttctgacaa cgatcggagg accgaaggag ctaaccgctt ttttgcacaa   1380
catgggggat catgtaactc gccttgatcg ttgggaaccg gagctgaatg aagccatacc   1440
aaacgacgag cgtgacacca cgatgcctgt agcaatggca acaacgttgc gcaaactatt   1500
aactggcgaa ctacttactc tagcttcccg gcaacaatta atagactgga tggaggcgga   1560
taaagttgca ggaccacttc tgcgctcggc ccttccggct ggctggttta ttgctgataa   1620
atctggagcc ggtgagcgtg ggtctcgcgg tatcattgca gcactggggc cagatggtaa   1680
gccctcccgt atcgtagtta tctacacgac ggggagtcag gcaactatgg atgaacgaaa   1740
tagacagatc gctgagatag gtgcctcact gattaagcat tggtaactgt cagaccaagt   1800
ttactcatat atactttaga ttgatttaaa acttcatttt taatttaaaa ggatctaggt   1860
gaagatcctt tttgataatc tcatgaccaa aatcccttaa cgtgagtttt cgttccactg   1920
agcgtcagac cccgtagaaa agatcaaagg atcttcttga gatccttttt ttctgcgcgt   1980
aatctgctgc ttgcaaacaa aaaaaccacc gctaccagcg gtggtttgtt tgccggatca   2040
agagctacca actctttttc cgaaggtaac tggcttcagc agagcgcaga taccaaatac   2100
tgtccttcta gtgtagccgt agttaggcca ccacttcaag aactctgtag caccgcctac   2160
atacctcgct ctgctaatcc tgttaccagt ggctgctgcc agtggcgata agtcgtgtct   2220
taccgggttg gactcaagac gatagttacc ggataaggcg cagcggtcgg gctgaacggg   2280
gggttcgtgc acacagccca gcttggagcg aacgacctac accgaactga gatacctaca   2340
gcgtgagcat tgagaaagcg ccacgcttcc cgaagggaga aaggcggaca ggtatccggt   2400
aagcggcagg gtcggaacag gagagcgcac gagggagctt ccagggggaa acgcctggta   2460
tctttatagt cctgtcgggt ttcgccacct ctgacttgag cgtcgatttt tgtgatgctc   2520
gtcagggggg cggagcctat ggaaaaacgc cagcaacgcg gcctttttac ggttcctggc   2580
cttttgctgg ccttttgctc acatgttctt tcctgcgtta tcccctgatt ctgtggataa   2640
ccgtattacc gcctttgagt gagctgatac cgctcgccgc agccgaacga ccgagcgcag   2700
cgagtcagtg agcgaggaag cggaagagcg cccaatacgc aaaccgcctc tccccgcgcg   2760
ttggccgatt cattaatgca gctgtggaat gtgtgtcagt tagggtgtgg aaagtcccca   2820
ggctccccag caggcagaag tatgcaaagc atgcatctca attagtcagc aaccaggtgt   2880
ggaaagtccc caggctcccc agcaggcaga agtatgcaaa gcatgcatct caattagtca   2940
gcaaccatag tcccgcccct aactccgccc atcccgcccc taactccgcc cagttccgcc   3000
cattctccgc cccatggctg actaattttt tttatttatg cagaggccga ggccgcctcg   3060
gcctctgagc tattccagaa gtagtgagga ggcttttttg gaggcctagg cttttgcaaa   3120
aagcttggac acaagacagg cttgcgagat atgtttgaga ataccacttt atcccgcgtc   3180
agggagaggc agtgcgtaaa aagacgcgga ctcatgtgaa atactggttt ttagtgcgcc   3240
```

```
agatctctat aatctcgcgc aacctatttt cccctcgaac actttttaag ccgtagataa   3300
acaggctggg acacttcaca tgagcgaaaa atacatcgtc acctgggaca tgttgcagat   3360
ccatgcacgt aaactcgcaa gccgactgat gccttctgaa caatggaaag gcattattgc   3420
cgtaagccgt ggcggtctgt accgggtgcg ttactggcgc gtgaactggg tattcgtcat   3480
gtcgataccg tttgtatttc cagctacgat cacgacaacc agcgcgagct taaagtgctg   3540
aaacgcgcag aaggcgatgg cgaaggcttc atcgttattg atgacctggt ggataccggt   3600
ggtactgcgg ttgcgattcg tgaaatgtat ccaaaagcgc actttgtcac catcttcgca   3660
aaaccggctg gtcgtccgct ggttgatgac tatgttgttg atatcccgca agatacctgg   3720
attgaacagc cgtgggatat gggcgtcgta ttcgtcccgc caatctccgg tcgctaatct   3780
tttcaacgcc tggcactgcc gggcgttgtt ctttttaact tcaggcgggt tacaatagtt   3840
tccagtaagt attctggagg ctgcatccat gacacaggca aacctgagcg aaaccctgtt   3900
caaaccccgc tttaaacatc ctgaaacctc gacgctagtc cgccgcttta atcacggcgc   3960
acaaccgcct gtgcagtcgg cccttgatgg taaaaccatc cctcactggt atcgcatgat   4020
taaccgtctg atgtggatct ggcgcggcat tgacccacgc gaaatcctcg acgtccaggc   4080
acgtattgtg atgagcgatg ccgaacgtac cgacgatgat ttatacgata cggtgattgg   4140
ctaccgtggc ggcaactgga tttatgagtg ggccccggat ctttgtgaag gaaccttact   4200
tctgtggtgt gacataattg gacaaactac ctacagagat ttaaagctct aaggtaaata   4260
taaaattttt aagtgtataa tgtgttaaac tactgattct aattgtttgt gtattttaga   4320
ttccaaccta tggaactgat gaatgggagc agtggtggaa tgcctttaat gaggaaaacc   4380
tgttttgctc agaagaaatg ccatctagtg atgatgaggc tactgctgac tctcaacatt   4440
ctactcctcc aaaaaagaag agaaaggtag aagaccccaa ggactttcct tcagaattgc   4500
taagtttttt gagtcatgct gtgtttagta atagaactct tgcttgcttt gctatttaca   4560
ccacaaagga aaaagctgca ctgctataca agaaaattat ggaaaaatat tctgtaacct   4620
ttataagtag gcataacagt tataatcata acatactgtt ttttcttact ccacacaggc   4680
atagagtgtc tgctattaat aactatgctc aaaaattgtg tacctttagc tttttaattt   4740
gtaaaggggt taataaggaa tatttgatgt atagtgcctt gactagagat cataatcagc   4800
cataccacat ttgtagaggt tttacttgct ttaaaaaacc tcccacacct cccctgaac    4860
ctgaaacata aaatgaatgc aattgttgtt gttaacttgt ttattgcagc ttataatggt   4920
tacaaataaa gcaatagcat cacaaatttc acaaataaag catttttttc actgcattct   4980
agttgtggtt tgtccaaact catcaatgta tcttatcatg tctggatcaa ctggataact   5040
caagctaacc aaaatcatcc caaacttccc accccatacc ctattaccac tgccaattac   5100
ctagtggttt catttactct aaacctgtga ttcctctgaa ttattttcat tttaaagaaa   5160
ttgtatttgt taaatatgta ctacaaactt agtagttgga agggctaatt cactcccaaa   5220
gaagacaaga tatccttgat ctgtggatct accacacaca aggctacttc cctgattagc   5280
agaactacac accagggcca ggggtcagat atccactgac ctttggatgg tgctacaagc   5340
tagtaccagt tgagccagat aaggtagaag aggccaataa aggagagaac accagcttgt   5400
tacaccctgt gagcctgcat gggatggatg acccggagag agaagtgtta gagtggaggt   5460
ttgacagccg cctagcattt catcacgtgg cccgagagct gcatccggag tacttcaaga   5520
actgctgata tcgagcttgc tacaagggac tttccgctgg ggactttcca gggaggcgtg   5580
gcctgggcgg gactggggag tggcgagccc tcagatcctg catataagca gctgcttttt   5640
```

-continued

```
gcctgtactg ggtctctctg gttagaccag atctgagcct gggagctctc tggctaacta   5700
gggaacccac tgcttaagcc tcaataaagc ttgccttgag tgcttcaagt agtgtgtgcc   5760
cgtctgttgt gtgactctgg taactagaga tccctcagac ccttttagtc agtgtggaaa   5820
atctctagca gtggcgcccg aacagggact tgaaagcgaa agggaaacca gaggagctct   5880
ctcgacgcag gactcggctt gctgaagcgc gcacggcaag aggcgagggg cggcgactgg   5940
tgagtacgcc aaaaattttg actagcggag gctagaagga gagagatggg tgcgagagcg   6000
tcagtattaa gcgggggaga attagatcgc gatgggaaaa aattcggtta aggccagggg   6060
gaaagaaaaa atataaatta aaacatatag tatgggcaag cagggagcta gaacgattcg   6120
cagttaatcc tggcctgtta gaaacatcag aaggctgtag acaaatactg ggacagctac   6180
aaccatccct tcagacagga tcagaagaac ttagatcatt atataataca gtagcaaccc   6240
tctattgtgt gcatcaaagg atagagataa aagacaccaa ggaagcttta gacaagatag   6300
aggaagagca aaacaaaagt aagaccaccg cacagcaagc ggccgctgat cttcagacct   6360
ggaggaggag atatgaggga caattggaga agtgaattat ataaatataa agtagtaaaa   6420
attgaaccat taggagtagc acccaccaag gcaaagagaa gagtggtgca gagagaaaaa   6480
agagcagtgg gaataggagc tttgttcctt gggttcttgg gagcagcagg aagcactatg   6540
ggcgcagcgt caatgacgct gacggtacag gccagacaat tattgtctgg tatagtgcag   6600
cagcagaaca atttgctgag ggctattgag gcgcaacagc atctgttgca actcacagtc   6660
tggggcatca agcagctcca ggcaagaatc ctggctgtgg aaagatacct aaaggatcaa   6720
cagctcctgg ggatttgggg ttgctctgga aaactcattt gcaccactgc tgtgccttgg   6780
aatgctagtt ggagtaataa atctctggaa cagatttgga atcacacgac ctggatggag   6840
tgggacagag aaattaacaa ttacacaagc ttaatacact ccttaattga agaatcgcaa   6900
aaccagcaag aaaagaatga acaagaatta ttggaattag ataaatgggc aagtttgtgg   6960
aattggttta acataacaaa ttggctgtgg tatataaaat tattcataat gatagtagga   7020
ggcttggtag gtttaagaat agtttttgct gtactttcta tagtgaatag agttaggcag   7080
ggatattcac cattatcgtt tcagacccac ctcccaaccc cgaggggacc cgacaggccc   7140
gaaggaatag aagaagaagg tggagagaga gacagagaca gatccattcg attagtgaac   7200
ggatctcgac ggtatcgccg aattcacaaa tggcagtatt catccacaat tttaaaagaa   7260
aaggggggat tggggggtac agtgcagggg aaagaatagt agacataata gcaacagaca   7320
tacaaactaa agaattacaa aaacaaatta caaaaattca aaattttcgg gtttattaca   7380
gggacagcag agatccactt tatcgataag cttgggagtt ccgcgttaca taacttacgg   7440
taaatggccc gcctggctga ccgcccaacg acccccgccc attgacgtca ataatgacgt   7500
atgttcccat agtaacgcca atagggactt tccattgacg tcaatgggtg gagtatttac   7560
ggtaaactgc ccacttggca gtacatcaag tgtatcatat gccaagtacg ccccctattg   7620
acgtcaatga cggtaaatgg cccgcctggc attatgccca gtacatgacc ttacgggact   7680
ttcctacttg gcagtacatc tacgtattag tcatcgctat taccatggtg atgcggtttt   7740
ggcagtacac caatgggcgt ggatagcggt ttgactcacg gggatttcca agtctccacc   7800
ccattgacgt caatgggagt ttgttttggc accaaaatca acgggacttt ccaaaatgtc   7860
gtaacaactc cgccccattg acgcaaatgg gcggtaggcg tgtacggtgg gaggtctata   7920
taagcagagc tcgtttagtg aaccgtcaga tcgcctggag acgccatcca cgctgttttg   7980
```

-continued

```
acctccatag aagacaccga ctctagctag aggatccgga ctagtaactc gaggatgggg   8040
actgacccgg gctgcaggaa ttcataactt cgtataatgt atgctatacg aagttatagt   8100
taagccttat tgtttatcat cctcattcaa cgacgcgaag gtgtaccttg gcgagaataa   8160
cttcgtatag gatactttat acgaagttat ttatctgtgc cccagtttgc tagggaggtc   8220
gcagtacttg gccacagcca tctcgtgctg ctcgacgtag gtctctttgt cggcctcctt   8280
gattctttcc agtctgtggt ccacgaagtg gaagccgggc atcttgaggt tcttagcggg   8340
tttcttggat ctgtatgtgg tcttgaagga gcagtgcagg tagcccccgc ccacgagctt   8400
cagggccatc tggctgtggc ctctcaggcc gccgtcagcg gggtacagca tctcggtgtt   8460
ggcctcccag ccgcgtgttt tcttctgcat cacagggccg ttggatggga agttcacccc   8520
gttgatcttg acgttgtaga tgatgcagcc gttctggaag ctggtgtcct gggtagcggt   8580
cagcacgccc ccgtcttcgt atgtggtgat tctctcccat gtgaagccct cagggaagga   8640
ctgcttaaag aagtcgggga tgccctgggt gtggttgatg aaggctttgc tgccgtacat   8700
gaagctggta gccaggatgt cgaaggcgaa ggggagaggg ccgccctcga ccaccttgat   8760
cttcatggtc tgggtgccct cgtagggctt gccttcgccc tcggatgtgc acttgaagtg   8820
gtggttgttc acggtgccct ccatgtacag cttcatgtgc atgttctcct tgatcagctc   8880
gctcatggtg gcatatgata acttcgtata gcatacatta tacgaagtta tattaagggt   8940
tattgaatat gatcggaagt caacgggtcg atggtgatgc ttggctcgaa taacttcgta   9000
taaagtatcc tatacgaagt tatactttgg ccgcggctcg agggggttgg ggttgcgcct   9060
tttccaaggc agccctgggt ttgcgcaggg acgcggctgc tctgggcgtg gttccgggaa   9120
acgcagcggc gccgaccctg ggtctcgcac attcttcacg tccgttcgca gcgtcacccg   9180
gatcttcgcc gctacccttg tgggcccccc ggcgacgctt cctgctccgc ccctaagtcg   9240
ggaaggttcc ttgcggttcg cggcgtgccg gacgtgacaa acggaagccg cacgtctcac   9300
tagtaccctc gcagacggac agcgccaggg agcaatggca gcgcgccgac cgcgatgggc   9360
tgtggccaat agcggctgct cagcagggcg cgccgagagc agcggccggg aaggggcggt   9420
gcgggaggcg gggtgtgggg cggtagtgtg ggccctgttc ctgcccgcgc ggtgttccgc   9480
attctgcaag cctccggagc gcacgtcggc agtcggctcc ctcgttgacc gaatcaccga   9540
cctctctccc caggggggatc caccggtcgc caccatggtg agcaagggcg aggagctgtt   9600
caccggggtg gtgcccatcc tggtcgagct ggacggcgac gtaaacggcc acaagttcag   9660
cgtgtccggc gagggcgagg gcgatgccac ctacggcaag ctgaccctga agttcatctg   9720
caccaccggc aagctgcccg tgccctggcc caccctcgtg accaccctga cctacggcgt   9780
gcagtgcttc agccgctacc ccgaccacat gaagcagcac gacttcttca agtccgccat   9840
gcccgaaggc tacgtccagg agcgcaccat cttcttcaag gacgacggca actacaagac   9900
ccgcgccgag gtgaagttcg agggcgacac cctggtgaac cgcatcgagc tgaagggcat   9960
cgacttcaag gaggacggca acatcctggg gcacaagctg gagtacaact acaacagcca  10020
caacgtctat atcatggccg acaagcagaa gaacggcatc aaggtgaact tcaagatccg  10080
ccacaacatc gaggacggca gcgtgcagct cgccgaccac taccagcaga acacccccat  10140
cggcgacggc cccgtgctgc tgcccgacaa ccactacctg agcacccagt ccgccctgag  10200
caaagacccc aacgagaagc gcgatcacat ggtcctgctg gagttcgtga ccgccgccgg  10260
gatcactctc ggcatggacg agctgtacaa gtaagatatc aagcttatcg ataatcaacc  10320
tctggattac aaaatttgtg aaagattgac tggtattctt aactatgttg ctccttttac  10380
```

gctatgtgga tacgctgctt taatgccttt gtatcatgct attgcttccc gtatggcttt 10440
cattttctcc tccttgtata aatcctggtt gctgtctctt tatgaggagt tgtggcccgt 10500
tgtcaggcaa cgtggcgtgg tgtgcactgt gtttgctgac gcaaccccca ctggttgggg 10560
cattgccacc acctgtcagc tcctttccgg gactttcgct ttccccctcc ctattgccac 10620
ggcggaactc atcgccgcct gccttgcccg ctgctggaca ggggctcggc tgttgggcac 10680
tgacaattcc gtggtgttgt cggggaaatc atcgtccttt ccttggctgc tcgcctgtgt 10740
tgccacctgg attctgcgcg ggacgtcctt ctgctacgtc ccttcggccc tcaatccagc 10800
ggaccttcct tcccgcggcc tgctgccggc tctgcggcct cttccgcgtc ttcgccttcg 10860
ccctcagacg agtcggatct ccctttgggc cgcctccccg catcgatacc gtcgacctcg 10920
agaacctaga aaaacatgga gcaatcacaa gtagcaatac agcagctacc aatgctgatt 10980
gtgcctggct agaagcacaa gaggaggagg aggtgggttt tccagtcaca cctcaggtac 11040
ctttaagacc aatgacttac aaggcagctg tagatcttag ccacttttta aaagaaaagg 11100
ggggactgga agggctaatt cactcccaac gaagacaaga tctttttgct tgtactgggt 11160
ctctctggtt agaccagatc tgagcctggg agctctctgg ctaactaggg aacccactgc 11220
ttaagcctca ataaagcttg ccttgagtgc ttcaagtagt gtgtgcccgt ctgttgtgtg 11280
actctggtaa ctagagatcc ctcagaccct tttagtcagt gtggaaaatc tctaga 11336

<210> SEQ ID NO 33
<211> LENGTH: 11223
<212> TYPE: DNA
<213> ORGANISM: Artificial Sequence
<220> FEATURE:
<223> OTHER INFORMATION: sequence for screening human cells

<400> SEQUENCE: 33
ttaattccgt gtattctata gtgtcaccta aatcgtatgt gtatgataca taaggttatg 60
tattaattgt agccgcgttc taacgacaat atgtacaagc ctaattgtgt agcatctggc 120
ttactgaagc agaccctatc atctctctcg taaactgccg tcagagtcgg tttggttgga 180
cgaaccttct gagtttctgg taacgccgtc ccgcacccgg aaatggtcag cgaaccaatc 240
agcagggtca tcgctagcca gatcctctac gccggacgca tcgtggccgg catcaccggc 300
gccacaggtg cggttgctgg cgcctatatc gccgacatca ccgatgggga agatcgggct 360
cgccacttcg ggctcatgag cgcttgtttc ggcgtgggta tggtggcagg ccccgtggcc 420
gggggactgt tgggcgccat ctccttgcat gcaccattcc ttgcggcggc ggtgctcaac 480
ggcctcaacc tactactggg ctgcttccta atgcaggagt cgcataaggg agagcgtcga 540
atggtgcact ctcagtacaa tctgctctga tgccgcatag ttaagccagc cccgacaccc 600
gccaacaccc gctgacgcgc cctgacgggc ttgtctgctc ccggcatccg cttacagaca 660
agctgtgacc gtctccggga gctgcatgtg tcagaggttt tcaccgtcat caccgaaacg 720
cgcgagacga aagggcctcg tgatacgcct atttttatag gttaatgtca tgataataat 780
ggtttcttag acgtcaggtg gcacttttcg gggaaatgtg cgcggaaccc ctatttgttt 840
atttttctaa atacattcaa atatgtatcc gctcatgaga caataaccct gataaatgct 900
tcaataatat tgaaaaagga agagtatgag tattcaacat ttccgtgtcg cccttattcc 960
cttttttgcg gcattttgcc ttcctgtttt tgctcaccca gaaacgctgg tgaaagtaaa 1020
agatgctgaa gatcagttgg gtgcacgagt gggttacatc gaactggatc tcaacagcgg 1080

-continued

```
taagatcctt gagagttttc gccccgaaga acgttttcca atgatgagca cttttaaagt   1140
tctgctatgt ggcgcggtat tatcccgtat tgacgccggg caagagcaac tcggtcgccg   1200
catacactat tctcagaatg acttggttga gtactcacca gtcacagaaa agcatcttac   1260
ggatggcatg acagtaagag aattatgcag tgctgccata accatgagtg ataacactgc   1320
ggccaactta cttctgacaa cgatcggagg accgaaggag ctaaccgctt ttttgcacaa   1380
catgggggat catgtaactc gccttgatcg ttgggaaccg gagctgaatg aagccatacc   1440
aaacgacgag cgtgacacca cgatgcctgt agcaatggca acaacgttgc gcaaactatt   1500
aactggcgaa ctacttactc tagcttcccg gcaacaatta atagactgga tggaggcgga   1560
taaagttgca ggaccacttc tgcgctcggc ccttccggct ggctggttta ttgctgataa   1620
atctggagcc ggtgagcgtg ggtctcgcgg tatcattgca gcactggggc cagatggtaa   1680
gccctcccgt atcgtagtta tctacacgac ggggagtcag gcaactatgg atgaacgaaa   1740
tagacagatc gctgagatag gtgcctcact gattaagcat tggtaactgt cagaccaagt   1800
ttactcatat atactttaga ttgatttaaa acttcatttt taatttaaaa ggatctaggt   1860
gaagatcctt tttgataatc tcatgaccaa aatcccttaa cgtgagtttt cgttccactg   1920
agcgtcagac cccgtagaaa agatcaaagg atcttcttga gatccttttt ttctgcgcgt   1980
aatctgctgc ttgcaaacaa aaaaaccacc gctaccagcg gtggtttgtt tgccggatca   2040
agagctacca actctttttc cgaaggtaac tggcttcagc agagcgcaga taccaaatac   2100
tgtccttcta gtgtagccgt agttaggcca ccacttcaag aactctgtag caccgcctac   2160
atacctcgct ctgctaatcc tgttaccagt ggctgctgcc agtggcgata agtcgtgtct   2220
taccgggttg gactcaagac gatagttacc ggataaggcg cagcggtcgg gctgaacggg   2280
gggttcgtgc acacagccca gcttggagcg aacgacctac accgaactga gatacctaca   2340
gcgtgagcat tgagaaagcg ccacgcttcc cgaagggaga aaggcggaca ggtatccggt   2400
aagcggcagg gtcggaacag gagagcgcac gagggagctt ccagggggaa acgcctggta   2460
tctttatagt cctgtcgggt ttcgccacct ctgacttgag cgtcgatttt tgtgatgctc   2520
gtcagggggg cggagcctat ggaaaaacgc cagcaacgcg gcctttttac ggttcctggc   2580
cttttgctgg ccttttgctc acatgttctt tcctgcgtta tcccctgatt ctgtggataa   2640
ccgtattacc gcctttgagt gagctgatac cgctcgccgc agccgaacga ccgagcgcag   2700
cgagtcagtg agcgaggaag cggaagagcg cccaatacgc aaaccgcctc tccccgcgcg   2760
ttggccgatt cattaatgca gctgtggaat gtgtgtcagt tagggtgtgg aaagtcccca   2820
ggctccccag caggcagaag tatgcaaagc atgcatctca attagtcagc aaccaggtgt   2880
ggaaagtccc caggctcccc agcaggcaga agtatgcaaa gcatgcatct caattagtca   2940
gcaaccatag tcccgcccct aactccgccc atcccgcccc taactccgcc cagttccgcc   3000
cattctccgc cccatggctg actaattttt tttatttatg cagaggccga ggccgcctcg   3060
gcctctgagc tattccagaa gtagtgagga ggcttttttg gaggcctagg cttttgcaaa   3120
aagcttggac acaagacagg cttgcgagat atgtttgaga ataccacttt atcccgcgtc   3180
agggagaggc agtgcgtaaa aagacgcgga ctcatgtgaa atactggttt ttagtgcgcc   3240
agatctctat aatctcgcgc aacctatttt cccctcgaac actttttaag ccgtagataa   3300
acaggctggg acacttcaca tgagcgaaaa atacatcgtc acctgggaca tgttgcagat   3360
ccatgcacgt aaactcgcaa gccgactgat gccttctgaa caatggaaag gcattattgc   3420
cgtaagccgt ggcggtctgt accgggtgcg ttactggcgc gtgaactggg tattcgtcat   3480
```

-continued

```
gtcgataccg tttgtatttc cagctacgat cacgacaacc agcgcgagct taaagtgctg   3540
aaacgcgcag aaggcgatgg cgaaggcttc atcgttattg atgacctggt ggataccggt   3600
ggtactgcgg ttgcgattcg tgaaatgtat ccaaaagcgc actttgtcac catcttcgca   3660
aaaccggctg gtcgtccgct ggttgatgac tatgttgttg atatcccgca agatacctgg   3720
attgaacagc cgtgggatat gggcgtcgta ttcgtcccgc caatctccgg tcgctaatct   3780
tttcaacgcc tggcactgcc gggcgttgtt ctttttaact tcaggcgggt tacaatagtt   3840
tccagtaagt attctggagg ctgcatccat gacacaggca aacctgagcg aaaccctgtt   3900
caaaccccgc tttaaacatc ctgaaacctc gacgctagtc cgccgcttta atcacggcgc   3960
acaaccgcct gtgcagtcgg cccttgatgg taaaaccatc cctcactggt atcgcatgat   4020
taaccgtctg atgtggatct ggcgcggcat tgacccacgc gaaatcctcg acgtccaggc   4080
acgtattgtg atgagcgatg ccgaacgtac cgacgatgat ttatacgata cggtgattgg   4140
ctaccgtggc ggcaactgga tttatgagtg ggccccggat ctttgtgaag gaaccttact   4200
tctgtggtgt gacataattg gacaaactac ctacagagat ttaaagctct aaggtaaata   4260
taaaattttt aagtgtataa tgtgttaaac tactgattct aattgtttgt gtattttaga   4320
ttccaaccta tggaactgat gaatgggagc agtggtggaa tgcctttaat gaggaaaacc   4380
tgttttgctc agaagaaatg ccatctagtg atgatgaggc tactgctgac tctcaacatt   4440
ctactcctcc aaaaaagaag agaaaggtag aagaccccaa ggactttcct tcagaattgc   4500
taagtttttt gagtcatgct gtgtttagta atagaactct tgcttgcttt gctatttaca   4560
ccacaaagga aaaagctgca ctgctataca agaaaattat ggaaaaatat tctgtaacct   4620
ttataagtag gcataacagt tataatcata acatactgtt ttttcttact ccacacaggc   4680
atagagtgtc tgctattaat aactatgctc aaaaattgtg tacctttagc tttttaattt   4740
gtaaaggggt taataaggaa tatttgatgt atagtgcctt gactagagat cataatcagc   4800
cataccacat ttgtagaggt tttacttgct ttaaaaaacc tcccacacct ccccctgaac   4860
ctgaaacata aaatgaatgc aattgttgtt gttaacttgt ttattgcagc ttataatggt   4920
tacaaataaa gcaatagcat cacaaatttc acaaataaag catttttttc actgcattct   4980
agttgtggtt tgtccaaact catcaatgta tcttatcatg tctggatcaa ctggataact   5040
caagctaacc aaaatcatcc caaacttccc accccatacc ctattaccac tgccaattac   5100
ctagtggttt catttactct aaacctgtga ttcctctgaa ttattttcat tttaaagaaa   5160
ttgtatttgt taaatatgta ctacaaactt agtagttgga agggctaatt cactcccaaa   5220
gaagacaaga tatccttgat ctgtggatct accacacaca aggctacttc cctgattagc   5280
agaactacac accagggcca ggggtcagat atccactgac ctttggatgg tgctacaagc   5340
tagtaccagt tgagccagat aaggtagaag aggccaataa aggagagaac accagcttgt   5400
tacaccctgt gagcctgcat gggatggatg acccggagag agaagtgtta gagtggaggt   5460
ttgacagccg cctagcattt catcacgtgg cccgagagct gcatccggag tacttcaaga   5520
actgctgata tcgagcttgc tacaagggac tttccgctgg ggactttcca gggaggcgtg   5580
gcctgggcgg gactggggag tggcgagccc tcagatcctg catataagca gctgcttttt   5640
gcctgtactg ggtctctctg gttagaccag atctgagcct gggagctctc tggctaacta   5700
gggaacccac tgcttaagcc tcaataaagc ttgccttgag tgcttcaagt agtgtgtgcc   5760
cgtctgttgt gtgactctgg taactagaga tccctcagac ccttttagtc agtgtggaaa   5820
```

-continued

```
atctctagca gtggcgcccg aacagggact tgaaagcgaa agggaaacca gaggagctct   5880
ctcgacgcag gactcggctt gctgaagcgc gcacggcaag aggcgagggg cggcgactgg   5940
tgagtacgcc aaaaattttg actagcggag gctagaagga gagagatggg tgcgagagcg   6000
tcagtattaa gcgggggaga attagatcgc gatgggaaaa aattcggtta aggccagggg   6060
gaaagaaaaa atataaatta aaacatatag tatgggcaag cagggagcta gaacgattcg   6120
cagttaatcc tggcctgtta gaaacatcag aaggctgtag acaaatactg ggacagctac   6180
aaccatccct tcagacagga tcagaagaac ttagatcatt atataataca gtagcaaccc   6240
tctattgtgt gcatcaaagg atagagataa aagacaccaa ggaagcttta gacaagatag   6300
aggaagagca aaacaaaagt aagaccaccg cacagcaagc ggccgctgat cttcagacct   6360
ggaggaggag atatgaggga caattggaga agtgaattat ataaatataa agtagtaaaa   6420
attgaaccat taggagtagc acccaccaag gcaaagagaa gagtggtgca gagagaaaaa   6480
agagcagtgg gaataggagc tttgttcctt gggttcttgg gagcagcagg aagcactatg   6540
ggcgcagcgt caatgacgct gacggtacag gccagacaat tattgtctgg tatagtgcag   6600
cagcagaaca atttgctgag ggctattgag gcgcaacagc atctgttgca actcacagtc   6660
tggggcatca agcagctcca ggcaagaatc ctggctgtgg aaagatacct aaaggatcaa   6720
cagctcctgg ggatttgggg ttgctctgga aaactcattt gcaccactgc tgtgccttgg   6780
aatgctagtt ggagtaataa atctctggaa cagatttgga atcacacgac ctggatggag   6840
tgggacagag aaattaacaa ttacacaagc ttaatacact ccttaattga agaatcgcaa   6900
aaccagcaag aaaagaatga acaagaatta ttggaattag ataaatgggc aagtttgtgg   6960
aattggttta acataacaaa ttggctgtgg tatataaaat tattcataat gatagtagga   7020
ggcttggtag gtttaagaat agtttttgct gtactttcta tagtgaatag agttaggcag   7080
ggatattcac cattatcgtt tcagacccac ctcccaaccc cgaggggacc cgacaggccc   7140
gaaggaatag aagaagaagg tggagagaga gacagagaca gatccattcg attagtgaac   7200
ggatctcgac ggtatcgccg aattcacaaa tggcagtatt catccacaat tttaaaagaa   7260
aaggggggat tggggggtac agtgcagggg aaagaatagt agacataata gcaacagaca   7320
tacaaactaa agaattacaa aaacaaatta caaaaattca aaattttcgg gtttattaca   7380
gggacagcag agatccactt tatcgatggt ccggtccgga attcctgcag ccccgataaa   7440
ataaaagatt ttatttagtc tccagaaaaa ggggggaatg aaagacccca cctgtaggtt   7500
tggcaagcta gctgcagtaa cgccattttg caaggcatgg aaaaatacca aaccaagaat   7560
agagaagttc agatcaaggg cgggtacatg aaaatagcta acgttgggcc aaacaggata   7620
tctgcggtga gcagtttcgg ccccggcccg gggccaagaa cagatggtca ccgcagtttc   7680
ggccccggcc cgaggccaag aacagatggt ccccagatat ggcccaaccc tcagcagttt   7740
cttaagaccc atcagatgtt tccaggctcc cccaaggacc tgaaatgacc ctgcgcctta   7800
tttgaattaa ccaatcagcc tgcttctcgc ttctgttcgc gcgcttctgc ttcccgagct   7860
ctataaaaga gctcacaacc cctcactcgg cgcgccagtc ctccgacaga ctgagtcgcc   7920
cggggggggat ccaccgggct gcaggaattc ataacttcgt ataatgtatg ctatacgaag   7980
ttatagttaa gccttattgt ttatcatcct cattcaacga cgcgaaggtg taccttggcg   8040
agaataactt cgtataggat actttatacg aagttattta tctgtgcccc agtttgctag   8100
ggaggtcgca gtacttggcc acagccatct cgtgctgctc gacgtaggtc tctttgtcgg   8160
cctccttgat tctttccagt ctgtggtcca cgaagtggaa gccgggcatc ttgaggttct   8220
```

```
tagcgggttt cttggatctg tatgtggtct tgaaggagca gtgcaggtag cccccgccca   8280
cgagcttcag ggccatctgg ctgtggcctc tcaggccgcc gtcagcgggg tacagcatct   8340
cggtgttggc ctcccagccg cgtgttttct tctgcatcac agggccgttg gatgggaagt   8400
tcaccccgtt gatcttgacg ttgtagatga tgcagccgtt ctggaagctg gtgtcctggg   8460
tagcggtcag cacgcccccg tcttcgtatg tggtgattct ctcccatgtg aagccctcag   8520
ggaaggactg cttaaagaag tcggggatgc cctgggtgtg gttgatgaag gctttgctgc   8580
cgtacatgaa gctggtagcc aggatgtcga aggcgaaggg gagagggccg ccctcgacca   8640
ccttgatctt catggtctgg gtgccctcgt agggcttgcc ttcgccctcg gatgtgcact   8700
tgaagtggtg gttgttcacg gtgccctcca tgtacagctt catgtgcatg ttctccttga   8760
tcagctcgct catggtggca tatgataact tcgtatagca tacattatac gaagttatat   8820
taagggttat tgaatatgat cggaagtcaa cgggtcgatg gtgatgcttg gctcgaataa   8880
cttcgtataa agtatcctat acgaagttat actttggccg cggctcgagg gggttggggt   8940
tgcgcctttt ccaaggcagc cctgggtttg cgcagggacg cggctgctct gggcgtggtt   9000
ccgggaaacg cagcggcgcc gaccctgggt ctcgcacatt cttcacgtcc gttcgcagcg   9060
tcacccggat cttcgccgct acccttgtgg gccccccggc gacgcttcct gctccgcccc   9120
taagtcggga aggttccttg cggttcgcgg cgtgccggac gtgacaaacg gaagccgcac   9180
gtctcactag taccctcgca gacggacagc gccagggagc aatggcagcg cgccgaccgc   9240
gatgggctgt ggccaatagc ggctgctcag cagggcgcgc cgagagcagc ggccgggaag   9300
gggcggtgcg ggaggcgggg tgtggggcgg tagtgtgggc cctgttcctg cccgcgcggt   9360
gttccgcatt ctgcaagcct ccggagcgca cgtcggcagt cggctccctc gttgaccgaa   9420
tcaccgacct ctctccccag ggggatccac cggtcgccac catggtgagc aagggcgagg   9480
agctgttcac cggggtggtg cccatcctgg tcgagctgga cggcgacgta aacggccaca   9540
agttcagcgt gtccggcgag ggcgagggcg atgccaccta cggcaagctg accctgaagt   9600
tcatctgcac caccggcaag ctgcccgtgc cctggcccac cctcgtgacc accctgacct   9660
acggcgtgca gtgcttcagc cgctaccccg accacatgaa gcagcacgac ttcttcaagt   9720
ccgccatgcc cgaaggctac gtccaggagc gcaccatctt cttcaaggac gacggcaact   9780
acaagacccg cgccgaggtg aagttcgagg gcgacaccct ggtgaaccgc atcgagctga   9840
agggcatcga cttcaaggag gacggcaaca tcctggggca caagctggag tacaactaca   9900
acagccacaa cgtctatatc atggccgaca agcagaagaa cggcatcaag gtgaacttca   9960
agatccgcca caacatcgag gacggcagcg tgcagctcgc cgaccactac cagcagaaca  10020
cccccatcgg cgacggcccc gtgctgctgc ccgacaacca ctacctgagc acccagtccg  10080
ccctgagcaa agaccccaac gagaagcgcg atcacatggt cctgctggag ttcgtgaccg  10140
ccgccgggat cactctcggc atggacgagc tgtacaagta agatatcaag cttatcgata  10200
atcaacctct ggattacaaa atttgtgaaa gattgactgg tattcttaac tatgttgctc  10260
cttttacgct atgtggatac gctgctttaa tgcctttgta tcatgctatt gcttcccgta  10320
tggctttcat tttctcctcc ttgtataaat cctggttgct gtctctttat gaggagttgt  10380
ggcccgttgt caggcaacgt ggcgtggtgt gcactgtgtt tgctgacgca acccccactg  10440
gttggggcat tgccaccacc tgtcagctcc tttccgggac tttcgctttc cccctcccta  10500
ttgccacggc ggaactcatc gccgcctgcc ttgcccgctg ctggacaggg gctcggctgt  10560
```

```
tgggcactga caattccgtg gtgttgtcgg ggaaatcatc gtcctttcct tggctgctcg  10620
cctgtgttgc cacctggatt ctgcgcggga cgtccttctg ctacgtccct tcggccctca  10680
atccagcgga ccttccttcc cgcggcctgc tgccggctct gcggcctctt ccgcgtcttc  10740
gccttcgccc tcagacgagt cggatctccc tttgggccgc ctccccgcat cgataccgtc  10800
gacctcgaga acctagaaaa acatggagca atcacaagta gcaatacagc agctaccaat  10860
gctgattgtg cctggctaga agcacaagag gaggaggagg tgggttttcc agtcacacct  10920
caggtacctt taagaccaat gacttacaag gcagctgtag atcttagcca ctttttaaaa  10980
gaaaaggggg gactggaagg gctaattcac tcccaacgaa gacaagatct tttgcttgt   11040
actgggtctc tctggttaga ccagatctga gcctgggagc tctctggcta actagggaac  11100
ccactgctta agcctcaata aagcttgcct tgagtgcttc aagtagtgtg tgcccgtctg  11160
ttgtgtgact ctggtaacta gagatccctc agaccctttt agtcagtgtg gaaaatctct  11220
aga                                                                11223
```

<210> SEQ ID NO 34
<211> LENGTH: 11357
<212> TYPE: DNA
<213> ORGANISM: Artificial Sequence
<220> FEATURE:
<223> OTHER INFORMATION: sequence for screeining human cells

<400> SEQUENCE: 34

```
ttaattccgt gtattctata gtgtcaccta aatcgtatgt gtatgataca taaggttatg     60
tattaattgt agccgcgttc taacgacaat atgtacaagc ctaattgtgt agcatctggc    120
ttactgaagc agaccctatc atctctctcg taaactgccg tcagagtcgg tttggttgga    180
cgaaccttct gagtttctgg taacgccgtc ccgcacccgg aaatggtcag cgaaccaatc    240
agcagggtca tcgctagcca gatcctctac gccggacgca tcgtggccgg catcaccggc    300
gccacaggtg cggttgctgg cgcctatatc gccgacatca ccgatgggga agatcgggct    360
cgccacttcg ggctcatgag cgcttgtttc ggcgtgggta tggtggcagg ccccgtggcc    420
gggggactgt tgggcgccat ctccttgcat gcaccattcc ttgcggcggc ggtgctcaac    480
ggcctcaacc tactactggg ctgcttccta atgcaggagt cgcataaggg agagcgtcga    540
atggtgcact ctcagtacaa tctgctctga tgccgcatag ttaagccagc cccgacaccc    600
gccaacaccc gctgacgcgc cctgacgggc ttgtctgctc ccggcatccg cttacagaca    660
agctgtgacc gtctccggga gctgcatgtg tcagaggttt tcaccgtcat caccgaaacg    720
cgcgagacga aagggcctcg tgatacgcct atttttatag gttaatgtca tgataataat    780
ggtttcttag acgtcaggtg gcacttttcg gggaaatgtg cgcggaaccc ctatttgttt    840
atttttctaa atacattcaa atatgtatcc gctcatgaga caataaccct gataaatgct    900
tcaataatat tgaaaaagga agagtatgag tattcaacat ttccgtgtcg cccttattcc    960
ctttttttgcg gcattttgcc ttcctgtttt tgctcaccca gaaacgctgg tgaaagtaaa   1020
agatgctgaa gatcagttgg gtgcacgagt gggttacatc gaactggatc tcaacagcgg   1080
taagatcctt gagagttttc gccccgaaga acgttttcca atgatgagca cttttaaagt   1140
tctgctatgt ggcgcggtat tatcccgtat tgacgccggg caagagcaac tcggtcgccg   1200
catacactat tctcagaatg acttggttga gtactcacca gtcacagaaa agcatcttac   1260
ggatggcatg acagtaagag aattatgcag tgctgccata accatgagtg ataacactgc   1320
ggccaactta cttctgacaa cgatcggagg accgaaggag ctaaccgctt ttttgcacaa   1380
```

```
catgggggat catgtaactc gccttgatcg ttgggaaccg gagctgaatg aagccatacc   1440
aaacgacgag cgtgacacca cgatgcctgt agcaatggca acaacgttgc gcaaactatt   1500
aactggcgaa ctacttactc tagcttcccg gcaacaatta atagactgga tggaggcgga   1560
taaagttgca ggaccacttc tgcgctcggc ccttccggct ggctggttta ttgctgataa   1620
atctggagcc ggtgagcgtg ggtctcgcgg tatcattgca gcactggggc cagatggtaa   1680
gccctcccgt atcgtagtta tctacacgac ggggagtcag gcaactatgg atgaacgaaa   1740
tagacagatc gctgagatag gtgcctcact gattaagcat tggtaactgt cagaccaagt   1800
ttactcatat atactttaga ttgatttaaa acttcatttt taatttaaaa ggatctaggt   1860
gaagatcctt tttgataatc tcatgaccaa aatcccttaa cgtgagtttt cgttccactg   1920
agcgtcagac cccgtagaaa agatcaaagg atcttcttga gatccttttt ttctgcgcgt   1980
aatctgctgc ttgcaaacaa aaaaaccacc gctaccagcg gtggtttgtt tgccggatca   2040
agagctacca actctttttc cgaaggtaac tggcttcagc agagcgcaga taccaaatac   2100
tgtccttcta gtgtagccgt agttaggcca ccacttcaag aactctgtag caccgcctac   2160
atacctcgct ctgctaatcc tgttaccagt ggctgctgcc agtggcgata agtcgtgtct   2220
taccgggttg gactcaagac gatagttacc ggataaggcg cagcggtcgg gctgaacggg   2280
gggttcgtgc acacagccca gcttggagcg aacgacctac accgaactga gatacctaca   2340
gcgtgagcat tgagaaagcg ccacgcttcc cgaagggaga aaggcggaca ggtatccggt   2400
aagcggcagg gtcggaacag gagagcgcac gagggagctt ccagggggaa acgcctggta   2460
tctttatagt cctgtcgggt ttcgccacct ctgacttgag cgtcgatttt tgtgatgctc   2520
gtcagggggg cggagcctat ggaaaaacgc cagcaacgcg gcctttttac ggttcctggc   2580
cttttgctgg ccttttgctc acatgttctt tcctgcgtta tcccctgatt ctgtggataa   2640
ccgtattacc gcctttgagt gagctgatac cgctcgccgc agccgaacga ccgagcgcag   2700
cgagtcagtg agcgaggaag cggaagagcg cccaatacgc aaaccgcctc tccccgcgcg   2760
ttggccgatt cattaatgca gctgtggaat gtgtgtcagt tagggtgtgg aaagtcccca   2820
ggctccccag caggcagaag tatgcaaagc atgcatctca attagtcagc aaccaggtgt   2880
ggaaagtccc caggctcccc agcaggcaga agtatgcaaa gcatgcatct caattagtca   2940
gcaaccatag tcccgcccct aactccgccc atcccgcccc taactccgcc cagttccgcc   3000
cattctccgc cccatggctg actaattttt tttatttatg cagaggccga ggccgcctcg   3060
gcctctgagc tattccagaa gtagtgagga ggcttttttg gaggcctagg cttttgcaaa   3120
aagcttggac acaagacagg cttgcgagat atgtttgaga ataccacttt atcccgcgtc   3180
agggagaggc agtgcgtaaa aagacgcgga ctcatgtgaa atactggttt ttagtgcgcc   3240
agatctctat aatctcgcgc aacctatttt cccctcgaac actttttaag ccgtagataa   3300
acaggctggg acacttcaca tgagcgaaaa atacatcgtc acctgggaca tgttgcagat   3360
ccatgcacgt aaactcgcaa gccgactgat gccttctgaa caatggaaag gcattattgc   3420
cgtaagccgt ggcggtctgt accgggtgcg ttactggcgc gtgaactggg tattcgtcat   3480
gtcgataccg tttgtatttc cagctacgat cacgacaacc agcgcgagct taaagtgctg   3540
aaacgcgcag aaggcgatgg cgaaggcttc atcgttattg atgacctggt ggataccggt   3600
ggtactgcgg ttgcgattcg tgaaatgtat ccaaaagcgc actttgtcac catcttcgca   3660
aaaccggctg gtcgtccgct ggttgatgac tatgttgttg atatcccgca agatacctgg   3720
```

-continued attgaacagc cgtgggatat gggcgtcgta ttcgtcccgc caatctccgg tcgctaatct 3780
tttcaacgcc tggcactgcc gggcgttgtt ctttttaact tcaggcgggt tacaatagtt 3840
tccagtaagt attctggagg ctgcatccat gacacaggca aacctgagcg aaaccctgtt 3900
caaaccccgc tttaaacatc ctgaaacctc gacgctagtc cgccgcttta atcacggcgc 3960
acaaccgcct gtgcagtcgg cccttgatgg taaaaccatc cctcactggt atcgcatgat 4020
taaccgtctg atgtggatct ggcgcggcat tgacccacgc gaaatcctcg acgtccaggc 4080
acgtattgtg atgagcgatg ccgaacgtac cgacgatgat ttatacgata cggtgattgg 4140
ctaccgtggc ggcaactgga tttatgagtg ggccccggat ctttgtgaag gaaccttact 4200
tctgtggtgt gacataattg gacaaactac ctacagagat ttaaagctct aaggtaaata 4260
taaaattttt aagtgtataa tgtgttaaac tactgattct aattgtttgt gtattttaga 4320
ttccaaccta tggaactgat gaatgggagc agtggtggaa tgcctttaat gaggaaaacc 4380
tgttttgctc agaagaaatg ccatctagtg atgatgaggc tactgctgac tctcaacatt 4440
ctactcctcc aaaaaagaag agaaaggtag aagaccccaa ggactttcct tcagaattgc 4500
taagtttttt gagtcatgct gtgtttagta atagaactct tgcttgcttt gctatttaca 4560
ccacaaagga aaaagctgca ctgctataca agaaaattat ggaaaaatat tctgtaacct 4620
ttataagtag gcataacagt tataatcata acatactgtt ttttcttact ccacacaggc 4680
atagagtgtc tgctattaat aactatgctc aaaaattgtg tacctttagc tttttaattt 4740
gtaaaggggt taataaggaa tatttgatgt atagtgcctt gactagagat cataatcagc 4800
cataccacat ttgtagaggt ttacttgct ttaaaaaacc tcccacacct cccccctgaac 4860
ctgaaacata aaatgaatgc aattgttgtt gttaacttgt ttattgcagc ttataatggt 4920
tacaaataaa gcaatagcat cacaaatttc acaaataaag catttttttc actgcattct 4980
agttgtggtt tgtccaaact catcaatgta tcttatcatg tctggatcaa ctggataact 5040
caagctaacc aaaatcatcc caaacttccc accccatacc ctattaccac tgccaattac 5100
ctagtggttt catttactct aaacctgtga ttcctctgaa ttattttcat tttaaagaaa 5160
ttgtatttgt taaatatgta ctacaaactt agtagttgga agggctaatt cactcccaaa 5220
gaagacaaga tatccttgat ctgtggatct accacacaca aggctacttc cctgattagc 5280
agaactacac accagggcca ggggtcagat atccactgac ctttggatgg tgctacaagc 5340
tagtaccagt tgagccagat aaggtagaag aggccaataa aggagagaac accagcttgt 5400
tacaccctgt gagcctgcat gggatggatg acccggagag agaagtgtta gagtggaggt 5460
ttgacagccg cctagcattt catcacgtgg cccgagagct gcatccggag tacttcaaga 5520
actgctgata tcgagcttgc tacaagggac tttccgctgg ggactttcca gggaggcgtg 5580
gcctgggcgg gactggggag tggcgagccc tcagatcctg catataagca gctgcttttt 5640
gcctgtactg ggtctctctg gttagaccag atctgagcct gggagctctc tggctaacta 5700
gggaacccac tgcttaagcc tcaataaagc ttgccttgag tgcttcaagt agtgtgtgcc 5760
cgtctgttgt gtgactctgg taactagaga tccctcagac ccttttagtc agtgtggaaa 5820
atctctagca gtggcgcccg aacagggact tgaaagcgaa agggaaacca gaggagctct 5880
ctcgacgcag gactcggctt gctgaagcgc gcacggcaag aggcgagggg cggcgactgg 5940
tgagtacgcc aaaaattttg actagcggag gctagaagga gagagatggg tgcgagagcg 6000
tcagtattaa gcgggggaga attagatcgc gatgggaaaa aattcggtta aggccagggg 6060
gaaagaaaaa atataaatta aaacatatag tatgggcaag cagggagcta gaacgattcg 6120

-continued

```
cagttaatcc tggcctgtta gaaacatcag aaggctgtag acaaatactg ggacagctac   6180
aaccatccct tcagacagga tcagaagaac ttagatcatt atataataca gtagcaaccc   6240
tctattgtgt gcatcaaagg atagagataa aagacaccaa ggaagcttta gacaagatag   6300
aggaagagca aaacaaaagt aagaccaccg cacagcaagc ggccgctgat cttcagacct   6360
ggaggaggag atatgaggga caattggaga agtgaattat ataaatataa agtagtaaaa   6420
attgaaccat taggagtagc acccaccaag gcaaagagaa gagtggtgca gagagaaaaa   6480
agagcagtgg gaataggagc tttgttcctt gggttcttgg gagcagcagg aagcactatg   6540
ggcgcagcgt caatgacgct gacggtacag gccagacaat tattgtctgg tatagtgcag   6600
cagcagaaca atttgctgag ggctattgag gcgcaacagc atctgttgca actcacagtc   6660
tggggcatca agcagctcca ggcaagaatc ctggctgtgg aaagatacct aaaggatcaa   6720
cagctcctgg ggatttgggg ttgctctgga aaactcattt gcaccactgc tgtgccttgg   6780
aatgctagtt ggagtaataa atctctggaa cagatttgga atcacacgac ctggatggag   6840
tgggacagag aaattaacaa ttacacaagc ttaatacact ccttaattga agaatcgcaa   6900
aaccagcaag aaaagaatga acaagaatta ttggaattag ataaatgggc aagtttgtgg   6960
aattggttta acataacaaa ttggctgtgg tatataaaat tattcataat gatagtagga   7020
ggcttggtag gtttaagaat agtttttgct gtactttcta tagtgaatag agttaggcag   7080
ggatattcac cattatcgtt tcagacccac ctcccaaccc cgaggggacc cgacaggccc   7140
gaaggaatag aagaagaagg tggagagaga gacagagaca gatccattcg attagtgaac   7200
ggatctcgac ggtatcgccg aattcacaaa tggcagtatt catccacaat tttaaaagaa   7260
aaggggggat tggggggtac agtgcagggg aaagaatagt agacataata gcaacagaca   7320
tacaaactaa agaattacaa aaacaaatta caaaaattca aaattttcgg gtttattaca   7380
gggacagcag agatccactt tatcgatggt ccggtccgga attcctgcag ccccgataaa   7440
ataaaagatt ttatttagtc tccagaaaaa ggggggaatg aaagacccca cctgtaggtt   7500
tggcaagcta gctgcagtaa cgccattttg caaggcatgg aaaaatacca aaccaagaat   7560
agagaagttc agatcaaggg cgggtacatg aaaatagcta acgttgggcc aaacaggata   7620
tctgcggtga gcagtttcgg ccccggcccg gggccaagaa cagatggtca ccgcagtttc   7680
ggccccggcc cgaggccaag aacagatggt ccccagatat ggcccaaccc tcagcagttt   7740
cttaagaccc atcagatgtt tccaggctcc cccaaggacc tgaaatgacc ctgcgcctta   7800
tttgaattaa ccaatcagcc tgcttctcgc ttctgttcgc gcgcttctgc ttcccgagct   7860
ctataaaaga gctcacaacc cctcactcgg cgcgccagtc ctccgacaga ctgagtcgcc   7920
cgggggggat ccaccgggct gcaggaattc ataacttcgt ataatgtatg ctatacgaag   7980
ttatagttaa gccttattgt ttatcatcct cattcaacga cgcgaaggtg taccttggcg   8040
agaataactt cgtataggat actttatacg aagttattta tctgtgcccc agtttgctag   8100
ggaggtcgca gtacttggcc acagccatct cgtgctgctc gacgtaggtc tctttgtcgg   8160
cctccttgat tctttccagt ctgtggtcca cgaagtggaa gccgggcatc ttgaggttct   8220
tagcgggttt cttggatctg tatgtggtct tgaaggagca gtgcaggtag cccccgccca   8280
cgagcttcag ggccatctgg ctgtggcctc tcaggccgcc gtcagcgggg tacagcatct   8340
cggtgttggc ctcccagccg cgtgttttct tctgcatcac agggccgttg gatgggaagt   8400
tcaccccgtt gatcttgacg ttgtagatga tgcagccgtt ctggaagctg gtgtcctggg   8460
```

```
tagcggtcag cacgcccccg tcttcgtatg tggtgattct ctcccatgtg aagccctcag   8520
ggaaggactg cttaaagaag tcggggatgc cctgggtgtg gttgatgaag gctttgctgc   8580
cgtacatgaa gctggtagcc aggatgtcga aggcgaaggg gagagggccg ccctcgacca   8640
ccttgatctt catggtctgg gtgccctcgt agggcttgcc ttcgccctcg gatgtgcact   8700
tgaagtggtg gttgttcacg gtgccctcca tgtacagctt catgtgcatg ttctccttga   8760
tcagctcgct catggtggca tatgataact tcgtatagca tacattatac gaagttatat   8820
taagggttat tgaatatgat cggaagtcaa cgggtcgatg gtgatgcttg gctcgaataa   8880
cttcgtataa agtatcctat acgaagttat actttggccg cggctcgaat ctacttaccg   8940
ataagcttgg gagttccgcg ttacataact tacggtaaat ggcccgcctg gctgaccgcc   9000
caacgacccc cgcccattga cgtcaataat gacgtatgtt cccatagtaa cgccaatagg   9060
gactttccat tgacgtcaat gggtggagta tttacggtaa actgcccact tggcagtaca   9120
tcaagtgtat catatgccaa gtacgccccc tattgacgtc aatgacggta aatggcccgc   9180
ctggcattat gcccagtaca tgaccttacg ggactttcct acttggcagt acatctacgt   9240
attagtcatc gctattacca tggtgatgcg gttttggcag tacaccaatg ggcgtggata   9300
gcggtttgac tcacggggat ttccaagtct ccaccccatt gacgtcaatg ggagtttgtt   9360
ttggcaccaa aatcaacggg actttccaaa atgtcgtaac aactccgccc cattgacgca   9420
aatgggcggt aggcgtgtac ggtgggaggt ctatataagc agagctcgtt tagtgaaccg   9480
tcagatcgcc tggagacgcc atccacgctg ttttgacctc catagaagac accgactcta   9540
gctagaggat ccggactagt aactcgagga tggggactga cccggacgcg tgccgccacc   9600
atggtgagca agggcgagga gctgttcacc ggggtggtgc ccatcctggt cgagctggac   9660
ggcgacgtaa acggccacaa gttcagcgtg tccggcgagg gcgagggcga tgccacctac   9720
ggcaagctga ccctgaagtt catctgcacc accggcaagc tgcccgtgcc ctggcccacc   9780
ctcgtgacca ccctgaccta cggcgtgcag tgcttcagcc gctaccccga ccacatgaag   9840
cagcacgact tcttcaagtc cgccatgccc gaaggctacg tccaggagcg caccatcttc   9900
ttcaaggacg acggcaacta caagacccgc gccgaggtga agttcgaggg cgacaccctg   9960
gtgaaccgca tcgagctgaa gggcatcgac ttcaaggagg acggcaacat cctggggcac  10020
aagctggagt acaactacaa cagccacaac gtctatatca tggccgacaa gcagaagaac  10080
ggcatcaagg tgaacttcaa gatccgccac aacatcgagg acggcagcgt gcagctcgcc  10140
gaccactacc agcagaacac ccccatcggc gacggccccg tgctgctgcc cgacaaccac  10200
tacctgagca cccagtccgc cctgagcaaa gaccccaacg agaagcgcga tcacatggtc  10260
ctgctggagt tcgtgaccgc cgccgggatc actctcggca tggacgagct gtacaagtaa  10320
gatatcaagc ttatcgataa tcaacctctg gattacaaaa tttgtgaaag attgactggt  10380
attcttaact atgttgctcc ttttacgcta tgtggatacg ctgctttaat gcctttgtat  10440
catgctattg cttcccgtat ggctttcatt ttctcctcct tgtataaatc ctggttgctg  10500
tctctttatg aggagttgtg gcccgttgtc aggcaacgtg gcgtggtgtg cactgtgttt  10560
gctgacgcaa cccccactgg ttggggcatt gccaccacct gtcagctcct ttccgggact  10620
ttcgctttcc ccctccctat tgccacggcg gaactcatcg ccgcctgcct tgcccgctgc  10680
tggacagggg ctcggctgtt gggcactgac aattccgtgg tgttgtcggg gaaatcatcg  10740
tcctttcctt ggctgctcgc ctgtgttgcc acctggattc tgcgcgggac gtccttctgc  10800
tacgtccctt cggccctcaa tccagcggac cttccttccc gcggcctgct gccggctctg  10860
```

```
cggcctcttc cgcgtcttcg ccttcgccct cagacgagtc ggatctccct ttgggccgcc  10920

tccccgcatc gataccgtcg acctcgagaa cctagaaaaa catggagcaa tcacaagtag  10980

caatacagca gctaccaatg ctgattgtgc ctggctagaa gcacaagagg aggaggaggt  11040

gggttttcca gtcacacctc aggtaccttt aagaccaatg acttacaagg cagctgtaga  11100

tcttagccac tttttaaaag aaaagggggg actggaaggg ctaattcact cccaacgaag  11160

acaagatctt tttgcttgta ctgggtctct ctggttagac cagatctgag cctgggagct  11220

ctctggctaa ctagggaacc cactgcttaa gcctcaataa agcttgcctt gagtgcttca  11280

agtagtgtgt gcccgtctgt tgtgtgactc tggtaactag agatccctca gacccttttta  11340

gtcagtgtgg aaaatct                                                  11357
```

<210> SEQ ID NO 35
<211> LENGTH: 12293
<212> TYPE: DNA
<213> ORGANISM: Artificial Sequence
<220> FEATURE:
<223> OTHER INFORMATION: sequence for screening human cells

<400> SEQUENCE: 35

```
ttaattccgt gtattctata gtgtcaccta aatcgtatgt gtatgataca taaggttatg     60

tattaattgt agccgcgttc taacgacaat atgtacaagc ctaattgtgt agcatctggc    120

ttactgaagc agaccctatc atctctctcg taaactgccg tcagagtcgg tttggttgga    180

cgaaccttct gagtttctgg taacgccgtc ccgcacccgg aaatggtcag cgaaccaatc    240

agcagggtca tcgctagcca gatcctctac gccggacgca tcgtggccgg catcaccggc    300

gccacaggtg cggttgctgg cgcctatatc gccgacatca ccgatgggga agatcgggct    360

cgccacttcg ggctcatgag cgcttgtttc ggcgtgggta tggtggcagg ccccgtggcc    420

gggggactgt tgggcgccat ctccttgcat gcaccattcc ttgcggcggc ggtgctcaac    480

ggcctcaacc tactactggg ctgcttccta atgcaggagt cgcataaggg agagcgtcga    540

atggtgcact ctcagtacaa tctgctctga tgccgcatag ttaagccagc cccgacaccc    600

gccaacaccc gctgacgcgc cctgacgggc ttgtctgctc ccggcatccg cttacagaca    660

agctgtgacc gtctccggga gctgcatgtg tcagaggttt tcaccgtcat caccgaaacg    720

cgcgagacga aagggcctcg tgatacgcct atttttatag gttaatgtca tgataataat    780

ggtttcttag acgtcaggtg gcacttttcg gggaaatgtg cgcggaaccc ctatttgttt    840

atttttctaa atacattcaa atatgtatcc gctcatgaga caataaccct gataaatgct    900

tcaataatat tgaaaaagga agagtatgag tattcaacat ttccgtgtcg cccttattcc    960

cttttttgcg gcattttgcc ttcctgtttt tgctcaccca gaaacgctgg tgaaagtaaa   1020

agatgctgaa gatcagttgg gtgcacgagt gggttacatc gaactggatc tcaacagcgg   1080

taagatcctt gagagttttc gccccgaaga acgttttcca atgatgagca cttttaaagt   1140

tctgctatgt ggcgcggtat tatcccgtat tgacgccggg caagagcaac tcggtcgccg   1200

catacactat tctcagaatg acttggttga gtactcacca gtcacagaaa agcatcttac   1260

ggatggcatg acagtaagag aattatgcag tgctgccata accatgagtg ataacactgc   1320

ggccaactta cttctgacaa cgatcggagg accgaaggag ctaaccgctt ttttgcacaa   1380

catgggggat catgtaactc gccttgatcg ttgggaaccg gagctgaatg aagccatacc   1440

aaacgacgag cgtgacacca cgatgcctgt agcaatggca acaacgttgc gcaaactatt   1500
```

-continued

```
aactggcgaa ctacttactc tagcttcccg gcaacaatta atagactgga tggaggcgga   1560
taaagttgca ggaccacttc tgcgctcggc ccttccggct ggctggttta ttgctgataa   1620
atctggagcc ggtgagcgtg ggtctcgcgg tatcattgca gcactggggc cagatggtaa   1680
gccctcccgt atcgtagtta tctacacgac ggggagtcag gcaactatgg atgaacgaaa   1740
tagacagatc gctgagatag gtgcctcact gattaagcat tggtaactgt cagaccaagt   1800
ttactcatat atactttaga ttgatttaaa acttcatttt taatttaaaa ggatctaggt   1860
gaagatcctt tttgataatc tcatgaccaa aatcccttaa cgtgagtttt cgttccactg   1920
agcgtcagac cccgtagaaa agatcaaagg atcttcttga gatccttttt ttctgcgcgt   1980
aatctgctgc ttgcaaacaa aaaaaccacc gctaccagcg gtggtttgtt tgccggatca   2040
agagctacca actctttttc cgaaggtaac tggcttcagc agagcgcaga taccaaatac   2100
tgtccttcta gtgtagccgt agttaggcca ccacttcaag aactctgtag caccgcctac   2160
atacctcgct ctgctaatcc tgttaccagt ggctgctgcc agtggcgata agtcgtgtct   2220
taccgggttg gactcaagac gatagttacc ggataaggcg cagcggtcgg gctgaacggg   2280
gggttcgtgc acacagccca gcttggagcg aacgacctac accgaactga gatacctaca   2340
gcgtgagcat tgagaaagcg ccacgcttcc cgaagggaga aaggcggaca ggtatccggt   2400
aagcggcagg gtcggaacag gagagcgcac gagggagctt ccagggggaa acgcctggta   2460
tctttatagt cctgtcgggt ttcgccacct ctgacttgag cgtcgatttt tgtgatgctc   2520
gtcagggggg cggagcctat ggaaaaacgc cagcaacgcg gcctttttac ggttcctggc   2580
cttttgctgg ccttttgctc acatgttctt tcctgcgtta tcccctgatt ctgtggataa   2640
ccgtattacc gcctttgagt gagctgatac cgctcgccgc agccgaacga ccgagcgcag   2700
cgagtcagtg agcgaggaag cggaagagcg cccaatacgc aaaccgcctc tccccgcgcg   2760
ttggccgatt cattaatgca gctgtggaat gtgtgtcagt tagggtgtgg aaagtcccca   2820
ggctccccag caggcagaag tatgcaaagc atgcatctca attagtcagc aaccaggtgt   2880
ggaaagtccc caggctcccc agcaggcaga agtatgcaaa gcatgcatct caattagtca   2940
gcaaccatag tcccgcccct aactccgccc atcccgcccc taactccgcc cagttccgcc   3000
cattctccgc cccatggctg actaattttt tttatttatg cagaggccga ggccgcctcg   3060
gcctctgagc tattccagaa gtagtgagga ggcttttttg gaggcctagg cttttgcaaa   3120
aagcttggac acaagacagg cttgcgagat atgtttgaga ataccacttt atcccgcgtc   3180
agggagaggc agtgcgtaaa aagacgcgga ctcatgtgaa atactggttt ttagtgcgcc   3240
agatctctat aatctcgcgc aacctatttt cccctcgaac actttttaag ccgtagataa   3300
acaggctggg acacttcaca tgagcgaaaa atacatcgtc acctgggaca tgttgcagat   3360
ccatgcacgt aaactcgcaa gccgactgat gccttctgaa caatggaaag gcattattgc   3420
cgtaagccgt ggcggtctgt accgggtgcg ttactggcgc gtgaactggg tattcgtcat   3480
gtcgataccg tttgtatttc cagctacgat cacgacaacc agcgcgagct taaagtgctg   3540
aaacgcgcag aaggcgatgg cgaaggcttc atcgttattg atgacctggt ggataccggt   3600
ggtactgcgg ttgcgattcg tgaaatgtat ccaaaagcgc actttgtcac catcttcgca   3660
aaaccggctg gtcgtccgct ggttgatgac tatgttgttg atatcccgca agatacctgg   3720
attgaacagc cgtgggatat gggcgtcgta ttcgtcccgc caatctccgg tcgctaatct   3780
tttcaacgcc tggcactgcc gggcgttgtt ctttttaact tcaggcgggt tacaatagtt   3840
tccagtaagt attctggagg ctgcatccat gacacaggca aacctgagcg aaaccctgtt   3900
```

```
caaaccccgc tttaaacatc ctgaaacctc gacgctagtc cgccgcttta atcacggcgc   3960
acaaccgcct gtgcagtcgg cccttgatgg taaaaccatc cctcactggt atcgcatgat   4020
taaccgtctg atgtggatct ggcgcggcat tgacccacgc gaaatcctcg acgtccaggc   4080
acgtattgtg atgagcgatg ccgaacgtac cgacgatgat ttatacgata cggtgattgg   4140
ctaccgtggc ggcaactgga tttatgagtg ggccccggat ctttgtgaag gaaccttact   4200
tctgtggtgt gacataattg gacaaactac ctacagagat ttaaagctct aaggtaaata   4260
taaaattttt aagtgtataa tgtgttaaac tactgattct aattgtttgt gtattttaga   4320
ttccaaccta tggaactgat gaatgggagc agtggtggaa tgcctttaat gaggaaaacc   4380
tgttttgctc agaagaaatg ccatctagtg atgatgaggc tactgctgac tctcaacatt   4440
ctactcctcc aaaaaagaag agaaaggtag aagaccccaa ggactttcct tcagaattgc   4500
taagtttttt gagtcatgct gtgtttagta atagaactct tgcttgcttt gctatttaca   4560
ccacaaagga aaaagctgca ctgctataca agaaaattat ggaaaaatat tctgtaacct   4620
ttataagtag gcataacagt tataatcata acatactgtt ttttcttact ccacacaggc   4680
atagagtgtc tgctattaat aactatgctc aaaaattgtg tacctttagc tttttaattt   4740
gtaaaggggt taataaggaa tatttgatgt atagtgcctt gactagagat cataatcagc   4800
cataccacat ttgtagaggt tttacttgct ttaaaaaacc tcccacacct cccccctgaac   4860
ctgaaacata aaatgaatgc aattgttgtt gttaacttgt ttattgcagc ttataatggt   4920
tacaaataaa gcaatagcat cacaaatttc acaaataaag catttttttc actgcattct   4980
agttgtggtt tgtccaaact catcaatgta tcttatcatg tctggatcaa ctggataact   5040
caagctaacc aaaatcatcc caaacttccc accccatacc ctattaccac tgccaattac   5100
ctagtggttt catttactct aaacctgtga ttcctctgaa ttattttcat tttaaagaaa   5160
ttgtatttgt taaatatgta ctacaaactt agtagttgga agggctaatt cactcccaaa   5220
gaagacaaga tatccttgat ctgtggatct accacacaca aggctacttc cctgattagc   5280
agaactacac accagggcca ggggtcagat atccactgac ctttggatgg tgctacaagc   5340
tagtaccagt tgagccagat aaggtagaag aggccaataa aggagagaac accagcttgt   5400
tacaccctgt gagcctgcat gggatggatg acccggagag agaagtgtta gagtggaggt   5460
ttgacagccg cctagcattt catcacgtgg cccgagagct gcatccggag tacttcaaga   5520
actgctgata tcgagcttgc tacaagggac tttccgctgg ggactttcca gggaggcgtg   5580
gcctgggcgg gactggggag tggcgagccc tcagatcctg catataagca gctgcttttt   5640
gcctgtactg ggtctctctg gttagaccag atctgagcct gggagctctc tggctaacta   5700
gggaacccac tgcttaagcc tcaataaagc ttgccttgag tgcttcaagt agtgtgtgcc   5760
cgtctgttgt gtgactctgg taactagaga tccctcagac ccttttagtc agtgtggaaa   5820
atctctagca gtggcgcccg aacagggact tgaaagcgaa agggaaacca gaggagctct   5880
ctcgacgcag gactcggctt gctgaagcgc gcacggcaag aggcgagggg cggcgactgg   5940
tgagtacgcc aaaaattttg actagcggag gctagaagga gagagatggg tgcgagagcg   6000
tcagtattaa gcgggggaga attagatcgc gatgggaaaa aattcggtta aggccagggg   6060
gaaagaaaaa atataaatta aaacatatag tatgggcaag cagggagcta gaacgattcg   6120
cagttaatcc tggcctgtta gaaacatcag aaggctgtag acaaatactg ggacagctac   6180
aaccatccct tcagacagga tcagaagaac ttagatcatt atataataca gtagcaaccc   6240
```

```
tctattgtgt gcatcaaagg atagagataa aagacaccaa ggaagcttta gacaagatag   6300
aggaagagca aaacaaaagt aagaccaccg cacagcaagc ggccgctgat cttcagacct   6360
ggaggaggag atatgaggga caattggaga agtgaattat ataaatataa agtagtaaaa   6420
attgaaccat taggagtagc acccaccaag gcaaagagaa gagtggtgca gagagaaaaa   6480
agagcagtgg gaataggagc tttgttcctt gggttcttgg gagcagcagg aagcactatg   6540
ggcgcagcgt caatgacgct gacggtacag gccagacaat tattgtctgg tatagtgcag   6600
cagcagaaca atttgctgag ggctattgag gcgcaacagc atctgttgca actcacagtc   6660
tggggcatca agcagctcca ggcaagaatc ctggctgtgg aaagatacct aaaggatcaa   6720
cagctcctgg ggatttgggg ttgctctgga aaactcattt gcaccactgc tgtgccttgg   6780
aatgctagtt ggagtaataa atctctggaa cagatttgga atcacacgac ctggatggag   6840
tgggacagag aaattaacaa ttacacaagc ttaatacact ccttaattga agaatcgcaa   6900
aaccagcaag aaaagaatga acaagaatta ttggaattag ataaatgggc aagtttgtgg   6960
aattggttta acataacaaa ttggctgtgg tatataaaat tattcataat gatagtagga   7020
ggcttggtag gtttaagaat agtttttgct gtactttcta tagtgaatag agttaggcag   7080
ggatattcac cattatcgtt tcagacccac ctcccaaccc cgaggggacc cgacaggccc   7140
gaaggaatag aagaagaagg tggagagaga gacagagaca gatccattcg attagtgaac   7200
ggatctcgac ggtatcgccg aattcacaaa tggcagtatt catccacaat tttaaaagaa   7260
aaggggggat tggggggtac agtgcagggg aaagaatagt agacataata gcaacagaca   7320
tacaaactaa agaattacaa aaacaaatta caaaaattca aaattttcgg gtttattaca   7380
gggacagcag agatccactt tatcgataag cttgggagtt ccgcgttaca taacttacgg   7440
taaatggccc gcctggctga ccgcccaacg acccccgccc attgacgtca ataatgacgt   7500
atgttcccat agtaacgcca atagggactt tccattgacg tcaatgggtg gagtatttac   7560
ggtaaactgc ccacttggca gtacatcaag tgtatcatat gccaagtacg ccccctattg   7620
acgtcaatga cggtaaatgg cccgcctggc attatgccca gtacatgacc ttacgggact   7680
ttcctacttg gcagtacatc tacgtattag tcatcgctat taccatggtg atgcggtttt   7740
ggcagtacac caatgggcgt ggatagcggt ttgactcacg gggatttcca agtctccacc   7800
ccattgacgt caatgggagt ttgttttggc accaaaatca acgggacttt ccaaaatgtc   7860
gtaacaactc cgccccattg acgcaaatgg gcggtaggcg tgtacggtgg gaggtctata   7920
taagcagagc tcgtttagtg aaccgtcaga tcgcctggag acgccatcca cgctgttttg   7980
acctccatag aagacaccga ctctagctag aggatccgga ctagtaactc gaggatgggg   8040
actgacccgg gctgcaggaa ttcataactt cgtataatgt atgctatacg aagttatagt   8100
taagccttat tgtttatcat cctcattcaa cgacgcgaag gtgtaccttg gcgagaataa   8160
cttcgtatag gatactttat acgaagttat ttacacggcg atctttccgc ccttcttggc   8220
ctttatgagg atctctctga tttttcttgc gtcgagtttt ccggtaagac ctttcggtac   8280
ttcgtccaca aacacaactc ctccgcgcaa ctttttcgcg gttgttactt gactggcgac   8340
gtaatccacg atctcttttt ccgtcatcgt ctttccgtgc tccaaaacaa caacggcggc   8400
gggaagttca ccggcgtcat cgtcgggaag acctgcgaca cctgcgtcga agatgttggg   8460
gtgttggagc aagatggatt ccaattcagc gggagccacc tgatagcctt tgtacttaat   8520
cagagacttc aggcggtcaa cgatgaagaa gtgttcgtct tcgtcccagt aagctatgtc   8580
tccagaatgt agccatccat ccttgtcaat caaggcgttg gtcgcttccg gattgtttac   8640
```

```
ataaccggac ataatcatag gacctctcac acacagttcg cctctttgat taacgcccag   8700
cgttttcccg gtatccagat ccacaacctt cgcttcaaaa aatggaacaa ctttaccgac   8760
cgcgcccggt ttatcatccc cctcgggtgt aatcagaata gctgatgtag tctcagtgag   8820
cccatatcct tgcctgatac ctggcagatg gaacctcttg gcaaccgctt ccccgacttc   8880
cttagagagg ggagcgccac cagaagcaat ttcgtgtaaa ttagataaat cgtatttgtc   8940
aatcagagtg cttttggcga agaaggagaa tagggttggc accagcagcg cactttgaat   9000
cttgtaatcc tgaaggctcc tcagaaacag ctcttcttca aatctataca ttaagacgac   9060
tcgaaatcca catatcaaat atccgagtgt agtaaacatt ccaaaaccgt gatggaatgg   9120
aacaacactt aaaatcgcag tatccggaat gatttgattg ccaaaaatag gatctctggc   9180
atgcgagaat ctcacgcagg cagttctatg aggcagagcg acacctttag gcagaccagt   9240
agatccagag gagttcatga tcagtgcaat tgtcttgtcc ctatcgaagg actctggcac   9300
aaaatcgtat tcattaaaac cgggaggtag atgagatgtg acgaacgtgt acatcgactg   9360
aaatccctgg taatccgttt tagaatccat gataataatt ttttggatga ttgggagctt   9420
tttttgcacg ttcaaaattt tttgcaaccc ctttttggaa acgaacacca cggtaggctg   9480
cgaaatgccc atactgttga gcaattcacg ttcattataa atgtcgttcg cgggcgcaac   9540
tgcaactccg ataaataacg cgcccaacac cggcataaag aattgaagag agttttcact   9600
gcatacgacg attctgtgat ttgtattcag cccatatcgt ttcatagctt ctgccaaccg   9660
aacggacatt tcgaagtact cagcgtaagt gatgtccacc tcgatatgtg catctgtaaa   9720
agcaattgtt ccaggaacca gggcgtatct cttcatagcc ttatgcagtt gctctccagc   9780
ggttccatct tccagcggat agaatggcgc cgggcctttc tttatgtttt tggcgtcttc   9840
catggtggca tatgataact tcgtatagca tacattatac gaagttatat taagggttat   9900
tgaatatgat cggaagtcaa cgggtcgatg gtgatgcttg gctcgaataa cttcgtataa   9960
agtatcctat acgaagttat actttggccg cggctcgagg gggttggggt tgcgcctttt  10020
ccaaggcagc cctgggtttg cgcagggacg cggctgctct gggcgtggtt ccgggaaacg  10080
cagcggcgcc gaccctgggt ctcgcacatt cttcacgtcc gttcgcagcg tcacccggat  10140
cttcgccgct acccttgtgg gccccccggc gacgcttcct gctccgcccc taagtcggga  10200
aggttccttg cggttcgcgg cgtgccggac gtgacaaacg gaagccgcac gtctcactag  10260
taccctcgca gacggacagc gccagggagc aatggcagcg cgccgaccgc gatgggctgt  10320
ggccaatagc ggctgctcag cagggcgcgc cgagagcagc ggccgggaag ggcggtgcg   10380
ggaggcgggg tgtggggcgg tagtgtgggc cctgttcctg cccgcgcggt gttccgcatt  10440
ctgcaagcct ccggagcgca cgtcggcagt cggctccctc gttgaccgaa tcaccgacct  10500
ctctccccag gggatccac cggtcgccac catggtgagc aagggcgagg agctgttcac  10560
cggggtggtg cccatcctgg tcgagctgga cggcgacgta aacggccaca agttcagcgt  10620
gtccggcgag ggcgagggcg atgccaccta cggcaagctg accctgaagt tcatctgcac  10680
caccggcaag ctgcccgtgc cctggcccac cctcgtgacc accctgacct acggcgtgca  10740
gtgcttcagc cgctaccccg accacatgaa gcagcacgac ttcttcaagt ccgccatgcc  10800
cgaaggctac gtccaggagc gcaccatctt cttcaaggac gacggcaact acaagacccg  10860
cgccgaggtg aagttcgagg gcgacaccct ggtgaaccgc atcgagctga agggcatcga  10920
cttcaaggag gacggcaaca tcctggggca caagctggag tacaactaca acagccacaa  10980
```

```
cgtctatatc atggccgaca agcagaagaa cggcatcaag gtgaacttca agatccgcca  11040
caacatcgag gacggcagcg tgcagctcgc cgaccactac cagcagaaca cccccatcgg  11100
cgacggcccc gtgctgctgc ccgacaacca ctacctgagc acccagtccg ccctgagcaa  11160
agaccccaac gagaagcgcg atcacatggt cctgctggag ttcgtgaccg ccgccgggat  11220
cactctcggc atggacgagc tgtacaagta agatatcaag cttatcgata atcaacctct  11280
ggattacaaa atttgtgaaa gattgactgg tattcttaac tatgttgctc cttttacgct  11340
atgtggatac gctgctttaa tgcctttgta tcatgctatt gcttcccgta tggctttcat  11400
tttctcctcc ttgtataaat cctggttgct gtctctttat gaggagttgt ggcccgttgt  11460
caggcaacgt ggcgtggtgt gcactgtgtt tgctgacgca acccccactg gttggggcat  11520
tgccaccacc tgtcagctcc tttccgggac tttcgctttc cccctcccta ttgccacggc  11580
ggaactcatc gccgcctgcc ttgcccgctg ctggacaggg gctcggctgt tgggcactga  11640
caattccgtg gtgttgtcgg ggaaatcatc gtcctttcct tggctgctcg cctgtgttgc  11700
cacctggatt ctgcgcggga cgtccttctg ctacgtccct tcggccctca atccagcgga  11760
ccttccttcc cgcggcctgc tgccggctct gcggcctctt ccgcgtcttc gccttcgccc  11820
tcagacgagt cggatctccc tttgggccgc ctccccgcat cgataccgtc gacctcgaga  11880
acctagaaaa acatggagca atcacaagta gcaatacagc agctaccaat gctgattgtg  11940
cctggctaga agcacaagag gaggaggagg tgggttttcc agtcacacct caggtacctt  12000
taagaccaat gacttacaag gcagctgtag atcttagcca ctttttaaaa gaaaaggggg  12060
gactggaagg gctaattcac tcccaacgaa gacaagatct tttgcttgt actgggtctc  12120
tctggttaga ccagatctga gcctgggagc tctctggcta actagggaac ccactgctta  12180
agcctcaata aagcttgcct tgagtgcttc aagtagtgtg tgcccgtctg ttgtgtgact  12240
ctggtaacta gagatccctc agaccctttt agtcagtgtg gaaaatctct aga         12293
```

<210> SEQ ID NO 36
<211> LENGTH: 6135
<212> TYPE: DNA
<213> ORGANISM: Artificial Sequence
<220> FEATURE:
<223> OTHER INFORMATION: sequence for screening human cells

<400> SEQUENCE: 36

```
gggctaattc actcccaaag aagacaagat atccttgatc tgtggatcta ccacacacaa     60
ggctacttcc ctgattagca gaactacaca ccagggccag gggtcagata tccactgacc    120
tttggatggt gctacaagct agtaccagtt gagccagata aggtagaaga ggccaataaa    180
ggagagaaca ccagcttgtt acaccctgtg agcctgcatg ggatggatga cccggagaga    240
gaagtgttag agtggaggtt tgacagccgc ctagcatttc atcacgtggc ccgagagctg    300
catccggagt acttcaagaa ctgctgatat cgagcttgct acaagggact ttccgctggg    360
gactttccag ggaggcgtgg cctgggcggg actggggagt ggcgagccct cagatcctgc    420
atataagcag ctgctttttg cctgtactgg gtctctctgg ttagaccaga tctgagcctg    480
ggagctctct ggctaactag ggaacccact gcttaagcct caataaagct tgccttgagt    540
gcttcaagta gtgtgtgccc gtctgttgtg tgactctggt aactagagat ccctcagacc    600
cttttagtca gtgtggaaaa tctctagcag tggcgcccga acagggactt gaaagcgaaa    660
gggaaaccag aggagctctc tcgacgcagg actcggcttg ctgaagcgcg cacggcaaga    720
ggcgaggggc ggcgactggt gagtacgcca aaaattttga ctagcggagg ctagaaggag    780
```

```
agagatgggt gcgagagcgt cagtattaag cgggggagaa ttagatcgcg atgggaaaaa    840
attcggttaa ggccaggggg aaagaaaaaa tataaattaa aacatatagt atgggcaagc    900
agggagctag aacgattcgc agttaatcct ggcctgttag aaacatcaga aggctgtaga    960
caaatactgg gacagctaca accatccctt cagacaggat cagaagaact tagatcatta   1020
tataatacag tagcaaccct ctattgtgtg catcaaagga tagagataaa agacaccaag   1080
gaagctttag acaagataga ggaagagcaa aacaaaagta agaccaccgc acagcaagcg   1140
gccgctgatc ttcagacctg gaggaggaga tatgagggac aattggagaa gtgaattata   1200
taaatataaa gtagtaaaaa ttgaaccatt aggagtagca cccaccaagg caaagagaag   1260
agtggtgcag agagaaaaaa gagcagtggg aataggagct ttgttccttg ggttcttggg   1320
agcagcagga agcactatgg gcgcagcgtc aatgacgctg acggtacagg ccagacaatt   1380
attgtctggt atagtgcagc agcagaacaa tttgctgagg gctattgagg cgcaacagca   1440
tctgttgcaa ctcacagtct ggggcatcaa gcagctccag gcaagaatcc tggctgtgga   1500
aagataccta aaggatcaac agctcctggg gatttggggt tgctctggaa aactcatttg   1560
caccactgct gtgccttgga atgctagttg gagtaataaa tctctggaac agatttggaa   1620
tcacacgacc tggatggagt gggacagaga aattaacaat tacacaagct taatacactc   1680
cttaattgaa gaatcgcaaa accagcaaga aaagaatgaa caagaattat tggaattaga   1740
taaatgggca agtttgtgga attggtttaa cataacaaat tggctgtggt atataaaatt   1800
attcataatg atagtaggag gcttggtagg tttaagaata gtttttgctg tactttctat   1860
agtgaataga gttaggcagg gatattcacc attatcgttt cagacccacc tcccaacccc   1920
gaggggaccc gacaggcccg aaggaataga agaagaaggt ggagagagag acagagacag   1980
atccattcga ttagtgaacg gatctcgacg gtatcgccga attcacaaat ggcagtattc   2040
atccacaatt ttaaaagaaa aggggggatt ggggggtaca gtgcagggga aagaatagta   2100
gacataatag caacagacat acaaactaaa gaattacaaa aacaaattac aaaaattcaa   2160
aattttcggg tttattacag ggacagcaga gatccacttt atcgataagc ttgggagttc   2220
cgcgttacat aacttacggt aaatggcccg cctggctgac cgcccaacga cccccgccca   2280
ttgacgtcaa taatgacgta tgttcccata gtaacgccaa tagggacttt ccattgacgt   2340
caatgggtgg agtatttacg gtaaactgcc cacttggcag tacatcaagt gtatcatatg   2400
ccaagtacgc cccctattga cgtcaatgac ggtaaatggc ccgcctggca ttatgcccag   2460
tacatgacct tacgggactt tcctacttgg cagtacatct acgtattagt catcgctatt   2520
accatggtga tgcggttttg gcagtacacc aatgggcgtg gatagcggtt tgactcacgg   2580
ggatttccaa gtctccaccc cattgacgtc aatgggagtt tgttttggca ccaaaatcaa   2640
cgggactttc caaaatgtcg taacaactcc gccccattga cgcaaatggg cggtaggcgt   2700
gtacggtggg aggtctatat aagcagagct cgtttagtga accgtcagat cgcctggaga   2760
cgccatccac gctgttttga cctccataga agacaccgac tctagctaga ggatccggac   2820
tagtaactcg aggatgggga ctgacccggg ctgcaggaat tcataacttc gtataatgta   2880
tgctatacga agttatagtt aagccttatt gtttatcatc ctcattcaac gacgcgaagg   2940
tgtaccttgg cgagaataac ttcgtatagg atactttata cgaagttatt tatctgtgcc   3000
ccagtttgct agggaggtcg cagtacttgg ccacagccat ctcgtgctgc tcgacgtagg   3060
tctctttgtc ggcctccttg attctttcca gtctgtggtc cacgaagtgg aagccgggca   3120
```

-continued

```
tcttgaggtt cttagcgggt ttcttggatc tgtatgtggt cttgaaggag cagtgcaggt   3180
agcccccgcc cacgagcttc agggccatct ggctgtggcc tctcaggccg ccgtcagcgg   3240
ggtacagcat ctcggtgttg gcctcccagc cgcgtgtttt cttctgcatc acagggccgt   3300
tggatgggaa gttcaccccg ttgatcttga cgttgtagat gatgcagccg ttctggaagc   3360
tggtgtcctg ggtagcggtc agcacgcccc cgtcttcgta tgtggtgatt ctctcccatg   3420
tgaagccctc agggaaggac tgcttaaaga agtcggggat gccctgggtg tggttgatga   3480
aggctttgct gccgtacatg aagctggtag ccaggatgtc gaaggcgaag gggagagggc   3540
cgccctcgac caccttgatc ttcatggtct gggtgccctc gtagggcttg ccttcgccct   3600
cggatgtgca cttgaagtgg tggttgttca cggtgccctc catgtacagc ttcatgtgca   3660
tgttctcctt gatcagctcg ctcatggtgg catatgataa cttcgtatag catacattat   3720
acgaagttat attaagggtt attgaatatg atcggaagtc aacgggtcga tggtgatgct   3780
tggctcgaat aacttcgtat aaagtatcct atacgaagtt atactttggc cgcggctcga   3840
gggggttggg gttgcgcctt ttccaaggca gccctgggtt tgcgcaggga cgcggctgct   3900
ctgggcgtgg ttccgggaaa cgcagcggcg ccgaccctgg gtctcgcaca ttcttcacgt   3960
ccgttcgcag cgtcacccgg atcttcgccg ctacccttgt gggccccccg gcgacgcttc   4020
ctgctccgcc cctaagtcgg gaaggttcct tgcggttcgc ggcgtgccgg acgtgacaaa   4080
cggaagccgc acgtctcact agtaccctcg cagacggaca gcgccaggga gcaatggcag   4140
cgcgccgacc gcgatgggct gtggccaata gcggctgctc agcagggcgc gccgagagca   4200
gcggccggga aggggcggtg cgggaggcgg ggtgtggggc ggtagtgtgg gccctgttcc   4260
tgcccgcgcg gtgttccgca ttctgcaagc ctccggagcg cacgtcggca gtcggctccc   4320
tcgttgaccg aatcaccgac ctctctcccc agggggatcc accggtcgcc accatggtga   4380
gcaagggcga ggagctgttc accggggtgg tgcccatcct ggtcgagctg gacggcgacg   4440
taaacggcca caagttcagc gtgtccggcg agggcgaggg cgatgccacc tacggcaagc   4500
tgaccctgaa gttcatctgc accaccggca agctgcccgt gccctggccc accctcgtga   4560
ccaccctgac ctacggcgtg cagtgcttca gccgctaccc cgaccacatg aagcagcacg   4620
acttcttcaa gtccgccatg cccgaaggct acgtccagga gcgcaccatc ttcttcaagg   4680
acgacggcaa ctacaagacc cgcgccgagg tgaagttcga gggcgacacc ctggtgaacc   4740
gcatcgagct gaagggcatc gacttcaagg aggacggcaa catcctgggg cacaagctgg   4800
agtacaacta caacagccac aacgtctata tcatggccga caagcagaag aacggcatca   4860
aggtgaactt caagatccgc cacaacatcg aggacggcag cgtgcagctc gccgaccact   4920
accagcagaa cacccccatc ggcgacggcc ccgtgctgct gcccgacaac cactacctga   4980
gcacccagtc cgccctgagc aaagacccca acgagaagcg cgatcacatg gtcctgctgg   5040
agttcgtgac cgccgccggg atcactctcg gcatggacga gctgtacaag taagatatca   5100
agcttatcga taatcaacct ctggattaca aaatttgtga aagattgact ggtattctta   5160
actatgttgc tccttttacg ctatgtggat acgctgcttt aatgcctttg tatcatgcta   5220
ttgcttcccg tatggctttc attttctcct ccttgtataa atcctggttg ctgtctcttt   5280
atgaggagtt gtggcccgtt gtcaggcaac gtggcgtggt gtgcactgtg tttgctgacg   5340
caacccccac tggttggggc attgccacca cctgtcagct cctttccggg actttcgctt   5400
tccccctccc tattgccacg gcggaactca tcgccgcctg ccttgcccgc tgctggacag   5460
gggctcggct gttgggcact gacaattccg tggtgttgtc ggggaaatca tcgtcctttc   5520
```

```
cttggctgct cgcctgtgtt gccacctgga ttctgcgcgg gacgtccttc tgctacgtcc   5580

cttcggccct caatccagcg gaccttcctt cccgcggcct gctgccggct ctgcggcctc   5640

ttccgcgtct tcgccttcgc cctcagacga gtcggatctc cctttgggcc gcctccccgc   5700

atcgataccg tcgacctcga gaacctagaa aaacatggag caatcacaag tagcaataca   5760

gcagctacca atgctgattg tgcctggcta gaagcacaag aggaggagga ggtgggtttt   5820

ccagtcacac ctcaggtacc tttaagacca atgacttaca aggcagctgt agatcttagc   5880

cactttttaa aagaaaaggg gggactggaa gggctaattc actcccaacg aagacaagat   5940

ctttttgctt gtactgggtc tctctggtta gaccagatct gagcctggga gctctctggc   6000

taactaggga acccactgct taagcctcaa taaagcttgc cttgagtgct tcaagtagtg   6060

tgtgcccgtc tgttgtgtga ctctggtaac tagagatccc tcagaccctt ttagtcagtg   6120

tggaaaatct ctaga                                                    6135
```

<210> SEQ ID NO 37
<211> LENGTH: 6022
<212> TYPE: DNA
<213> ORGANISM: Artificial Sequence
<220> FEATURE:
<223> OTHER INFORMATION: sequence for screening human cells

<400> SEQUENCE: 37

```
gggctaattc actcccaaag aagacaagat atccttgatc tgtggatcta ccacacacaa     60

ggctacttcc ctgattagca gaactacaca ccagggccag gggtcagata tccactgacc    120

tttggatggt gctacaagct agtaccagtt gagccagata aggtagaaga ggccaataaa    180

ggagagaaca ccagcttgtt acaccctgtg agcctgcatg ggatggatga cccggagaga    240

gaagtgttag agtggaggtt tgacagccgc ctagcatttc atcacgtggc ccgagagctg    300

catccggagt acttcaagaa ctgctgatat cgagcttgct acaagggact ttccgctggg    360

gactttccag ggaggcgtgg cctgggcggg actggggagt ggcgagccct cagatcctgc    420

atataagcag ctgctttttg cctgtactgg gtctctctgg ttagaccaga tctgagcctg    480

ggagctctct ggctaactag ggaacccact gcttaagcct caataaagct tgccttgagt    540

gcttcaagta gtgtgtgccc gtctgttgtg tgactctggt aactagagat ccctcagacc    600

cttttagtca gtgtggaaaa tctctagcag tggcgcccga acagggactt gaaagcgaaa    660

gggaaaccag aggagctctc tcgacgcagg actcggcttg ctgaagcgcg cacggcaaga    720

ggcgaggggc ggcgactggt gagtacgcca aaaattttga ctagcggagg ctagaaggag    780

agagatgggt gcgagagcgt cagtattaag cgggggagaa ttagatcgcg atgggaaaaa    840

attcggttaa ggccaggggg aaagaaaaaa tataaattaa aacatatagt atgggcaagc    900

agggagctag aacgattcgc agttaatcct ggcctgttag aaacatcaga aggctgtaga    960

caaatactgg gacagctaca accatccctt cagacaggat cagaagaact tagatcatta   1020

tataatacag tagcaaccct ctattgtgtg catcaaagga tagagataaa agacaccaag   1080

gaagctttag acaagataga ggaagagcaa aacaaaagta agaccaccgc acagcaagcg   1140

gccgctgatc ttcagacctg gaggaggaga tatgagggac aattggagaa gtgaattata   1200

taaatataaa gtagtaaaaa ttgaaccatt aggagtagca cccaccaagg caaagagaag   1260

agtggtgcag agagaaaaaa gagcagtggg aataggagct ttgttccttg ggttcttggg   1320

agcagcagga agcactatgg gcgcagcgtc aatgacgctg acggtacagg ccagacaatt   1380
```

```
attgtctggt atagtgcagc agcagaacaa tttgctgagg gctattgagg cgcaacagca   1440
tctgttgcaa ctcacagtct ggggcatcaa gcagctccag gcaagaatcc tggctgtgga   1500
aagataccta aaggatcaac agctcctggg gatttggggt tgctctggaa aactcatttg   1560
caccactgct gtgccttgga atgctagttg gagtaataaa tctctggaac agatttggaa   1620
tcacacgacc tggatggagt gggacagaga aattaacaat tacacaagct taatacactc   1680
cttaattgaa gaatcgcaaa accagcaaga aaagaatgaa caagaattat tggaattaga   1740
taaatgggca agtttgtgga attggtttaa cataacaaat tggctgtggt atataaaatt   1800
attcataatg atagtaggag gcttggtagg tttaagaata gtttttgctg tactttctat   1860
agtgaataga gttaggcagg gatattcacc attatcgttt cagacccacc tcccaacccc   1920
gaggggaccc gacaggcccg aaggaataga agaagaaggt ggagagagag acagagacag   1980
atccattcga ttagtgaacg gatctcgacg gtatcgccga attcacaaat ggcagtattc   2040
atccacaatt ttaaaagaaa aggggggatt ggggggtaca gtgcagggga aagaatagta   2100
gacataatag caacagacat acaaactaaa gaattacaaa aacaaattac aaaaattcaa   2160
aattttcggg tttattacag ggacagcaga gatccacttt atcgatggtc cggtccggaa   2220
ttcctgcagc cccgataaaa taaaagattt tatttagtct ccagaaaaag gggggaatga   2280
aagaccccac ctgtaggttt ggcaagctag ctgcagtaac gccattttgc aaggcatgga   2340
aaaataccaa accaagaata gagaagttca gatcaagggc gggtacatga aaatagctaa   2400
cgttgggcca aacaggatat ctgcggtgag cagtttcggc cccggcccgg ggccaagaac   2460
agatggtcac cgcagtttcg gccccggccc gaggccaaga acagatggtc cccagatatg   2520
gcccaaccct cagcagtttc ttaagaccca tcagatgttt ccaggctccc ccaaggacct   2580
gaaatgaccc tgcgccttat ttgaattaac caatcagcct gcttctcgct tctgttcgcg   2640
cgcttctgct tcccgagctc tataaaagag ctcacaaccc ctcactcggc gcgccagtcc   2700
tccgacagac tgagtcgccc ggggggggatc caccgggctg caggaattca taacttcgta   2760
taatgtatgc tatacgaagt tatagttaag ccttattgtt tatcatcctc attcaacgac   2820
gcgaaggtgt accttggcga gaataacttc gtataggata ctttatacga agttatttat   2880
ctgtgcccca gtttgctagg gaggtcgcag tacttggcca cagccatctc gtgctgctcg   2940
acgtaggtct ctttgtcggc ctccttgatt ctttccagtc tgtggtccac gaagtggaag   3000
ccgggcatct tgaggttctt agcgggtttc ttggatctgt atgtggtctt gaaggagcag   3060
tgcaggtagc ccccgcccac gagcttcagg gccatctggc tgtggcctct caggccgccg   3120
tcagcggggt acagcatctc ggtgttggcc tcccagccgc gtgttttctt ctgcatcaca   3180
gggccgttgg atgggaagtt caccccgttg atcttgacgt tgtagatgat gcagccgttc   3240
tggaagctgg tgtcctgggt agcggtcagc acgcccccgt cttcgtatgt ggtgattctc   3300
tcccatgtga agccctcagg gaaggactgc ttaaagaagt cggggatgcc ctgggtgtgg   3360
ttgatgaagg ctttgctgcc gtacatgaag ctggtagcca ggatgtcgaa ggcgaagggg   3420
agagggccgc cctcgaccac cttgatcttc atggtctggg tgccctcgta gggcttgcct   3480
tcgccctcgg atgtgcactt gaagtggtgg ttgttcacgg tgccctccat gtacagcttc   3540
atgtgcatgt tctccttgat cagctcgctc atggtggcat atgataactt cgtatagcat   3600
acattatacg aagttatatt aagggttatt gaatatgatc ggaagtcaac gggtcgatgg   3660
tgatgcttgg ctcgaataac ttcgtataaa gtatcctata cgaagttata ctttggccgc   3720
ggctcgaggg ggttggggtt gcgccttttc caaggcagcc ctgggtttgc gcagggacgc   3780
```

```
ggctgctctg ggcgtggttc cgggaaacgc agcggcgccg accctgggtc tcgcacattc   3840
ttcacgtccg ttcgcagcgt cacccggatc ttcgccgcta cccttgtggg ccccccggcg   3900
acgcttcctg ctccgcccct aagtcgggaa ggttccttgc ggttcgcggc gtgccggacg   3960
tgacaaacgg aagccgcacg tctcactagt accctcgcag acggacagcg ccagggagca   4020
atggcagcgc gccgaccgcg atgggctgtg gccaatagcg gctgctcagc agggcgcgcc   4080
gagagcagcg gccgggaagg ggcggtgcgg gaggcggggt gtggggcggt agtgtgggcc   4140
ctgttcctgc ccgcgcggtg ttccgcattc tgcaagcctc cggagcgcac gtcggcagtc   4200
ggctccctcg ttgaccgaat caccgacctc tctccccagg gggatccacc ggtcgccacc   4260
atggtgagca agggcgagga gctgttcacc ggggtggtgc ccatcctggt cgagctggac   4320
ggcgacgtaa acggccacaa gttcagcgtg tccggcgagg gcgagggcga tgccacctac   4380
ggcaagctga ccctgaagtt catctgcacc accggcaagc tgcccgtgcc ctggcccacc   4440
ctcgtgacca ccctgaccta cggcgtgcag tgcttcagcc gctaccccga ccacatgaag   4500
cagcacgact tcttcaagtc cgccatgccc gaaggctacg tccaggagcg caccatcttc   4560
ttcaaggacg acggcaacta caagacccgc gccgaggtga agttcgaggg cgacaccctg   4620
gtgaaccgca tcgagctgaa gggcatcgac ttcaaggagg acggcaacat cctggggcac   4680
aagctggagt acaactacaa cagccacaac gtctatatca tggccgacaa gcagaagaac   4740
ggcatcaagg tgaacttcaa gatccgccac aacatcgagg acggcagcgt gcagctcgcc   4800
gaccactacc agcagaacac ccccatcggc gacggccccg tgctgctgcc cgacaaccac   4860
tacctgagca cccagtccgc cctgagcaaa gaccccaacg agaagcgcga tcacatggtc   4920
ctgctggagt tcgtgaccgc cgccgggatc actctcggca tggacgagct gtacaagtaa   4980
gatatcaagc ttatcgataa tcaacctctg gattacaaaa tttgtgaaag attgactggt   5040
attcttaact atgttgctcc ttttacgcta tgtggatacg ctgctttaat gcctttgtat   5100
catgctattg cttcccgtat ggctttcatt ttctcctcct tgtataaatc ctggttgctg   5160
tctctttatg aggagttgtg gcccgttgtc aggcaacgtg gcgtggtgtg cactgtgttt   5220
gctgacgcaa cccccactgg ttggggcatt gccaccacct gtcagctcct ttccgggact   5280
ttcgctttcc ccctccctat tgccacggcg gaactcatcg ccgcctgcct tgcccgctgc   5340
tggacagggg ctcggctgtt gggcactgac aattccgtgg tgttgtcggg gaaatcatcg   5400
tcctttcctt ggctgctcgc ctgtgttgcc acctggattc tgcgcgggac gtccttctgc   5460
tacgtccctt cggccctcaa tccagcggac cttccttccc gcggcctgct gccggctctg   5520
cggcctcttc cgcgtcttcg ccttcgccct cagacgagtc ggatctccct ttgggccgcc   5580
tccccgcatc gataccgtcg acctcgagaa cctagaaaaa catggagcaa tcacaagtag   5640
caatacagca gctaccaatg ctgattgtgc ctggctagaa gcacaagagg aggaggaggt   5700
gggttttcca gtcacacctc aggtaccttt aagaccaatg acttacaagg cagctgtaga   5760
tcttagccac tttttaaaag aaaagggggg actggaaggg ctaattcact cccaacgaag   5820
acaagatctt tttgcttgta ctgggtctct ctggttagac cagatctgag cctgggagct   5880
ctctggctaa ctagggaacc cactgcttaa gcctcaataa agcttgcctt gagtgcttca   5940
agtagtgtgt gcccgtctgt tgtgtgactc tggtaactag agatccctca gaccctttta   6000
gtcagtgtgg aaaatctcta ga                                            6022
```

<210> SEQ ID NO 38

<211> LENGTH: 6156
<212> TYPE: DNA
<213> ORGANISM: Artificial Sequence
<220> FEATURE:
<223> OTHER INFORMATION: sequence for screening human cells

<400> SEQUENCE: 38
gggctaattc actcccaaag aagacaagat atccttgatc tgtggatcta ccacacacaa 60
ggctacttcc ctgattagca gaactacaca ccagggccag gggtcagata tccactgacc 120
tttggatggt gctacaagct agtaccagtt gagccagata aggtagaaga ggccaataaa 180
ggagagaaca ccagcttgtt acaccctgtg agcctgcatg ggatggatga cccggagaga 240
gaagtgttag agtggaggtt tgacagccgc ctagcatttc atcacgtggc ccgagagctg 300
catccggagt acttcaagaa ctgctgatat cgagcttgct acaagggact ttccgctggg 360
gactttccag ggaggcgtgg cctgggcggg actggggagt ggcgagccct cagatcctgc 420
atataagcag ctgctttttg cctgtactgg gtctctctgg ttagaccaga tctgagcctg 480
ggagctctct ggctaactag ggaacccact gcttaagcct caataaagct tgccttgagt 540
gcttcaagta gtgtgtgccc gtctgttgtg tgactctggt aactagagat ccctcagacc 600
cttttagtca gtgtggaaaa tctctagcag tggcgcccga acagggactt gaaagcgaaa 660
gggaaaccag aggagctctc tcgacgcagg actcggcttg ctgaagcgcg cacggcaaga 720
ggcgaggggc ggcgactggt gagtacgcca aaaattttga ctagcggagg ctagaaggag 780
agagatgggt gcgagagcgt cagtattaag cgggggagaa ttagatcgcg atgggaaaaa 840
attcggttaa ggccaggggg aaagaaaaaa tataaattaa aacatatagt atgggcaagc 900
agggagctag aacgattcgc agttaatcct ggcctgttag aaacatcaga aggctgtaga 960
caaatactgg gacagctaca accatccctt cagacaggat cagaagaact tagatcatta 1020
tataatacag tagcaaccct ctattgtgtg catcaaagga tagagataaa agacaccaag 1080
gaagctttag acaagataga ggaagagcaa aacaaaagta agaccaccgc acagcaagcg 1140
gccgctgatc ttcagacctg gaggaggaga tatgagggac aattggagaa gtgaattata 1200
taaatataaa gtagtaaaaa ttgaaccatt aggagtagca cccaccaagg caaagagaag 1260
agtggtgcag agagaaaaaa gagcagtggg aataggagct ttgttccttg ggttcttggg 1320
agcagcagga agcactatgg gcgcagcgtc aatgacgctg acggtacagg ccagacaatt 1380
attgtctggt atagtgcagc agcagaacaa tttgctgagg gctattgagg cgcaacagca 1440
tctgttgcaa ctcacagtct ggggcatcaa gcagctccag gcaagaatcc tggctgtgga 1500
aagataccta aaggatcaac agctcctggg gatttggggt tgctctggaa aactcatttg 1560
caccactgct gtgccttgga atgctagttg gagtaataaa tctctggaac agatttggaa 1620
tcacacgacc tggatggagt gggacagaga aattaacaat tacacaagct taatacactc 1680
cttaattgaa gaatcgcaaa accagcaaga aaagaatgaa caagaattat tggaattaga 1740
taaatgggca agtttgtgga attggtttaa cataacaaat tggctgtggt atataaaatt 1800
attcataatg atagtaggag gcttggtagg tttaagaata gtttttgctg tactttctat 1860
agtgaataga gttaggcagg gatattcacc attatcgttt cagacccacc tcccaacccc 1920
gaggggaccc gacaggcccg aaggaataga agaagaaggt ggagagagag acagagacag 1980
atccattcga ttagtgaacg gatctcgacg gtatcgccga attcacaaat ggcagtattc 2040
atccacaatt ttaaaagaaa aggggggatt ggggggtaca gtgcagggga aagaatagta 2100
gacataatag caacagacat acaaactaaa gaattacaaa aacaaattac aaaaattcaa 2160

-continued

```
aattttcggg tttattacag ggacagcaga gatccacttt atcgatggtc cggtccggaa   2220
ttcctgcagc cccgataaaa taaaagattt tatttagtct ccagaaaaag gggggaatga   2280
aagaccccac ctgtaggttt ggcaagctag ctgcagtaac gccattttgc aaggcatgga   2340
aaaataccaa accaagaata gagaagttca gatcaagggc gggtacatga aaatagctaa   2400
cgttgggcca aacaggatat ctgcggtgag cagtttcggc cccggcccgg ggccaagaac   2460
agatggtcac cgcagtttcg gccccggccc gaggccaaga acagatggtc cccagatatg   2520
gcccaaccct cagcagtttc ttaagaccca tcagatgttt ccaggctccc ccaaggacct   2580
gaaatgaccc tgcgccttat ttgaattaac caatcagcct gcttctcgct tctgttcgcg   2640
cgcttctgct tcccgagctc tataaaagag ctcacaaccc ctcactcggc gcgccagtcc   2700
tccgacagac tgagtcgccc ggggggggatc caccgggctg caggaattca taacttcgta   2760
taatgtatgc tatacgaagt tatagttaag ccttattgtt tatcatcctc attcaacgac   2820
gcgaaggtgt accttggcga gaataacttc gtataggata ctttatacga agttatttat   2880
ctgtgcccca gtttgctagg gaggtcgcag tacttggcca cagccatctc gtgctgctcg   2940
acgtaggtct ctttgtcggc ctccttgatt ctttccagtc tgtggtccac gaagtggaag   3000
ccgggcatct tgaggttctt agcgggtttc ttggatctgt atgtggtctt gaaggagcag   3060
tgcaggtagc ccccgcccac gagcttcagg gccatctggc tgtggcctct caggccgccg   3120
tcagcggggt acagcatctc ggtgttggcc tcccagccgc gtgttttctt ctgcatcaca   3180
gggccgttgg atgggaagtt caccccgttg atcttgacgt tgtagatgat gcagccgttc   3240
tggaagctgg tgtcctgggt agcggtcagc acgcccccgt cttcgtatgt ggtgattctc   3300
tcccatgtga agccctcagg gaaggactgc ttaaagaagt cggggatgcc ctgggtgtgg   3360
ttgatgaagg ctttgctgcc gtacatgaag ctggtagcca ggatgtcgaa ggcgaagggg   3420
agagggccgc cctcgaccac cttgatcttc atggtctggg tgccctcgta gggcttgcct   3480
tcgccctcgg atgtgcactt gaagtggtgg ttgttcacgg tgccctccat gtacagcttc   3540
atgtgcatgt tctccttgat cagctcgctc atggtggcat atgataactt cgtatagcat   3600
acattatacg aagttatatt aagggttatt gaatatgatc ggaagtcaac gggtcgatgg   3660
tgatgcttgg ctcgaataac ttcgtataaa gtatcctata cgaagttata ctttggccgc   3720
ggctcgaatc tacttaccga taagcttggg agttccgcgt tacataactt acggtaaatg   3780
gcccgcctgg ctgaccgccc aacgaccccc gcccattgac gtcaataatg acgtatgttc   3840
ccatagtaac gccaataggg actttccatt gacgtcaatg ggtggagtat ttacggtaaa   3900
ctgcccactt ggcagtacat caagtgtatc atatgccaag tacgccccct attgacgtca   3960
atgacggtaa atggcccgcc tggcattatg cccagtacat gaccttacgg gactttccta   4020
cttggcagta catctacgta ttagtcatcg ctattaccat ggtgatgcgg ttttggcagt   4080
acaccaatgg gcgtggatag cggtttgact cacggggatt tccaagtctc caccccattg   4140
acgtcaatgg gagtttgttt tggcaccaaa atcaacggga ctttccaaaa tgtcgtaaca   4200
actccgcccc attgacgcaa atgggcggta ggcgtgtacg gtgggaggtc tatataagca   4260
gagctcgttt agtgaaccgt cagatcgcct ggagacgcca tccacgctgt tttgacctcc   4320
atagaagaca ccgactctag ctagaggatc cggactagta actcgaggat ggggactgac   4380
ccggacgcgt gccgccacca tggtgagcaa gggcgaggag ctgttcaccg ggtggtgcc   4440
catcctggtc gagctggacg gcgacgtaaa cggccacaag ttcagcgtgt ccggcgaggg   4500
```

cgagggcgat gccacctacg gcaagctgac cctgaagttc atctgcacca ccggcaagct 4560
gcccgtgccc tggcccaccc tcgtgaccac cctgacctac ggcgtgcagt gcttcagccg 4620
ctaccccgac cacatgaagc agcacgactt cttcaagtcc gccatgcccg aaggctacgt 4680
ccaggagcgc accatcttct tcaaggacga cggcaactac aagacccgcg ccgaggtgaa 4740
gttcgagggc gacaccctgg tgaaccgcat cgagctgaag ggcatcgact tcaaggagga 4800
cggcaacatc ctggggcaca agctggagta caactacaac agccacaacg tctatatcat 4860
ggccgacaag cagaagaacg gcatcaaggt gaacttcaag atccgccaca acatcgagga 4920
cggcagcgtg cagctcgccg accactacca gcagaacacc cccatcggcg acggccccgt 4980
gctgctgccc gacaaccact acctgagcac ccagtccgcc ctgagcaaag accccaacga 5040
gaagcgcgat cacatggtcc tgctggagtt cgtgaccgcc gccgggatca ctctcggcat 5100
ggacgagctg tacaagtaag atatcaagct tatcgataat caacctctgg attacaaaat 5160
ttgtgaaaga ttgactggta ttcttaacta tgttgctcct tttacgctat gtggatacgc 5220
tgctttaatg cctttgtatc atgctattgc ttcccgtatg gctttcattt tctcctcctt 5280
gtataaatcc tggttgctgt ctctttatga ggagttgtgg cccgttgtca ggcaacgtgg 5340
cgtggtgtgc actgtgtttg ctgacgcaac ccccactggt tggggcattg ccaccacctg 5400
tcagctcctt tccgggactt tcgctttccc cctccctatt gccacggcgg aactcatcgc 5460
cgcctgcctt gcccgctgct ggacaggggc tcggctgttg ggcactgaca attccgtggt 5520
gttgtcgggg aaatcatcgt cctttccttg gctgctcgcc tgtgttgcca cctggattct 5580
gcgcgggacg tccttctgct acgtcccttc ggccctcaat ccagcggacc ttccttcccg 5640
cggcctgctg ccggctctgc ggcctcttcc gcgtcttcgc cttcgccctc agacgagtcg 5700
gatctccctt tgggccgcct ccccgcatcg ataccgtcga cctcgagaac ctagaaaaac 5760
atggagcaat cacaagtagc aatacagcag ctaccaatgc tgattgtgcc tggctagaag 5820
cacaagagga ggaggaggtg ggttttccag tcacacctca ggtaccttta agaccaatga 5880
cttacaaggc agctgtagat cttagccact ttttaaaaga aaaggggga ctggaagggc 5940 taattcactc ccaacgaaga caagatcttt ttgcttgtac tgggtctctc tggttagacc 6000
agatctgagc ctgggagctc tctggctaac tagggaaccc actgcttaag cctcaataaa 6060
gcttgccttg agtgcttcaa gtagtgtgtg cccgtctgtt gtgtgactct ggtaactaga 6120
gatccctcag acccttttag tcagtgtgga aaatct 6156

<210> SEQ ID NO 39
<211> LENGTH: 7092
<212> TYPE: DNA
<213> ORGANISM: Artificial Sequence
<220> FEATURE:
<223> OTHER INFORMATION: sequence for screening human cells

<400> SEQUENCE: 39
gggctaattc actcccaaag aagacaagat atccttgatc tgtggatcta ccacacacaa 60
ggctacttcc ctgattagca gaactacaca ccagggccag gggtcagata tccactgacc 120
tttggatggt gctacaagct agtaccagtt gagccagata aggtagaaga ggccaataaa 180
ggagagaaca ccagcttgtt acaccctgtg agcctgcatg ggatggatga cccggagaga 240
gaagtgttag agtggaggtt tgacagccgc ctagcatttc atcacgtggc ccgagagctg 300
catccggagt acttcaagaa ctgctgatat cgagcttgct acaagggact ttccgctggg 360
gactttccag ggaggcgtgg cctgggcggg actggggagt ggcgagccct cagatcctgc 420

-continued

```
atataagcag ctgctttttg cctgtactgg gtctctctgg ttagaccaga tctgagcctg    480
ggagctctct ggctaactag ggaacccact gcttaagcct caataaagct tgccttgagt    540
gcttcaagta gtgtgtgccc gtctgttgtg tgactctggt aactagagat ccctcagacc    600
cttttagtca gtgtggaaaa tctctagcag tggcgcccga acagggactt gaaagcgaaa    660
gggaaaccag aggagctctc tcgacgcagg actcggcttg ctgaagcgcg cacggcaaga    720
ggcgaggggc ggcgactggt gagtacgcca aaaattttga ctagcggagg ctagaaggag    780
agagatgggt gcgagagcgt cagtattaag cgggggagaa ttagatcgcg atgggaaaaa    840
attcggttaa ggccaggggg aaagaaaaaa tataaattaa aacatatagt atgggcaagc    900
agggagctag aacgattcgc agttaatcct ggcctgttag aaacatcaga aggctgtaga    960
caaatactgg gacagctaca accatccctt cagacaggat cagaagaact tagatcatta   1020
tataatacag tagcaaccct ctattgtgtg catcaaagga tagagataaa agacaccaag   1080
gaagctttag acaagataga ggaagagcaa aacaaaagta agaccaccgc acagcaagcg   1140
gccgctgatc ttcagacctg gaggaggaga tatgagggac aattggagaa gtgaattata   1200
taaatataaa gtagtaaaaa ttgaaccatt aggagtagca cccaccaagg caaagagaag   1260
agtggtgcag agagaaaaaa gagcagtggg aataggagct ttgttccttg ggttcttggg   1320
agcagcagga agcactatgg gcgcagcgtc aatgacgctg acggtacagg ccagacaatt   1380
attgtctggt atagtgcagc agcagaacaa tttgctgagg gctattgagg cgcaacagca   1440
tctgttgcaa ctcacagtct ggggcatcaa gcagctccag gcaagaatcc tggctgtgga   1500
aagataccta aaggatcaac agctcctggg gatttggggt tgctctggaa aactcatttg   1560
caccactgct gtgccttgga atgctagttg gagtaataaa tctctggaac agatttggaa   1620
tcacacgacc tggatggagt gggacagaga aattaacaat tacacaagct taatacactc   1680
cttaattgaa gaatcgcaaa accagcaaga aaagaatgaa caagaattat tggaattaga   1740
taaatgggca agtttgtgga attggtttaa cataacaaat tggctgtggt atataaaatt   1800
attcataatg atagtaggag gcttggtagg tttaagaata gtttttgctg tactttctat   1860
agtgaataga gttaggcagg gatattcacc attatcgttt cagacccacc tcccaacccc   1920
gaggggaccc gacaggcccg aaggaataga agaagaaggt ggagagagag acagagacag   1980
atccattcga ttagtgaacg gatctcgacg gtatcgccga attcacaaat ggcagtattc   2040
atccacaatt ttaaaagaaa aggggggatt ggggggtaca gtgcagggga aagaatagta   2100
gacataatag caacagacat acaaactaaa gaattacaaa aacaaattac aaaaattcaa   2160
aattttcggg tttattacag ggacagcaga gatccacttt atcgataagc ttgggagttc   2220
cgcgttacat aacttacggt aaatggcccg cctggctgac cgcccaacga cccccgccca   2280
ttgacgtcaa taatgacgta tgttcccata gtaacgccaa tagggacttt ccattgacgt   2340
caatgggtgg agtatttacg gtaaactgcc cacttggcag tacatcaagt gtatcatatg   2400
ccaagtacgc cccctattga cgtcaatgac ggtaaatggc ccgcctggca ttatgcccag   2460
tacatgacct tacgggactt tcctacttgg cagtacatct acgtattagt catcgctatt   2520
accatggtga tgcggttttg gcagtacacc aatgggcgtg gatagcggtt tgactcacgg   2580
ggatttccaa gtctccaccc cattgacgtc aatgggagtt tgttttggca ccaaaatcaa   2640
cgggactttc caaaatgtcg taacaactcc gccccattga cgcaaatggg cggtaggcgt   2700
gtacggtggg aggtctatat aagcagagct cgtttagtga accgtcagat cgcctggaga   2760
```

```
cgccatccac gctgttttga cctccataga agacaccgac tctagctaga ggatccggac   2820
tagtaactcg aggatgggga ctgacccggg ctgcaggaat tcataacttc gtataatgta   2880
tgctatacga agttatagtt aagccttatt gtttatcatc ctcattcaac gacgcgaagg   2940
tgtaccttgg cgagaataac ttcgtatagg atactttata cgaagttatt tacacggcga   3000
tctttccgcc cttcttggcc tttatgagga tctctctgat tttcttgcg tcgagttttc   3060
cggtaagacc tttcggtact tcgtccacaa acacaactcc tccgcgcaac tttttcgcgg   3120
ttgttacttg actggcgacg taatccacga tctcttttc cgtcatcgtc tttccgtgct   3180
ccaaaacaac aacggcggcg ggaagttcac cggcgtcatc gtcgggaaga cctgcgacac   3240
ctgcgtcgaa gatgttgggg tgttggagca agatggattc caattcagcg ggagccacct   3300
gatagccttt gtacttaatc agagacttca ggcggtcaac gatgaagaag tgttcgtctt   3360
cgtcccagta agctatgtct ccagaatgta gccatccatc cttgtcaatc aaggcgttgg   3420
tcgcttccgg attgtttaca taaccggaca taatcatagg acctctcaca cacagttcgc   3480
ctctttgatt aacgcccagc gttttcccgg tatccagatc cacaaccttc gcttcaaaaa   3540
atggaacaac tttaccgacc gcgcccggtt tatcatcccc ctcgggtgta atcagaatag   3600
ctgatgtagt ctcagtgagc ccatatcctt gcctgatacc tggcagatgg aacctcttgg   3660
caaccgcttc cccgacttcc ttagagaggg gagcgccacc agaagcaatt tcgtgtaaat   3720
tagataaatc gtatttgtca atcagagtgc ttttggcgaa gaaggagaat agggttggca   3780
ccagcagcgc actttgaatc ttgtaatcct gaaggctcct cagaaacagc tcttcttcaa   3840
atctatacat taagacgact cgaaatccac atatcaaata tccgagtgta gtaaacattc   3900
caaaaccgtg atggaatgga acaacactta aaatcgcagt atccggaatg atttgattgc   3960
caaaaatagg atctctggca tgcgagaatc tcacgcaggc agttctatga ggcagagcga   4020
cacctttagg cagaccagta gatccagagg agttcatgat cagtgcaatt gtcttgtccc   4080
tatcgaagga ctctggcaca aaatcgtatt cattaaaacc gggaggtaga tgagatgtga   4140
cgaacgtgta catcgactga aatccctggt aatccgtttt agaatccatg ataataattt   4200
tttggatgat tgggagcttt ttttgcacgt tcaaaatttt ttgcaacccc tttttggaaa   4260
cgaacaccac ggtaggctgc gaaatgccca tactgttgag caattcacgt tcattataaa   4320
tgtcgttcgc gggcgcaact gcaactccga taaataacgc gcccaacacc ggcataaaga   4380
attgaagaga gttttcactg catacgacga ttctgtgatt tgtattcagc ccatatcgtt   4440
tcatagcttc tgccaaccga acggacattt cgaagtactc agcgtaagtg atgtccacct   4500
cgatatgtgc atctgtaaaa gcaattgttc caggaaccag ggcgtatctc ttcatagcct   4560
tatgcagttg ctctccagcg gttccatctt ccagcggata gaatggcgcc gggcctttct   4620
ttatgttttt ggcgtcttcc atggtggcat atgataactt cgtatagcat acattatacg   4680
aagttatatt aagggttatt gaatatgatc ggaagtcaac gggtcgatgg tgatgcttgg   4740
ctcgaataac ttcgtataaa gtatcctata cgaagttata ctttggccgc ggctcgaggg   4800
ggttggggtt gcgccttttc caaggcagcc ctgggtttgc gcagggacgc ggctgctctg   4860
ggcgtggttc cgggaaacgc agcggcgccg accctgggtc tcgcacattc ttcacgtccg   4920
ttcgcagcgt cacccggatc ttcgccgcta cccttgtggg ccccccggcg acgcttcctg   4980
ctccgcccct aagtcgggaa ggttccttgc ggttcgcggc gtgccggacg tgacaaacgg   5040
aagccgcacg tctcactagt accctcgcag acggacagcg ccagggagca atggcagcgc   5100
gccgaccgcg atgggctgtg gccaatagcg gctgctcagc agggcgcgcc gagagcagcg   5160
```

gccgggaagg ggcggtgcgg gaggcggggt gtggggcggt agtgtgggcc ctgttcctgc 5220
ccgcgcggtg ttccgcattc tgcaagcctc cggagcgcac gtcggcagtc ggctccctcg 5280
ttgaccgaat caccgacctc tctccccagg gggatccacc ggtcgccacc atggtgagca 5340
agggcgagga gctgttcacc ggggtggtgc ccatcctggt cgagctggac ggcgacgtaa 5400
acggccacaa gttcagcgtg tccggcgagg gcgagggcga tgccacctac ggcaagctga 5460
ccctgaagtt catctgcacc accggcaagc tgcccgtgcc ctggcccacc ctcgtgacca 5520
ccctgaccta cggcgtgcag tgcttcagcc gctaccccga ccacatgaag cagcacgact 5580
tcttcaagtc cgccatgccc gaaggctacg tccaggagcg caccatcttc ttcaaggacg 5640
acggcaacta caagacccgc gccgaggtga agttcgaggg cgacaccctg gtgaaccgca 5700
tcgagctgaa gggcatcgac ttcaaggagg acggcaacat cctggggcac aagctggagt 5760
acaactacaa cagccacaac gtctatatca tggccgacaa gcagaagaac ggcatcaagg 5820
tgaacttcaa gatccgccac aacatcgagg acggcagcgt gcagctcgcc gaccactacc 5880
agcagaacac ccccatcggc gacggccccg tgctgctgcc cgacaaccac tacctgagca 5940
cccagtccgc cctgagcaaa gaccccaacg agaagcgcga tcacatggtc ctgctggagt 6000
tcgtgaccgc cgccgggatc actctcggca tggacgagct gtacaagtaa gatatcaagc 6060
ttatcgataa tcaacctctg gattacaaaa tttgtgaaag attgactggt attcttaact 6120
atgttgctcc ttttacgcta tgtggatacg ctgctttaat gcctttgtat catgctattg 6180
cttcccgtat ggctttcatt ttctcctcct tgtataaatc ctggttgctg tctctttatg 6240
aggagttgtg gcccgttgtc aggcaacgtg gcgtggtgtg cactgtgttt gctgacgcaa 6300
cccccactgg ttggggcatt gccaccacct gtcagctcct ttccgggact ttcgctttcc 6360
ccctccctat tgccacggcg gaactcatcg ccgcctgcct tgcccgctgc tggacagggg 6420
ctcggctgtt gggcactgac aattccgtgg tgttgtcggg gaaatcatcg tcctttcctt 6480
ggctgctcgc ctgtgttgcc acctggattc tgcgcgggac gtccttctgc tacgtccctt 6540
cggccctcaa tccagcggac cttccttccc gcggcctgct gccggctctg cggcctcttc 6600
cgcgtcttcg ccttcgccct cagacgagtc ggatctccct ttgggccgcc tccccgcatc 6660
gataccgtcg acctcgagaa cctagaaaaa catggagcaa tcacaagtag caatacagca 6720
gctaccaatg ctgattgtgc ctggctagaa gcacaagagg aggaggaggt gggttttcca 6780
gtcacacctc aggtaccttt aagaccaatg acttacaagg cagctgtaga tcttagccac 6840
tttttaaaag aaaagggggg actggaaggg ctaattcact cccaacgaag acaagatctt 6900
tttgcttgta ctgggtctct ctggttagac cagatctgag cctgggagct ctctggctaa 6960
ctagggaacc cactgcttaa gcctcaataa agcttgcctt gagtgcttca agtagtgtgt 7020
gcccgtctgt tgtgtgactc tggtaactag agatccctca gaccctttta gtcagtgtgg 7080
aaaatctcta ga 7092

<210> SEQ ID NO 40
<211> LENGTH: 5672
<212> TYPE: DNA
<213> ORGANISM: Artificial Sequence
<220> FEATURE:
<223> OTHER INFORMATION: sequence for screening simian cells

<400> SEQUENCE: 40
cctagtcgcc gcctggtcaa ctcggtactc ggtaataaga agaccctggt ctgttaggac 60

-continued

```
cctttctgct ttgagaaacc gaagcaggaa aatccctagc agattggcgc ccgaacaggg    120
acttgaagga gagtgagaga ctcctgagta cggctgagtg aaggcagtaa gggcggcagg    180
aaccaaccac gacggagtgc tcctataaag gcgcgggtcg gtaccagacg gcgtgaggag    240
cgggagagga ggaggcctcc ggttgcagta agtgcaacac aaaaaagaaa tagctgtctt    300
gttatccagg aagggataat aagatagagt gggagatggg cgcgagaaac tccgtcttgt    360
cagggaagaa agcagatgaa ttgaaaaaat tattaatcgc atgaatttta aaagaagggg    420
aggaataggg gatatgactc cagcagaaag attaattaac atgatcacta cagaacaaga    480
aatacaattt caacaatcaa aaaactcaaa atttaaaaat tttcgggtct attacagagc    540
tcacgcgtga ttggagttgg gagattataa attagtagag atcactccga ttggcttggc    600
ccccacagat gtgaagaggt acactactgg tggcacctca agaaataaaa gaggggtctt    660
tgtgctaggg ttcttgggtt ttctcgcaac ggcaggttct gcaatgggcg cggcgtcgtt    720
gacgctgacc gctcagtccc ggactttatt ggctgggata gtgcagcaac agcaacagct    780
gttggacgtg gtcaagagac aacaagaatt gttgcgactg accgtctggg gaacaaagaa    840
cctccagact agggtcactg ccatcgagaa gtacttaaag gaccaggcgc agctaaatgc    900
ttggggatgt gcgtttagac aagtctgcca cactactgta ccatggccaa atgcaagtct    960
aacaccagac tggaacaatg atacttggca agagtgggag cgaaaggttg acttcttgga   1020
ggaaaatata acagccctcc tagaagaggc acaaattcaa caagagaaga acatgtatga   1080
attacaaaag ttgaatagct gggatgtgtt tggcaattgg tttgaccttg cttcttggat   1140
aaagtatata caatatggaa tttatgtagt tgtaggagta atactgttaa gaatagtgat   1200
ctatatagta caaatgctag ctaagttaag gcaggggtat aggccagtgt tctcttcccc   1260
accctcttat ttccagtaga ctcataccca acaggacccg gcactgccaa ccagagaagg   1320
caaagaagga gacggtggag aaggcggtgg atcctattat cgaattcctg cagccccgat   1380
aaaataaaag attttattta gtctccagaa aaagggggga atgaaagacc ccacctgtag   1440
gtttggcaag ctagctgcag taacgccatt ttgcaaggca tggaaaaata ccaaaccaag   1500
aatagagaag ttcagatcaa gggcgggtac atgaaaatag ctaacgttgg gccaaacagg   1560
atatctgcgg tgagcagttt cggccccggc ccggggccaa gaacagatgg tcaccgcagt   1620
ttcggccccg gcccgaggcc aagaacagat ggtccccaga tatggcccaa ccctcagcag   1680
tttcttaaga cccatcagat gtttccaggc tcccccaagg acctgaaatg accctgcgcc   1740
ttatttgaat taaccaatca gcctgcttct cgcttctgtt cgcgcgcttc tgcttcccga   1800
gctctataaa agagctcaca acccctcact cggcgcgcca gtcctccgac agactgagtc   1860
gcccgggggg gatccaccgg gctgcaggaa ttcgatatca agcttatcga tgattctaga   1920
catgcatatc tagcgtcccg ggctgcagga attcataact tcgtataatg tatgctatac   1980
gaagttatag ttaagcctta ttgtttatca tcctcattca acgacgcgaa ggtgtacctt   2040
ggcgagaata acttcgtata ggatacttta tacgaagtta tttatctgtg ccccagtttg   2100
ctagggaggt cgcagtactt ggccacagcc atctcgtgct gctcgacgta ggtctctttg   2160
tcggcctcct tgattctttc cagtctgtgg tccacgaagt ggaagccggg catcttgagg   2220
ttcttagcgg gtttcttgga tctgtatgtg gtcttgaagg agcagtgcag gtagcccccg   2280
cccacgagct tcagggccat ctggctgtgg cctctcaggc cgccgtcagc ggggtacagc   2340
atctcggtgt tggcctccca gccgcgtgtt ttcttctgca tcacagggcc gttggatggg   2400
aagttcaccc cgttgatctt gacgttgtag atgatgcagc cgttctggaa gctggtgtcc   2460
```

```
tgggtagcgg tcagcacgcc cccgtcttcg tatgtggtga ttctctccca tgtgaagccc   2520
tcagggaagg actgcttaaa gaagtcgggg atgccctggg tgtggttgat gaaggctttg   2580
ctgccgtaca tgaagctggt agccaggatg tcgaaggcga aggggagagg gccgccctcg   2640
accaccttga tcttcatggt ctgggtgccc tcgtagggct tgccttcgcc ctcggatgtg   2700
cacttgaagt ggtggttgtt cacggtgccc tccatgtaca gcttcatgtg catgttctcc   2760
ttgatcagct cgctcatggt ggcatatgat aacttcgtat agcatacatt atacgaagtt   2820
atattaaggg ttattgaata tgatcggaag tcaacgggtc gatggtgatg cttggctcga   2880
ataacttcgt ataaagtatc ctatacgaag ttatactttg gccgcggctc gaggggggttg   2940
gggttgcgcc ttttccaagg cagccctggg tttgcgcagg gacgcggctg ctctgggcgt   3000
ggttccggga aacgcagcgg cgccgaccct gggtctcgca cattcttcac gtccgttcgc   3060
agcgtcaccc ggatcttcgc cgctaccctt gtgggccccc cggcgacgct tcctgctccg   3120
cccctaagtc gggaaggttc cttgcggttc gcggcgtgcc ggacgtgaca aacggaagcc   3180
gcacgtctca ctagtaccct cgcagacgga cagcgccagg gagcaatggc agcgcgccga   3240
ccgcgatggg ctgtggccaa tagcggctgc tcagcagggc gcgccgagag cagcggccgg   3300
gaaggggcgg tgcgggaggc ggggtgtggg gcggtagtgt gggccctgtt cctgcccgcg   3360
cggtgttccg cattctgcaa gcctccggag cgcacgtcgg cagtcggctc cctcgttgac   3420
cgaatcaccg acctctctcc ccagggggat ccaccggtcg ccaccatggt gagcaagggc   3480
gaggagctgt tcaccggggt ggtgcccatc ctggtcgagc tggacggcga cgtaaacggc   3540
cacaagttca gcgtgtccgg cgagggcgag ggcgatgcca cctacggcaa gctgaccctg   3600
aagttcatct gcaccaccgg caagctgccc gtgccctggc ccaccctcgt gaccaccctg   3660
acctacggcg tgcagtgctt cagccgctac cccgaccaca tgaagcagca cgacttcttc   3720
aagtccgcca tgcccgaagg ctacgtccag gagcgcacca tcttcttcaa ggacgacggc   3780
aactacaaga cccgcgccga ggtgaagttc gagggcgaca ccctggtgaa ccgcatcgag   3840
ctgaagggca tcgacttcaa ggaggacggc aacatcctgg ggcacaagct ggagtacaac   3900
tacaacagcc acaacgtcta tatcatggcc gacaagcaga agaacggcat caaggtgaac   3960
ttcaagatcc gccacaacat cgaggacggc agcgtgcagc tcgccgacca ctaccagcag   4020
aacaccccca tcggcgacgg ccccgtgctg ctgcccgaca accactacct gagcacccag   4080
tccgccctga gcaaagaccc caacgagaag cgcgatcaca tggtcctgct ggagttcgtg   4140
accgccgccg ggatcactct cggcatggac gagctgtaca agtaaagcgg ccgcgactct   4200
agagtcgacc tgcaggcatg caagcttgat atcaagctta tcgataatca acctctggat   4260
tacaaaattt gtgaaagatt gactggtatt cttaactatg ttgctccttt tacgctatgt   4320
ggatacgctg ctttaatgcc tttgtatcat gctattgctt cccgtatggc tttcattttc   4380
tcctccttgt ataaatcctg gttgctgtct ctttatgagg agttgtggcc cgttgtcagg   4440
caacgtggcg tggtgtgcac tgtgtttgct gacgcaaccc ccactggttg gggcattgcc   4500
accacctgtc agctcctttc cgggactttc gctttccccc tccctattgc cacggcggaa   4560
ctcatcgccg cctgccttgc ccgctgctgg acaggggctc ggctgttggg cactgacaat   4620
tccgtggtgt tgtcggggaa atcatcgtcc tttccttggc tgctcgcctg tgttgccacc   4680
tggattctgc gcgggacgtc cttctgctac gtcccttcgg ccctcaatcc agcggacctt   4740
ccttcccgcg gcctgctgcc ggctctgcgg cctcttccgc gtcttcgcct tcgccctcag   4800
```

-continued

```
acgagtcgga tctccctttg ggccgcctcc ccgcatcgat accgtcgacc tcgagtttta   4860

taaaagaaaa ggggggactg gaagggattt attacagtgc aagaagacat agaatcttag   4920

acatgtactt agaaaaggaa gaaggcatca taccagattg gcaggattac acctcaggac   4980

caggaattag atacccaaag acatttggct ggctatggaa attagtccct gtaaatgtat   5040

cagatgaggc acaggaggat gagaggcatt atttaatgca gccagctcaa acttccaagt   5100

gggatgaccc ttggggagag gttctagcgt ggaagtttga tccaactcta gcctacactt   5160

atgaggcata tgctagatac ccagaagagt tggaagcaag tcaggcctgt cagaactgca   5220

tttcgctctg tattcagtcg ctctgcggag aggctggcag attgagccct gggaggttct   5280

ctccagcact agcaggtaga gcctgggtgt tccctgctag actctcacca gcacttggcc   5340

agtgctgggc agagtggctc cacgcttgct tgcttaaaga cctcttcaat aaagctgcca   5400

ttttagaagt aagccagtgt gtgttcccat ctctcctagt cgccgcctgg tcaactcggt   5460

actcggtaat aagaagaccc tggtctgtta ggaccctttc tgctttgaga aaccgaagca   5520

ggaaaatccc tagcatggta cccagctttt gttcccttta gtgagggtta attccgagct   5580

tggcgtaatc atggtcatag ctgtttcctg tgtgaaattg ttatccgctc acaattccac   5640

acaacatacg agccggaagc ataaagtgta aa                                 5672
```

<210> SEQ ID NO 41
<211> LENGTH: 5950
<212> TYPE: DNA
<213> ORGANISM: Artificial Sequence
<220> FEATURE:
<223> OTHER INFORMATION: sequence for screening human cells floxed

<400> SEQUENCE: 41

```
gggctaattc actcccaaag aagacaagat atccttgatc tgtggatcta ccacacacaa     60

ggctacttcc ctgattagca gaactacaca ccagggccag gggtcagata tccactgacc    120

tttggatggt gctacaagct agtaccagtt gagccagata aggtagaaga ggccaataaa    180

ggagagaaca ccagcttgtt acaccctgtg agcctgcatg ggatggatga cccggagaga    240

gaagtgttag agtggaggtt tgacagccgc ctagcatttc atcacgtggc ccgagagctg    300

catccggagt acttcaagaa ctgctgatat cgagcttgct acaagggact ttccgctggg    360

gactttccag ggaggcgtgg cctgggcggg actggggagt ggcgagccct cagatcctgc    420

atataagcag ctgctttttg cctgtactgg gtctctctgg ttagaccaga tctgagcctg    480

ggagctctct ggctaactag ggaacccact gcttaagcct caataaagct tgccttgagt    540

gcttcaagta gtgtgtgccc gtctgttgtg tgactctggt aactagagat ccctcagacc    600

cttttagtca gtgtggaaaa tctctagcag tggcgcccga acagggactt gaaagcgaaa    660

gggaaaccag aggagctctc tcgacgcagg actcggcttg ctgaagcgcg cacggcaaga    720

ggcgaggggc ggcgactggt gagtacgcca aaaattttga ctagcggagg ctagaaggag    780

agagatgggt gcgagagcgt cagtattaag cgggggagaa ttagatcgcg atgggaaaaa    840

attcggttaa ggccaggggg aaagaaaaaa tataaattaa aacatatagt atgggcaagc    900

agggagctag aacgattcgc agttaatcct ggcctgttag aaacatcaga aggctgtaga    960

caaatactgg gacagctaca accatccctt cagacaggat cagaagaact tagatcatta   1020

tataatacag tagcaaccct ctattgtgtg catcaaagga tagagataaa agacaccaag   1080

gaagctttag acaagataga ggaagagcaa aacaaaagta agaccaccgc acagcaagcg   1140

gccgctgatc ttcagacctg gaggaggaga tatgagggac aattggagaa gtgaattata   1200
```

```
taaatataaa gtagtaaaaa ttgaaccatt aggagtagca cccaccaagg caaagagaag   1260
agtggtgcag agagaaaaaa gagcagtggg aataggagct ttgttccttg ggttcttggg   1320
agcagcagga agcactatgg gcgcagcgtc aatgacgctg acggtacagg ccagacaatt   1380
attgtctggt atagtgcagc agcagaacaa tttgctgagg gctattgagg cgcaacagca   1440
tctgttgcaa ctcacagtct ggggcatcaa gcagctccag gcaagaatcc tggctgtgga   1500
aagataccta aaggatcaac agctcctggg gatttggggt tgctctggaa aactcatttg   1560
caccactgct gtgccttgga atgctagttg gagtaataaa tctctggaac agatttggaa   1620
tcacacgacc tggatggagt gggacagaga aattaacaat tacacaagct taatacactc   1680
cttaattgaa gaatcgcaaa accagcaaga aaagaatgaa caagaattat tggaattaga   1740
taaatgggca agtttgtgga attggtttaa cataacaaat tggctgtggt atataaaatt   1800
attcataatg atagtaggag gcttggtagg tttaagaata gtttttgctg tactttctat   1860
agtgaataga gttaggcagg gatattcacc attatcgttt cagacccacc tcccaacccc   1920
gaggggaccc gacaggcccg aaggaataga agaagaaggt ggagagagag acagagacag   1980
atccattcga ttagtgaacg gatctcgacg gtatcgccga attcacaaat ggcagtattc   2040
atccacaatt ttaaaagaaa aggggggatt ggggggtaca gtgcagggga aagaatagta   2100
gacataatag caacagacat acaaactaaa gaattacaaa aacaaattac aaaaattcaa   2160
aattttcggg tttattacag ggacagcaga gatccacttt atcgataagc ttgggagttc   2220
cgcgttacat aacttacggt aaatggcccg cctggctgac cgcccaacga cccccgccca   2280
ttgacgtcaa taatgacgta tgttcccata gtaacgccaa tagggacttt ccattgacgt   2340
caatgggtgg agtatttacg gtaaactgcc cacttggcag tacatcaagt gtatcatatg   2400
ccaagtacgc cccctattga cgtcaatgac ggtaaatggc ccgcctggca ttatgcccag   2460
tacatgacct tacgggactt tcctacttgg cagtacatct acgtattagt catcgctatt   2520
accatggtga tgcggttttg gcagtacacc aatgggcgtg gatagcggtt tgactcacgg   2580
ggatttccaa gtctccaccc cattgacgtc aatgggagtt tgttttggca ccaaaatcaa   2640
cgggactttc caaaatgtcg taacaactcc gccccattga cgcaaatggg cggtaggcgt   2700
gtacggtggg aggtctatat aagcagagct cgtttagtga accgtcagat cgcctggaga   2760
cgccatccac gctgttttga cctccataga agacaccgac tctagctaga ggatccggac   2820
tagtaactcg aggatgggga ctgacccggg ctgcaggaat tcataacttc gtataatgta   2880
tgctatacga agttatcata tgccaccatg agcgagctga tcaaggagaa catgcacatg   2940
aagctgtaca tggagggcac cgtgaacaac caccacttca agtgcacatc cgagggcgaa   3000
ggcaagccct acgagggcac ccagaccatg aagatcaagg tggtcgaggg cggccctctc   3060
cccttcgcct tcgacatcct ggctaccagc ttcatgtacg gcagcaaagc cttcatcaac   3120
cacacccagg gcatccccga cttctttaag cagtccttcc ctgagggctt cacatgggag   3180
agaatcacca catacgaaga cgggggcgtg ctgaccgcta cccaggacac cagcttccag   3240
aacggctgca tcatctacaa cgtcaagatc aacggggtga acttcccatc caacggccct   3300
gtgatgcaga agaaaacacg cggctgggag gccaacaccg agatgctgta ccccgctgac   3360
ggcggcctga gaggccacag ccagatggcc ctgaagctcg tgggcggggg ctacctgcac   3420
tgctccttca agaccacata cagatccaag aaacccgcta agaacctcaa gatgcccggc   3480
ttccacttcg tggaccacag actggaaaga atcaaggagg ccgacaaaga gacctacgtc   3540
```

-continued

```
gagcagcacg agatggctgt ggccaagtac tgcgacctcc ctagcaaact ggggcacaga   3600
taaataactt cgtataaagt atcctatacg aagttatact ttggccgcgg ctcgaggggg   3660
ttggggttgc gccttttcca aggcagccct gggtttgcgc agggacgcgg ctgctctggg   3720
cgtggttccg ggaaacgcag cggcgccgac cctgggtctc gcacattctt cacgtccgtt   3780
cgcagcgtca cccggatctt cgccgctacc cttgtgggcc ccccggcgac gcttcctgct   3840
ccgcccctaa gtcgggaagg ttccttgcgg ttcgcggcgt gccggacgtg acaaacggaa   3900
gccgcacgtc tcactagtac cctcgcagac ggacagcgcc agggagcaat ggcagcgcgc   3960
cgaccgcgat gggctgtggc caatagcggc tgctcagcag ggcgcgccga gagcagcggc   4020
cgggaagggg cggtgcggga ggcggggtgt ggggcggtag tgtgggccct gttcctgccc   4080
gcgcggtgtt ccgcattctg caagcctccg gagcgcacgt cggcagtcgg ctccctcgtt   4140
gaccgaatca ccgacctctc tccccagggg gatccaccgg tcgccaccat ggtgagcaag   4200
ggcgaggagc tgttcaccgg ggtggtgccc atcctggtcg agctggacgg cgacgtaaac   4260
ggccacaagt tcagcgtgtc cggcgagggc gagggcgatg ccacctacgg caagctgacc   4320
ctgaagttca tctgcaccac cggcaagctg cccgtgccct ggcccaccct cgtgaccacc   4380
ctgacctacg gcgtgcagtg cttcagccgc taccccgacc acatgaagca gcacgacttc   4440
ttcaagtccg ccatgcccga aggctacgtc caggagcgca ccatcttctt caaggacgac   4500
ggcaactaca agacccgcgc cgaggtgaag ttcgagggcg acaccctggt gaaccgcatc   4560
gagctgaagg gcatcgactt caaggaggac ggcaacatcc tggggcacaa gctggagtac   4620
aactacaaca gccacaacgt ctatatcatg gccgacaagc agaagaacgg catcaaggtg   4680
aacttcaaga tccgccacaa catcgaggac ggcagcgtgc agctcgccga ccactaccag   4740
cagaacaccc ccatcggcga cggccccgtg ctgctgcccg acaaccacta cctgagcacc   4800
cagtccgccc tgagcaaaga ccccaacgag aagcgcgatc acatggtcct gctggagttc   4860
gtgaccgccg ccgggatcac tctcggcatg gacgagctgt acaagtaaga tatcaagctt   4920
atcgataatc aacctctgga ttacaaaatt tgtgaaagat tgactggtat tcttaactat   4980
gttgctcctt ttacgctatg tggatacgct gctttaatgc ctttgtatca tgctattgct   5040
tcccgtatgg ctttcatttt ctcctccttg tataaatcct ggttgctgtc tctttatgag   5100
gagttgtggc ccgttgtcag gcaacgtggc gtggtgtgca ctgtgtttgc tgacgcaacc   5160
cccactggtt ggggcattgc caccacctgt cagctccttt ccgggacttt cgctttcccc   5220
ctccctattg ccacggcgga actcatcgcc gcctgccttg cccgctgctg gacaggggct   5280
cggctgttgg gcactgacaa ttccgtggtg ttgtcgggga aatcatcgtc ctttccttgg   5340
ctgctcgcct gtgttgccac ctggattctg cgcgggacgt ccttctgcta cgtcccttcg   5400
gccctcaatc cagcggacct tccttcccgc ggcctgctgc cggctctgcg gcctcttccg   5460
cgtcttcgcc ttcgccctca gacgagtcgg atctcccttt gggccgcctc cccgcatcga   5520
taccgtcgac ctcgagaacc tagaaaaaca tggagcaatc acaagtagca atacagcagc   5580
taccaatgct gattgtgcct ggctagaagc acaagaggag gaggaggtgg gttttccagt   5640
cacacctcag gtacctttaa gaccaatgac ttacaaggca gctgtagatc ttagccactt   5700
tttaaaagaa aaggggggac tggaagggct aattcactcc caacgaagac aagatctttt   5760
tgcttgtact gggtctctct ggttagacca gatctgagcc tgggagctct ctggctaact   5820
agggaaccca ctgcttaagc ctcaataaag cttgccttga gtgcttcaag tagtgtgtgc   5880
ccgtctgttg tgtgactctg gtaactagag atccctcaga cccttttagt cagtgtggaa   5940
```

aatctctaga 5950

<210> SEQ ID NO 42
<211> LENGTH: 5837
<212> TYPE: DNA
<213> ORGANISM: Artificial Sequence
<220> FEATURE:
<223> OTHER INFORMATION: sequence fr screening human cells floxed

<400> SEQUENCE: 42
gggctaattc actcccaaag aagacaagat atccttgatc tgtggatcta ccacacacaa 60
ggctacttcc ctgattagca gaactacaca ccagggccag gggtcagata tccactgacc 120
tttggatggt gctacaagct agtaccagtt gagccagata aggtagaaga ggccaataaa 180
ggagagaaca ccagcttgtt acaccctgtg agcctgcatg ggatggatga cccggagaga 240
gaagtgttag agtggaggtt tgacagccgc ctagcatttc atcacgtggc ccgagagctg 300
catccggagt acttcaagaa ctgctgatat cgagcttgct acaagggact ttccgctggg 360
gactttccag ggaggcgtgg cctgggcggg actggggagt ggcgagccct cagatcctgc 420
atataagcag ctgctttttg cctgtactgg gtctctctgg ttagaccaga tctgagcctg 480
ggagctctct ggctaactag ggaacccact gcttaagcct caataaagct tgccttgagt 540
gcttcaagta gtgtgtgccc gtctgttgtg tgactctggt aactagagat ccctcagacc 600
cttttagtca gtgtggaaaa tctctagcag tggcgcccga acagggactt gaaagcgaaa 660
gggaaaccag aggagctctc tcgacgcagg actcggcttg ctgaagcgcg cacggcaaga 720
ggcgaggggc ggcgactggt gagtacgcca aaaattttga ctagcggagg ctagaaggag 780
agagatgggt gcgagagcgt cagtattaag cgggggagaa ttagatcgcg atgggaaaaa 840
attcggttaa ggccaggggg aaagaaaaaa tataaattaa aacatatagt atgggcaagc 900
agggagctag aacgattcgc agttaatcct ggcctgttag aaacatcaga aggctgtaga 960
caaatactgg gacagctaca accatccctt cagacaggat cagaagaact tagatcatta 1020
tataatacag tagcaaccct ctattgtgtg catcaaagga tagagataaa agacaccaag 1080
gaagctttag acaagataga ggaagagcaa aacaaaagta agaccaccgc acagcaagcg 1140
gccgctgatc ttcagacctg gaggaggaga tatgagggac aattggagaa gtgaattata 1200
taaatataaa gtagtaaaaa ttgaaccatt aggagtagca cccaccaagg caaagagaag 1260
agtggtgcag agagaaaaaa gagcagtggg aataggagct ttgttccttg ggttcttggg 1320
agcagcagga agcactatgg gcgcagcgtc aatgacgctg acggtacagg ccagacaatt 1380
attgtctggt atagtgcagc agcagaacaa tttgctgagg gctattgagg cgcaacagca 1440
tctgttgcaa ctcacagtct ggggcatcaa gcagctccag gcaagaatcc tggctgtgga 1500
aagataccta aaggatcaac agctcctggg gatttggggt tgctctggaa aactcatttg 1560
caccactgct gtgccttgga atgctagttg gagtaataaa tctctggaac agatttggaa 1620
tcacacgacc tggatggagt gggacagaga aattaacaat tacacaagct taatacactc 1680
cttaattgaa gaatcgcaaa accagcaaga aaagaatgaa caagaattat tggaattaga 1740
taaatgggca agtttgtgga attggtttaa cataacaaat tggctgtggt atataaaatt 1800
attcataatg atagtaggag gcttggtagg tttaagaata gtttttgctg tactttctat 1860
agtgaataga gttaggcagg gatattcacc attatcgttt cagacccacc tcccaacccc 1920
gaggggaccc gacaggcccg aaggaataga agaagaaggt ggagagagag acagagacag 1980

-continued

```
atccattcga ttagtgaacg gatctcgacg gtatcgccga attcacaaat ggcagtattc   2040
atccacaatt ttaaaagaaa aggggggatt ggggggtaca gtgcagggga aagaatagta   2100
gacataatag caacagacat acaaactaaa gaattacaaa aacaaattac aaaaattcaa   2160
aattttcggg tttattacag ggacagcaga gatccacttt atcgatggtc cggtccggaa   2220
ttcctgcagc cccgataaaa taaaagattt tatttagtct ccagaaaaag gggggaatga   2280
aagaccccac ctgtaggttt ggcaagctag ctgcagtaac gccattttgc aaggcatgga   2340
aaaataccaa accaagaata gagaagttca gatcaagggc gggtacatga aaatagctaa   2400
cgttgggcca aacaggatat ctgcggtgag cagtttcggc cccggcccgg ggccaagaac   2460
agatggtcac cgcagtttcg gccccggccc gaggccaaga acagatggtc cccagatatg   2520
gcccaaccct cagcagtttc ttaagaccca tcagatgttt ccaggctccc ccaaggacct   2580
gaaatgaccc tgcgccttat ttgaattaac caatcagcct gcttctcgct tctgttcgcg   2640
cgcttctgct tcccgagctc tataaaagag ctcacaaccc ctcactcggc gcgccagtcc   2700
tccgacagac tgagtcgccc ggggggggatc caccgggctg caggaattca taacttcgta   2760
taatgtatgc tatacgaagt tatcatatgc caccatgagc gagctgatca aggagaacat   2820
gcacatgaag ctgtacatgg agggcaccgt gaacaaccac cacttcaagt gcacatccga   2880
gggcgaaggc aagccctacg agggcaccca gaccatgaag atcaaggtgg tcgagggcgg   2940
ccctctcccc ttcgccttcg acatcctggc taccagcttc atgtacggca gcaaagcctt   3000
catcaaccac acccagggca tccccgactt ctttaagcag tccttccctg agggcttcac   3060
atgggagaga atcaccacat acgaagacgg gggcgtgctg accgctaccc aggacaccag   3120
cttccagaac ggctgcatca tctacaacgt caagatcaac ggggtgaact tcccatccaa   3180
cggccctgtg atgcagaaga aaacacgcgg ctgggaggcc aacaccgaga tgctgtaccc   3240
cgctgacggc ggcctgagag gccacagcca gatggccctg aagctcgtgg gcgggggcta   3300
cctgcactgc tccttcaaga ccacatacag atccaagaaa cccgctaaga acctcaagat   3360
gcccggcttc cacttcgtgg accacagact ggaaagaatc aaggaggccg acaaagagac   3420
ctacgtcgag cagcacgaga tggctgtggc caagtactgc gacctcccta gcaaactggg   3480
gcacagataa ataacttcgt ataaagtatc ctatacgaag ttatactttg gccgcggctc   3540
gagggggttg ggttgcgcc ttttccaagg cagccctggg tttgcgcagg gacgcggctg   3600
ctctgggcgt ggttccggga aacgcagcgg cgccgaccct gggtctcgca cattcttcac   3660
gtccgttcgc agcgtcaccc ggatcttcgc cgctaccctt gtgggccccc cggcgacgct   3720
tcctgctccg cccctaagtc gggaaggttc cttgcggttc gcggcgtgcc ggacgtgaca   3780
aacggaagcc gcacgtctca ctagtaccct cgcagacgga cagcgccagg gagcaatggc   3840
agcgcgccga ccgcgatggg ctgtggccaa tagcggctgc tcagcagggc gcgccgagag   3900
cagcggccgg gaaggggcgg tgcgggaggc ggggtgtggg gcggtagtgt gggccctgtt   3960
cctgcccgcg cggtgttccg cattctgcaa gcctccggag cgcacgtcgg cagtcggctc   4020
cctcgttgac cgaatcaccg acctctctcc ccagggggat ccaccggtcg ccaccatggt   4080
gagcaagggc gaggagctgt tcaccggggt ggtgcccatc ctggtcgagc tggacggcga   4140
cgtaaacggc cacaagttca gcgtgtccgg cgagggcgag ggcgatgcca cctacggcaa   4200
gctgaccctg aagttcatct gcaccaccgg caagctgccc gtgccctggc ccaccctcgt   4260
gaccaccctg acctacggcg tgcagtgctt cagccgctac cccgaccaca tgaagcagca   4320
cgacttcttc aagtccgcca tgcccgaagg ctacgtccag gagcgcacca tcttcttcaa   4380
```

```
ggacgacggc aactacaaga cccgcgccga ggtgaagttc gagggcgaca ccctggtgaa   4440

ccgcatcgag ctgaagggca tcgacttcaa ggaggacggc aacatcctgg ggcacaagct   4500

ggagtacaac tacaacagcc acaacgtcta tatcatggcc gacaagcaga agaacggcat   4560

caaggtgaac ttcaagatcc gccacaacat cgaggacggc agcgtgcagc tcgccgacca   4620

ctaccagcag aacaccccca tcggcgacgg ccccgtgctg ctgcccgaca accactacct   4680

gagcacccag tccgccctga gcaaagaccc caacgagaag cgcgatcaca tggtcctgct   4740

ggagttcgtg accgccgccg ggatcactct cggcatggac gagctgtaca agtaagatat   4800

caagcttatc gataatcaac ctctggatta caaaatttgt gaaagattga ctggtattct   4860

taactatgtt gctcctttta cgctatgtgg atacgctgct ttaatgcctt tgtatcatgc   4920

tattgcttcc cgtatggctt tcattttctc ctccttgtat aaatcctggt tgctgtctct   4980

ttatgaggag ttgtggcccg ttgtcaggca acgtggcgtg gtgtgcactg tgtttgctga   5040

cgcaaccccc actggttggg gcattgccac cacctgtcag ctcctttccg ggactttcgc   5100

tttccccctc cctattgcca cggcggaact catcgccgcc tgccttgccc gctgctggac   5160

aggggctcgg ctgttgggca ctgacaattc cgtggtgttg tcggggaaat catcgtcctt   5220

tccttggctg ctcgcctgtg ttgccacctg gattctgcgc gggacgtcct tctgctacgt   5280

cccttcggcc ctcaatccag cggaccttcc ttcccgcggc ctgctgccgg ctctgcggcc   5340

tcttccgcgt cttcgccttc gccctcagac gagtcggatc tccctttggg ccgcctcccc   5400

gcatcgatac cgtcgacctc gagaacctag aaaaacatgg agcaatcaca agtagcaata   5460

cagcagctac caatgctgat tgtgcctggc tagaagcaca agaggaggag gaggtgggtt   5520

ttccagtcac acctcaggta cctttaagac caatgactta caaggcagct gtagatctta   5580

gccacttttt aaaagaaaag gggggactgg aagggctaat tcactcccaa cgaagacaag   5640

atctttttgc ttgtactggg tctctctggt tagaccagat ctgagcctgg gagctctctg   5700

gctaactagg gaacccactg cttaagcctc aataaagctt gccttgagtg cttcaagtag   5760

tgtgtgcccg tctgttgtgt gactctggta actagagatc cctcagaccc ttttagtcag   5820

tgtggaaaat ctctaga                                                  5837
```

<210> SEQ ID NO 43
<211> LENGTH: 5971
<212> TYPE: DNA
<213> ORGANISM: Artificial Sequence
<220> FEATURE:
<223> OTHER INFORMATION: sequence for screening human cells floxed

<400> SEQUENCE: 43

```
gggctaattc actcccaaag aagacaagat atccttgatc tgtggatcta ccacacacaa     60

ggctacttcc ctgattagca gaactacaca ccagggccag gggtcagata tccactgacc    120

tttggatggt gctacaagct agtaccagtt gagccagata aggtagaaga ggccaataaa    180

ggagagaaca ccagcttgtt acaccctgtg agcctgcatg ggatggatga cccggagaga    240

gaagtgttag agtggaggtt tgacagccgc ctagcatttc atcacgtggc ccgagagctg    300

catccggagt acttcaagaa ctgctgatat cgagcttgct acaagggact ttccgctggg    360

gactttccag ggaggcgtgg cctgggcggg actggggagt ggcgagccct cagatcctgc    420

atataagcag ctgctttttg cctgtactgg gtctctctgg ttagaccaga tctgagcctg    480

ggagctctct ggctaactag ggaacccact gcttaagcct caataaagct tgccttgagt    540
```

-continued

```
gcttcaagta gtgtgtgccc gtctgttgtg tgactctggt aactagagat ccctcagacc    600
cttttagtca gtgtggaaaa tctctagcag tggcgcccga acagggactt gaaagcgaaa    660
gggaaaccag aggagctctc tcgacgcagg actcggcttg ctgaagcgcg cacggcaaga    720
ggcgaggggc ggcgactggt gagtacgcca aaaattttga ctagcggagg ctagaaggag    780
agagatgggt gcgagagcgt cagtattaag cgggggagaa ttagatcgcg atgggaaaaa    840
attcggttaa ggccaggggg aaagaaaaaa tataaattaa aacatatagt atgggcaagc    900
agggagctag aacgattcgc agttaatcct ggcctgttag aaacatcaga aggctgtaga    960
caaatactgg gacagctaca accatccctt cagacaggat cagaagaact tagatcatta   1020
tataatacag tagcaaccct ctattgtgtg catcaaagga tagagataaa agacaccaag   1080
gaagctttag acaagataga ggaagagcaa aacaaaagta agaccaccgc acagcaagcg   1140
gccgctgatc ttcagacctg gaggaggaga tatgagggac aattggagaa gtgaattata   1200
taaatataaa gtagtaaaaa ttgaaccatt aggagtagca cccaccaagg caaagagaag   1260
agtggtgcag agagaaaaaa gagcagtggg aataggagct ttgttccttg ggttcttggg   1320
agcagcagga agcactatgg gcgcagcgtc aatgacgctg acggtacagg ccagacaatt   1380
attgtctggt atagtgcagc agcagaacaa tttgctgagg gctattgagg cgcaacagca   1440
tctgttgcaa ctcacagtct ggggcatcaa gcagctccag gcaagaatcc tggctgtgga   1500
aagataccta aaggatcaac agctcctggg gatttggggt tgctctggaa aactcatttg   1560
caccactgct gtgccttgga atgctagttg gagtaataaa tctctggaac agatttggaa   1620
tcacacgacc tggatggagt gggacagaga aattaacaat tacacaagct taatacactc   1680
cttaattgaa gaatcgcaaa accagcaaga aaagaatgaa caagaattat tggaattaga   1740
taaatgggca agtttgtgga attggtttaa cataacaaat tggctgtggt atataaaatt   1800
attcataatg atagtaggag gcttggtagg tttaagaata gtttttgctg tactttctat   1860
agtgaataga gttaggcagg gatattcacc attatcgttt cagacccacc tcccaacccc   1920
gaggggaccc gacaggcccg aaggaataga agaagaaggt ggagagagag acagagacag   1980
atccattcga ttagtgaacg gatctcgacg gtatcgccga attcacaaat ggcagtattc   2040
atccacaatt ttaaaagaaa aggggggatt ggggggtaca gtgcagggga aagaatagta   2100
gacataatag caacagacat acaaactaaa gaattacaaa aacaaattac aaaaattcaa   2160
aattttcggg tttattacag ggacagcaga gatccacttt atcgatggtc cggtccggaa   2220
ttcctgcagc cccgataaaa taaaagattt tatttagtct ccagaaaaag gggggaatga   2280
aagaccccac ctgtaggttt ggcaagctag ctgcagtaac gccattttgc aaggcatgga   2340
aaaataccaa accaagaata gagaagttca gatcaagggc gggtacatga aaatagctaa   2400
cgttgggcca aacaggatat ctgcggtgag cagtttcggc cccggcccgg ggccaagaac   2460
agatggtcac cgcagtttcg gccccggccc gaggccaaga acagatggtc cccagatatg   2520
gcccaaccct cagcagtttc ttaagaccca tcagatgttt ccaggctccc ccaaggacct   2580
gaaatgaccc tgcgccttat ttgaattaac caatcagcct gcttctcgct tctgttcgcg   2640
cgcttctgct tcccgagctc tataaaagag ctcacaaccc ctcactcggc gcgccagtcc   2700
tccgacagac tgagtcgccc ggggggggatc caccgggctg caggaattca taacttcgta   2760
taatgtatgc tatacgaagt tatcatatgc caccatgagc gagctgatca aggagaacat   2820
gcacatgaag ctgtacatgg agggcaccgt gaacaaccac cacttcaagt gcacatccga   2880
gggcgaaggc aagccctacg agggcaccca gaccatgaag atcaaggtgg tcgagggcgg   2940
```

ccctctcccc ttcgccttcg acatcctggc taccagcttc atgtacggca gcaaagcctt 3000
catcaaccac acccagggca tccccgactt ctttaagcag tccttccctg agggcttcac 3060
atgggagaga atcaccacat acgaagacgg gggcgtgctg accgctaccc aggacaccag 3120
cttccagaac ggctgcatca tctacaacgt caagatcaac ggggtgaact tcccatccaa 3180
cggccctgtg atgcagaaga aaacacgcgg ctgggaggcc aacaccgaga tgctgtaccc 3240
cgctgacggc ggcctgagag gccacagcca gatggccctg aagctcgtgg gcgggggcta 3300
cctgcactgc tccttcaaga ccacatacag atccaagaaa cccgctaaga acctcaagat 3360
gcccggcttc cacttcgtgg accacagact ggaaagaatc aaggaggccg acaaagagac 3420
ctacgtcgag cagcacgaga tggctgtggc caagtactgc gacctcccta gcaaactggg 3480
gcacagataa ataacttcgt ataaagtatc ctatacgaag ttatactttg gccgcggctc 3540
gaatctactt accgataagc ttgggagttc cgcgttacat aacttacggt aaatggcccg 3600
cctggctgac cgcccaacga cccccgccca ttgacgtcaa taatgacgta tgttcccata 3660
gtaacgccaa tagggacttt ccattgacgt caatgggtgg agtatttacg gtaaactgcc 3720
cacttggcag tacatcaagt gtatcatatg ccaagtacgc cccctattga cgtcaatgac 3780
ggtaaatggc ccgcctggca ttatgcccag tacatgacct tacgggactt tcctacttgg 3840
cagtacatct acgtattagt catcgctatt accatggtga tgcggttttg gcagtacacc 3900
aatgggcgtg gatagcggtt tgactcacgg ggatttccaa gtctccaccc cattgacgtc 3960
aatgggagtt tgttttggca ccaaaatcaa cgggactttc caaaatgtcg taacaactcc 4020
gccccattga cgcaaatggg cggtaggcgt gtacggtggg aggtctatat aagcagagct 4080
cgtttagtga accgtcagat cgcctggaga cgccatccac gctgttttga cctccataga 4140
agacaccgac tctagctaga ggatccggac tagtaactcg aggatgggga ctgacccgga 4200
cgcgtgccgc caccatggtg agcaagggcg aggagctgtt caccggggtg gtgcccatcc 4260
tggtcgagct ggacggcgac gtaaacggcc acaagttcag cgtgtccggc gagggcgagg 4320
gcgatgccac ctacggcaag ctgaccctga agttcatctg caccaccggc aagctgcccg 4380
tgccctggcc caccctcgtg accaccctga cctacggcgt gcagtgcttc agccgctacc 4440
ccgaccacat gaagcagcac gacttcttca agtccgccat gcccgaaggc tacgtccagg 4500
agcgcaccat cttcttcaag gacgacggca actacaagac ccgcgccgag gtgaagttcg 4560
agggcgacac cctggtgaac cgcatcgagc tgaagggcat cgacttcaag gaggacggca 4620
acatcctggg gcacaagctg gagtacaact acaacagcca caacgtctat atcatggccg 4680
acaagcagaa gaacggcatc aaggtgaact tcaagatccg ccacaacatc gaggacggca 4740
gcgtgcagct cgccgaccac taccagcaga acacccccat cggcgacggc cccgtgctgc 4800
tgcccgacaa ccactacctg agcacccagt ccgccctgag caaagacccc aacgagaagc 4860
gcgatcacat ggtcctgctg gagttcgtga ccgccgccgg gatcactctc ggcatggacg 4920
agctgtacaa gtaagatatc aagcttatcg ataatcaacc tctggattac aaaatttgtg 4980
aaagattgac tggtattctt aactatgttg ctccttttac gctatgtgga tacgctgctt 5040
taatgccttt gtatcatgct attgcttccc gtatggcttt cattttctcc tccttgtata 5100
aatcctggtt gctgtctctt tatgaggagt tgtggcccgt tgtcaggcaa cgtggcgtgg 5160
tgtgcactgt gtttgctgac gcaaccccca ctggttgggg cattgccacc acctgtcagc 5220
tcctttccgg gactttcgct ttccccctcc ctattgccac ggcggaactc atcgccgcct 5280

```
gccttgcccg ctgctggaca ggggctcggc tgttgggcac tgacaattcc gtggtgttgt   5340

cggggaaatc atcgtccttt ccttggctgc tcgcctgtgt tgccacctgg attctgcgcg   5400

ggacgtcctt ctgctacgtc ccttcggccc tcaatccagc ggaccttcct tcccgcggcc   5460

tgctgccggc tctgcggcct cttccgcgtc ttcgccttcg ccctcagacg agtcggatct   5520

ccctttgggc cgcctccccg catcgatacc gtcgacctcg agaacctaga aaaacatgga   5580

gcaatcacaa gtagcaatac agcagctacc aatgctgatt gtgcctggct agaagcacaa   5640

gaggaggagg aggtgggttt tccagtcaca cctcaggtac ctttaagacc aatgacttac   5700

aaggcagctg tagatcttag ccactttta aaagaaaagg ggggactgga agggctaatt   5760

cactcccaac gaagacaaga tctttttgct tgtactgggt ctctctggtt agaccagatc   5820

tgagcctggg agctctctgg ctaactaggg aacccactgc ttaagcctca ataaagcttg   5880

ccttgagtgc ttcaagtagt gtgtgcccgt ctgttgtgtg actctggtaa ctagagatcc   5940

ctcagaccct tttagtcagt gtggaaaatc t                                   5971
```

<210> SEQ ID NO 44
<211> LENGTH: 6907
<212> TYPE: DNA
<213> ORGANISM: Artificial Sequence
<220> FEATURE:
<223> OTHER INFORMATION: sequence for screening human cells floxed

<400> SEQUENCE: 44

```
gggctaattc actcccaaag aagacaagat atccttgatc tgtggatcta ccacacacaa     60

ggctacttcc ctgattagca gaactacaca ccagggccag gggtcagata tccactgacc    120

tttggatggt gctacaagct agtaccagtt gagccagata aggtagaaga ggccaataaa    180

ggagagaaca ccagcttgtt acaccctgtg agcctgcatg ggatggatga cccggagaga    240

gaagtgttag agtggaggtt tgacagccgc ctagcatttc atcacgtggc ccgagagctg    300

catccggagt acttcaagaa ctgctgatat cgagcttgct acaagggact ttccgctggg    360

gactttccag ggaggcgtgg cctgggcggg actggggagt ggcgagccct cagatcctgc    420

atataagcag ctgctttttg cctgtactgg gtctctctgg ttagaccaga tctgagcctg    480

ggagctctct ggctaactag ggaacccact gcttaagcct caataaagct tgccttgagt    540

gcttcaagta gtgtgtgccc gtctgttgtg tgactctggt aactagagat ccctcagacc    600

cttttagtca gtgtggaaaa tctctagcag tggcgcccga acagggactt gaaagcgaaa    660

gggaaaccag aggagctctc tcgacgcagg actcggcttg ctgaagcgcg cacggcaaga    720

ggcgaggggc ggcgactggt gagtacgcca aaaattttga ctagcggagg ctagaaggag    780

agagatgggt gcgagagcgt cagtattaag cgggggagaa ttagatcgcg atgggaaaaa    840

attcggttaa ggccaggggg aaagaaaaaa tataaattaa aacatatagt atgggcaagc    900

agggagctag aacgattcgc agttaatcct ggcctgttag aaacatcaga aggctgtaga    960

caaatactgg gacagctaca accatccctt cagacaggat cagaagaact tagatcatta   1020

tataatacag tagcaaccct ctattgtgtg catcaaagga tagagataaa agacaccaag   1080

gaagctttag acaagataga ggaagagcaa aacaaaagta agaccaccgc acagcaagcg   1140

gccgctgatc ttcagacctg gaggaggaga tatgagggac aattggagaa gtgaattata   1200

taaatataaa gtagtaaaaa ttgaaccatt aggagtagca cccaccaagg caaagagaag   1260

agtggtgcag agagaaaaaa gagcagtggg aataggagct ttgttccttg ggttcttggg   1320

agcagcagga agcactatgg gcgcagcgtc aatgacgctg acggtacagg ccagacaatt   1380
```

-continued

```
attgtctggt atagtgcagc agcagaacaa tttgctgagg gctattgagg cgcaacagca   1440
tctgttgcaa ctcacagtct ggggcatcaa gcagctccag gcaagaatcc tggctgtgga   1500
aagataccta aaggatcaac agctcctggg gatttggggt tgctctggaa aactcatttg   1560
caccactgct gtgccttgga atgctagttg gagtaataaa tctctggaac agatttggaa   1620
tcacacgacc tggatggagt gggacagaga aattaacaat tacacaagct taatacactc   1680
cttaattgaa gaatcgcaaa accagcaaga aaagaatgaa caagaattat tggaattaga   1740
taaatgggca agtttgtgga attggtttaa cataacaaat tggctgtggt atataaaatt   1800
attcataatg atagtaggag gcttggtagg tttaagaata gtttttgctg tactttctat   1860
agtgaataga gttaggcagg gatattcacc attatcgttt cagacccacc tcccaacccc   1920
gaggggaccc gacaggcccg aaggaataga agaagaaggt ggagagagag acagagacag   1980
atccattcga ttagtgaacg gatctcgacg gtatcgccga attcacaaat ggcagtattc   2040
atccacaatt ttaaaagaaa aggggggatt ggggggtaca gtgcagggga aagaatagta   2100
gacataatag caacagacat acaaactaaa gaattacaaa aacaaattac aaaaattcaa   2160
aattttcggg tttattacag ggacagcaga gatccacttt atcgataagc ttgggagttc   2220
cgcgttacat aacttacggt aaatggcccg cctggctgac cgcccaacga cccccgccca   2280
ttgacgtcaa taatgacgta tgttcccata gtaacgccaa tagggacttt ccattgacgt   2340
caatgggtgg agtatttacg gtaaactgcc cacttggcag tacatcaagt gtatcatatg   2400
ccaagtacgc cccctattga cgtcaatgac ggtaaatggc ccgcctggca ttatgcccag   2460
tacatgacct tacgggactt tcctacttgg cagtacatct acgtattagt catcgctatt   2520
accatggtga tgcggttttg gcagtacacc aatgggcgtg gatagcggtt tgactcacgg   2580
ggatttccaa gtctccaccc cattgacgtc aatgggagtt tgttttggca ccaaaatcaa   2640
cgggactttc caaaatgtcg taacaactcc gccccattga cgcaaatggg cggtaggcgt   2700
gtacggtggg aggtctatat aagcagagct cgtttagtga accgtcagat cgcctggaga   2760
cgccatccac gctgttttga cctccataga agacaccgac tctagctaga ggatccggac   2820
tagtaactcg aggatgggga ctgacccggg ctgcaggaat tcataacttc gtataatgta   2880
tgctatacga agttatcata tgccaccatg gaagacgcca aaaacataaa gaaaggcccg   2940
gcgccattct atccgctgga agatggaacc gctggagagc aactgcataa ggctatgaag   3000
agatacgccc tggttcctgg aacaattgct tttacagatg cacatatcga ggtggacatc   3060
acttacgctg agtacttcga aatgtccgtt cggttggcag aagctatgaa acgatatggg   3120
ctgaatacaa atcacagaat cgtcgtatgc agtgaaaact ctcttcaatt ctttatgccg   3180
gtgttgggcg cgttatttat cggagttgca gttgcgcccg cgaacgacat ttataatgaa   3240
cgtgaattgc tcaacagtat gggcatttcg cagcctaccg tggtgttcgt ttccaaaaag   3300
gggttgcaaa aaattttgaa cgtgcaaaaa aagctcccaa tcatccaaaa aattattatc   3360
atggattcta aaacggatta ccagggattt cagtcgatgt acacgttcgt cacatctcat   3420
ctacctcccg gttttaatga atacgatttt gtgccagagt ccttcgatag ggacaagaca   3480
attgcactga tcatgaactc ctctggatct actggtctgc ctaaaggtgt cgctctgcct   3540
catagaactg cctgcgtgag attctcgcat gccagagatc ctatttttgg caatcaaatc   3600
attccggata ctgcgatttt aagtgttgtt ccattccatc acggttttgg aatgtttact   3660
acactcggat atttgatatg tggatttcga gtcgtcttaa tgtatagatt tgaagaagag   3720
```

-continued

```
ctgtttctga ggagccttca ggattacaag attcaaagtg cgctgctggt gccaacccta   3780
ttctccttct tcgccaaaag cactctgatt gacaaatacg atttatctaa tttacacgaa   3840
attgcttctg gtggcgctcc cctctctaag gaagtcgggg aagcggttgc caagaggttc   3900
catctgccag gtatcaggca aggatatggg ctcactgaga ctacatcagc tattctgatt   3960
acacccgagg gggatgataa accgggcgcg gtcggtaaag ttgttccatt ttttgaagcg   4020
aaggttgtgg atctggatac cgggaaaacg ctgggcgtta atcaaagagg cgaactgtgt   4080
gtgagaggtc ctatgattat gtccggttat gtaaacaatc cggaagcgac caacgccttg   4140
attgacaagg atggatggct acattctgga gacatagctt actgggacga agacgaacac   4200
ttcttcatcg ttgaccgcct gaagtctctg attaagtaca aaggctatca ggtggctccc   4260
gctgaattgg aatccatctt gctccaacac cccaacatct tcgacgcagg tgtcgcaggt   4320
cttcccgacg atgacgccgg tgaacttccc gccgccgttg ttgttttgga gcacggaaag   4380
acgatgacgg aaaaagagat cgtggattac gtcgccagtc aagtaacaac cgcgaaaaag   4440
ttgcgcggag gagttgtgtt tgtggacgaa gtaccgaaag gtcttaccgg aaaactcgac   4500
gcaagaaaaa tcagagagat cctcataaag gccaagaagg gcggaaagat cgccgtgtaa   4560
ataacttcgt ataaagtatc ctatacgaag ttatactttg gccgcggctc gagggggttg   4620
gggttgcgcc ttttccaagg cagccctggg tttgcgcagg gacgcggctg ctctgggcgt   4680
ggttccggga aacgcagcgg cgccgaccct gggtctcgca cattcttcac gtccgttcgc   4740
agcgtcaccc ggatcttcgc cgctaccctt gtgggccccc cggcgacgct tcctgctccg   4800
cccctaagtc gggaaggttc cttgcggttc gcggcgtgcc ggacgtgaca aacggaagcc   4860
gcacgtctca ctagtaccct cgcagacgga cagcgccagg gagcaatggc agcgcgccga   4920
ccgcgatggg ctgtggccaa tagcggctgc tcagcagggc gcgccgagag cagcggccgg   4980
gaaggggcgg tgcgggaggc ggggtgtggg gcggtagtgt gggccctgtt cctgcccgcg   5040
cggtgttccg cattctgcaa gcctccggag cgcacgtcgg cagtcggctc cctcgttgac   5100
cgaatcaccg acctctctcc ccagggggat ccaccggtcg ccaccatggt gagcaagggc   5160
gaggagctgt tcaccggggt ggtgcccatc ctggtcgagc tggacggcga cgtaaacggc   5220
cacaagttca gcgtgtccgg cgagggcgag ggcgatgcca cctacggcaa gctgaccctg   5280
aagttcatct gcaccaccgg caagctgccc gtgccctggc ccaccctcgt gaccaccctg   5340
acctacggcg tgcagtgctt cagccgctac cccgaccaca tgaagcagca cgacttcttc   5400
aagtccgcca tgcccgaagg ctacgtccag gagcgcacca tcttcttcaa ggacgacggc   5460
aactacaaga cccgcgccga ggtgaagttc gagggcgaca ccctggtgaa ccgcatcgag   5520
ctgaagggca tcgacttcaa ggaggacggc aacatcctgg ggcacaagct ggagtacaac   5580
tacaacagcc acaacgtcta tatcatggcc gacaagcaga agaacggcat caaggtgaac   5640
ttcaagatcc gccacaacat cgaggacggc agcgtgcagc tcgccgacca ctaccagcag   5700
aacaccccca tcggcgacgg ccccgtgctg ctgcccgaca accactacct gagcacccag   5760
tccgccctga gcaaagaccc caacgagaag cgcgatcaca tggtcctgct ggagttcgtg   5820
accgccgccg ggatcactct cggcatggac gagctgtaca agtaagatat caagcttatc   5880
gataatcaac ctctggatta caaaatttgt gaaagattga ctggtattct taactatgtt   5940
gctcctttta cgctatgtgg atacgctgct ttaatgcctt tgtatcatgc tattgcttcc   6000
cgtatggctt tcattttctc ctccttgtat aaatcctggt tgctgtctct ttatgaggag   6060
ttgtggcccg ttgtcaggca acgtggcgtg gtgtgcactg tgtttgctga cgcaaccccc   6120
```

actggttggg gcattgccac cacctgtcag ctcctttccg ggactttcgc tttccccctc 6180
cctattgcca cggcggaact catcgccgcc tgccttgccc gctgctggac aggggctcgg 6240
ctgttgggca ctgacaattc cgtggtgttg tcggggaaat catcgtcctt tccttggctg 6300
ctcgcctgtg ttgccacctg gattctgcgc gggacgtcct tctgctacgt cccttcggcc 6360
ctcaatccag cggaccttcc ttcccgcggc ctgctgccgg ctctgcggcc tcttccgcgt 6420
cttcgccttc gccctcagac gagtcggatc tccctttggg ccgcctcccc gcatcgatac 6480
cgtcgacctc gagaacctag aaaaacatgg agcaatcaca agtagcaata cagcagctac 6540
caatgctgat tgtgcctggc tagaagcaca agaggaggag gaggtgggtt ttccagtcac 6600
acctcaggta cctttaagac caatgactta caaggcagct gtagatctta gccacttttt 6660
aaaagaaaag gggggactgg aagggctaat tcactcccaa cgaagacaag atctttttgc 6720
ttgtactggg tctctctggt tagaccagat ctgagcctgg gagctctctg gctaactagg 6780
gaacccactg cttaagcctc aataaagctt gccttgagtg cttcaagtag tgtgtgcccg 6840
tctgttgtgt gactctggta actagagatc cctcagaccc ttttagtcag tgtggaaaat 6900
ctctaga 6907

<210> SEQ ID NO 45
<211> LENGTH: 5872
<212> TYPE: DNA
<213> ORGANISM: Artificial Sequence
<220> FEATURE:
<223> OTHER INFORMATION: sequence for screening simian cells floxed

<400> SEQUENCE: 45
cagtcgctct gcggagaggc tggcagattg agccctggga ggttctctcc agcactagca 60
ggtagagcct gggtgttccc tgctagactc tcaccagcac ttggccagtg ctgggcagag 120
tggctccacg cttgcttgct taaagacctc ttcaataaag ctgccatttt agaagtaagc 180
cagtgtgtgt tcccatctct cctagtcgcc gcctggtcaa ctcggtactc ggtaataaga 240
agaccctggt ctgttaggac cctttctgct ttgagaaacc gaagcaggaa aatccctagc 300
agattggcgc ccgaacaggg acttgaagga gagtgagaga ctcctgagta cggctgagtg 360
aaggcagtaa gggcggcagg aaccaaccac gacggagtgc tcctataaag gcgcgggtcg 420
gtaccagacg gcgtgaggag cgggagagga ggaggcctcc ggttgcagta agtgcaacac 480
aaaaaagaaa tagctgtctt gttatccagg aagggataat aagatagagt gggagatggg 540
cgcgagaaac tccgtcttgt cagggaagaa agcagatgaa ttgaaaaaat tattaatcgc 600
atgaatttta aaagaagggg aggaataggg gatatgactc cagcagaaag attaattaac 660
atgatcacta cagaacaaga aatacaattt caacaatcaa aaaactcaaa atttaaaaat 720
tttcgggtct attacagagc tcacgcgtga ttggagttgg gagattataa attagtagag 780
atcactccga ttggcttggc ccccacagat gtgaagaggt acactactgg tggcacctca 840
agaaataaaa gaggggtctt tgtgctaggg ttcttgggtt ttctcgcaac ggcaggttct 900
gcaatgggcg cggcgtcgtt gacgctgacc gctcagtccc ggactttatt ggctgggata 960
gtgcagcaac agcaacagct gttggacgtg gtcaagagac aacaagaatt gttgcgactg 1020
accgtctggg gaacaaagaa cctccagact agggtcactg ccatcgagaa gtacttaaag 1080
gaccaggcgc agctaaatgc ttggggatgt gcgtttagac aagtctgcca cactactgta 1140
ccatggccaa atgcaagtct aacaccagac tggaacaatg atacttggca agagtgggag 1200

```
cgaaaggttg acttcttgga ggaaaatata acagccctcc tagaagaggc acaaattcaa   1260
caagagaaga acatgtatga attacaaaag ttgaatagct gggatgtgtt tggcaattgg   1320
tttgaccttg cttcttggat aaagtatata caatatggaa tttatgtagt tgtaggagta   1380
atactgttaa gaatagtgat ctatatagta caaatgctag ctaagttaag gcaggggtat   1440
aggccagtgt tctcttcccc accctcttat ttccagtaga ctcataccca acaggacccg   1500
gcactgccaa ccagagaagg caaagaagga gacggtggag aaggcggtgg atcctattat   1560
cgaattcctg cagccccgat aaaataaaag attttattta gtctccagaa aaagggggga   1620
atgaaagacc ccacctgtag gtttggcaag ctagctgcag taacgccatt ttgcaaggca   1680
tggaaaaata ccaaaccaag aatagagaag ttcagatcaa gggcgggtac atgaaaatag   1740
ctaacgttgg gccaaacagg atatctgcgg tgagcagttt cggccccggc ccggggccaa   1800
gaacagatgg tcaccgcagt ttcggccccg gcccgaggcc aagaacagat ggtccccaga   1860
tatggcccaa ccctcagcag tttcttaaga cccatcagat gtttccaggc tcccccaagg   1920
acctgaaatg accctgcgcc ttatttgaat taaccaatca gcctgcttct cgcttctgtt   1980
cgcgcgcttc tgcttcccga gctctataaa agagctcaca acccctcact cggcgcgcca   2040
gtcctccgac agactgagtc gcccgggggg gatccaccgg gctgcaggaa ttcgatatca   2100
agcttatcga tgattctaga catgcatatc tagcgtcccg ggctgcagga attcataact   2160
tcgtataatg tatgctatac gaagttatca tatgccacca tgagcgagct gatcaaggag   2220
aacatgcaca tgaagctgta catggagggc accgtgaaca accaccactt caagtgcaca   2280
tccgagggcg aaggcaagcc ctacgagggc acccagacca tgaagatcaa ggtggtcgag   2340
ggcggccctc tcccctttcgc cttcgacatc ctggctacca gcttcatgta cggcagcaaa   2400
gccttcatca accacaccca gggcatcccc gacttcttta agcagtcctt ccctgagggc   2460
ttcacatggg agagaatcac cacatacgaa gacgggggcg tgctgaccgc tacccaggac   2520
accagcttcc agaacggctg catcatctac aacgtcaaga tcaacggggt gaacttccca   2580
tccaacggcc ctgtgatgca gaagaaaaca cgcggctggg aggccaacac cgagatgctg   2640
taccccgctg acggcggcct gagaggccac agccagatgg ccctgaagct cgtgggcggg   2700
ggctacctgc actgctcctt caagaccaca tacagatcca agaaacccgc taagaacctc   2760
aagatgcccg gcttccactt cgtggaccac agactggaaa gaatcaagga ggccgacaaa   2820
gagacctacg tcgagcagca cgagatggct gtggccaagt actgcgacct ccctagcaaa   2880
ctggggcaca gataaataac ttcgtataaa gtatcctata cgaagttata ctttggccgc   2940
ggctcgaggg ggttggggtt gcgccttttc caaggcagcc ctgggtttgc gcagggacgc   3000
ggctgctctg ggcgtggttc cgggaaacgc agcggcgccg accctgggtc tcgcacattc   3060
ttcacgtccg ttcgcagcgt cacccggatc ttcgccgcta cccttgtggg ccccccggcg   3120
acgcttcctg ctccgcccct aagtcgggaa ggttccttgc ggttcgcggc gtgccggacg   3180
tgacaaacgg aagccgcacg tctcactagt accctcgcag acggacagcg ccagggagca   3240
atggcagcgc gccgaccgcg atgggctgtg gccaatagcg gctgctcagc agggcgcgcc   3300
gagagcagcg gccgggaagg ggcggtgcgg gaggcggggt gtggggcggt agtgtgggcc   3360
ctgttcctgc ccgcgcggtg ttccgcattc tgcaagcctc cggagcgcac gtcggcagtc   3420
ggctccctcg ttgaccgaat caccgacctc tctccccagg gggatccacc ggtcgccacc   3480
atggtgagca agggcgagga gctgttcacc ggggtggtgc ccatcctggt cgagctggac   3540
ggcgacgtaa acggccacaa gttcagcgtg tccggcgagg gcgagggcga tgccacctac   3600
```

ggcaagctga ccctgaagtt catctgcacc accggcaagc tgcccgtgcc ctggcccacc 3660
ctcgtgacca ccctgaccta cggcgtgcag tgcttcagcc gctaccccga ccacatgaag 3720
cagcacgact tcttcaagtc cgccatgccc gaaggctacg tccaggagcg caccatcttc 3780
ttcaaggacg acggcaacta caagacccgc gccgaggtga agttcgaggg cgacaccctg 3840
gtgaaccgca tcgagctgaa gggcatcgac ttcaaggagg acggcaacat cctggggcac 3900
aagctggagt acaactacaa cagccacaac gtctatatca tggccgacaa gcagaagaac 3960
ggcatcaagg tgaacttcaa gatccgccac aacatcgagg acggcagcgt gcagctcgcc 4020
gaccactacc agcagaacac ccccatcggc gacggccccg tgctgctgcc cgacaaccac 4080
tacctgagca cccagtccgc cctgagcaaa gaccccaacg agaagcgcga tcacatggtc 4140
ctgctggagt tcgtgaccgc cgccgggatc actctcggca tggacgagct gtacaagtaa 4200
agcggccgcg actctagagt cgacctgcag gcatgcaagc ttgatatcaa gcttatcgat 4260
aatcaacctc tggattacaa aatttgtgaa agattgactg gtattcttaa ctatgttgct 4320
ccttttacgc tatgtggata cgctgcttta atgcctttgt atcatgctat tgcttcccgt 4380
atggctttca ttttctcctc cttgtataaa tcctggttgc tgtctcttta tgaggagttg 4440
tggcccgttg tcaggcaacg tggcgtggtg tgcactgtgt ttgctgacgc aacccccact 4500
ggttggggca ttgccaccac ctgtcagctc ctttccggga ctttcgcttt ccccctccct 4560
attgccacgg cggaactcat cgccgcctgc cttgcccgct gctggacagg ggctcggctg 4620
ttgggcactg acaattccgt ggtgttgtcg gggaaatcat cgtcctttcc ttggctgctc 4680
gcctgtgttg ccacctggat tctgcgcggg acgtccttct gctacgtccc ttcggccctc 4740
aatccagcgg accttccttc ccgcggcctg ctgccggctc tgcggcctct tccgcgtctt 4800
cgccttcgcc ctcagacgag tcggatctcc ctttgggccg cctccccgca tcgataccgt 4860
cgacctcgag ttttataaaa gaaaaggggg gactggaagg gatttattac agtgcaagaa 4920
gacatagaat cttagacatg tacttagaaa aggaagaagg catcatacca gattggcagg 4980
attacacctc aggaccagga attagatacc caaagacatt tggctggcta tggaaattag 5040
tccctgtaaa tgtatcagat gaggcacagg aggatgagag gcattattta atgcagccag 5100
ctcaaacttc caagtgggat gacccttggg gagaggttct agcgtggaag tttgatccaa 5160
ctctagccta cacttatgag gcatatgcta gatacccaga agagttggaa gcaagtcagg 5220
cctgtcagaa ctgcatttcg ctctgtattc agtcgctctg cggagaggct ggcagattga 5280
gccctgggag gttctctcca gcactagcag gtagagcctg ggtgttccct gctagactct 5340
caccagcact tggccagtgc tgggcagagt ggctccacgc ttgcttgctt aaagacctct 5400
tcaataaagc tgccatttta gaagtaagcc agtgtgtgtt cccatctctc ctagtcgccg 5460
cctggtcaac tcggtactcg gtaataagaa gaccctggtc tgttaggacc ctttctgctt 5520
tgagaaaccg aagcaggaaa atccctagca tggtacccag cttttgttcc ctttagtgag 5580
ggttaattcc gagcttggcg taatcatggt catagctgtt tcctgtgtga aattgttatc 5640
cgctcacaat tccacacaac atacgagccg gaagcataaa gtgtaaagcc tggggtgcct 5700
aatgagtgag ctaactcaca ttaattgcgt tgcgctcact gcccgctttc cagtcgggaa 5760
acctgtcgtg ccagctgcat taatgaatcg gccaacgcgc ggggagaggc ggtttgcgta 5820
ttgggcgctc ttccgcttcc tcgctcactg actcgctgcg ctcggtcgtt cg 5872

<210> SEQ ID NO 46

<211> LENGTH: 1653
<212> TYPE: DNA
<213> ORGANISM: Lampyris noctiluca
<220> FEATURE:
<221> NAME/KEY: CDS
<222> LOCATION: (1)..(1653)

<400> SEQUENCE: 46

```
atg gaa gac gcc aaa aac ata aag aaa ggc ccg gcg cca ttc tat ccg       48
Met Glu Asp Ala Lys Asn Ile Lys Lys Gly Pro Ala Pro Phe Tyr Pro
1               5                   10                  15

ctg gaa gat gga acc gct gga gag caa ctg cat aag gct atg aag aga       96
Leu Glu Asp Gly Thr Ala Gly Glu Gln Leu His Lys Ala Met Lys Arg
            20                  25                  30

tac gcc ctg gtt cct gga aca att gct ttt aca gat gca cat atc gag      144
Tyr Ala Leu Val Pro Gly Thr Ile Ala Phe Thr Asp Ala His Ile Glu
        35                  40                  45

gtg gac atc act tac gct gag tac ttc gaa atg tcc gtt cgg ttg gca      192
Val Asp Ile Thr Tyr Ala Glu Tyr Phe Glu Met Ser Val Arg Leu Ala
    50                  55                  60

gaa gct atg aaa cga tat ggg ctg aat aca aat cac aga atc gtc gta      240
Glu Ala Met Lys Arg Tyr Gly Leu Asn Thr Asn His Arg Ile Val Val
65                  70                  75                  80

tgc agt gaa aac tct ctt caa ttc ttt atg ccg gtg ttg ggc gcg tta      288
Cys Ser Glu Asn Ser Leu Gln Phe Phe Met Pro Val Leu Gly Ala Leu
                85                  90                  95

ttt atc gga gtt gca gtt gcg ccc gcg aac gac att tat aat gaa cgt      336
Phe Ile Gly Val Ala Val Ala Pro Ala Asn Asp Ile Tyr Asn Glu Arg
            100                 105                 110

gaa ttg ctc aac agt atg ggc att tcg cag cct acc gtg gtg ttc gtt      384
Glu Leu Leu Asn Ser Met Gly Ile Ser Gln Pro Thr Val Val Phe Val
        115                 120                 125

tcc aaa aag ggg ttg caa aaa att ttg aac gtg caa aaa aag ctc cca      432
Ser Lys Lys Gly Leu Gln Lys Ile Leu Asn Val Gln Lys Lys Leu Pro
    130                 135                 140

atc atc caa aaa att att atc atg gat tct aaa acg gat tac cag gga      480
Ile Ile Gln Lys Ile Ile Ile Met Asp Ser Lys Thr Asp Tyr Gln Gly
145                 150                 155                 160

ttt cag tcg atg tac acg ttc gtc aca tct cat cta cct ccc ggt ttt      528
Phe Gln Ser Met Tyr Thr Phe Val Thr Ser His Leu Pro Pro Gly Phe
                165                 170                 175

aat gaa tac gat ttt gtg cca gag tcc ttc gat agg gac aag aca att      576
Asn Glu Tyr Asp Phe Val Pro Glu Ser Phe Asp Arg Asp Lys Thr Ile
            180                 185                 190

gca ctg atc atg aac tcc tct gga tct act ggt ctg cct aaa ggt gtc      624
Ala Leu Ile Met Asn Ser Ser Gly Ser Thr Gly Leu Pro Lys Gly Val
        195                 200                 205

gct ctg cct cat aga act gcc tgc gtg aga ttc tcg cat gcc aga gat      672
Ala Leu Pro His Arg Thr Ala Cys Val Arg Phe Ser His Ala Arg Asp
    210                 215                 220

cct att ttt ggc aat caa atc att ccg gat act gcg att tta agt gtt      720
Pro Ile Phe Gly Asn Gln Ile Ile Pro Asp Thr Ala Ile Leu Ser Val
225                 230                 235                 240

gtt cca ttc cat cac ggt ttt gga atg ttt act aca ctc gga tat ttg      768
Val Pro Phe His His Gly Phe Gly Met Phe Thr Thr Leu Gly Tyr Leu
                245                 250                 255

ata tgt gga ttt cga gtc gtc tta atg tat aga ttt gaa gaa gag ctg      816
Ile Cys Gly Phe Arg Val Val Leu Met Tyr Arg Phe Glu Glu Glu Leu
            260                 265                 270

ttt ctg agg agc ctt cag gat tac aag att caa agt gcg ctg ctg gtg      864
Phe Leu Arg Ser Leu Gln Asp Tyr Lys Ile Gln Ser Ala Leu Leu Val
```

-continued

```
        275                 280                 285

cca acc cta ttc tcc ttc ttc gcc aaa agc act ctg att gac aaa tac      912
Pro Thr Leu Phe Ser Phe Phe Ala Lys Ser Thr Leu Ile Asp Lys Tyr
    290                 295                 300

gat tta tct aat tta cac gaa att gct tct ggt ggc gct ccc ctc tct      960
Asp Leu Ser Asn Leu His Glu Ile Ala Ser Gly Gly Ala Pro Leu Ser
305                 310                 315                 320

aag gaa gtc ggg gaa gcg gtt gcc aag agg ttc cat ctg cca ggt atc     1008
Lys Glu Val Gly Glu Ala Val Ala Lys Arg Phe His Leu Pro Gly Ile
                325                 330                 335

agg caa gga tat ggg ctc act gag act aca tca gct att ctg att aca     1056
Arg Gln Gly Tyr Gly Leu Thr Glu Thr Thr Ser Ala Ile Leu Ile Thr
            340                 345                 350

ccc gag ggg gat gat aaa ccg ggc gcg gtc ggt aaa gtt gtt cca ttt     1104
Pro Glu Gly Asp Asp Lys Pro Gly Ala Val Gly Lys Val Val Pro Phe
        355                 360                 365

ttt gaa gcg aag gtt gtg gat ctg gat acc ggg aaa acg ctg ggc gtt     1152
Phe Glu Ala Lys Val Val Asp Leu Asp Thr Gly Lys Thr Leu Gly Val
    370                 375                 380

aat caa aga ggc gaa ctg tgt gtg aga ggt cct atg att atg tcc ggt     1200
Asn Gln Arg Gly Glu Leu Cys Val Arg Gly Pro Met Ile Met Ser Gly
385                 390                 395                 400

tat gta aac aat ccg gaa gcg acc aac gcc ttg att gac aag gat gga     1248
Tyr Val Asn Asn Pro Glu Ala Thr Asn Ala Leu Ile Asp Lys Asp Gly
                405                 410                 415

tgg cta cat tct gga gac ata gct tac tgg gac gaa gac gaa cac ttc     1296
Trp Leu His Ser Gly Asp Ile Ala Tyr Trp Asp Glu Asp Glu His Phe
            420                 425                 430

ttc atc gtt gac cgc ctg aag tct ctg att aag tac aaa ggc tat cag     1344
Phe Ile Val Asp Arg Leu Lys Ser Leu Ile Lys Tyr Lys Gly Tyr Gln
        435                 440                 445

gtg gct ccc gct gaa ttg gaa tcc atc ttg ctc caa cac ccc aac atc     1392
Val Ala Pro Ala Glu Leu Glu Ser Ile Leu Leu Gln His Pro Asn Ile
    450                 455                 460

ttc gac gca ggt gtc gca ggt ctt ccc gac gat gac gcc ggt gaa ctt     1440
Phe Asp Ala Gly Val Ala Gly Leu Pro Asp Asp Asp Ala Gly Glu Leu
465                 470                 475                 480

ccc gcc gcc gtt gtt gtt ttg gag cac gga aag acg atg acg gaa aaa     1488
Pro Ala Ala Val Val Val Leu Glu His Gly Lys Thr Met Thr Glu Lys
                485                 490                 495

gag atc gtg gat tac gtc gcc agt caa gta aca acc gcg aaa aag ttg     1536
Glu Ile Val Asp Tyr Val Ala Ser Gln Val Thr Thr Ala Lys Lys Leu
            500                 505                 510

cgc gga gga gtt gtg ttt gtg gac gaa gta ccg aaa ggt ctt acc gga     1584
Arg Gly Gly Val Val Phe Val Asp Glu Val Pro Lys Gly Leu Thr Gly
        515                 520                 525

aaa ctc gac gca aga aaa atc aga gag atc ctc ata aag gcc aag aag     1632
Lys Leu Asp Ala Arg Lys Ile Arg Glu Ile Leu Ile Lys Ala Lys Lys
    530                 535                 540

ggc gga aag atc gcc gtg taa                                         1653
Gly Gly Lys Ile Ala Val
545                 550


<210> SEQ ID NO 47
<211> LENGTH: 550
<212> TYPE: PRT
<213> ORGANISM: Lampyris noctiluca

<400> SEQUENCE: 47

Met Glu Asp Ala Lys Asn Ile Lys Lys Gly Pro Ala Pro Phe Tyr Pro
```

-continued

```
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430
```

-continued

```
Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
    530                 535                 540

Gly Gly Lys Ile Ala Val
545                 550
```